(12) United States Patent
Bhide et al.

(10) Patent No.: US 10,544,133 B2
(45) Date of Patent: Jan. 28, 2020

(54) HETEROARYL SUBSTITUTED PYRIDYL COMPOUNDS USEFUL AS KINASE MODULATORS

(71) Applicant: BRISTOL-MYERS SQUIBB COMPANY, Princeton, NJ (US)

(72) Inventors: Rajeev S. Bhide, Princeton Junction, NJ (US); John V. Duncia, Newtown, PA (US); John Hynes, Washington Crossing, PA (US); Satheesh Kesavan Nair, Bangalore (IN); William J. Pitts, Newtown, PA (US); Sreekantha Ratna Kumar, Bangalore (IN); Daniel S. Gardner, Furlong, PA (US); Natesan Murugesan, Princeton Junction, NJ (US); Venkatram Reddy Paidi, Karnataka (IN); Joseph B. Santella, Springfield, PA (US); Ramesh Kumar Sistla, Bangalore (IN); Hong Wu, New Hope, PA (US)

(73) Assignee: Bristol-Myers Squibb Company, Princeton, NJ (US)

( * ) Notice: Subject to any disclaimer, the term of this patent is extended or adjusted under 35 U.S.C. 154(b) by 0 days.

(21) Appl. No.: 16/009,389

(22) Filed: Jun. 15, 2018

(65) Prior Publication Data

US 2018/0370956 A1     Dec. 27, 2018

Related U.S. Application Data

(60) Continuation of application No. 15/480,682, filed on Apr. 6, 2017, now Pat. No. 10,023,562, which is a division of application No. 14/441,705, filed as application No. PCT/US2013/068875 on Nov. 7, 2013, now Pat. No. 9,657,009.

(60) Provisional application No. 61/723,848, filed on Nov. 8, 2012.

(51) Int. Cl.
| | | |
|---|---|---|
| C07D 407/14 | (2006.01) |
| C07D 401/14 | (2006.01) |
| C07D 401/12 | (2006.01) |
| C07D 417/14 | (2006.01) |
| C07D 213/74 | (2006.01) |
| C07D 405/12 | (2006.01) |
| C07D 405/14 | (2006.01) |

(52) U.S. Cl.
CPC ......... *C07D 407/14* (2013.01); *C07D 213/74* (2013.01); *C07D 401/12* (2013.01); *C07D 401/14* (2013.01); *C07D 405/12* (2013.01); *C07D 405/14* (2013.01); *C07D 417/14* (2013.01)

(58) Field of Classification Search
CPC .................................................. C07D 407/14
USPC ........................................... 546/256; 514/333
See application file for complete search history.

(56) References Cited

U.S. PATENT DOCUMENTS

| | | | |
|---|---|---|---|
| 8,058,045 | B2 | 11/2011 | Collins et al. |
| 8,148,411 | B2 | 4/2012 | Bothe et al. |
| 8,586,751 | B2 | 11/2013 | De Lucca et al. |
| 8,987,311 | B2 | 3/2015 | Dodd et al. |
| 9,315,494 | B2 | 4/2016 | Moslin |
| 2005/0272753 | A1 | 12/2005 | Nagashima et al. |
| 2006/0148800 | A1 | 7/2006 | Stadtmueller et al. |
| 2009/0082329 | A1 | 3/2009 | Halley et al. |
| 2009/0203715 | A1 | 8/2009 | Bothe et al. |
| 2011/0224225 | A1 | 9/2011 | Zeitlmann et al. |
| 2011/0237590 | A1 | 9/2011 | Kitamura et al. |
| 2015/0011532 | A1 | 1/2015 | Paidi et al. |
| 2015/0018344 | A1 | 1/2015 | Paidi et al. |

FOREIGN PATENT DOCUMENTS

| | | |
|---|---|---|
| EP | 2532656 | 12/2012 |
| GB | 2388596 | 11/2003 |
| WO | WO 02/102800 A1 | 12/2002 |
| WO | WO 03/013523 A1 | 2/2003 |
| WO | WO 2004/065378 A1 | 8/2004 |
| WO | WO 2005/007646 A1 | 1/2005 |
| WO | WO 2005/075468 A2 | 8/2005 |
| WO | WO 2008/148889 A1 | 12/2008 |
| WO | WO 2009/046416 A1 | 4/2009 |
| WO | WO 2011/053701 A1 | 5/2011 |
| WO | WO 2012/149567 A1 | 11/2012 |
| WO | WO 2014/074675 A1 | 5/2014 |
| WO | WO 2015/103453 A1 | 7/2015 |

OTHER PUBLICATIONS

Buckley, G. M. et al., "IRAK-4 inhibitors: Part I: A series of amides," Bioorganic & Medicinal Chemistry Letters, 18(11), pp. 3211-3214 (2008).

Buckley, G. M. et al., "IRAK-4 inhibitors: Part II: A structure-based assessment of imidazo[1,2-a]pyridine binding," Bioorganic & Medicinal Chemistry Letters, 18(11), pp. 3291-3295 (2008).

(Continued)

*Primary Examiner* — Patricia L Morris
(74) *Attorney, Agent, or Firm* — Gary Greenblatt

(57) ABSTRACT

Compounds having the following formula:

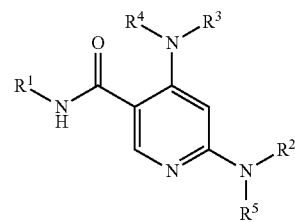

or a stereoisomer or a pharmaceutically-acceptable salt thereof, wherein $R^2$ is a monocyclic heteroaryl group, and $R^1$, $R^3$, $R^4$, $R^5$ and $R^6$ are as defined herein, are useful as kinase modulators, including IRAK-4 inhibition.

9 Claims, No Drawings

Specification includes a Sequence Listing.

(56) References Cited

OTHER PUBLICATIONS

Buckley, G. M. et al., "IRAK-4 inhibitors. Part III: A series of imidazo[1,2-a]pyridines," Bioorganic & Medicinal Chemistry Letters, 18(12), pp. 3656-3660 (2008).
International Search Report for PCT/US2013/068875 dated Mar. 4, 2014.
International Preliminary Report on Patentability for PCT/US2013/068875 dated May 12, 2015.
Hynes Jr., J. et al., "Chapter Nine—Advances in the Discovery of Small-Molecule IRAK4 inhibitors," Annual Reports in Medicinal Chemistry, vol. 49, pp. 117-133.
Hussein, W.M., et al., Toll-like receptor agonists: a patent review (2011-2013), Expert Opinion on Therapeutic Patents, 24(4) pp. 453-470 (2014).
Quesniaux, V.F.J., et al., "Toll-like receptors: emerging targets of immunomodulation," Expert Opinion on Therapeutic Patents, 14(1), pp. 85-100 (2004).
Flannery, S., et al., "The interleukin-1 receptor-associated kinases: Critical regulators of innate immune signaling," Biochemical Pharmacology 80, pp. 1981-1991 (2010).

HETEROARYL SUBSTITUTED PYRIDYL COMPOUNDS USEFUL AS KINASE MODULATORS

This application is a continuation application of U.S. patent application Ser. No. 15/480,682, filed Apr. 6, 2017, which is a divisional application of U.S. patent application Ser. No. 14/441,705, filed May 8, 2015, which claims priority to national phase application under 35 U.S.C. § 371 of International Patent Application No. PCT/US2013/068875, filed Nov. 7, 2013, which claims priority to provisional application U.S. 61/723,848, filed Nov. 8, 2012, the contents of which are herein incorporated by reference.

FIELD OF THE INVENTION

This invention relates to compounds useful as kinase inhibitors, including the modulation of IRAK-4. Provided herein are monocyclic heteroaryl-substituted pyridyl compounds, compositions comprising such compounds, and methods of their use. The invention further pertains to pharmaceutical compositions containing at least one compound according to the invention that are useful for the treatment of conditions related to kinase modulation and methods of inhibiting the activity of kinases, including IRAK-4 in a mammal.

BACKGROUND OF THE INVENTION

Toll/IL-1 receptor family members are important regulators of inflammation and host resistance. The Toll like receptor (TLR) family recognizes molecular patterns derived from infectious organisms including bacteria, fungi, parasites, and viruses (reviewed in Kawai, T. et al., *Nature Immunol.*, 11:373-384 (2010)). Ligand binding to the receptor induces dimerization and recruitment of adaptor molecules to a conserved cytoplasmic motif in the receptor termed the Toll/IL-1 receptor (TIR) domain. With the exception of TLR3, all TLRs recruit the adaptor molecule MyD88. The IL-1 receptor family also contains a cytoplasmic TIR motif and recruits MyD88 upon ligand binding (reviewed in Sims, J. E. et al., *Nature Rev. Immunol.*, 10:89-102 (2010)).

Members of the IRAK family of serine/threonine kinases are recruited to the receptor via interactions with MyD88. The family consists of four members. Several lines of evidence indicate that IRAK4 plays a critical and non-redundant role in initiating signaling via MyD88 dependent TLRs and IL-R family members. Structural data confirms that IRAK4 directly interacts with MyD88 and subsequently recruits either IRAK1 or IRAK2 to the receptor complex to facilitate downstream signaling (Lin, S. et al., *Nature*, 465:885-890 (2010)). IRAK4 directly phosphorylates IRAK1 to facilitate downstream signaling to the E3 ubiquitin ligase TRAF6, resulting in activation of the serine/threonine kinase TAK1 with subsequent activation of the NFκB pathway and MAPK cascade (Flannery, S. et al., *Biochem. Pharmacol.*, 80:1981-1991 (2010)). A subset of human patients was identified who lack IRAK4 expression (Picard, C. et al., *Science*, 299:2076-2079 (2003)). Cells from these patients fail to respond to all TLR agonists with the exception of TLR3 as well as to members of the IL-1 family including IL-1β and IL-18 (Ku, C. et al., *J. Exp. Med.*, 204:2407-2422 (2007)). Deletion of IRAK4 in mice results in a severe block in IL-1, IL-18 and all TLR dependent responses with the exception of TLR3 (Suzuki, N. et al., *Nature*, 416:750-754 (2002)). In contrast, deletion of either IRAK1 (Thomas, J. A. et al., *J. Immunol.*, 163:978-984 (1999); Swantek, J. L. et al., *J. Immunol.*, 164:4301-4306 (2000) or IRAK2 (Wan, Y. et al., *J. Biol. Chem.*, 284:10367-10375 (2009)) results in partial loss of signaling. Furthermore, IRAK4 is the only member of the IRAK family whose kinase activity has been shown to be required for initiation of signaling. Replacement of wild type IRAK4 in the mouse genome with a kinase inactive mutant (KDKI) impairs signaling via all MyD88 dependent receptors including IL-1, IL-18 and all TLRs with the exception of TLR3 (Koziczak-Holbro, M. et al., *J. Biol. Chem.*, 282:13552-13560 (2007); Kawagoe, T. et al., *J. Exp. Med.*, 204:1013-1024 (2007); and Fraczek, J. et al., *J. Biol. Chem.*, 283:31697-31705 (2008)).

As compared to wild type animals, IRAK4 KDKI mice show greatly reduced disease severity in mouse models of multiple sclerosis (Staschke, K. A. et al., *J. Immunol.*, 183:568-577 (2009)), rheumatoid arthritis (Koziczak-Holbro, M. et al., *Arthritis Rheum.*, 60:1661-1671 (2009)), atherosclerosis (Kim, T. W. et al., *J. Immunol.*, 186:2871-2880 (2011) and Rekhter, M. et al., *Biochem. Biophys. Res. Comm.*, 367:642-648 (2008)), and myocardial infarction (Maekawa, Y. et al., *Circulation*, 120:1401-1414 (2009)). As described, IRAK4 inhibitors will block all MyD88 dependent signaling. MyD88 dependent TLRs have been shown to contribute to the pathogenesis of multiple sclerosis, rheumatoid arthritis, cardiovascular disease, metabolic syndrome, sepsis, systemic lupus erythematosus, inflammatory bowel diseases including Crohn's disease and ulcerative colitis, autoimmune uveitis, psoriasis, asthma, allergy, type I diabetes, and allograft rejection (Keogh, B. et al., *Trends Pharmacol. Sci.*, 32:435-442 (2011); Mann, D. L., *Circ. Res.*, 108:1133-1145 (2011); Jiang, W. et al., *J. Invest. Dermatol.* (2013) doi: 10.1038/jid.2013.57; Horton, C. G. et al., *Mediators Inflamm.*, Article ID 498980 (2010), doi: 10.1155/2010/498980; Goldstein, D. R. et al., *J. Heart Lung Transplant.*, 24:1721-1729 (2005); and Cario, E., *Inflamm. Bowel Dis.*, 16:1583-1597 (2010)). Oncogenically active MyD88 mutations in diffuse large B cell lymphomas have been identified that are sensitive to IRAK4 inhibition (Ngo, V. N. et al., *Nature*, 470:115-121 (2011)). Whole genome sequencing also identified mutations in MyD88 associated with chronic lymphatic leukemia and Waldenström's Macroglobulinemia suggesting that IRAK4 inhibitors may also have utility in treating leukemias (Puente, X. S. et al., *Nature*, 475:101-105 (2011); Treon, S. P. et. al., *New Engl. J. Med.*, 367:826-833 (2012)).

In addition to blocking TLR signaling, IRAK4 inhibitors will also block signaling by members of the IL-1 family. Neutralization of IL-1 has been shown to be efficacious in multiple diseases including gout; gouty arthritis; type 2 diabetes; auto-inflammatory diseases including Cryopyrin-Associated Periodic Syndromes (CAPS), TNF Receptor Associated Periodic Syndrome (TRAPS), Familial Mediterranean Fever (FMF), adult onset stills; systemic onset juvenile idiopathic arthritis; stroke; GVHD; smoldering multiple myeloma; recurrent pericarditis; osteoarthritis; emphysema (Dinarello, C. A., *Eur. J. Immunol.*, 41:1203-1217 (2011) and Couillin, I. et al., *J. Immunol.*, 183:8195-8202 (2009)). In a mouse model of Alzheimer's disease, blockade of IL-1 receptor improved cognitive defects, attenuated tau pathology and reduced oligomeric forms of amyloid-β (Kitazawa, M. et al., *J. Immunol.*, 187:6539-6549 (2011)). IL-1 has also been shown to be a critical link to adaptive immunity, driving differentiation of the TH17 effector T cell subset (Chung, Y. et al., *Immunity*, 30:576-587 (2009)). Therefore, IRAK4 inhibitors are predicted to have efficacy in TH17 associated diseases including multiple sclerosis, psoriasis, inflammatory bowel diseases, autoimmune uveitis, and rheumatoid arthritis (Wilke, C. M. et al., *Trends Immunol.*, 32:603-661 (2011)).

In view of the conditions that may benefit by treatment involving modulation of protein kinases, it is immediately apparent that new compounds capable of modulating protein kinases such as IRAK-4 and methods of using these compounds could provide substantial therapeutic benefits to a wide variety of patients.

The present invention relates to a new class of heterocyclic-substituted pyridyl compounds found to be effective inhibitors of protein kinases including IRAK-4.

SUMMARY OF THE INVENTION

Modulators of kinase activity which may generally be described as heterocyclic-substituted pyridyl compounds found are provided herein.

The invention is directed to compounds of Formula I that which are useful as inhibitors of IRAK-4, and are useful for the treatment of proliferative diseases, allergic diseases, autoimmune diseases and inflammatory diseases, or stereoisomers, tautomers, pharmaceutically acceptable slats, solvates or prodrugs thereof.

The present invention also provides processes and intermediates for making the compounds of the present invention or stereoisomers, tautomers, pharmaceutically acceptable salts, solvates, or prodrugs thereof.

The present invention also provides pharmaceutical compositions comprising a pharmaceutically acceptable carrier and at least one of the compounds of the present invention or stereoisomers, tautomers, pharmaceutically acceptable salts, solvates, or prodrugs thereof.

The present invention also provides a method for inhibition of IRAK-4 comprising administering to a host in need of such treatment a therapeutically effective amount of at least one of the compounds of the present invention or stereoisomers, tautomers, pharmaceutically acceptable salts, solvates, or prodrugs thereof.

The present invention also provides a method for treating proliferative, metabolic, allergic, autoimmune and inflammatory diseases, comprising administering to a host in need of such treatment a therapeutically effective amount of at least one of the compounds of the present invention or stereoisomers, tautomers, pharmaceutically acceptable salts, solvates, or prodrugs thereof.

A preferred embodiment is a method for treating inflammatory and autoimmune diseases wherein the treatment of inflammatory diseases is even more preferred. Particular, inflammatory and autoimmune diseases include, but are not limited to, Crohn's disease, ulcerative colitis, asthma, graft versus host disease, allograft rejection, chronic obstructive pulmonary disease; Graves' disease, rheumatoid arthritis, systemic lupus erythematosis, psoriasis; CAPS, TRAPS, FMF, adult onset stills, systemic onset juvenile idiopathic arthritis, multiple sclerosis, neuropathic pain, gout, and gouty arthritis.

An alternate preferred embodiment is a method for treating metabolic diseases, including type 2 diabetes and atherosclerosis.

The present invention also provides the compounds of the present invention or stereoisomers, tautomers, pharmaceutically acceptable salts, solvates, or prodrugs thereof, for use in therapy.

The present invention also provides the use of the compounds of the present invention or stereoisomers, tautomers, pharmaceutically acceptable salts, solvates, or prodrugs thereof, for the manufacture of a medicament for the treatment of cancers.

These and other features of the invention will be set forth in the expanded form as the disclosure continues.

DETAILED DESCRIPTION OF THE EMBODIMENTS OF THE INVENTION

Provided herein is at least one chemical entity chosen from compounds of Formula (I):

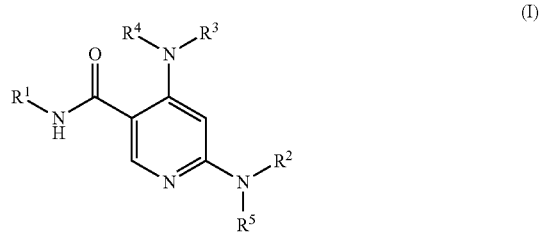

(I)

or a stereoisomer or pharmaceutically-acceptable salt thereof, wherein:

$R^1$ is $C_{1-6}$ alkyl substituted with 0-7 $R^{1a}$, $C_{1-6}$ haloalkyl, $C_{2-6}$ alkenyl substituted with 0-7 $R^{1a}$, $C_{2-6}$ alkynyl substituted with 0-7 $R^{1a}$, —$(CH_2)_r$—$C_{3-10}$ cycloalkyl substituted with 0-7 $R^{1a}$, —$(CH_2)_r C_{6-10}$ aryl substituted with 0-7 $R^{1a}$, or —$(CH_2)_r$-5-10 membered heterocycle containing 1-4 heteroatoms selected from N, O, and S, substituted with 0-7 $R^{1a}$;

$R^{1a}$ at each occurrence is independently hydrogen, =O, F, Cl, Br, $OCF_3$, $CF_3$, $CHF_2$, CN, $NO_2$, —$(CH_2)_rOR^b$, —$(CH_2)_rSR^b$, —$(CH_2)_rC(O)R^b$, —$(CH_2)_rC(O)OR^b$, —$(CH_2)_rOC(O)R^b$, —$(CH_2)_rNR^{11}R^{11}$, —$(CH_2)_rC(O)NR^{11}R^{11}$, —$(CH_2)_rNR^bC(O)R^c$, —$(CH_2)_rNR^bC(O)OR^c$, —$NR^bC(O)NR^{11}R^{11}$, —$S(O)_pNR^{11}R^{11}$, —$NR^bS(O)_pR^c$, —$S(O)R^c$, —$S(O)_2R^c$, $C_{1-6}$ alkyl substituted with 0-2 $R^a$, $C_{1-6}$ haloalkyl, —$(CH_2)_r$-3-14 membered carbocycle substituted with 0-3 $R^a$, or —$(CH_2)_r$-5-7 membered heterocycle comprising carbon atoms and 1-4 heteroatoms selected from N, O, and $S(O)_p$ substituted with 0-3 $R^a$;

$R^2$ is 5-6 membered heteroaryl containing 1-3 heteroatoms selected from N, O, and S, substituted with 0-4 $R^{2a}$;

$R^{2a}$ at each occurrence is independently hydrogen, =O, halo, $OCF_3$, CN, $NO_2$, —$(CH_2)OR^b$, —$(CH_2)_rSR^b$, —$(CH_2)_rC(O)R^b$, —$(CH_2)C(O)OR^b$, —$(CH_2)_rOC(O)R^b$, —$(CH_2)_rNR^{11}R^{11}$, —$(CH_2)_rC(O)NR^{11}R^{11}$, —$(CH_2)_r NR^bC(O)R^c$, —$(CH_2)_rNR^bC(O)OR^c$, —$NR^bC(O)NR^{11}R^{11}$, —$S(O)_pNR^{11}R^{11}$, —$NR^bS(O)_pR^c$, —$S(O)R^c$, —$S(O)_2R^c$, $C_{1-6}$ alkyl substituted with 0-2 $R^a$, $C_{1-6}$ haloalkyl, —$(CH_2)_r$-3-14 membered carbocycle substituted with 0-1 $R^a$, or —$(CH_2)_r$-5-7 membered heterocycle comprising carbon atoms and 1-4 heteroatoms selected from N, O, and $S(O)_p$, substituted with 0-2 $R^a$;

$R^3$ is $C_{1-6}$ alkyl substituted with 0-3 $R^{3a}$, $C_{1-6}$ haloalkyl, $C_{2-6}$ alkenyl substituted with 0-3 $R^{3a}$, $C_{2-6}$ alkynyl substituted with 0-3 $R^{3a}$, $C_{3-10}$ cycloalkyl substituted with 0-3 $R^{3a}$, $C_{6-10}$ aryl substituted with 0-3 $R^{3a}$, or 5-10 membered heterocycle containing 1-4 heteroatoms selected from N, O, and S, substituted with 0-3 $R^{3a}$;

$R^{3a}$ at each occurrence is independently hydrogen, =O, F, Cl, Br, $OCF_3$, $CF_3$, $CHF_2$, CN, $NO_2$, —$(CH_2)_rOR^b$, —$(CH_2)_rSR^b$, —$(CH_2)_rC(O)R^b$, —$(CH_2)_rC(O)OR^b$, —$(CH_2)_rOC(O)R^b$, —$(CH_2)_rNR^{11}R^{11}$, —$(CH_2)_rC(O)

NR$^{11}$R$^{11}$, —(CH$_2$)$_r$NR$^b$C(O)R$^c$, —(CH$_2$)$_r$NR$^b$C(O)OR$^c$, —NR$^b$C(O)NR$^{11}$R$^{11}$, —S(O)$_p$NR$^{11}$R$^{11}$, —NR$^b$S(O)$_p$R$^c$, —S(O)R$^c$, —S(O)$_2$R$^c$, C$_{1-6}$ alkyl substituted with 0-3 R$^a$, C$_{1-6}$ haloalkyl, —(CH$_2$)$_r$-3-14 membered carbocycle substituted with 0-3 R$^a$, or —(CH$_2$)$_r$-5-10 membered heterocycle comprising carbon atoms and 1-4 heteroatoms selected from N, O, and S(O)$_p$, substituted with 0-3 R$^a$;

R$^4$ and R$^5$ are independently hydrogen or C$_{1-4}$ alkyl substituted with 0-1 R$^f$;

R$^{11}$ at each occurrence is independently (i) hydrogen, C$_{1-6}$ alkyl substituted with 0-1 R$^f$, CF$_3$, C$_{3-10}$ cycloalkyl substituted with 0-1 R$^f$, —(CH)$_r$-phenyl substituted with 0-3 R$^d$, or —(CH$_2$)$_r$-5-7 membered heterocycle comprising carbon atoms and 1-4 heteroatoms selected from N, O, and S(O)$_p$, substituted with 0-3 R$^d$; or (ii) one R$^{11}$ together with a second R$^{11}$ and the nitrogen atom to which they are both attached may be combined to form an azetidinyl, pyrrolidinyl, piperidinyl, morpholinyl, or 4-(C$_{1-6}$ alkyl)piperazinyl ring;

R$^a$ at each occurrence is independently hydrogen, F, Cl, Br, OCF$_3$, CF$_3$, CHF$_2$, CN, NO$_2$, —(CH$_2$)$_r$OR$^b$, —(CH$_2$)$_r$SR$^b$, —(CH$_2$)$_r$C(O)R$^b$, —(CH$_2$)$_r$C(O)OR$^b$, —(CH$_2$)$_r$OC(O)R$^b$, —(CH$_2$)$_r$NR$^{11}$R$^{11}$, —(CH$_2$)$_r$C(O)NR$^{11}$R$^{11}$, —(CH$_2$)$_r$NR$^b$C(O)R$^c$, —(CH$_2$)$_r$NR$^b$C(O)OR$^c$, —NR$^b$C(O)NR$^{11}$R$^{11}$, —S(O)$_p$NR$^{11}$R$^{11}$, —NR$^b$S(O)$_p$R$^c$, —S(O)R$^c$, —S(O)$_2$R$^c$, C$_{1-6}$ alkyl substituted with 0-3 R$^f$, C$_{1-6}$ haloalkyl, —(CH$_2$)$_r$-3-14 membered carbocycle, or —(CH$_2$)$_r$-5-7 membered heterocycle comprising carbon atoms and 1-4 heteroatoms selected from N, O, and S(O)$_p$, substituted with 0-3 R$^f$, alternatively two R$^a$ on adjacent or the same carbon atom form a cyclic acetal of the formula —O—(CH$_2$)$_n$—O— or —O—CF$_2$—O—, wherein n is 1 or 2;

R$^b$ is hydrogen, C$_{1-6}$ alkyl substituted with 0-2 R$^d$, C$_{1-6}$ haloalkyl, C$_{3-6}$ cycloalkyl substituted with 0-2 R$^d$, or (CH$_2$)$_r$-phenyl substituted with 0-3 R$^d$;

R$^c$ is C$_{1-6}$ alkyl substituted with 0-3 R$^f$, —(CH$_2$)$_r$—C$_{3-6}$ cycloalkyl substituted with 0-3 R$^f$, or —(CH$_2$)$_r$-phenyl substituted with 0-3 R$^f$;

R$^d$ at each occurrence is independently hydrogen, F, Cl, Br, OCF$_3$, CF$_3$, CN, NO$_2$, —OR$^e$, —(CH$_2$)$_r$C(O)R$^c$, —NR$^e$R$^e$, —NR$^e$C(O)OR$^e$, C$_{1-6}$ alkyl, or —(CH$_2$)$_r$-phenyl substituted with 0-3 R$^f$;

R$^e$ is hydrogen, C$_{1-6}$ alkyl, C$_{3-6}$ cycloalkyl, or —(CH$_2$)$_r$-phenyl substituted with 0-3 R$^f$;

R$^f$ at each occurrence is independently hydrogen, halo, NH$_2$, OH, C$_{3-6}$ cycloalkyl, CF$_3$ or O(C$_{1-6}$ alkyl);

p is 0, 1, or 2; and r is 0, 1, 2, 3, or 4.

In another embodiment are provided compounds of formula I, or a stereoisomer or pharmaceutically-acceptable salt thereof, wherein R$^2$ is pyridyl, thiazolyl, pyrimidinyl, pyrrolyl, pyrazolyl, imidazolyl, oxazolyl, isoxazolyl, thiadiazolyl, isothiazolyl, furanyl, thienyl, oxadiazolyl, pyrazinyl, pyridazinyl or triazinyl, each group substituted by 0-4 groups selected from R$^{2a}$.

In another embodiment, there is provided a compound of formula I, or a stereoisomer or pharmaceutically-acceptable salt thereof, wherein both R$^4$ and R$^5$ are hydrogen.

In another embodiment, there is provided a compound of formula I having the structure of formula II:

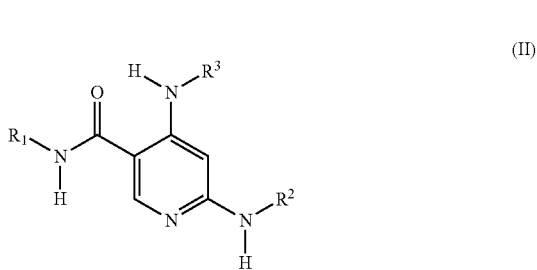

(II)

or a stereoisomer or pharmaceutically-acceptable salt thereof, wherein:

R$^1$ is C$_{1-6}$ alkyl, —(CH$_2$)$_r$C$_{3-10}$ cycloalkyl, —(CH$_2$)$_r$-5-7 membered heterocycle containing 1-4 heteroatoms selected from N, O and S, or —(CH$_2$)$_r$-phenyl, each group substituted with 0-4 R$^{1a}$;

R$^{1a}$ at each occurrence is independently hydrogen, =O, F, Cl, Br, OCF$_3$, CF$_3$, CHF$_2$, CN, NO$_2$, —(CH$_2$)$_r$OR$^b$, —(CH$_2$)$_r$SR$^b$, —(CH$_2$)$_r$C(O)R$^b$, —(CH$_2$)$_r$C(O)OR$^b$, —(CH$_2$) OC(O)R$^b$, —(CH$_2$)$_r$NR$^{11}$R$^{11}$, —(CH$_2$)C(O)NR$^{11}$R$^{11}$, —(CH$_2$)$_r$NR$^b$C(O)R$^c$, —(CH$_2$)$_r$NR$^b$C(O)OR$^c$, —NR$^b$C(O)NR$^{11}$R$^{11}$, —S(O)$_p$NR$^{11}$R$^{11}$, —NR$^b$S(O)$_p$R$^c$, —S(O)R$^c$, —S(O)$_2$R$^c$, C$_{1-6}$ alkyl substituted with 0-2 R$^a$, C$_{1-6}$ haloalkyl, —(CH$_2$)$_r$-3-14 membered carbocycle substituted with 0-3 R$^a$ (hydrogen or —C(O)NHCH$_2$), or —(CH$_2$)$_r$-5-7 membered heterocycle comprising carbon atoms and 1-4 heteroatoms selected from N, O, and S(O)$_p$ substituted with 0-3 R$^a$;

R$^2$ is pyridyl, thiazolyl, pyrimidinyl, pyrrolyl, pyrazolyl, imidazolyl, oxazolyl, isoxazolyl, thiadiazolyl, isothiazolyl, furanyl, thienyl, oxadiazolyl, pyrazinyl, pyridazinyl or triazinyl, each group substituted by 0-4 groups selected from R$^{2a}$;

R$^{2a}$ at each occurrence is independently hydrogen, =O, F, Cl, Br, OCF$_3$, CN, NO$_2$, —(CH$_2$)$_r$OR$^b$, —(CH$_2$)$_r$SR$^b$, —(CH$_2$)$_r$C(O)R$^b$, —(CH$_2$)$_r$C(O)OR$^b$, —(CH$_2$) OC(O)R$^b$, —(CH$_2$)$_r$NR$^{11}$R$^{11}$, —(CH$_2$)$_r$C(O)NR$^{11}$R$^{11}$, —(CH$_2$)$_r$NR$^b$C(O)R$^c$, —(CH$_2$)$_r$NR$^b$C(O)OR$^c$, —NR$^b$C(O)NR$^{11}$R$^{11}$, —S(O)$_p$NR$^{11}$R$^{11}$, —NR$^b$S(O)$_p$R$^c$, —S(O)R$^c$, —S(O)$_2$R$^c$, C$_{1-6}$ alkyl substituted with 0-2 R$^a$, C$_{1-6}$ haloalkyl, —(CH$_2$)$_r$-3-14 membered carbocycle substituted with 0-1 R$^a$, or —(CH$_2$)$_r$-5-7 membered heterocycle comprising carbon atoms and 1-4 heteroatoms selected from N, O, and S(O)$_p$ substituted with 0-1 R$^a$;

R$^3$ is C$_{1-6}$ alkyl, C$_{3-10}$ cycloalkyl, phenyl, or a 5-10 membered heterocycle containing 1-4 heteroatoms selected from N, O, and S substituted with 0-3 R$^{3a}$;

R$^{3a}$ at each occurrence is independently hydrogen, =O, F, Cl, Br, OCF$_3$, CF$_3$, CHF$_2$, CN, NO$_2$, —(CH$_2$)O)R$^b$, —(CH$_2$)$_r$SR$^b$, —(CH$_2$)$_r$C(O)R$^b$, —(CH$_2$)$_r$C(O)OR$^b$, —(CH$_2$)$_r$OC(O)R$^b$, —(CH$_2$)$_r$NR$^{11}$R$^{11}$, —(CH$_2$)$_r$C(O) NR$^{11}$R$^{11}$, —(CH$_2$)$_r$NR$^b$C(O)R$^c$, —(CH$_2$)$_r$NR$^b$C(O)OR$^c$, —NR$^b$C(O)NR$^{11}$R$^{11}$, —S(O)$_p$NR$^{11}$R$^{11}$, —NR$^b$S(O)$_p$R$^c$, —S(O)R$^c$, —S(O)$_2$R$^c$, C$_{1-6}$ alkyl substituted with 0-3 R$^a$, C$_{1-6}$ haloalkyl, —(CH$_2$)$_r$-3-14 membered carbocycle substituted with 0-3 R$^a$, or —(CH$_2$)$_r$-5-10 membered heterocycle comprising carbon atoms and 1-4 heteroatoms selected from N, O, and S(O)$_p$ substituted with 0-3 R$^a$;

R$^{11}$ at each occurrence is independently hydrogen, C$_{1-6}$ alkyl substituted with 0-1 R$^f$, CF$_3$, a C$_{3-10}$ cycloalkyl substituted with 0-1 R$^f$, —CH$_2$-phenyl substituted with 0-3 R$^d$, or —(CH$_2$)-5-7 membered heterocycle comprising carbon atoms and 1-4 heteroatoms selected from N, O, and S(O)$_p$, substituted with 0-3 R$^d$;

$R^a$ at each occurrence is independently:
  (i) hydrogen, F, Cl, Br, $OCF_3$, $CF_3$, $CHF_2$, CN, $NO_2$, —$(CH_2)_rOR^b$, —$(CH_2)_rSR^b$, —$(CH_2)_rC(O)R^b$, —$(CH_2)_rC(O)OR^b$, —$(CH_2)_rOC(O)R^b$, —$(CH_2)_rNR^{11}R^{11}$, —$(CH_2)_rC(O)NR^{11}R^{11}$, —$(CH_2)_rNR^bC(O)R^c$, —$(CH_2)_rNR^bC(O)OR^c$, —$NR^bC(O)NR^{11}R^{11}$, —$S(O)_pNR^{11}R^{11}$, —$NR^bS(O)_pR^c$, —$S(O)R^c$, —$S(O)_2R^c$,
  $C_{1-6}$ alkyl, $C_{1-6}$ haloalkyl, —$(CH_2)_r$-3-14 membered carbocycle, or —$(CH_2)_r$-5-7 membered heterocycle comprising carbon atoms and 1-4 heteroatoms selected from N, O, and $S(O)_p$; or
  (ii) two $R^a$, two $R^a$ on adjacent or the same carbon atom form a cyclic acetal of the formula —O—$(CH_2)_n$—O— or —O—$CF_2$—O—, wherein n is 1 or 2;
$R^b$ is hydrogen, $C_{1-6}$ alkyl substituted with 0-2 $R^d$, $C_{1-6}$ haloalkyl, $C_{3-6}$ cycloalkyl substituted with 0-2 $R^d$, or —$(CH_2)_r$-phenyl substituted with 0-3 $R^d$;
$R^c$ is $C_{1-6}$ alkyl, $C_{3-6}$ cycloalkyl or —$(CH_2)_r$-phenyl substituted with 0-3 $R^f$;
$R^d$ at each occurrence is independently hydrogen, F, Cl, Br, $OCF_3$, $CF_3$, CN, $NO_2$, —$OR^e$, —$(CH_2)_rC(O)R^e$, —$NR^eR^e$, —$NR^eC(O)OR^e$, $C_{1-6}$ alkyl, or —$(CH_2)_r$-phenyl substituted with 0-3 $R^f$;
$R^e$ is hydrogen, $C_{1-6}$ alkyl, $C_{3-6}$ cycloalkyl, or —$(CH_2)_r$-phenyl substituted with 0-3 $R^f$;
$R^f$ is hydrogen, halo, $NH_2$, OH, or $O(C_{1-6}$ alkyl);
r is 0, 1, 2, 3, or 4; and
p is 0, 1, or 2.

In another embodiment, there is provided a compound, or a stereoisomer or pharmaceutically-acceptable salt thereof, wherein $R^2$ is thiazolyl, pyridyl, or pyrimidinyl, each group substituted by 0-4 $R^{2a}$.

In a preferred embodiment, there is provided a compound, or a stereoisomer or pharmaceutically-acceptable salt thereof, where $R^a$ is independently =O, F, Cl, CN, —$(CH_2)OR^b$, —$(CH_2)C(O)R^b$, —$(CH_2)_rC(O)OR^b$, —$(CH_2)_rNR^{11}R^{11}$, $C_{1-6}$ alkyl substituted with 0-2 $R^a$, or pyridyl.

In an especially preferred embodiment, there is provided a compound, or a stereoisomer or pharmaceutically-acceptable salt thereof, wherein $R^b$ is ethyl or methyl, $R^{11}$ is hydrogen, and r is 0.

In a more preferred embodiment compounds of Formula (I), or a stereoisomer or pharmaceutically-acceptable salt thereof, are provided wherein $R^2$ is

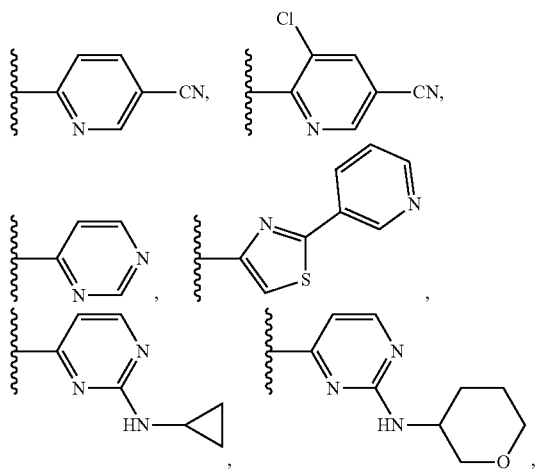

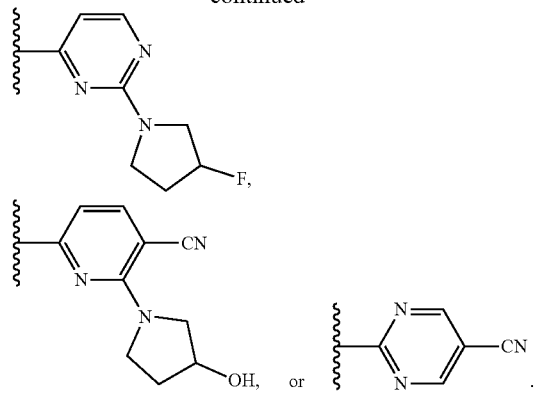

In yet another more preferred embodiment there are provided compounds of Formula (I), or a stereoisomer or pharmaceutically-acceptable salt thereof, wherein:
$R^1$ is $C_{1-6}$ alkyl, —$(CH_2)_rC_{3-10}$ cycloalkyl, —$(CH_2)_r$-6-membered heterocycle containing 1-4 heteroatoms selected from N, S and O, or —$(CH_2)_r$-phenyl, each group substituted by 0-4 $R^{1a}$; and
$R^{1a}$ at each occurrence is independently:
  (i) F, $CF_3$, CN, —$(CH_2)_rOR^b$, —$(CH_2)_rC(O)NR^{11}R^{11}$, —$(CH_2)_rNR^bC(O)R^c$, or —$NR^bC(O)NR^{11}R^{11}$; or
  (ii) $C_{1-6}$ alkyl, $C_{3-10}$ cycloalkyl (especially cyclopropyl or cyclobutyl), phenyl, or a 5-7 membered heterocycle comprising carbon atoms and 1-3 heteroatoms selected from N and O (especially pyrrolidinyl, or morpholinyl), each group substituted with 0-4 $R^a$;
$R^a$ is independently hydrogen, —$(CH_2)_rC(O)NR^{11}R^{11}$, $C_{1-4}$ alkyl, or a 5-7 membered heterocycle comprising carbon atoms and 1-3 heteroatoms selected from N and O (especially triazolyl);
$R^b$ is hydrogen or methyl;
$R^c$ independently, at each occurrence is:
  (i) $C_{1-4}$ alkyl; or
  (ii) $C_{3-6}$ cycloalkyl (especially cyclopentyl or cyclohexyl) or phenyl;
$R^{11}$ at each occurrence is independently hydrogen or $C_{1-4}$ alkyl; and
r is 0, 1, 2, 3, or 4.

In another embodiment, there is provided a compound of Formula (I), or a stereoisomer or pharmaceutically-acceptable salt thereof, wherein $R^1$ is $C_{1-6}$ alkyl or cyclohexyl, each substituted by 0-4 R.

In a further embodiment, there is provided a compound of formula I, or a stereoisomer or pharmaceutically-acceptable salt thereof, wherein $R^1$ is

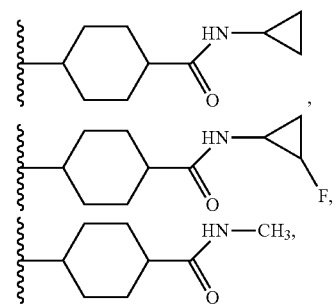

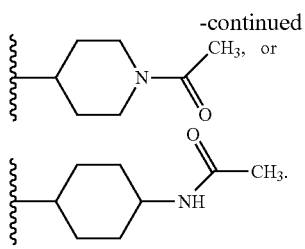

In another embodiment there are provided compounds of Formula (I), or a stereoisomer or pharmaceutically-acceptable salt thereof, in which
$R^3$ is $C_{1-6}$ alkyl, $C_{3-10}$ cycloalkyl, phenyl, or a 5-7-membered heterocycle containing 1-3 heteroatoms selected from N, O and S, (especially tetrahydropyranyl, tetrahydrofuranyl, or oxetanyl), each group optionally substituted with 0-3 $R^{3a}$;
$R^{3a}$ is, independently at each occurrence:
  (i) hydrogen, F, Cl, $CF_3$, $CHF_2$, —$(CH_2)_rOR^b$, —$(CH_2)_rC(O)OR^b$, —$(CH_2)_r NR^{11}R^{11}$, or —$(CH_2)_rC(O)NR^{11}R^{11}$; or
  (ii) $C_{1-6}$ alkyl, —$(CH_2)_r$-phenyl, $C_{3-10}$ cycloalkyl, or —$(CH_2)_r$-5-7 membered heterocycle comprising carbon atoms and 1-4 heteroatoms selected from N, O, and $S(O)_p$, each group substituted with 0-3 $R^a$;
$R^a$ is hydrogen, F, Cl, or —$(CH_2)OR^b$;
$R^b$ is hydrogen, $CHF_2$, or $C_{1-4}$ alkyl;
$R^{11}$ is independently hydrogen, $C_{3-10}$ cycloalkyl, —$CF_3$, or $C_{1-4}$ alkyl optionally substituted with OH; and
r is 0, 1, 2, 3, or 4.

In another preferred embodiment there are provided compounds of Formula (I), or a stereoisomer or pharmaceutically-acceptable salt thereof, in which $R^3$ is methyl, ethyl, isopropyl, isobutyl, cyclopropyl, cyclopentyl, or tetrahydropyranyl, each group substituted by 0-2 groups independently selected from F and —$CF_3$.

In another embodiment, there is provided a compound of Formula (I), wherein $R^3$ is selected from the following groups: —$CH_2CH_3$, —$CH(CH_3)_2$, —$CH_2CF_3$,

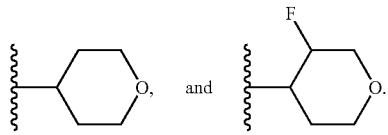

In one embodiment, a compound of Formula (II) or a stereoisomer or pharmaceutically-acceptable salt thereof is provided wherein $R^1$ is $C_{1-6}$ alkyl, cyclohexyl, or piperidinyl, each substituted by 0-4 $R^{1a}$.

In one embodiment, a compound of Formula (II) or a stereoisomer or pharmaceutically-acceptable salt thereof is provided wherein:
$R^1$ is —$CH_3$, —$CH_2CHFC(CH_3)_2OH$,

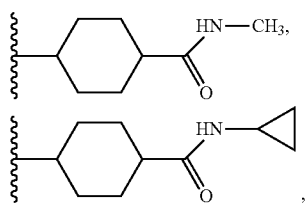

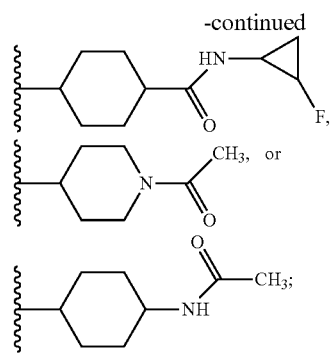

$R^2$ is

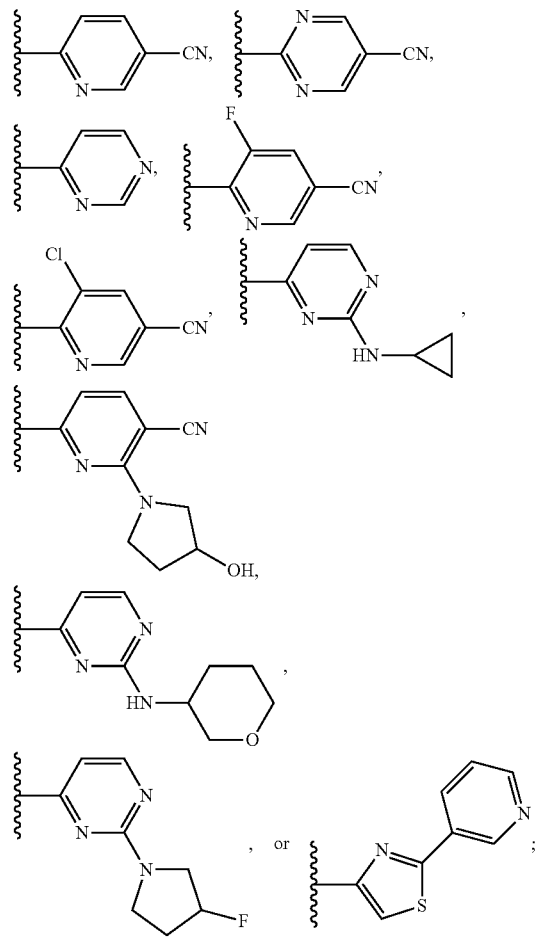

and
$R^3$ is —$CH_2CH_3$, —$CH(CH_3)_2$, —$CH_2CF_3$, cyclopropyl, cyclobutyl, —$CH(phenyl)CH(OH)CH_2(OH)$,

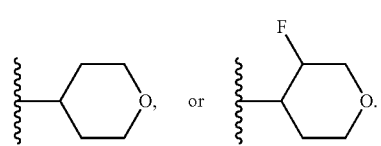 [SMILES: *C1CCOCC1 ; *C1CCOCC1F]

In one embodiment, a compound of Formula (II) or a stereoisomer or pharmaceutically-acceptable salt thereof, is provided wherein: R¹ is —CH₃ or —CH₂CHFC(CH₃)₂OH.

In one embodiment, a compound of Formula (II) or a stereoisomer or pharmaceutically-acceptable salt thereof, is provided wherein R¹ is —CH₂CHFC(CH₃)₂OH.

In one embodiment, a compound of Formula (II) or a stereoisomer or pharmaceutically-acceptable salt thereof, is provided wherein R¹ is —CH₂CHFC(CH₃)₂OH.

In one embodiment, a compound of Formula (II) or pharmaceutically-acceptable salt thereof, is provided wherein R¹ is

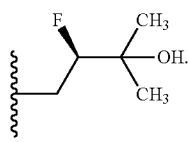 [SMILES: *C[C@@H](F)C(C)(C)O]

In one embodiment, a compound of Formula (II) or a stereoisomer or pharmaceutically-acceptable salt thereof, is provided wherein R¹ is

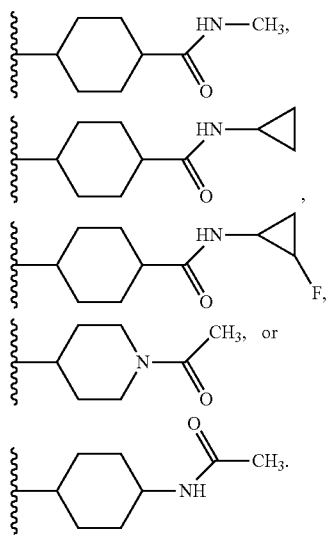

In one embodiment, a compound of Formula (II) or a stereoisomer or pharmaceutically-acceptable salt thereof, is provided wherein R¹ is

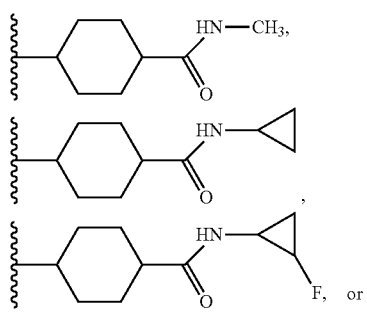

-continued

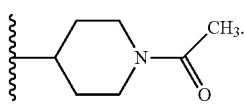

In one embodiment, a compound of Formula (II) or a stereoisomer or pharmaceutically-acceptable salt thereof, is provided wherein R¹ is

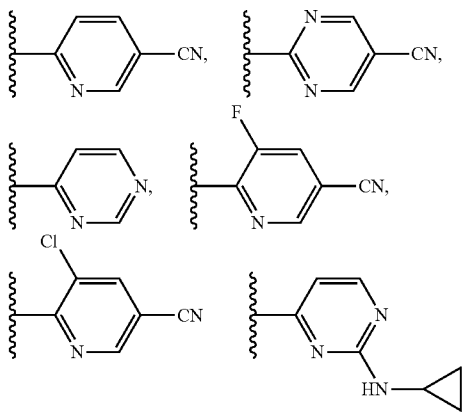

In one embodiment, a compound of Formula (II) or a stereoisomer or pharmaceutically-acceptable salt thereof, is provided wherein R² is a 5-6 membered heteroaryl containing 1-3 heteroatoms selected from N, O, and S, substituted with 0-4 R²ᵃ.

In one embodiment, a compound of Formula (II) or a stereoisomer or pharmaceutically-acceptable salt thereof, is provided wherein R² is 5-6 membered heteroaryl containing 1 nitrogen heteroatom and 0-1 additional heteroatom selected from N, O, and S, substituted with 0-4 R²ᵃ.

In one embodiment, a compound of Formula (II) or a stereoisomer or pharmaceutically-acceptable salt thereof, is provided wherein R² is thiazolyl, pyridyl, or pyrimidinyl, each group substituted with 0-4 R²ᵃ.

In one embodiment, a compound of Formula (II) or a stereoisomer or pharmaceutically-acceptable salt thereof, is provided wherein R² is

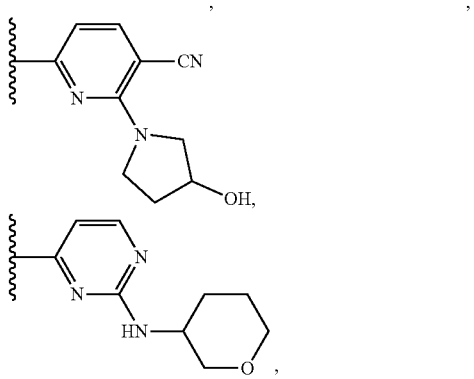

-continued

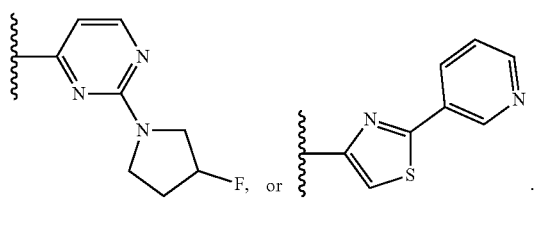

In one embodiment, a compound of Formula (II) or a stereoisomer or pharmaceutically-acceptable salt thereof, is provided wherein R² is

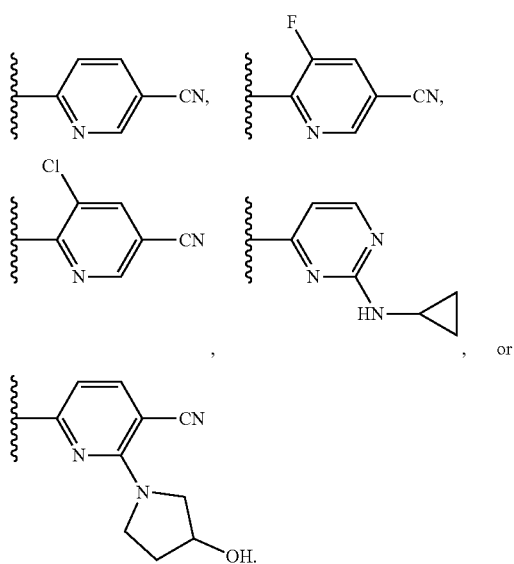

In one embodiment, a compound of Formula (II) or a stereoisomer or pharmaceutically-acceptable salt thereof, is provided wherein R² is

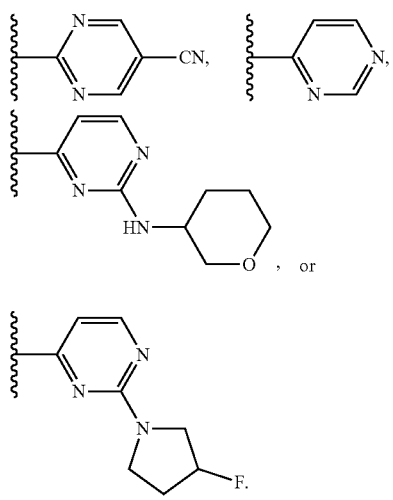

In one embodiment, a compound of Formula (II) or a stereoisomer or pharmaceutically-acceptable salt thereof, is provided wherein R² is

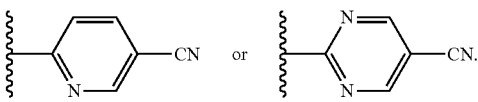

In one embodiment, a compound of Formula (II) or a stereoisomer or pharmaceutically-acceptable salt thereof, is provided wherein R² is

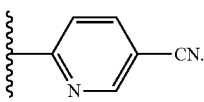

In one embodiment, a compound of Formula (II) or a stereoisomer or pharmaceutically-acceptable salt thereof, is provided wherein R² is

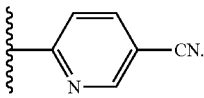 [SMILES: *c1ccc(C#N)cn1]

In one embodiment, a compound of Formula (II) or a stereoisomer or pharmaceutically-acceptable salt thereof, is provided wherein R² is

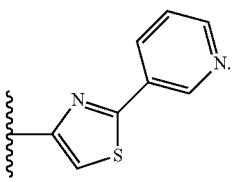 [SMILES: *c1csc(-c2cccnc2)n1]

In one embodiment, a compound of Formula (II) or a stereoisomer or pharmaceutically-acceptable salt thereof, is provided wherein R³ is $C_{1-6}$ alkyl substituted with 0-3 $R^{3a}$, $C_{1-6}$ haloalkyl, $C_{3-6}$ cycloalkyl substituted with 0-3 $R^{3a}$, or tetrahydropyranyl substituted with 0-3 $R^{3a}$.

In one embodiment, a compound of Formula (II) or a stereoisomer or pharmaceutically-acceptable salt thereof, is provided wherein $R^3$ is —CH$_2$CH$_3$, —CH(CH$_3$)$_2$, or —CH$_2$CF$_3$.

In one embodiment, a compound of Formula (II) or a stereoisomer or pharmaceutically-acceptable salt thereof, is provided wherein $R^3$ is —CH$_2$CH$_3$ or —CH(CH$_3$)$_2$.

In one embodiment, a compound of Formula (II) or a stereoisomer or pharmaceutically-acceptable salt thereof, is provided wherein $R^3$ is —CH(CH$_3$)$_2$.

In one embodiment, a compound of Formula (II) or a stereoisomer or pharmaceutically-acceptable salt thereof, is provided wherein $R^3$ is cyclopropyl, cyclobutyl,

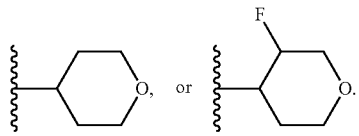 [SMILES: *C1CCOCC1 ; "or" ; *C1CCOCC1F]

In one embodiment, a compound of Formula (II) or a stereoisomer or pharmaceutically-acceptable salt thereof, is provided wherein $R^3$ is cyclopropyl or cyclobutyl.

In one embodiment, a compound of Formula (II) or a stereoisomer or pharmaceutically-acceptable salt thereof, is provided wherein $R^3$ is —CH(phenyl)CH(OH)CH$_2$(OH).

In one embodiment, a compound of Formula (II) or a stereoisomer or pharmaceutically-acceptable salt thereof, is provided wherein: $R^1$ is C$_{1-6}$ alkyl substituted by 0-4 $R^{1a}$; $R^2$ is pyrimidinyl, each group substituted by 0-1 groups selected from $R^{2a}$; $R^3$ is C$_{1-4}$ alkyl substituted with 0-3 $R^{3a}$; each $R^{1a}$ is independently F, Cl, OH, OCF$_3$, CF$_3$, CHF$_2$, or CN; $R^{2a}$ is CN or —NR$^{11}$R$^{11}$; and each $R^{3a}$ is independently F, Cl, Br, OCF$_3$, CF$_3$, CHF$_2$, or CN.

In one embodiment, a compound of Formula (II) or a stereoisomer or pharmaceutically-acceptable salt thereof, is provided wherein: $R^1$ is C$_{4-6}$ alkyl substituted by 0-2 $R^{1a}$; each $R^{1a}$ is independently F or OH; $R^2$ is pyrimidinyl substituted by CN; and $R^3$ is C$_{2-3}$ alkyl.

In one embodiment, a compound of Formula (II) or a stereoisomer or pharmaceutically-acceptable salt thereof, is provided wherein: $R^1$ is C$_{1-6}$ alkyl substituted by 0-4 $R^{1a}$; $R^2$ is pyrimidinyl, each group substituted by 0-1 groups selected from $R^{2a}$; and $R^3$ is C$_{1-6}$ alkyl substituted with 0-3 $R^{3a}$.

In one embodiment, a compound of Formula (II) or a stereoisomer or pharmaceutically-acceptable salt thereof, is provided wherein:
$R^1$ is —CH$_3$ or —CH$_2$CHFC(CH$_3$)$_2$OH;
$R^2$ is

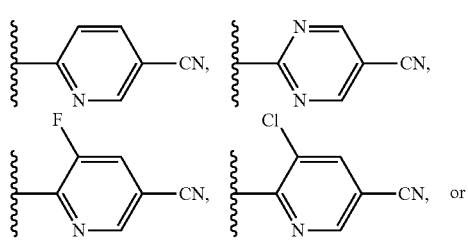

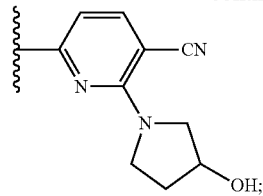

and
$R^3$ is —CH$_2$CH$_3$, —CH(CH$_3$)$_2$, or —CH$_2$CF$_3$.

In one embodiment, a compound of Formula (II) or a stereoisomer or pharmaceutically-acceptable salt thereof, is provided wherein:
$R^1$ is —CH$_3$ or —CH$_2$CHFC(CH$_3$)$_2$OH;
$R^2$ is

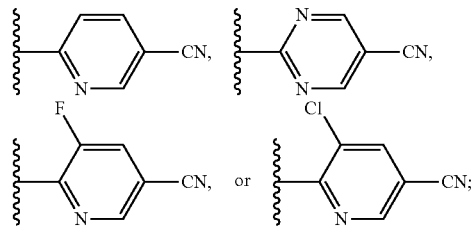

and
$R^3$ is —CH$_2$CH$_3$ or —CH(CH$_3$)$_2$.

In one embodiment, a compound of Formula (II) or a stereoisomer or pharmaceutically-acceptable salt thereof, is provided wherein:
$R^1$ is —CH$_2$CHFC(CH$_3$)$_2$OH;
$R^2$ is

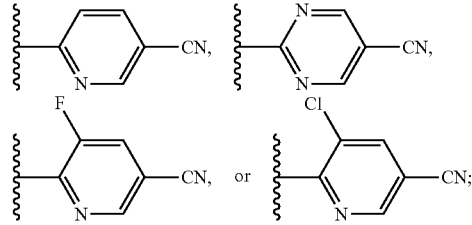

and
$R^3$ is —CH$_2$CH$_3$, —CH(CH$_3$)$_2$, or —CH$_2$CF$_3$.

In one embodiment, a compound of Formula (II) or a stereoisomer or pharmaceutically-acceptable salt thereof, is provided wherein:
$R^1$ is —CH$_3$ or —CH$_2$CHFC(CH$_3$)$_2$OH;
$R^2$ is

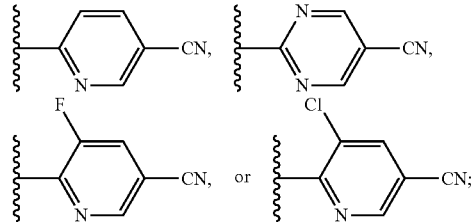

and

R³ is —CH(CH₃)₂.

In one embodiment, a compound of Formula (II) or a stereoisomer or pharmaceutically-acceptable salt thereof, is provided wherein:

R¹ is —CH₃ or —CH₂CHFC(CH₃)₂OH;

R² is

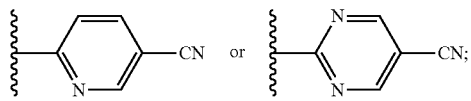

and

R³ is —CH(CH₃)₂.

In one embodiment, a compound of Formula (II) or a stereoisomer or pharmaceutically-acceptable salt thereof, is provided wherein:

R¹ is —CH₂CHFC(CH₃)₂OH;

R² is

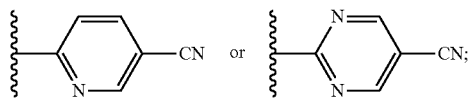

and

R³ is —CH(CH₃)₂.

In one embodiment, a compound of Formula (II) or a pharmaceutically-acceptable salt thereof is provided having the following formula:

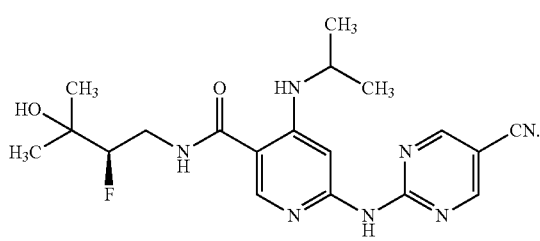 [SMILES: CC(C)Nc1cc(Nc2ncc(C#N)cn2)ncc1C(=O)NC[C@@H](F)C(C)(C)O]

In one embodiment, a compound of Formula (II) is provided having the following formula:

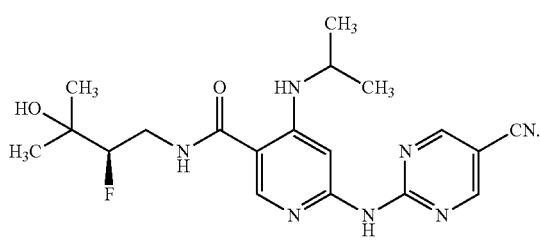 [SMILES: CC(C)Nc1cc(Nc2ncc(C#N)cn2)ncc1C(=O)NC[C@@H](F)C(C)(C)O]

In one embodiment, a compound of Formula (II) having the following formula is provided as an HCl salt:

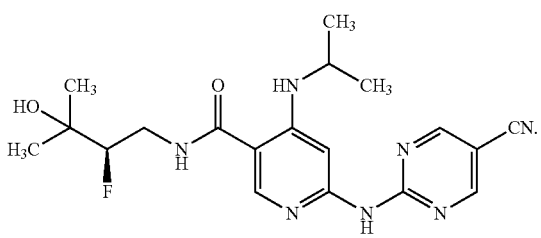 [SMILES: CC(C)Nc1cc(Nc2ncc(C#N)cn2)ncc1C(=O)NC[C@@H](F)C(C)(C)O]

In one embodiment, a compound of Formula (II) or a stereoisomer or pharmaceutically-acceptable salt thereof, is provided wherein:

R¹ is:
  (a) C₂₋₃ hydroxyalkyl substituted with zero to 4 R¹ᵃ wherein R¹ᵃ is independently selected from F, Cl, —OH, —CHF₂, —CN, —CF₃, —OCH₃, and cyclopropyl;
  (b) C₁₋₃ alkyl substituted with —O(C₁₋₃ alkyl) and zero to 4 R¹ᵃ wherein R¹ᵃ is independently selected from F, Cl, —OH, —CHF₂, —CN, —CF₃, and cyclopropyl;
  (c) C₄₋₈ alkyl substituted with zero to 7 R¹ᵃ wherein R¹ᵃ is independently selected from F, Cl, —OH, —CHF₂, —CF₃, —CN—OCH₃, cyclopropyl, and —OP(O)(OH)₂;
  (d) —(CH₂)₂₋₄NHC(O)(C₁₋₆ alkyl), —(CH₂)₂CH(CH₃)NHC(O)(C₁₋₆ alkyl), —(CH₂)₂CH(CH₃)NHC(O)(CH₂)₀₋₁NH(C₁₋₆ alkyl), or —(CH₂)₂CH(CH₃)NHC(O)(CH₂)₀₋₁N(C₁₋₄ alkyl)₂;
  (e) cyclohexyl substituted with zero to 2 substituents independently selected from —OH, —OCH₃, C₁₋₆ alkyl, C₁₋₆ hydroxyalkyl, —C(O)NH₂, —C(O)NH(C₃₋₆ alkyl), —C(O)NH(C₁₋₆ hydroxyalkyl), —C(O)NH(C₃₋₆ cycloalkyl), —C(O)NH(C₃₋₆ fluoro cycloalkyl), —NHC(O)(C₁₋₃ alkyl), —NHC(O)O(C₁₋₃ alkyl), —NHS(O)₂CH₃, —S(O)₂NH₂, —S(O)₂(C₁₋₃ alkyl), —S(C₁₋₃ alkyl), thiazolyl, methyl pyrazolyl, and C₁₋₃ alkyl substituted with —OH and cyclopropyl;
  (f) —(CH₂)₂(phenyl) wherein said phenyl is substituted with —C(O)NH₂, —C(O)NH(C₁₋₃ alkyl), or —S(O)₂NH₂; or
  (g) piperidinyl substituted with —C(O)(C₁₋₃ alkyl);

R² is phenyl, pyridinyl, pyridazinyl, pyrimidinyl, pyrazolyl, thiazolyl, or triazolyl, each substituted with zero to 2 substituents independently selected from F, Cl, —OH, —CN, C₁₋₃ alkyl, —CH₂C(O)OCH₃, —O(C₁₋₃ alkyl), —NH₂, —NH(C₁₋₃ alkyl), —NH(cyclopropyl), —C(O)NH₂, —NHC(O)(C₁₋₃ alkyl), —NH(tetrahydropyranyl), hydroxypyrrolidinyl, =O, —O(piperidinyl), and pyridinyl; and R³ is:
  (a) C₁₋₆ alkyl substituted with zero to 4 substituents independently selected from F, —OH, —CH₃, —CF₃, and C₃₋₆ cycloalkyl;
  (b) C₃₋₆ cycloalkyl substituted with zero to 2 substituents independently selected from F, —OH, C₁₋₃ hydroxyalkyl, —CH₃, —CF₂H, —NH₂, and —C(O)OCH₂CH₃;
  (c) oxetanyl, tetrahydropyranyl, or fluoro tetrahydropyranyl;
  (d) phenyl substituted with zero to 2 substituents independently selected from —OH, —CN, —O(C₁₋₃ alkyl), C₁₋₃ hydroxyalkyl, —C(O)NH₂, —S(O)₂NH₂, —NHS(O)₂(C₁₋₃ alkyl), pyrazolyl, imidazolyl, and methyl tetrazolyl; or (e)

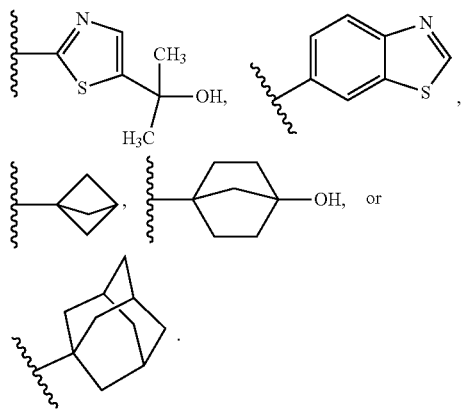

In one embodiment, a compound of Formula (II) or a stereoisomer or pharmaceutically-acceptable salt thereof, is provided wherein:

$R^1$ is:
(a) $C_{1-3}$ alkyl substituted with —O($C_{1-3}$ alkyl) and zero to 4 $R^{1a}$ wherein $R^{1a}$ is independently selected from F, —OH, and —$CF_3$;
(b) $C_{4-8}$ alkyl substituted with zero to 5 $R^{1a}$ wherein $R^{1a}$ is independently selected from F, Cl, —OH, —$CHF_2$, —$CF_3$, —CN—$OCH_3$, cyclopropyl, and —OP(O)(OH)$_2$;
(c) —($CH_2$)$_{2-4}$NHC(O)($C_{1-3}$ alkyl), —($CH_2$)$_2$CH($CH_3$)NHC(O)($C_{1-3}$ alkyl), —($CH_2$)$_2$CH($CH_3$)NHC(O)NH($C_{1-3}$ alkyl), or —($CH_2$)$_2$CH($CH_3$)NHC(O)N($C_{1-3}$ alkyl)$_2$;
(d) cyclohexyl substituted with zero to 2 substituents independently selected from —OH, —$OCH_3$, $C_{1-3}$ alkyl, —$OCH_3$, $C_{1-3}$ hydroxyalkyl, —C(O)$NH_2$, —C(O)NH($C_{1-3}$ alkyl), —C(O)NH($C_{3-5}$ cycloalkyl), —C(O)NH(fluoro cyclopropyl), —NHC(O)($C_{1-3}$ alkyl), —NHC(O)O($C_{1-3}$ alkyl), —S(O)$_2$NH$_2$, —S(O)$_2$($C_{1-2}$ alkyl), —S($C_{1-2}$ alkyl), thiazolyl, methyl pyrazolyl, and $C_{1-3}$ alkyl substituted with —OH and cyclopropyl;
(e) —($CH_2$)$_2$(phenyl) wherein said phenyl is substituted with —C(O)$NH_2$, —C(O)NH($CH_3$), or —S(O)$_2$NH$_2$; or
(f) piperidinyl substituted with —C(O)($C_{1-3}$ alkyl);

$R^2$ is phenyl, pyridinyl, pyrimidinyl, pyrazolyl, thiazolyl, or triazolyl, each substituted with zero to 2 substituents independently selected from F, Cl, —OH, —CN, $C_{1-3}$ alkyl, —$CH_2$C(O)$OCH_3$, —O($C_{1-3}$ alkyl), —$NH_2$, —NH($C_{1-3}$ alkyl), —NH(cyclopropyl), —C(O)$NH_2$, —NHC(O)($C_{1-3}$ alkyl), —NH(tetrahydropyranyl), hydroxypyrrolidinyl, —O(piperidinyl), and pyridinyl; or pyridazinyl substituted with =O; and $R^3$ is:
(a) $C_{1-5}$ alkyl substituted with zero to 3 substituents independently selected from F, —OH, —$CH_3$, —$CF_3$, and cyclopropyl;
(b) $C_{3-6}$ cycloalkyl substituted with zero to 2 substituents independently selected from F, —OH, $C_{1-3}$ hydroxyalkyl, —$CH_3$, —$CF_2$H, —$NH_2$, and —C(O)$OCH_2CH_3$;
(c) oxetanyl, tetrahydropyranyl, or fluoro tetrahydropyranyl;
(d) phenyl substituted with zero to 2 substituents independently selected from —OH, —CN, —$OCH_3$, $C_{1-2}$ hydroxyalkyl, —C(O)$NH_2$, —S(O)$_2$NH$_2$, —NHS(O)$_2$$CH_3$, pyrazolyl, imidazolyl, and methyl tetrazolyl; or (e)

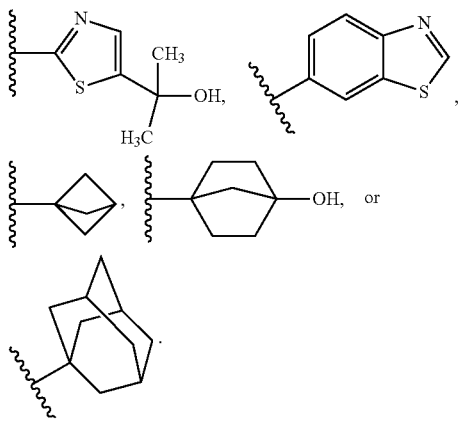

In one embodiment, a compound of Formula (II) or a stereoisomer or pharmaceutically-acceptable salt thereof, is provided wherein:

$R^1$ is —$CH_2$CHFC($CH_3$)$_2$OH, —$CH_2$CHFC($CH_3$)$_2$$OCH_3$, —$CH_2$CHFC($CH_2CH_3$)$_2$OH, —$CH_2$CHFCH$_2$$OCH_3$, —($CH_2$)$_3$$OCH_3$, —($CH_2$)$_3$OC($CH_3$)$_3$, —$CH_2$$CF_2$C($CH_3$)$_2$OH, —($CH_2$)$_2$CH($CH_3$)NHC(O)$CH_3$, —($CH_2$)$_2$CH($CH_3$)NHC(O)NHCH($CH_3$)$_2$, —$CH_2$CHFC($CH_3$)$_2$OP(O)(OH)$_2$,

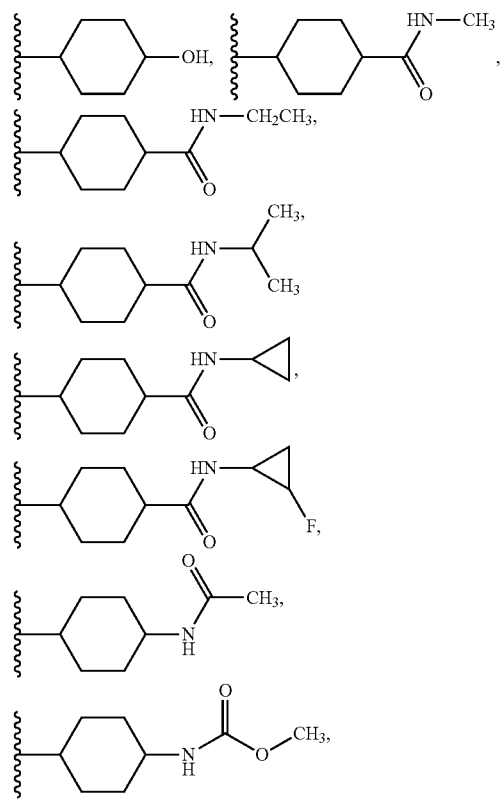

-continued
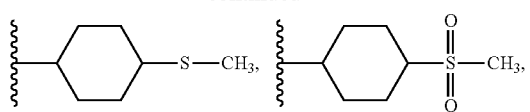
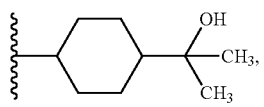
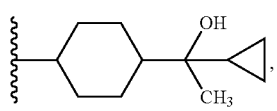
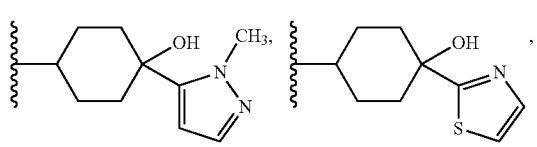
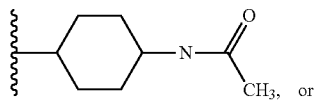 or
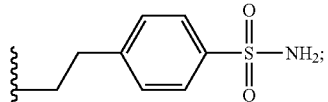;
$R^2$ is
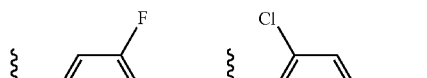
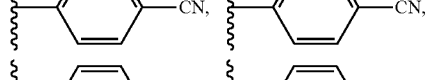
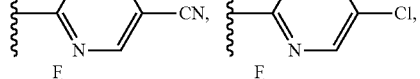
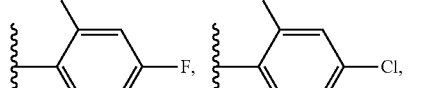
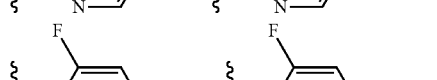
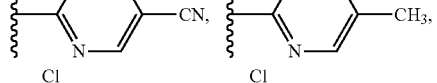
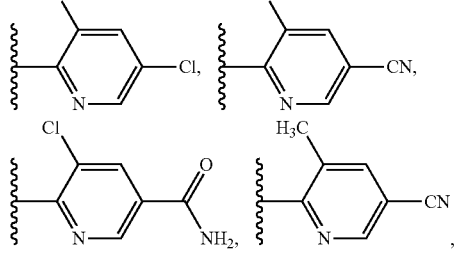
-continued
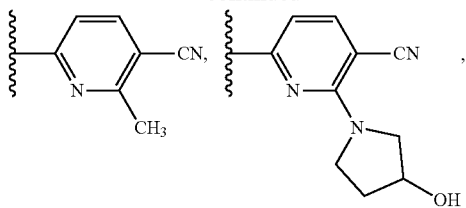
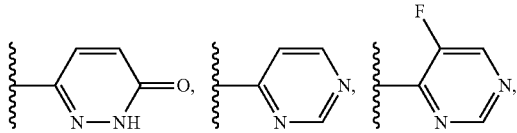
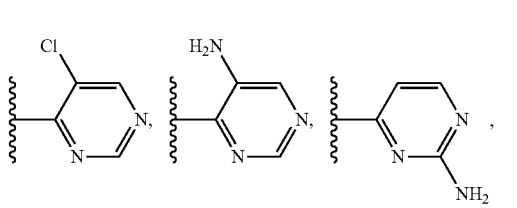
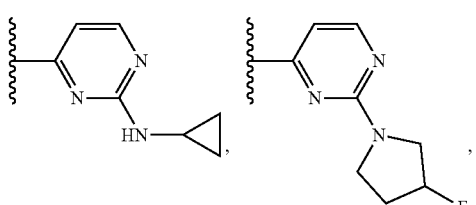
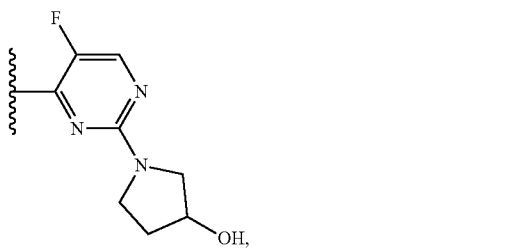
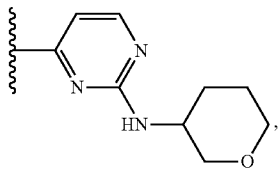
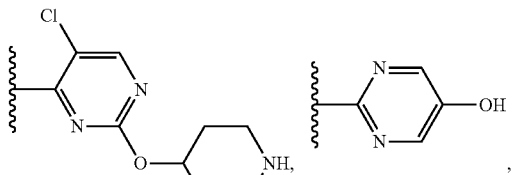
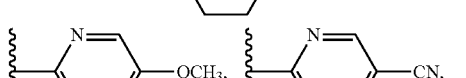
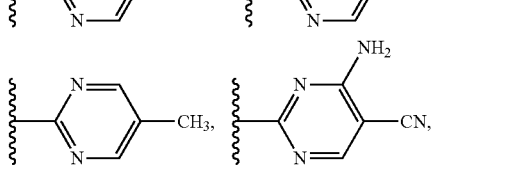

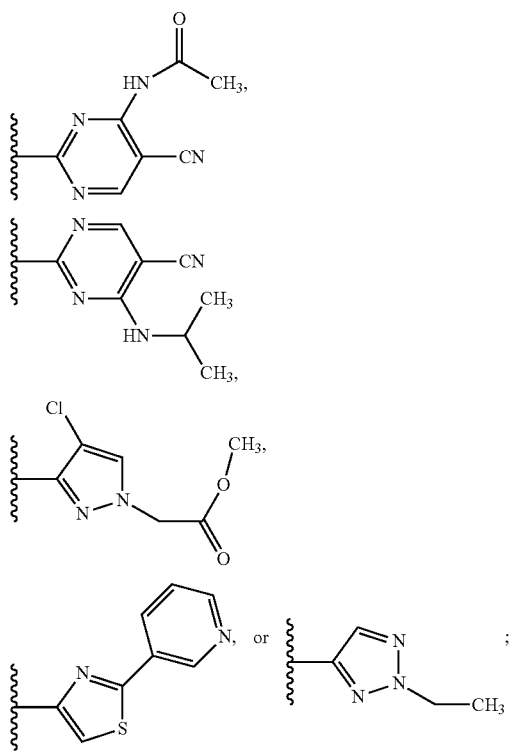

and
R³ is C₂₋₅ alkyl, —CH₂CF₃, —CH₂C(CH₃)₂F, —CH(CH₃)CHFCH₃, —CH(CH₃)CH₂F, —CH(CH₃)CH₂CH₂F, —CH(CH₃)CH₂OH, —CH₂C(CH₃)₂OH, —CH₂CF₂C(CH₃)₂OH, —CH(CH₃(cyclopropyl), C₃₋₄ cycloalkyl,

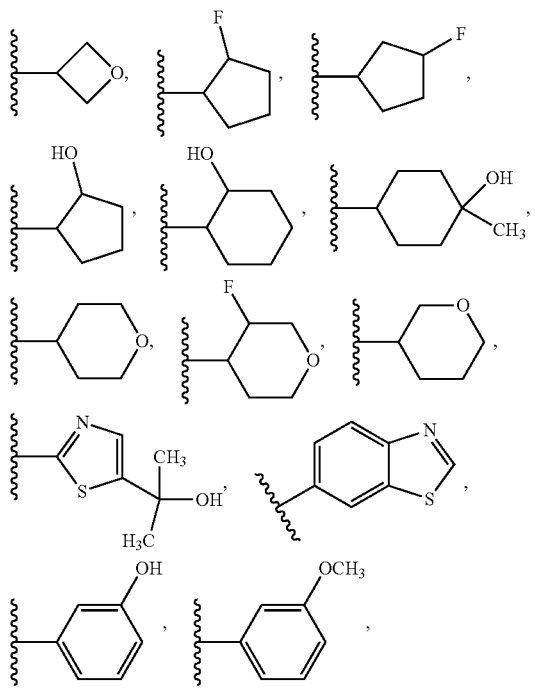

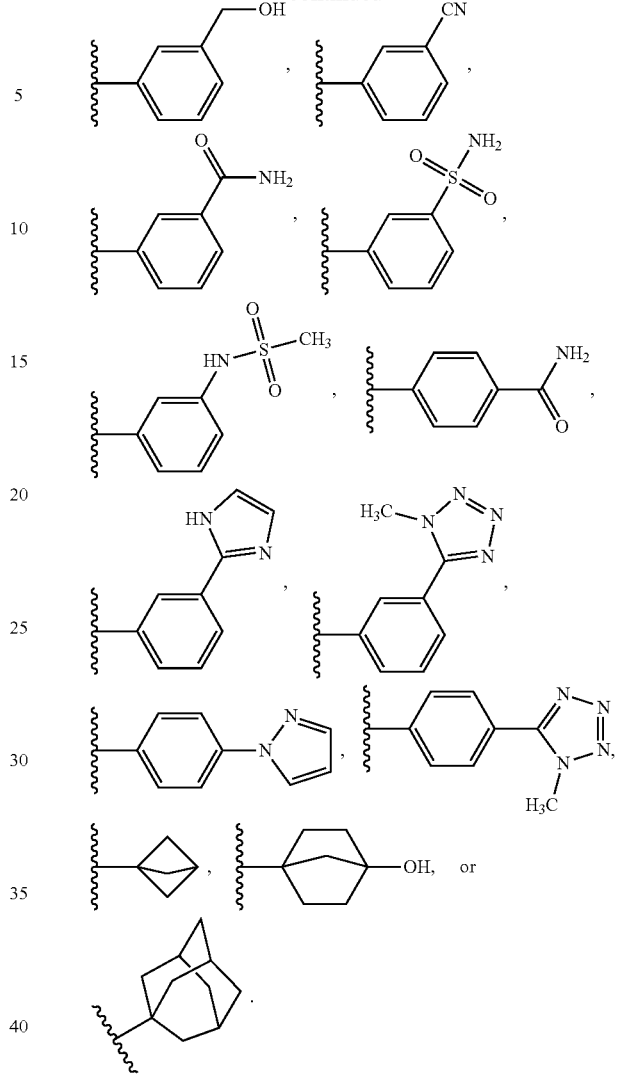

In one embodiment, a compound of Formula (II) or a stereoisomer or pharmaceutically-acceptable salt thereof, is provided wherein R¹ is:
(a) C₁₋₃ alkyl substituted with —O(C₁₋₃ alkyl) and zero to 4 R¹ᵃ wherein R¹ᵃ is independently selected from F, —OH, and —CF₃;
(b) C₄₋₈ alkyl substituted with zero to 5 R¹ᵃ wherein R¹ᵃ is independently selected from F, Cl, —OH, —CHF₂, —CF₃, —CN—OCH₃, cyclopropyl, and —OP(O)OH)₂; or
(c) —(CH₂)₂₋₄NHC(O)(C₁₋₃ alkyl), —(CH₂)₂CH(CH₃)NHC(O)(C₁₋₃ alkyl), —(CH₂)₂CH(CH₃)NHC(O)NH(C₁₋₃ alkyl), or —(CH₂)₂CH(CH₃)NHC(O)N(C₁₋₃ alkyl)₂.

In one embodiment, a compound of Formula (II) or a stereoisomer or pharmaceutically-acceptable salt thereof, is provided wherein R¹ is cyclohexyl substituted with zero to 2 substituents independently selected from —OH, —OCH₃, C₁₋₃ alkyl, —OCH₃, C₁₋₃ hydroxyalkyl, —C(O)NH₂, —C(O)NH(C₁₋₃ alkyl), —C(O)NH(C₃₋₅ cycloalkyl), —C(O)NH(fluoro cyclopropyl), —NHC(O)C₁₋₃ alkyl), —NHC(O)O(C₁₋₃ alkyl), —S(O)₂NH₂, —S(O)₂(C₁₋₂ alkyl), —S(C₁₋₂ alkyl), thiazolyl, methyl pyrazolyl, and C₁₋₃ alkyl substituted with —OH and cyclopropyl.

In one embodiment, a compound of Formula (II) or a stereoisomer or pharmaceutically-acceptable salt thereof, is provided wherein $R^3$ is $C_{2-5}$ alkyl, —$CH_2CF_3$, —$CH_2C(CH_3)_2F$, —$CH(CH_3)CHFCH_3$, —$CH(CH_3)CH_2F$, —$CH(CH_3)CH_2CH_2F$, —$CH(CH_3)CH_2OH$, —$CH_2C(CH_3)_2OH$, —$CH_2CF_2C(CH_3)_2OH$, or —$CH(CH_3(cyclopropyl))$.

In one embodiment, a compound of Formula (II) or a stereoisomer or pharmaceutically-acceptable salt thereof, is provided wherein $R^3$ is $C_{3-4}$ cycloalkyl,

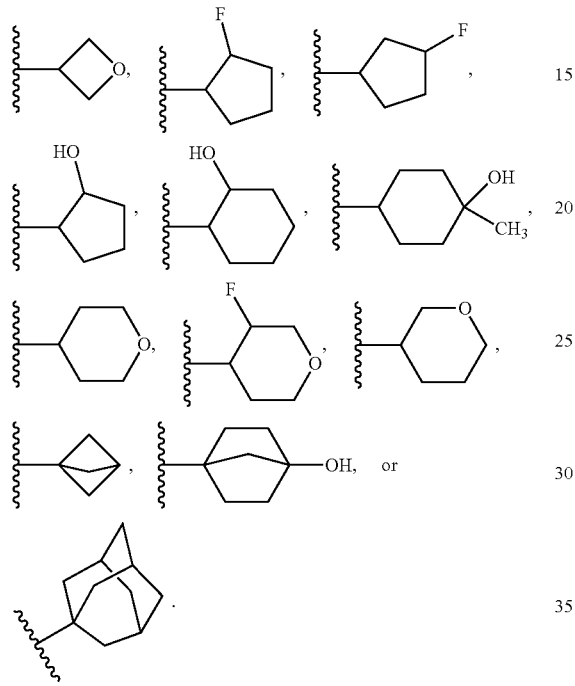

In one embodiment, a compound of Formula (II) or a stereoisomer or pharmaceutically-acceptable salt thereof, is provided wherein $R^3$ is

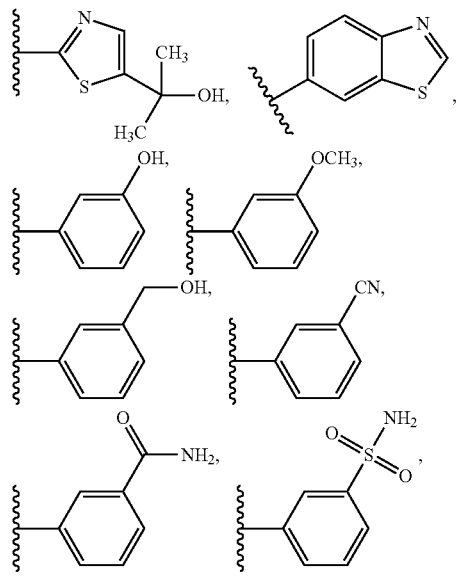

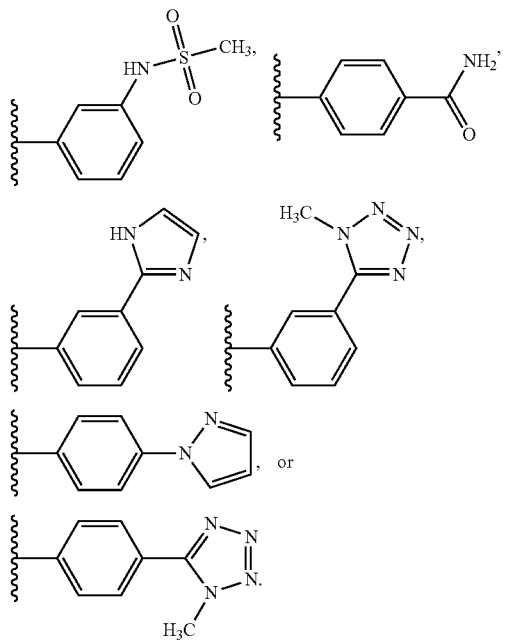

In one embodiment, a compound of Formula (II) or a stereoisomer or pharmaceutically-acceptable salt thereof, is provided wherein $R^2$ is

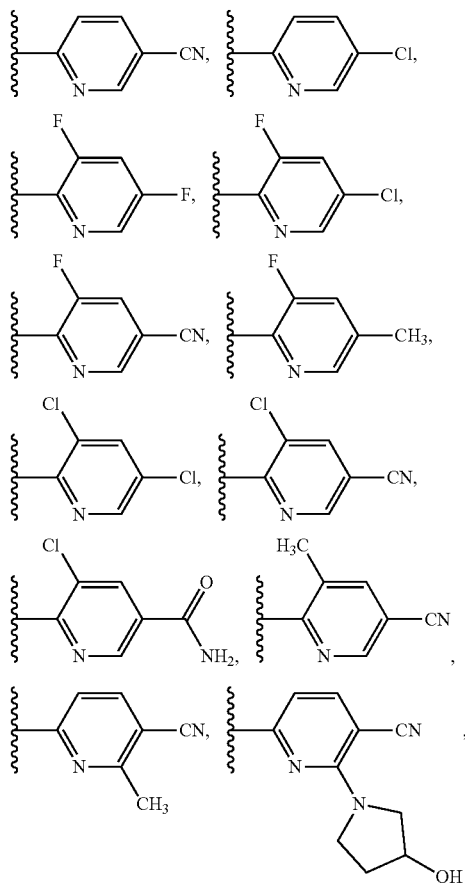

-continued

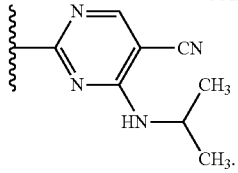

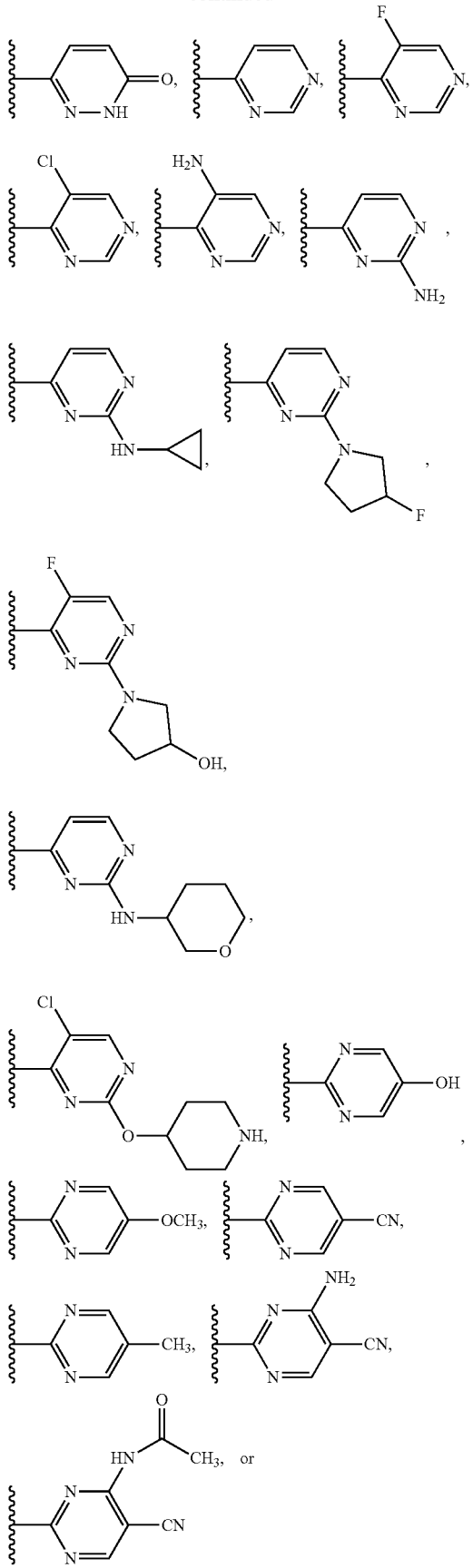

In one embodiment, a compound of Formula (II) or a stereoisomer or pharmaceutically-acceptable salt thereof, is provided wherein said compound is selected from Examples 2 to 168.

In one embodiment, a compound of Formula (II) or a stereoisomer or pharmaceutically-acceptable salt thereof, is provided wherein $R^1$ is (a) $C_{2-3}$ hydroxyalkyl substituted with zero to 4 $R^{1a}$ wherein $R^{1a}$ is independently selected from F, Cl, —OH, —CHF$_2$, —CN, —CF$_3$, —OCH$_3$, and cyclopropyl; (b) $C_{1-3}$ alkyl substituted with —O($C_{1-3}$ alkyl) and zero to 4 $R^{1a}$ wherein $R^{1a}$ is independently selected from F, Cl, —OH, —CHF$_2$, —CN, —CF$_3$, and cyclopropyl; or (c) $C_{4-8}$ alkyl substituted with zero to 7 $R^{1a}$ wherein $R^{1a}$ is independently selected from F, Cl, —OH, —CHF$_2$, —CF$_3$, —CN—OCH$_3$, cyclopropyl, and —OP(O)(OH)$_2$. Included in this embodiment are compounds in which $R^1$ is $C_{1-3}$ alkyl substituted with —O($C_{1-3}$ alkyl) and zero to 4 $R^{1a}$ wherein $R^{1a}$ is independently selected from F, —OH, and —CF$_3$; or $C_{4-8}$ alkyl substituted with zero to 5 $R^{1a}$ wherein $R^{1a}$ is independently selected from F, Cl, —OH, —CHF$_2$, —CF$_3$, —CN—OCH$_3$, cyclopropyl, and —OP(O)(OH)$_2$. Also included in this embodiment are compounds in which $R^1$ is —CH$_2$CHFC(CH$_3$)$_2$OH, —CH$_2$CHFC(CH$_3$)$_2$OCH$_3$, —CH$_2$CHFC(CH$_2$CH$_3$)$_2$OH, —CH$_2$CHF CH$_2$OCH$_3$, —(CH$_2$)$_3$OCH$_3$, —(CH$_2$)$_3$OC(CH$_3$)$_3$, —CH$_2$CF$_2$C(CH$_3$)$_2$OH, or —CH$_2$CHFC(CH$_3$)$_2$OP(O)(OH)$_2$.

In one embodiment, a compound of Formula (II) or a stereoisomer or pharmaceutically-acceptable salt thereof, is provided wherein $R^1$ is —(CH$_2$)$_{2-4}$NHC(O)(C$_{1-6}$ alkyl), —(CH$_2$)$_2$CH(CH$_3$)NHC(O)(C$_{1-6}$ alkyl), —(CH$_2$)$_2$CH(CH$_3$)NHC(O)(CH$_2$)$_{0-1}$NH(C$_{1-6}$ alkyl), or —(CH$_2$)$_2$CH(CH$_3$)NHC(O)(CH$_2$)$_{0-1}$N(C$_{1-4}$ alkyl)$_2$. Included in this embodiment are compounds in which $R^1$ is —(CH$_2$)$_{2-4}$NHC(O)(C$_{1-3}$ alkyl), —(CH$_2$)$_2$CH(CH$_3$)NHC(O)(C$_{1-3}$ alkyl), —(CH$_2$)$_2$CH(CH$_3$)NHC(O)NH(C$_{1-3}$ alkyl), or —(CH$_2$)$_2$CH(CH$_3$)NHC(O)N(C$_{1-3}$ alkyl)$_2$. Also included in this embodiment are compounds in which $R^1$ is —(CH$_2$)$_2$CH(CH$_3$)NHC(O)CH$_3$ or —(CH$_2$)$_2$CH(CH$_3$)NHC(O)NHCH(CH$_3$)$_2$.

In one embodiment, a compound of Formula (II) or a stereoisomer or pharmaceutically-acceptable salt thereof, is provided wherein $R^1$ is cyclohexyl substituted with zero to 2 substituents independently selected from —OH, —OCH$_3$, $C_{1-6}$ alkyl, $C_{1-6}$ hydroxyalkyl, —C(O)NH$_2$, —C(O)NH(C$_{1-3}$ alkyl), —C(O)NH(C$_{1-6}$ hydroxyalkyl), —C(O)NH(C$_{3-6}$ cycloalkyl), —C(O)NH(C$_{3-6}$ fluoro cycloalkyl), —NHC(O)(C$_{1-3}$ alkyl), —NHC(O)O(C$_{1-3}$ alkyl), —NHS(O)$_2$CH$_3$, —S(O)$_2$NH$_2$, —S(O)$_2$(C$_{1-3}$ alkyl), —S(C$_{1-3}$ alkyl), thiazolyl, methyl pyrazolyl, and $C_{1-3}$ alkyl substituted with —OH and cyclopropyl. Included in this embodiment are compounds in which $R^1$ is cyclohexyl substituted with zero to 2 substituents independently selected from —OH, —OCH$_3$, $C_{1-3}$ alkyl, —OCH$_3$, $C_{1-3}$ hydroxyalkyl, —C(O)NH$_2$, —C(O)NH(C$_{1-3}$ alkyl), —C(O)NH(C$_{3-5}$ cycloalkyl), —C(O)NH(fluoro cyclopropyl), —NHC(O)(C$_{1-3}$ alkyl), —NHC(O)O(C$_{1-3}$ alkyl), —S(O)$_2$NH$_2$, —S(O)$_2$(C$_{1-2}$ alkyl), —S(C$_{1-2}$ alkyl), thiazolyl, methyl pyrazolyl, and $C_{1-3}$ alkyl substituted with —OH and cyclopropyl. Also included in this embodiment are compounds in which $R^1$ is

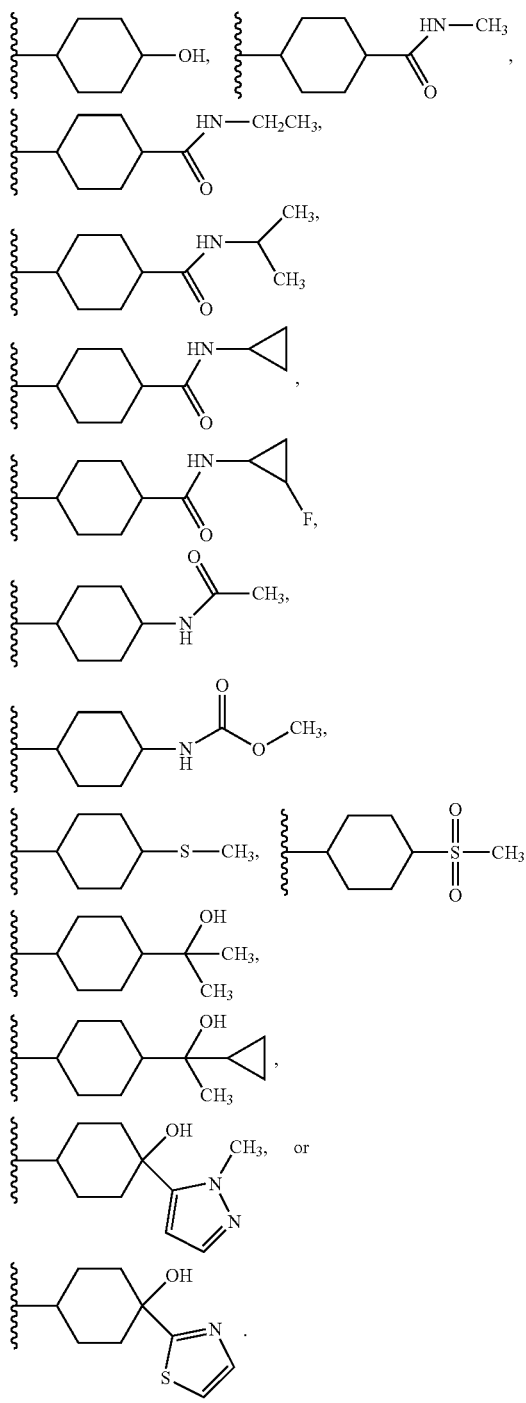

In one embodiment, a compound of Formula (II) or a stereoisomer or pharmaceutically-acceptable salt thereof, is provided wherein $R^1$ is —CH$_2$CHFC(CH$_3$)$_2$OH, —CH$_2$CHFC(CH$_3$)$_2$OCH$_3$, —CH$_2$CHFC(CH$_2$CH$_3$)$_2$OH, —CH$_2$CHF CH$_2$OCH$_3$, —(CH$_2$)$_3$OCH$_3$, —(CH$_2$)$_3$OC(CH$_3$)$_3$, —CH$_2$CF$_2$C(CH$_3$)$_2$OH, —(CH$_2$)$_2$CH(CH$_3$)NHC(O)CH$_3$, —(CH$_2$)$_2$CH(CH$_3$)NHC(O)NHCH(CH$_3$)$_2$, —CH$_2$CHFC(CH$_3$)$_2$OP(O)(OH)$_2$, In one embodiment, a compound of Formula (II) or a stereoisomer or pharmaceutically-acceptable salt thereof, is provided wherein $R^1$ is —(CH$_2$)$_2$(phenyl) wherein said phenyl is substituted with —C(O)NH$_2$, —C(O)NH(C$_{1-3}$ alkyl), or —S(O)$_2$NH$_2$; or piperidinyl substituted with —C(O)(C$_{1-3}$ alkyl). Included in this embodiment are compounds in which $R^1$ is —(CH$_2$)$_2$(phenyl) wherein said phenyl is substituted with —C(O)NH$_2$, —C(O)NH(CH$_3$), or —S(O)$_2$NH$_2$; or piperidinyl substituted with —C(O)(C$_{1-3}$ alkyl). Also included in this embodiment are compounds in which $R^1$ is

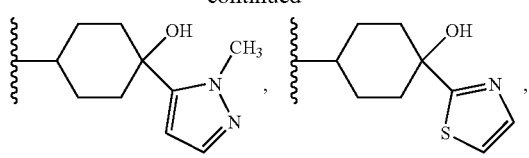
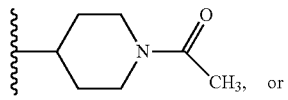
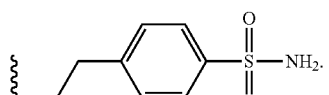
In one embodiment, a compound of Formula (II) or a stereoisomer or pharmaceutically-acceptable salt thereof, is provided wherein R² is
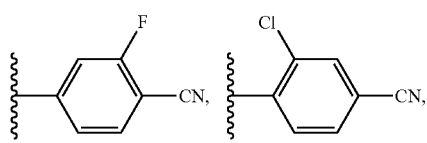
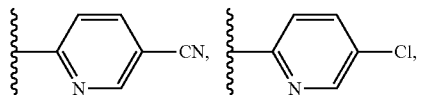
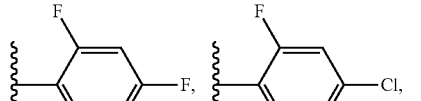
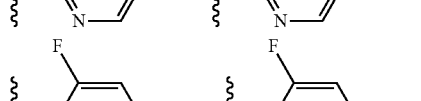
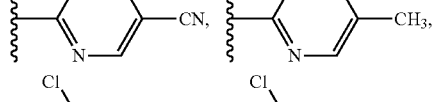
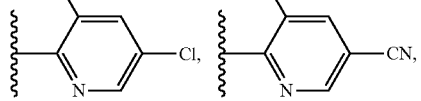
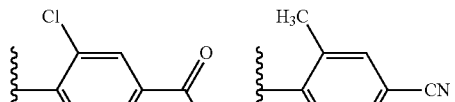
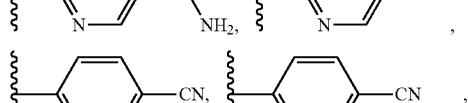
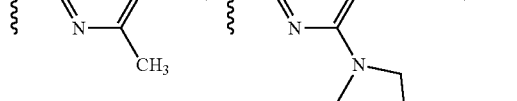
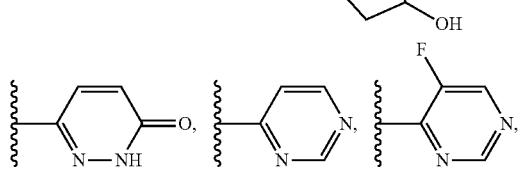
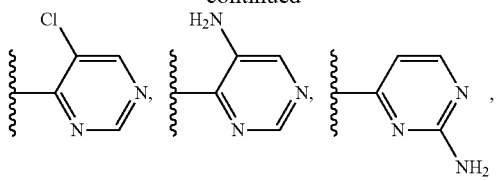
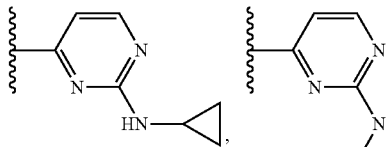
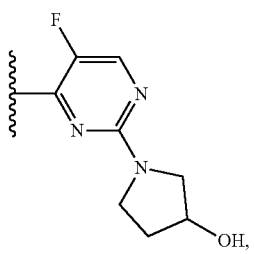
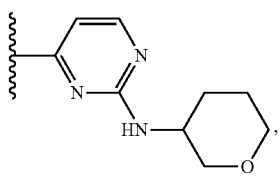
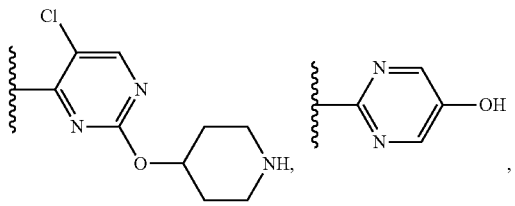
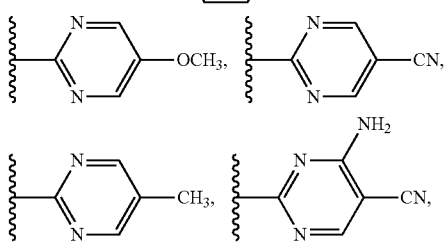
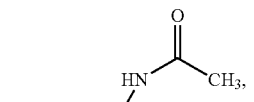
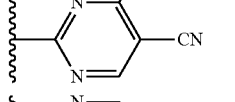
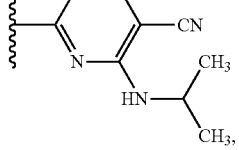

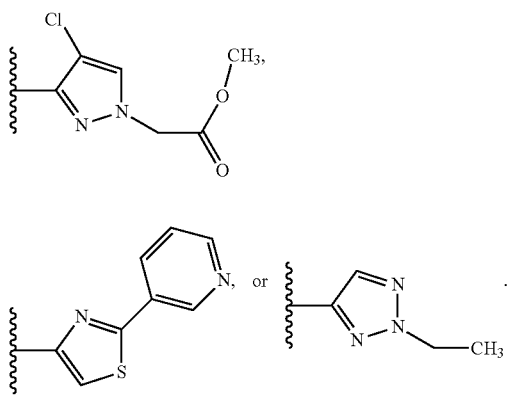

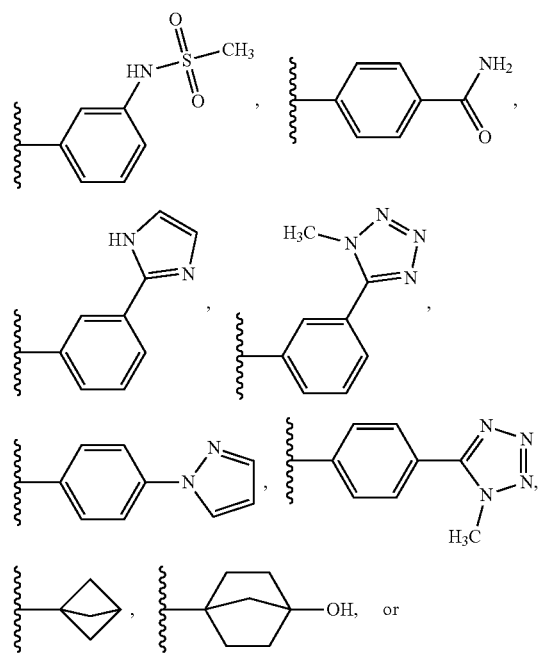

In one embodiment, a compound of Formula (II) or a stereoisomer or pharmaceutically-acceptable salt thereof, is provided wherein $R^3$ is: $C_{2-5}$ alkyl, —$CH_2CF_3$, —$CH_2C(CH_3)_2F$, —$CH(CH_3)CHFCH_3$, —$CH(CH_3)CH_2F$, —$CH(CH_3)CH_2CH_2F$, —$CH(CH_3)CH_2OH$, —$CH_2C(CH_3)_2OH$, —$CH_2CF_2C(CH_3)_2OH$, —$CH(CH_3)(cyclopropyl)$, $C_{3-4}$ cycloalkyl,

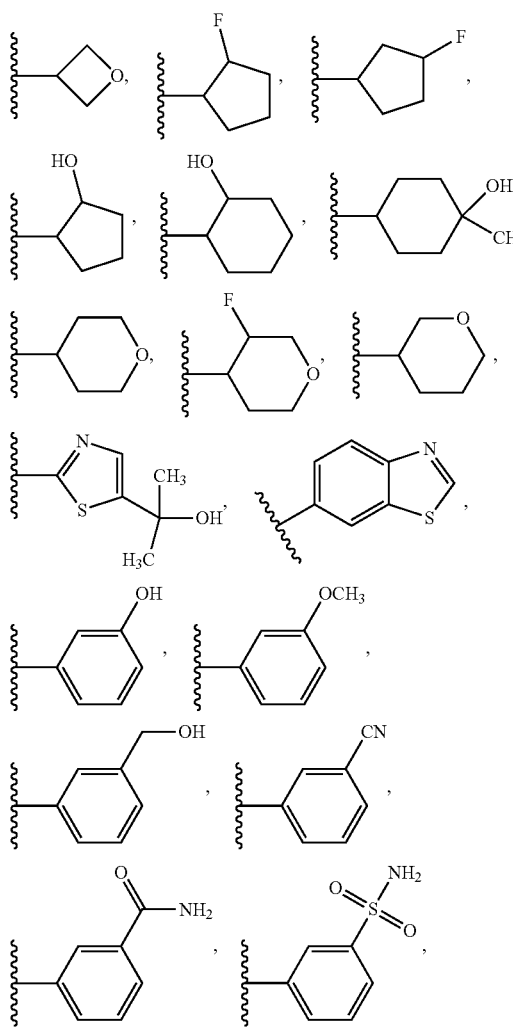

In one embodiment, a compound of Formula (II) or a stereoisomer or pharmaceutically-acceptable salt thereof, is provided wherein $R^2$ is phenyl, pyridinyl, pyridazinyl, pyrimidinyl, pyrazolyl, thiazolyl, or triazolyl, each substituted with zero to 2 substituents independently selected from F, Cl, —OH, —CN, $C_{1-3}$ alkyl, —$CH_2C(O)OCH_3$, —$O(C_{1-3}$ alkyl), —$NH_2$, —$NH(C_{1-3}$ alkyl), —$NH(cyclopropyl)$, —$C(O)NH_2$, —$NH)C_{1-3}$ alkyl), —$NH(cyclopropyl)$, —$C(O)NH_2$, —$NHC(O)(C_{1-3}$ alkyl), —$NH(tetrahydropyranyl)$, hydroxypyrrolidinyl, =O, —O(piperidinyl), and pyridinyl. Included in this embodiment are compounds in which $R^2$ is phenyl, pyridinyl, pyrimidinyl, pyrazolyl, thiazolyl, or triazolyl, each substituted with zero to 2 substituents independently selected from F, Cl, —OH, —CN, $C_{1-3}$ alkyl, —$CH_2C(O)OCH_3$, —$O(C_{1-3}$ alkyl), —$NH_2$, —$NH(C_{1-3}$ alkyl), —$NH(cyclopropyl)$, —$C(O)NH_2$, —$NHC(O)(C_{1-3}$ alkyl), —$NH(tetrahydropyranyl)$, hydroxypyrrolidinyl, —O(piperidinyl), and pyridinyl; or pyridazinyl substituted with =O. Also included in this embodiment are compounds in which $R^2$ is

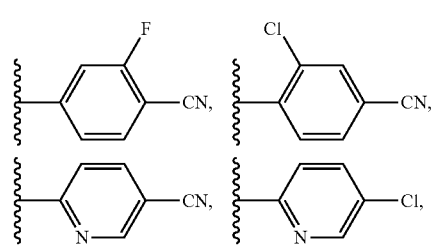

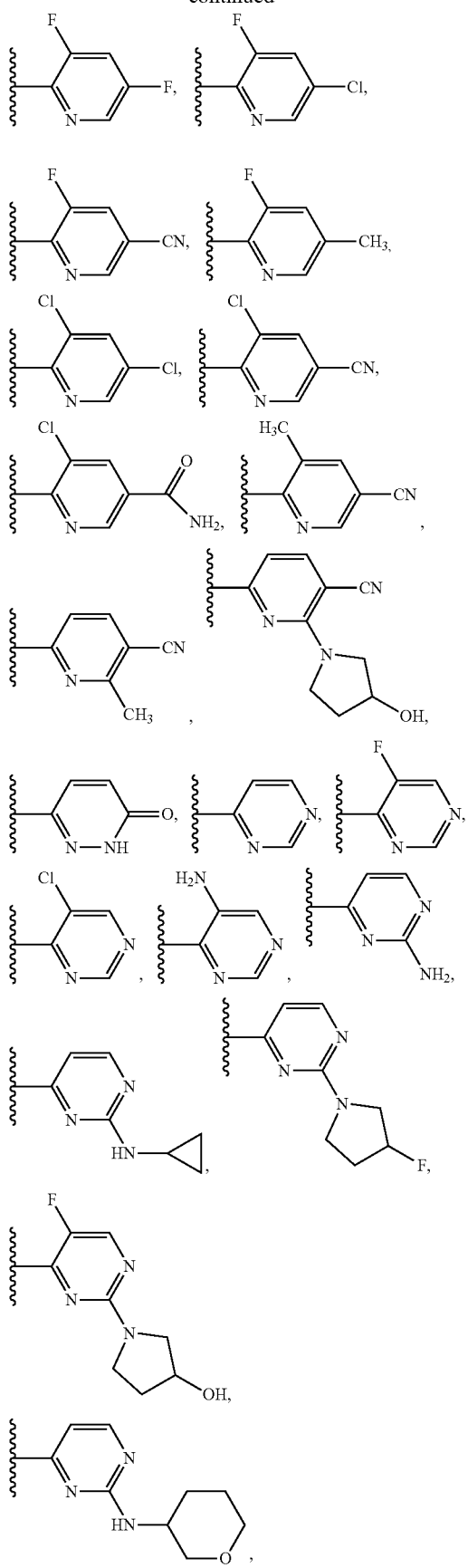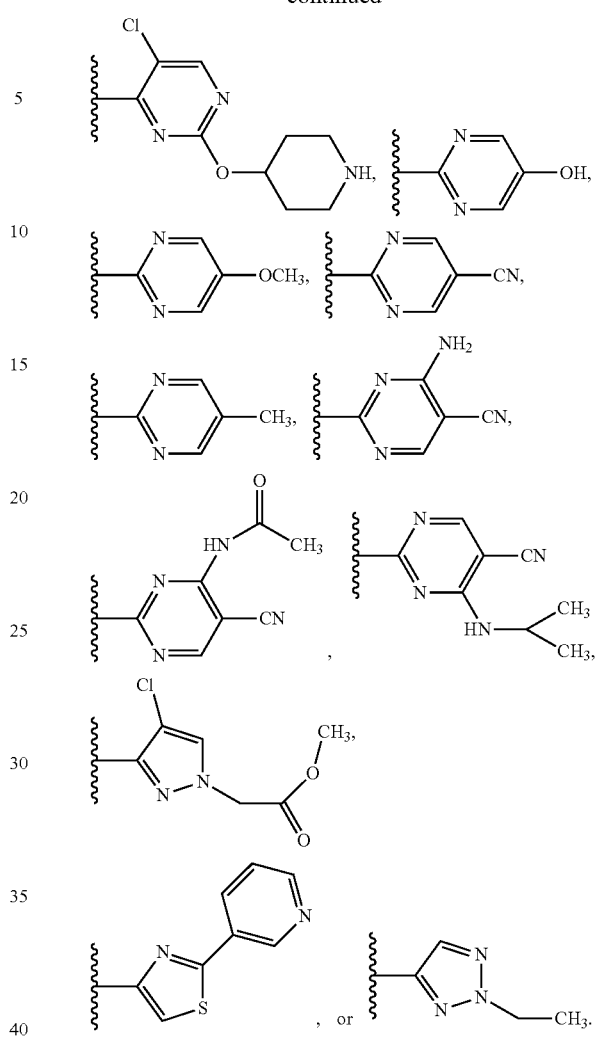

In one embodiment, a compound of Formula (II) or a stereoisomer or pharmaceutically-acceptable salt thereof, is provided wherein $R^3$ is (a) $C_{1-6}$ alkyl substituted with zero to 4 substituents independently selected from F, —OH, —CH₃, —CF₃, and $C_{3-6}$ cycloalkyl; (b) $C_{3-6}$ cycloalkyl substituted with zero to 2 substituents independently selected from F, —OH, $C_{1-3}$ hydroxyalkyl, —CH₃, —CF₂H, —NH₂, and —C(O)OCH₂CH₃; (c) oxetanyl, tetrahydropyranyl, or fluoro tetrahydropyranyl; (d) phenyl substituted with zero to 2 substituents independently selected from —OH, —CN, —O($C_{1-3}$ alkyl), $C_{1-3}$ hydroxyalkyl, —C(O)NH₂, —S(O)₂NH₂, —NHS(O)₂($C_{1-3}$ alkyl), pyrazolyl, imidazolyl, and methyl tetrazolyl; or (e)

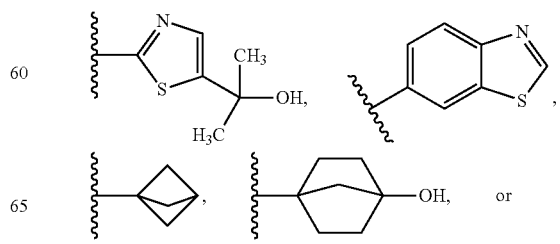

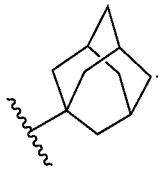

Included in this embodiment are compounds in which $R^3$ is (a) $C_{1-5}$ alkyl substituted with zero to 3 substituents independently selected from F, —OH, —CH$_3$, —CF$_3$, and cyclopropyl; (b) $C_{3-6}$ cycloalkyl substituted with zero to 2 substituents independently selected from F, —OH, $C_{1-3}$ hydroxyalkyl, —CH$_3$, —CF$_2$H, —NH$_2$, and —C(O)OCH$_2$CH$_3$; (c) oxetanyl, tetrahydropyranyl, or fluoro tetrahydropyranyl; (d) phenyl substituted with zero to 2 substituents independently selected from —OH, —CN, —OCH$_3$, $C_{1-2}$ hydroxyalkyl, —C(O)NH$_2$, —S(O)$_2$NH$_2$, —NHS(O)$_2$CH$_3$, pyrazolyl, imidazolyl, and methyl tetrazolyl; or (e)

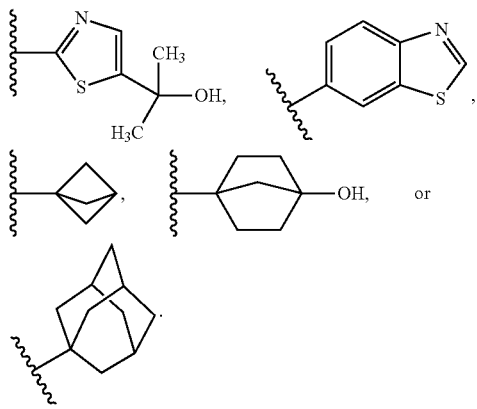

Also included in this embodiment are compounds in which $R^3$ is $C_{2-5}$ alkyl, —CH$_2$CF$_3$, —CH$_2$C(CH$_3$)$_2$F, —CH(CH$_3$)CHFCH$_3$, —CH(CH$_3$)CH$_2$F, —CH(CH$_3$)CH$_2$CH$_2$F, —CH(CH$_3$)CH$_2$OH, —CH$_2$C(CH$_3$)$_2$OH, —CH$_2$CF$_2$C(CH$_3$)$_2$OH, —CH(CH$_3$)(cyclopropyl), $C_{3-4}$ cycloalkyl,

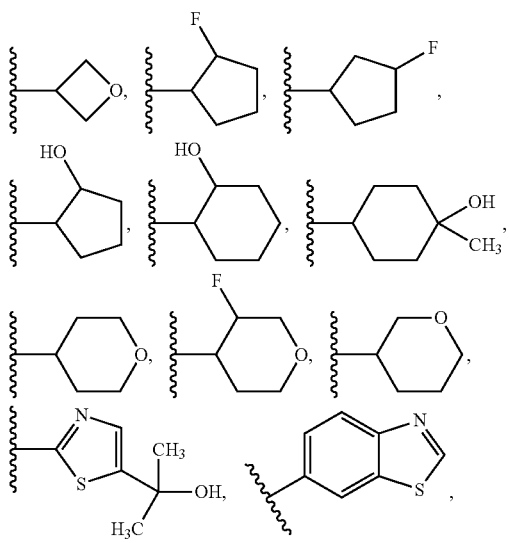

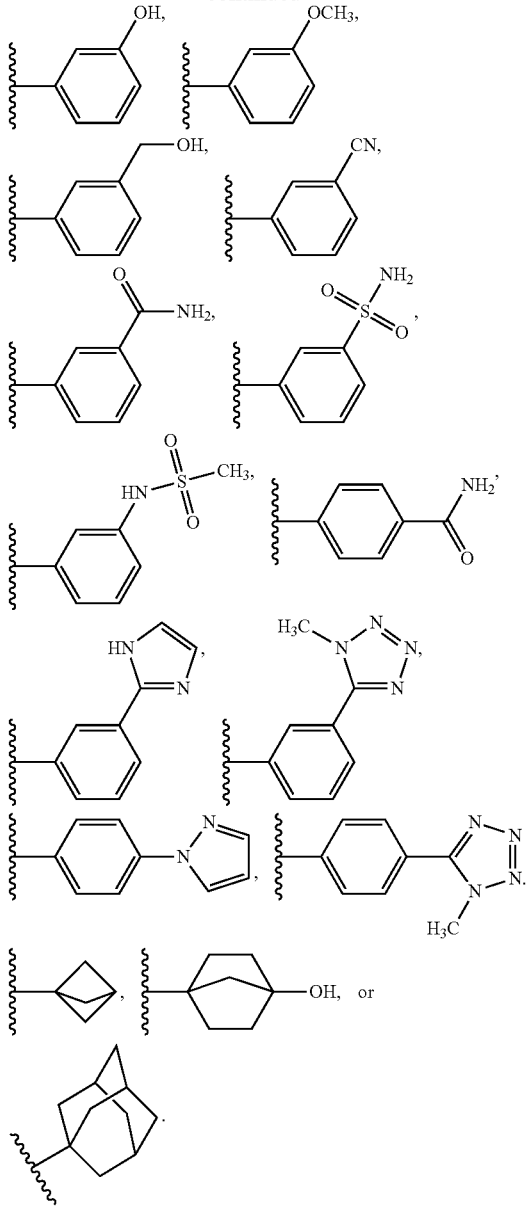

One embodiment provides a compound of Formula (I) or pharmaceutically-acceptable salt thereof, selected from: 6-((5-cyano-2-pyridinyl)amino)-4-(((1S,2S)-2,3-dihydroxy-1-phenylpropyl)amino)-N-methylnicotinamide (1); 6-((5-cyano-2-pyridinyl)amino)-N-((2R)-2-fluoro-3-hydroxy-3-methylbutyl)-4-(isopropylamino)nicotinamide (2); 6-((5-cyano-2-pyridinyl)amino)-N-((2R)-2-fluoro-3-hydroxy-3-methylbutyl)-4-((2,2,2-trifluoroethyl)amino)nicotinamide (3); 6-((5-cyano-2-pyridinyl)amino)-4-(ethylamino)-N-((2R)-2-fluoro-3-hydroxy-3-methylbutyl)nicotinamide (4); 6-((5-cyano-2-pyridinyl)amino)-4-(isopropylamino)-N-(trans-4-(methylcarbamoyl)cyclohexyl)nicotinamide (5); 6-((5-cyanopyridin-2-yl)amino)-N-((1R,4R)-4-(cyclopropylcarbamoyl)cyclohexyl)-4-(isopropylamino)nicotinamide (6); 6-((5-cyano-2-pyridinyl)amino)-N-(trans-4-(((1S,2R)-2-fluorocyclopropyl)carbamoyl)cyclohexyl)-4-(isopropylamino)nicotinamide (7); N-(1-acetyl-4-piperidinyl)-6-((5-cyano-2-pyridinyl)amino)-4-(isopropylamino)nicotinamide (8); N-(trans-4-acetamidocyclohexyl)-6-((5-cyano-2-pyridinyl)amino)-4-(isopropylamino)nicotinamide (9); 6-((5-cyano-2-pyridinyl)amino)-4-(cyclobutylamino)-N-(trans-4-(methylcarbamoyl)cyclohexyl)nicotinamide (10); N-((1R,4R)-4-acetamidocyclohexyl)-6-(5-cyanopyridin-2-yl)amino)-4-(((3 S,4R)-3-fluorotetrahydro-2H-pyran-4-yl)amino)nicotinamide (11); 6-((3-chloro-5-cyano-2-pyridinyl)amino)-N-((2R)-2-fluoro-3-hydroxy-3-methylbutyl)-4-(isopropylamino)nicotinamide (12); 6-((3-chloro-5-cyano-2-pyridinyl)amino)-N-((2R)-2-fluoro-3-hydroxy-3-methylbutyl)-4-(tetrahydro-2H-pyran-4-ylamino)nicotinamide (13); 6-((3-chloro-5-cyano-2-pyridinyl)amino)-4-(cyclopropylamino)-N-((2R)-2-fluoro-3-hydroxy-3-methylbutyl)nicotinamide (14); N-((1r,4r)-4-acetamidocyclohexyl)-6-((3-chloro-5-cyanopyridin-2-yl)amino)-4-(isopropylamino)nicotinamide (15); 6-((3-chloro-5-cyanopyridin-2-yl)amino)-4-(isopropylamino)-N-((1r,4r)-4-(methylcarbamoyl)cyclohexyl)nicotinamide (16); 6-((5-cyano-3-fluoro-2-pyridinyl)amino)-N-((2R)-2-fluoro-3-hydroxy-3-methylbutyl)-4-(isopropylamino)nicotinamide (17); 6-((5-cyano-3-fluoropyridin-2-yl)amino)-4-(isopropylamino)-N-((1r,4r)-4-(methylcarbamoyl)cyclohexyl)nicotinamide (18); N-(trans-4-acetamidocyclohexyl)-6-((5-cyano-3-fluoro-2-pyridinyl)amino)-4-(isopropylamino)nicotinamide (19); N-((2R)-2-fluoro-3-hydroxy-3-methylbutyl)-4-(isopropylamino)-6-(4-pyrimidinylamino)nicotinamide (20); 4-(cyclopropylamino)-N-((2R)-2-fluoro-3-hydroxy-3-methylbutyl)-6-(4-pyrimidinylamino)nicotinamide (21); 6-((5-cyano-2-pyrimidinyl)amino)-N-((2R)-2-fluoro-3-hydroxy-3-methylbutyl)-4-(isopropylamino)nicotinamide (22); 4-(cyclopropylamino)-N-((2R)-2-fluoro-3-hydroxy-3-methylbutyl)-6-((4-(3-pyridinyl)-1,3-thiazol-2-yl)amino)nicotinamide (23); 6-((2-(cyclopropylamino)-4-pyrimidinyl)amino)-N-((2R)-2-fluoro-3-hydroxy-3-methylbutyl)-4-(isopropylamino)nicotinamide (24); N-((2R)-2-fluoro-3-hydroxy-3-methylbutyl)-4-(isopropylamino)-6-((2-(tetrahydro-2H-pyran-3-ylamino)-4-pyrimidinyl)amino)nicotinamide (25); N-((2R)-2-fluoro-3-hydroxy-3-methylbutyl)-6-((2-(3-fluoro-1-pyrrolidinyl)-4-pyrimidinyl)amino)-4-(isopropylamino)nicotinamide (26); and 6-((5-cyano-6-((3S)-3-hydroxy-1-pyrrolidinyl)-2-pyridinyl)amino)-N-((2R)-2-fluoro-3-hydroxy-3-methylbutyl)-4-(isopropylamino)nicotinamide (27).

In another embodiment, there is provided a pharmaceutical composition comprising one or more compounds of Formula (I) and a pharmaceutically acceptable carrier or diluent.

The present invention is also directed to pharmaceutical compositions useful in treating diseases associated with kinase modulation, including modulation (especially inhibition) of IRAK-4, comprising compounds of Formula (I), or pharmaceutically-acceptable salts thereof, and pharmaceutically-acceptable carriers or diluents.

The invention further relates to methods of treating diseases associated with the kinase modulation, including the modulation of IRAK-4, comprising administering to a patient in need of such treatment a therapeutically-effective amount of a compound according to Formula (I).

The present invention also provides processes and intermediates for making the compounds of the present invention or stereoisomers, tautomers, pharmaceutically acceptable salts, solvates, or prodrugs thereof.

The present invention also provides a method for treating proliferative, metabolic, allergic, autoimmune and inflammatory diseases (or use of the compounds of the present invention or stereoisomers, tautomers, pharmaceutically acceptable salts, solvates, or prodrugs thereof, for the manufacture of a medicament for the treatment of these diseases), comprising administering to a host in need of such treatment a therapeutically effective amount of at least one of the compounds of the present invention or stereoisomers, tautomers, pharmaceutically acceptable salts, solvates, or prodrugs thereof.

The present invention also provides a method for treating a disease (or use of the compounds of the present invention or stereoisomers, tautomers, pharmaceutically acceptable salts, solvates, or prodrugs thereof, for the manufacture of a medicament for the treatment of these diseases), comprising administering to a patient in need of such treatment a therapeutically-effective amount of a compound of formula I, wherein the disease is Crohn's disease, ulcerative colitis, asthma, graft versus host disease, allograft rejection, chronic obstructive pulmonary disease; Graves' disease, rheumatoid arthritis, systemic lupus erythematosis, psoriasis; CAPS, TRAPS, FMF, adult onset stills, systemic onset juvenile idiopathic arthritis, multiple sclerosis, neuropathic pain, gout, and gouty arthritis.

The present invention also provides a method of treating an inflammatory or autoimmune disease (or use of the compounds of the present invention or stereoisomers, tautomers, pharmaceutically acceptable salts, solvates, or prodrugs thereof, for the manufacture of a medicament for the treatment of these diseases) comprising administering to a patient in need of such treatment a therapeutically-effective amount of a compound according to formula I.

The present invention also provides a method of treating an inflammatory or autoimmune disease (or use of the compounds of the present invention or stereoisomers, tautomers, pharmaceutically acceptable salts, solvates, or prodrugs thereof, for the manufacture of a medicament for the treatment of these diseases) wherein the disease is selected from Crohn's, ulcerative colitis, asthma, graft versus host disease, allograft rejection, chronic obstructive pulmonary disease; Graves' disease, rheumatoid arthritis, systemic lupus erythematosis, psoriasis; CAPS, TRAPS, FMF, adult onset stills, systemic onset juvenile idiopathic arthritis, multiple sclerosis, neuropathic pain, gout, and gouty arthritis.

In addition, the present invention provides a method of treating a condition (or use of the compounds of the present invention or stereoisomers, tautomers, pharmaceutically acceptable salts, solvates, or prodrugs thereof, for the manufacture of a medicament for the treatment of these conditions) comprising administering to a patient in need of such treatment a therapeutically-effective amount of a compound of formula I, wherein the condition is selected from acute myelogenous leukemia, chronic myelogenous leukemia, metastatic melanoma, Kaposi's sarcoma, multiple myeloma, solid tumors, ocular neovasculization, and infantile haemangiomas, B cell lymphoma, systemic lupus erythematosus (SLE), rheumatoid arthritis, psoriatic arthritis, multiple vasculitides, idiopathic thrombocytopenic purpura (ITP), myasthenia gravis, allergic rhinitis, multiple sclerosis (MS), transplant rejection, Type I diabetes, membranous nephritis, inflammatory bowel disease, autoimmune hemolytic anemia, autoimmune thyroiditis, cold and warm agglutinin diseases, Evans' syndrome, hemolytic uremic syndrome/thrombotic thrombocytopenic purpura (HUS/TTP), sarcoidosis, Sjögren's syndrome, peripheral neuropathies, pemphigus vulgaris and asthma.

The present invention also provides a method for treating a rheumatoid arthritis (or use of the compounds of the present invention or stereoisomers, tautomers, pharmaceutically acceptable salts, solvates, or prodrugs thereof, for the manufacture of a medicament for the treatment of rheumatoid arthritis), comprising administering to a patient in need of such treatment a therapeutically-effective amount of a compound of formula I.

The present invention also provides a method of treating a TLR/IL-1 mediated disease (or use of the compounds of the present invention or stereoisomers, tautomers, pharmaceutically acceptable salts, solvates, or prodrugs thereof, for the manufacture of a medicament for the treatment of these diseases), comprising administering to a patient in need of such treatment a therapeutically-effective amount of a compound of formula I The present invention also provides a method of treating a TLR/IL-1 mediated disease (or use of the compounds of the present invention or stereoisomers, tautomers, pharmaceutically acceptable salts, solvates, or prodrugs thereof, for the manufacture of a medicament for the treatment of these diseases), comprising administering to a patient in need of such treatment a therapeutically-effective amount of a compound of formula I, wherein the TLR/IL-1 mediated disease is a disease modulated by a kinase selected from IRAK-4.

The present invention also provides a method of treating diseases, comprising administering to a patient in need of such treatment a therapeutically-effective amount of a compound of formula I, or pharmaceutically acceptable salt thereof, in combination with other therapeutic agents.

The present invention also provides the compounds of the present invention or stereoisomers, tautomers, pharmaceutically acceptable salts, solvates, or prodrugs thereof, for use in therapy.

In another embodiment, compounds of formula I are selected from exemplified compounds or combinations of exemplified compounds or other embodiments herein.

In another embodiment are compounds having an $IC_{50}$<1000 nM in the IRAK-4 assay described below.

The present invention may be embodied in other specific forms without departing from the spirit or essential attributes thereof. This invention encompasses all combinations of preferred aspects and/or embodiments of the invention noted herein. It is understood that any and all embodiments of the present invention may be taken in conjunction with any other embodiment or embodiments to describe additional more preferred embodiments. It is also to be understood that each individual element of the preferred embodiments is its own independent preferred embodiment. Furthermore, any element of an embodiment is meant to be combined with any and all other elements from any embodiment to describe an additional embodiment.

DETAILED DESCRIPTION OF THE INVENTION

The following are definitions of terms used in this specification and appended claims. The initial definition provided for a group or term herein applies to that group or term throughout the specification and claims, individually or as part of another group, unless otherwise indicated.

Compounds of this invention may have one or more asymmetric centers. Unless otherwise indicated, all chiral (enantiomeric and diastereomeric) and racemic forms of compounds of the present invention are included in the present invention. Many geometric isomers of olefins, C=N double bonds, and the like can also be present in the compounds, and all such stable isomers are contemplated in the present invention. Cis- and trans-geometric isomers of the compounds of the present invention are described and may be isolated as a mixture of isomers or as separated isomeric forms. The present compounds can be isolated in optically active or racemic forms. It is well known in the art how to prepare optically active forms, such as by resolution of racemic forms or by synthesis from optically active starting materials. All chiral, (enantiomeric and diastereomeric) and racemic forms and all geometric isomeric forms of a structure are intended, unless the specific stereochemistry or isomer form is specifically indicated.

When any variable (e.g., $R^3$) occurs more than one time in any constituent or formula for a compound, its definition at each occurrence is independent of its definition at every other occurrence. Thus, for example, if a group is shown to be substituted with 0-2 $R^3$, then said group may optionally be substituted with up to two $R^3$ groups and $R^3$ at each occurrence is selected independently from the definition of $R^3$. Also, combinations of substituents and/or variables are permissible only if such combinations result in stable compounds.

When a bond to a substituent is shown to cross a bond connecting two atoms in a ring, then such substituent may be bonded to any atom on the ring. When a substituent is listed without indicating the atom via which such substituent is bonded to the rest of the compound of a given formula, then such substituent may be bonded via any atom in such substituent. Combinations of substituents and/or variables are permissible only if such combinations result in stable compounds.

In cases wherein there are nitrogen atoms (e.g., amines) on compounds of the present invention, these can be converted to N-oxides by treatment with an oxidizing agent (e.g., MCPBA and/or hydrogen peroxides) to afford other compounds of this invention. Thus, all shown and claimed nitrogen atoms are considered to cover both the shown nitrogen and its N-oxide (N→O) derivative.

In accordance with a convention used in the art,

is used in structural formulas herein to depict the bond that is the point of attachment of the moiety or substituent to the core or backbone structure.

A dash "-" that is not between two letters or symbols is used to indicate a point of attachment for a substituent. For example, —$CONH_2$ is attached through the carbon atom.

The term "optionally substituted" in reference to a particular moiety of the compound of Formula I (e.g., an optionally substituted heteroaryl group) refers to a moiety having 0, 1, 2, or more substituents. For example, "optionally substituted alkyl" encompasses both "alkyl" and "substituted alkyl" as defined below. It will be understood by those skilled in the art, with respect to any group containing one or more substituents, that such groups are not intended to introduce any substitution or substitution patterns that are sterically impractical, synthetically non-feasible and/or inherently unstable.

As used herein, the term "at least one chemical entity" is interchangeable with the term "a compound".

As used herein, the term "alkyl" or "alkylene" is intended to include both branched and straight-chain saturated aliphatic hydrocarbon groups having the specified number of carbon atoms. For example, "$C_{1-10}$ alkyl" (or alkylene), is intended to include $C_1$, $C_2$, $C_3$, $C_4$, $C_5$, $C_6$, $C_7$, $C_8$, $C_9$, and $C_{10}$ alkyl groups. Additionally, for example, "$C_1$-$C_6$ alkyl"

denotes alkyl having 1 to 6 carbon atoms. Alkyl groups can be unsubstituted or substituted so that one or more of its hydrogens are replaced by another chemical group. Example alkyl groups include, but are not limited to, methyl (Me), ethyl (Et), propyl (e.g., n-propyl and isopropyl), butyl (e.g., n-butyl, isobutyl, t-butyl), pentyl (e.g., n-pentyl, isopentyl, neopentyl), and the like.

Alkenyl" or "alkenylene" is intended to include hydrocarbon chains of either straight or branched configuration and having one or more double carbon-carbon bonds that may occur in any stable point along the chain. For example, "$C_{2-6}$ alkenyl" (or alkenylene), is intended to include $C_2$, $C_3$, $C_4$, $C_5$, and $C_6$ alkenyl groups. Examples of alkenyl include, but are not limited to, ethenyl, 1-propenyl, 2-propenyl, 2-butenyl, 3-butenyl, 2-pentenyl, 3-pentenyl, 4-pentenyl, 2-hexenyl, 3-hexenyl, 4-hexenyl, 5-hexenyl, 2-methyl-2-propenyl, 4-methyl-3-pentenyl, and the like.

"Alkynyl" or "alkynylene" is intended to include hydrocarbon chains of either straight or branched configuration and having one or more triple carbon-carbon bonds that may occur in any stable point along the chain. For example, "$C_{2-6}$ alkynyl" (or alkynylene), is intended to include $C_2$, $C_3$, $C_4$, $C_5$, and $C_6$ alkynyl groups; such as ethynyl, propynyl, butynyl, pentynyl, hexynyl and the like.

One skilled in the field will understand that, when the designation "$CO_2$" is used herein, this is intended to refer to the group

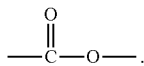

When the term "alkyl" is used together with another group, such as in "arylalkyl", this conjunction defines with more specificity at least one of the substituents that the substituted alkyl will contain. For example, "arylalkyl" refers to a substituted alkyl group as defined above where at least one of the substituents is an aryl, such as benzyl. Thus, the term aryl($C_{0-4}$)alkyl includes a substituted lower alkyl having at least one aryl substituent and also includes an aryl directly bonded to another group, i.e., aryl($C_0$)alkyl. The term "heteroarylalkyl" refers to a substituted alkyl group as defined above where at least one of the substituents is a heteroaryl.

When reference is made to a substituted alkenyl, alkynyl, alkylene, alkenylene, or alkynylene group, these groups are substituted with one to three substituents as defined above for substituted alkyl groups.

The term "alkoxy" refers to an oxygen atom substituted by alkyl or substituted alkyl, as defined herein. For example, the term "alkoxy" includes the group —O—$C_{1-6}$ alkyl such as methoxy, ethoxy, propoxy, isopropoxy, n-butoxy, sec-butoxy, tert-butoxy, pentoxy, 2-pentyloxy, isopentoxy, neopentoxy, hexoxy, 2-hexoxy, 3-hexoxy, 3-methylpentoxy, and the like. "Lower alkoxy" refers to alkoxy groups having one to four carbons.

It should be understood that the selections for all groups, including for example, alkoxy, thioalkyl, and aminoalkyl, will be made by one skilled in the field to provide stable compounds.

The term "substituted", as used herein, means that any one or more hydrogens on the designated atom or group is replaced with a selection from the indicated group, provided that the designated atom's normal valence is not exceeded. When a substituent is oxo, or keto, (i.e., =O) then 2 hydrogens on the atom are replaced. Keto substituents are not present on aromatic moieties. Unless otherwise specified, substituents are named into the core structure. For example, it is to be understood that when (cycloalkyl)alkyl is listed as a possible substituent, the point of attachment of this substituent to the core structure is in the alkyl portion. Ring double bonds, as used herein, are double bonds that are formed between two adjacent ring atoms (e.g., C=C, C=N, or N=N).

Combinations of substituents and/or variables are permissible only if such combinations result in stable compounds or useful synthetic intermediates. A stable compound or stable structure is meant to imply a compound that is sufficiently robust to survive isolation from a reaction mixture to a useful degree of purity, and subsequent formulation into an efficacious therapeutic agent. It is preferred that the presently recited compounds do not contain a N-halo, S(O)$_2$H, or S(O)H group.

The term "cycloalkyl" refers to cyclized alkyl groups, including mono-, bi- or poly-cyclic ring systems. $C_{3-7}$ cycloalkyl is intended to include $C_3$, $C_4$, $C_5$, $C_6$, and $C_7$ cycloalkyl groups. Example cycloalkyl groups include, but are not limited to, cyclopropyl, cyclobutyl, cyclopentyl, cyclohexyl, norbornyl, and the like. As used herein, "carbocycle" or "carbocyclic residue" is intended to mean any stable 3-, 4-, 5-, 6-, or 7-monocyclic or bicyclic or 7-, 8-, 9-, 10-, 11-, 12-, or 13-membered bicyclic or tricyclic ring, any of which may be saturated, partially unsaturated, unsaturated or aromatic. Examples of such carbocycles include, but are not limited to, cyclopropyl, cyclobutyl, cyclobutenyl, cyclopentyl, cyclopentenyl, cyclohexyl, cycloheptenyl, cycloheptyl, cycloheptenyl, adamantyl, cyclooctyl, cyclooctenyl, cyclooctadienyl, [3.3.0]bicyclooctane, [4.3.0]bicyclononane, [4.4.0]bicyclodecane, [2.2.2]bicyclooctane, fluorenyl, phenyl, naphthyl, indanyl, adamantyl, anthracenyl, and tetrahydronaphthyl (tetralin). As shown above, bridged rings are also included in the definition of carbocycle (e.g., [2.2.2]bicyclooctane). Preferred carbocycles, unless otherwise specified, are cyclopropyl, cyclobutyl, cyclopentyl, cyclohexyl, and phenyl. When the term "carbocycle" is used, it is intended to include "aryl". A bridged ring occurs when one or more carbon atoms link two non-adjacent carbon atoms. Preferred bridges are one or two carbon atoms. It is noted that a bridge always converts a monocyclic ring into a bicyclic ring. When a ring is bridged, the substituents recited for the ring may also be present on the bridge.

The term "aryl" refers to monocyclic or bicyclic aromatic hydrocarbon groups having 6 to 12 carbon atoms in the ring portion, such as phenyl, and naphthyl groups, each of which may be substituted.

Accordingly, in compounds of Formula (I), the term "cycloalkyl" includes cyclopropyl, cyclobutyl, cyclopentyl, cyclohexyl, cycloheptyl, bicyclooctyl, etc., as well as the following ring systems:

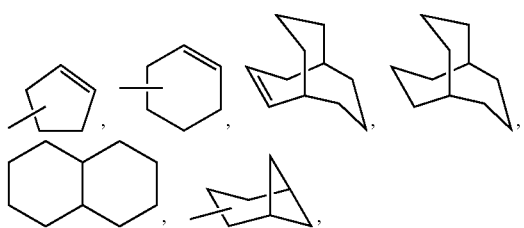

-continued

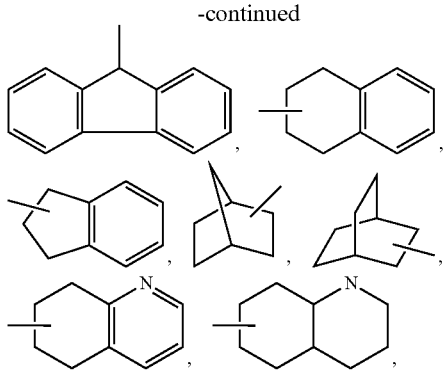

and the like, which optionally may be substituted at any available atoms of the ring(s). Preferred cycloalkyl groups include cyclopropyl, cyclopentyl, cyclohexyl, and

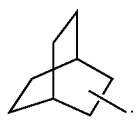

The term "halo" or "halogen" refers to chloro, bromo, fluoro and iodo.

The term "haloalkyl" means a substituted alkyl having one or more halo substituents. For example, "haloalkyl" includes mono, bi, and trifluoromethyl.

The term "haloalkoxy" means an alkoxy group having one or more halo substituents. For example, "haloalkoxy" includes $OCF_3$.

Thus, examples of aryl groups include:

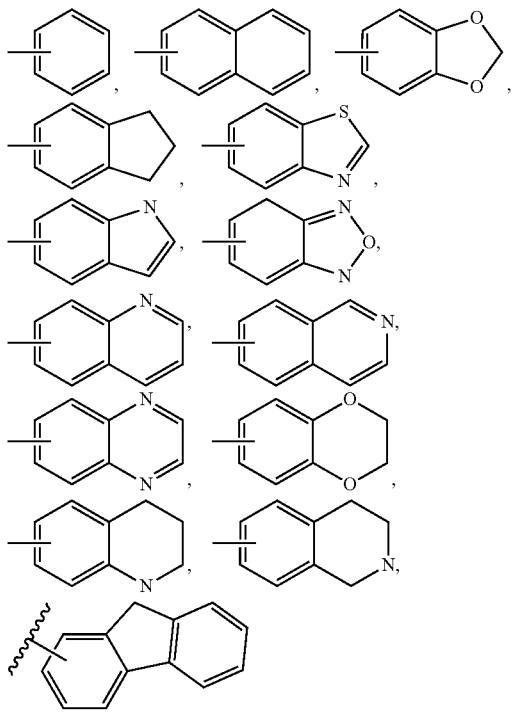

(fluorenyl) and the like, which optionally may be substituted at any available carbon or nitrogen atom. A preferred aryl group is optionally-substituted phenyl.

The terms "heterocycloalkyl", "heterocyclo", "heterocyclic", or "heterocyclyl" may be used interchangeably and refer to substituted and unsubstituted 3- to 7-membered monocyclic groups, 7- to 11-membered bicyclic groups, and 10- to 15-membered tricyclic groups, in which at least one of the rings has at least one heteroatom (0, S or N), said heteroatom containing ring preferably having 1, 2, or 3 heteroatoms selected from O, S, and N. Each ring of such a group containing a heteroatom can contain one or two oxygen or sulfur atoms and/or from one to four nitrogen atoms provided that the total number of heteroatoms in each ring is four or less, and further provided that the ring contains at least one carbon atom. The nitrogen and sulfur atoms may optionally be oxidized and the nitrogen atoms may optionally be quaternized. The fused rings completing the bicyclic and tricyclic groups may contain only carbon atoms and may be saturated, partially saturated, or unsaturated. The heterocyclo group may be attached at any available nitrogen or carbon atom. The term "heterocycle" includes "heteroaryl" groups. As valence allows, if said further ring is cycloalkyl or heterocyclo it is additionally optionally substituted with =O (oxo).

Exemplary monocyclic heterocyclyl groups include azetidinyl, pyrrolidinyl, oxetanyl, imidazolinyl, oxazolidinyl, isoxazolinyl, thiazolidinyl, isothiazolidinyl, tetrahydrofuranyl, piperidyl, piperazinyl, 2-oxopiperazinyl, 2-oxopiperidyl, 2-oxopyrrolodinyl, 2-oxoazepinyl, azepinyl, 1-pyridonyl, 4-piperidonyl, tetrahydropyranyl, morpholinyl, thiamorpholinyl, thiamorpholinyl sulfoxide, thiamorpholinyl sulfone, 1,3-dioxolane and tetrahydro-1,1-dioxothienyl and the like. Exemplary bicyclic heterocyclo groups include quinuclidinyl. Additional monocyclic heterocyclyl groups include

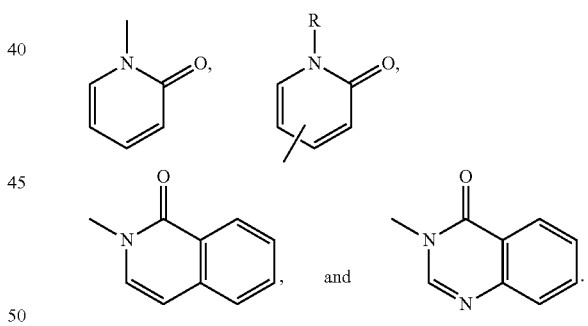

The term "heteroaryl" refers to substituted and unsubstituted aromatic 5- or 6-membered monocyclic groups, 9- or 10-membered bicyclic groups, and 11- to 14-membered tricyclic groups which have at least one heteroatom (O, S or N) in at least one of the rings, said heteroatom-containing ring preferably having 1, 2, or 3 heteroatoms selected from O, S, and N. Each ring of the heteroaryl group containing a heteroatom can contain one or two oxygen or sulfur atoms and/or from one to four nitrogen atoms provided that the total number of heteroatoms in each ring is four or less and each ring has at least one carbon atom. The fused rings completing the bicyclic and tricyclic groups may contain only carbon atoms and may be saturated, partially saturated, or unsaturated. The nitrogen and sulfur atoms may optionally be oxidized and the nitrogen atoms may optionally be quaternized. Heteroaryl groups which are bicyclic or tricyclic must include at least one fully aromatic ring but the other fused ring or rings may be aromatic or non-aromatic. The heteroaryl group may be attached at any available nitrogen or carbon atom of any ring. As valence allows, if said further ring is cycloalkyl or heterocyclo it is additionally optionally substituted with =O (oxo).

Exemplary monocyclic heteroaryl groups include pyrrolyl, pyrazolyl, pyrazolinyl, imidazolyl, oxazolyl, isoxazolyl, thiazolyl, thiadiazolyl, isothiazolyl, furanyl, thienyl, oxadiazolyl, pyridyl, pyrazinyl, pyrimidinyl, pyridazinyl, triazinyl and the like.

Exemplary bicyclic heteroaryl groups include indolyl, benzothiazolyl, benzodioxolyl, benzoxazolyl, benzothienyl, quinolinyl, tetrahydroisoquinolinyl, isoquinolinyl, benzimidazolyl, benzopyranyl, indolizinyl, benzofuranyl, chromonyl, coumarinyl, benzopyranyl, cinnolinyl, quinoxalinyl, indazolyl, pyrrolopyridyl, furopyridyl, dihydroisoindolyl, tetrahydroquinolinyl and the like.

Exemplary tricyclic heteroaryl groups include carbazolyl, benzindolyl, phenanthrollinyl, acridinyl, phenanthridinyl, xanthenyl and the like.

In compounds of Formula (I), preferred heteroaryl groups include

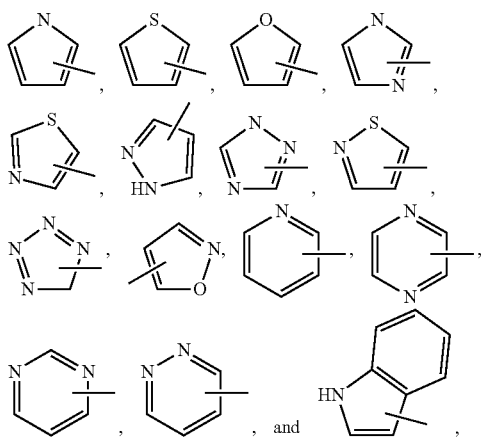

and the like, which optionally may be substituted at any available carbon or nitrogen atom.

Unless otherwise indicated, when reference is made to a specifically-named aryl (e.g., phenyl), cycloalkyl (e.g., cyclohexyl), heterocyclo (e.g., pyrrolidinyl, piperidinyl, and morpholinyl) or heteroaryl (e.g., tetrazolyl, imidazolyl, pyrazolyl, triazolyl, thiazolyl, and furyl) the reference is intended to include rings having 0 to 3, preferably 0 to 2, substituents selected from those recited above for the aryl, cycloalkyl, heterocyclo and/or heteroaryl groups, as appropriate.

The term "carbocyclyl" or "carbocyclic" refers to a saturated or unsaturated monocyclic or bicyclic ring in which all atoms of all rings are carbon. Thus, the term includes cycloalkyl and aryl rings. Monocyclic carbocycles have 3 to 6 ring atoms, still more typically 5 or 6 ring atoms. Bicyclic carbocycles have 7 to 12 ring atoms, e.g., arranged as a bicyclo [4,5], [5,5], [5,6] or [6,6] system, or 9 or 10 ring atoms arranged as a bicyclo [5,6] or [6,6] system. Examples of mono- and bicyclic carbocycles include cyclopropyl, cyclobutyl, cyclopentyl, 1-cyclopent-1-enyl, 1-cyclopent-2-enyl, 1-cyclopent-3-enyl, cyclohexyl, 1-cyclohex-1-enyl, 1-cyclohex-2-enyl, 1-cyclohex-3-enyl, phenyl and naphthyl.

The carbocyclic ring may be substituted in which case the substituents are selected from those recited above for cycloalkyl and aryl groups.

The term "heteroatoms" shall include oxygen, sulfur and nitrogen.

When the term "unsaturated" is used herein to refer to a ring or group, the ring or group may be fully unsaturated or partially unsaturated.

Throughout the specification, groups and substituents thereof may be chosen by one skilled in the field to provide stable moieties and compounds and compounds useful as pharmaceutically-acceptable compounds and/or intermediate compounds useful in making pharmaceutically-acceptable compounds.

The compounds of Formula (I) may exist in a free form (with no ionization) or can form salts which are also within the scope of this invention. Unless otherwise indicated, reference to an inventive compound is understood to include reference to the free form and to salts thereof. The term "salt(s)" denotes acidic and/or basic salts formed with inorganic and/or organic acids and bases. In addition, the term "salt(s) may include zwitterions (inner salts), e.g., when a compound of Formula (I), contains both a basic moiety, such as an amine or a pyridine or imidazole ring, and an acidic moiety, such as a carboxylic acid. Pharmaceutically acceptable (i.e., non-toxic, physiologically acceptable) salts are preferred, such as, for example, acceptable metal and amine salts in which the cation does not contribute significantly to the toxicity or biological activity of the salt. However, other salts may be useful, e.g., in isolation or purification steps which may be employed during preparation, and thus, are contemplated within the scope of the invention. Salts of the compounds of the Formula (I) may be formed, for example, by reacting a compound of the Formula (I) with an amount of acid or base, such as an equivalent amount, in a medium such as one in which the salt precipitates or in an aqueous medium followed by lyophilization.

Exemplary acid addition salts include acetates (such as those formed with acetic acid or trihaloacetic acid, for example, trifluoroacetic acid), adipates, alginates, ascorbates, aspartates, benzoates, benzenesulfonates, bisulfates, borates, butyrates, citrates, camphorates, camphorsulfonates, cyclopentanepropionates, digluconates, dodecylsulfates, ethanesulfonates, fumarates, glucoheptanoates, glycerophosphates, hemisulfates, heptanoates, hexanoates, hydrochlorides (formed with hydrochloric acid), hydrobromides (formed with hydrogen bromide), hydroiodides, 2-hydroxyethanesulfonates, lactates, maleates (formed with maleic acid), methanesulfonates (formed with methanesulfonic acid), 2-naphthalenesulfonates, nicotinates, nitrates, oxalates, pectinates, persulfates, 3-phenylpropionates, phosphates, picrates, pivalates, propionates, salicylates, succinates, sulfates (such as those formed with sulfuric acid), sulfonates (such as those mentioned herein), tartrates, thiocyanates, toluenesulfonates such as tosylates, undecanoates, and the like.

Exemplary basic salts include ammonium salts, alkali metal salts such as sodium, lithium, and potassium salts; alkaline earth metal salts such as calcium and magnesium salts; barium, zinc, and aluminum salts; salts with organic bases (for example, organic amines) such as trialkylamines such as triethylamine, procaine, dibenzylamine, N-benzyl-β-phenethylamine, 1-ephenamine, N,N'-dibenzylethylenediamine, dehydroabietylamine, N-ethylpiperidine, benzylamine, dicyclohexylamine or similar pharmaceutically acceptable amines and salts with amino acids such as arginine, lysine and the like. Basic nitrogen-containing groups may be quaternized with agents such as lower alkyl halides (e.g., methyl, ethyl, propyl, and butyl chlorides, bromides and iodides), dialkyl sulfates (e.g., dimethyl, diethyl, dibutyl, and diamyl sulfates), long chain halides (e.g., decyl, lauryl, myristyl and stearyl chlorides, bromides and iodides), aralkyl halides (e.g., benzyl and phenethyl bromides), and others. Preferred salts include monohydrochloride, hydrogensulfate, methanesulfonate, phosphate or nitrate salts.

The phrase "pharmaceutically acceptable" is employed herein to refer to those compounds, materials, compositions, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

As used herein, "pharmaceutically acceptable salts" refer to derivatives of the disclosed compounds wherein the parent compound is modified by making acid or base salts thereof. Examples of pharmaceutically acceptable salts include, but are not limited to, mineral or organic acid salts of basic groups such as amines; and alkali or organic salts of acidic groups such as carboxylic acids. The pharmaceutically acceptable salts include the conventional non-toxic salts or the quaternary ammonium salts of the parent compound formed, for example, from non-toxic inorganic or organic acids. For example, such conventional non-toxic salts include those derived from inorganic acids such as hydrochloric, hydrobromic, sulfuric, sulfamic, phosphoric, and nitric; and the salts prepared from organic acids such as acetic, propionic, succinic, glycolic, stearic, lactic, malic, tartaric, citric, ascorbic, pamoic, maleic, hydroxymaleic, phenylacetic, glutamic, benzoic, salicylic, sulfanilic, 2-acetoxybenzoic, fumaric, toluenesulfonic, methanesulfonic, ethane disulfonic, oxalic, and isethionic, and the like.

The pharmaceutically acceptable salts of the present invention can be synthesized from the parent compound which contains a basic or acidic moiety by conventional chemical methods. Generally, such salts can be prepared by reacting the free acid or base forms of these compounds with a stoichiometric amount of the appropriate base or acid in water or in an organic solvent, or in a mixture of the two; generally, nonaqueous media like ether, ethyl acetate, ethanol, isopropanol, or acetonitrile are preferred. Lists of suitable salts are found in Remington's Pharmaceutical Sciences, 18th Edition, Mack Publishing Company, Easton, Pa. (1990), the disclosure of which is hereby incorporated by reference.

All stereoisomers of the compounds of the instant invention are contemplated, either in admixture or in pure or substantially pure form. Stereoisomers may include compounds which are optical isomers through possession of one or more chiral atoms, as well as compounds which are optical isomers by virtue of limited rotation about one or more bonds (atropisomers). The definition of compounds according to the invention embraces all the possible stereoisomers and their mixtures. It very particularly embraces the racemic forms and the isolated optical isomers having the specified activity. The racemic forms can be resolved by physical methods, such as, for example, fractional crystallization, separation or crystallization of diastereomeric derivatives or separation by chiral column chromatography. The individual optical isomers can be obtained from the racemates from the conventional methods, such as, for example, salt formation with an optically active acid followed by crystallization.

The present invention is intended to include all isotopes of atoms occurring in the present compounds. Isotopes include those atoms having the same atomic number but different mass numbers. By way of general example and without limitation, isotopes of hydrogen include deuterium and tritium. Isotopes of carbon include $^{13}C$ and $^{14}C$. Isotopically-labeled compounds of the invention can generally be prepared by conventional techniques known to those skilled in the art or by processes analogous to those described herein, using an appropriate isotopically-labeled reagent in place of the non-labeled reagent otherwise employed.

Prodrugs and solvates of the inventive compounds are also contemplated. The term "prodrug" denotes a compound which, upon administration to a subject, undergoes chemical conversion by metabolic or chemical processes to yield a compound of the Formula (I), and/or a salt and/or solvate thereof. Any compound that will be converted in vivo to provide the bioactive agent (i.e., the compound for Formula (I)) is a prodrug within the scope and spirit of the invention. For example, compounds containing a carboxy group can form physiologically hydrolyzable esters which serve as prodrugs by being hydrolyzed in the body to yield Formula (I) compounds per se. Such prodrugs are preferably administered orally since hydrolysis in many instances occurs principally under the influence of the digestive enzymes. Parenteral administration may be used where the ester per se is active, or in those instances where hydrolysis occurs in the blood. Examples of physiologically hydrolyzable esters of compounds of Formula (I) include $C_{1-6}$ alkylbenzyl, 4-methoxybenzyl, indanyl, phthalyl, methoxymethyl, $C_{1-6}$ alkanoyloxy-$C_{1-6}$ alkyl, e.g., acetoxymethyl, pivaloyloxymethyl or propionyloxymethyl, $C_{1-6}$ alkoxycarbonyloxy-$C_{1-6}$ alkyl, e.g., methoxycarbonyl-oxymethyl or ethoxycarbonyloxymethyl, glycyloxymethyl, phenylglycyloxymethyl, (5-methyl-2-oxo-1,3-dioxolen-4-yl)-methyl and other well known physiologically hydrolyzable esters used, for example, in the penicillin and cephalosporin arts. Such esters may be prepared by conventional techniques known in the art.

Various forms of prodrugs are well known in the art. For examples of such prodrug derivatives, see:
a) Bundgaard, H., ed., *Design of Prodrugs*, Elsevier (1985), and Widder, K. et al., eds., *Methods in Enzymology*, 112:309-396, Academic Press (1985);
b) Bundgaard, H., Chapter 5, "Design and Application of Prodrugs", Krosgaard-Larsen, P. et al., eds., *A Textbook of Drug Design and Development*, pp. 113-191, Harwood Academic Publishers (1991); and
c) Bundgaard, H., *Adv. Drug Deliv. Rev.*, 8:1-38 (1992), each of which is incorporated herein by reference.

Compounds of the Formula (I) and salts thereof may exist in their tautomeric form, in which hydrogen atoms are transposed to other parts of the molecules and the chemical bonds between the atoms of the molecules are consequently rearranged. It should be understood that the all tautomeric forms, insofar as they may exist, are included within the invention. Additionally, inventive compounds may have trans and cis isomers.

It should further be understood that solvates (e.g., hydrates) of the compounds of Formula (I) are also with the scope of the present invention. Methods of solvation are generally known in the art.

Utility

The compounds of the invention modulate kinase activity, including the modulation of IRAK-4. Other types of kinase activity that may be modulated by the compounds of the instant invention include, but are not limited to, the Pelle/IRAK family and mutants thereof.

Accordingly, compounds of Formula (I) have utility in treating conditions associated with the modulation of kinase activity, and particularly the selective inhibition of IRAK-4 activity or the inhibition of IRAK and other Pelle family kinases. Such conditions include TLR/IL-1 family receptor associated diseases in which cytokine levels are modulated as a consequence of intracellular signaling. Moreover, the compounds of Formula (I) have advantageous selectivity for IRAK-4 activity, preferably from at least 20 fold to over 1,000 fold more selective.

As used herein, the terms "treating" or "treatment" encompass the treatment of a disease state in a mammal, particularly in a human, and include: (a) preventing or delaying the occurrence of the disease state in a mammal, in particular, when such mammal is predisposed to the disease state but has not yet been diagnosed as having it; (b) inhibiting the disease state, i.e., arresting its development; and/or (c) achieving a full or partial reduction of the symptoms or disease state, and/or alleviating, ameliorating, lessening, or curing the disease or disorder and/or its symptoms.

In view of their activity as selective inhibitors IRAK-4, compounds of Formula (I) are useful in treating TLR/IL-1 family receptor associated diseases, but not limited to, inflammatory diseases such as Crohn's disease, ulcerative colitis, asthma, graft versus host disease, allograft rejection, chronic obstructive pulmonary disease; autoimmune diseases such as Graves' disease, rheumatoid arthritis, systemic lupus erythematosis, psoriasis; auto-inflammatory diseases including CAPS, TRAPS, FMF, adult onset stills, systemic onset juvenile idiopathic arthritis, gout, gouty arthritis; metabolic diseases including type 2 diabetes, atherosclerosis, myocardial infarction; destructive bone disorders such as bone resorption disease, osteoarthritis, osteoporosis, multiple myeloma-related bone disorder; proliferative disorders such as acute myelogenous leukemia, chronic myelogenous leukemia; angiogenic disorders such as angiogenic disorders including solid tumors, ocular neovasculization, and infantile haemangiomas; infectious diseases such as sepsis, septic shock, and Shigellosis; neurodegenerative diseases such as Alzheimer's disease, Parkinson's disease, cerebral ischemias or neurodegenerative disease caused by traumatic injury, oncologic and viral diseases such as metastatic melanoma, Kaposi's sarcoma, multiple myeloma, and HIV infection and CMV retinitis, AIDS, respectively.

More particularly, the specific conditions or diseases that may be treated with the inventive compounds include, without limitation, pancreatitis (acute or chronic), asthma, allergies, adult respiratory distress syndrome, chronic obstructive pulmonary disease, glomerulonephritis, rheumatoid arthritis, systemic lupus erythematosis, scleroderma, chronic thyroiditis, Graves' disease, autoimmune gastritis, diabetes, autoimmune hemolytic anemia, autoimmune neutropenia, thrombocytopenia, atopic dermatitis, chronic active hepatitis, myasthenia gravis, multiple sclerosis, inflammatory bowel disease, ulcerative colitis, Crohn's disease, psoriasis, graft vs. host disease, inflammatory reaction induced by endotoxin, tuberculosis, atherosclerosis, muscle degeneration, cachexia, psoriatic arthritis, Reiter's syndrome, gout, traumatic arthritis, rubella arthritis, acute synovitis, pancreatic β-cell disease; diseases characterized by massive neutrophil infiltration; rheumatoid spondylitis, gouty arthritis and other arthritic conditions, cerebral malaria, chronic pulmonary inflammatory disease, silicosis, pulmonary sarcoidosis, bone resorption disease, allograft rejections, fever and myalgias due to infection, cachexia secondary to infection, keloid formation, scar tissue formation, ulcerative colitis, pyresis, influenza, osteoporosis, osteoarthritis, acute myelogenous leukemia, chronic myelogenous leukemia, metastatic melanoma, Kaposi's sarcoma, multiple myeloma, sepsis, septic shock, and Shigellosis; Alzheimer's disease, Parkinson's disease, cerebral ischemias or neurodegenerative disease caused by traumatic injury; angiogenic disorders including solid tumors, ocular neovasculization, and infantile haemangiomas; viral diseases including acute hepatitis infection (including hepatitis A, hepatitis B and hepatitis C), HIV infection and CMV retinitis, AIDS, ARC or malignancy, and herpes; stroke, myocardial ischemia, ischemia in stroke heart attacks, organ hypoxia, vascular hyperplasia, cardiac and renal reperfusion injury, thrombosis, cardiac hypertrophy, thrombin-induced platelet aggregation, endotoxemia and/or toxic shock syndrome, conditions associated with prostaglandin endoperoxidase syndase-2, and pemphigus vulgaris. Preferred methods of treatment are those wherein the condition is selected from Crohn's disease, ulcerative colitis, allograft rejection, rheumatoid arthritis, psoriasis, ankylosing spondylitis, psoriatic arthritis, and pemphigus vulgaris. Alternatively preferred methods of treatment are those wherein the condition is selected from ischemia reperfusion injury, including cerebral ischemia reperfusions injury arising from stroke and cardiac ischemia reperfusion injury arising from myocardial infarction. Another preferred method of treatment is one in which the condition is multiple myeloma.

In addition, the kinase inhibitors of the present invention inhibit the expression of inducible pro-inflammatory proteins such as prostaglandin endoperoxide synthase-2 (PGHS-2), also referred to as cyclooxygenase-2 (COX-2), IL-1, IL-6, IL-18, chemokines. Accordingly, additional IRAK-4-associated conditions include edema, analgesia, fever and pain, such as neuromuscular pain, headache, pain caused by cancer, dental pain and arthritis pain. The inventive compounds also may be used to treat veterinary viral infections, such as lentivirus infections, including, but not limited to equine infectious anemia virus; or retrovirus infections, including feline immunodeficiency virus, bovine immunodeficiency virus, and canine immunodeficiency virus.

When the terms "IRAK-4-associated condition" or "IRAK-4-associated disease or disorder" are used herein, each is intended to encompass all of the conditions identified above as if repeated at length, as well as any other condition that is affected by IRAK-4 kinase activity.

The present invention thus provides methods for treating such conditions, comprising administering to a subject in need thereof a therapeutically-effective amount of at least one compound of Formula (I) or a salt thereof. "Therapeutically effective amount" is intended to include an amount of a compound of the present invention that is effective when administered alone or in combination to inhibit IRAK-4 and/or treat diseases.

The methods of treating IRAK-4 kinase-associated conditions may comprise administering compounds of Formula (I) alone or in combination with each other and/or other suitable therapeutic agents useful in treating such conditions. Accordingly, "therapeutically effective amount" is also intended to include an amount of the combination of compounds claimed that is effective to inhibit IRAK-4 and/or treat diseases associated with IRAK-4.

Exemplary of such other therapeutic agents include corticosteroids, rolipram, calphostin, cytokine-suppressive anti-inflammatory drugs (CSAIDs), Interleukin-10, glucocorticoids, salicylates, nitric oxide, and other immunosuppressants; nuclear translocation inhibitors, such as deoxyspergualin (DSG); non-steroidal anti-inflammatory drugs (NSAIDs) such as ibuprofen, celecoxib and rofecoxib; steroids such as prednisone or dexamethasone; antiviral agents such as abacavir; antiproliferative agents such as methotrexate, leflunomide, FK506 (tacrolimus, PROGRAF®); anti-malarials such as hydroxychloroquine; cytotoxic drugs such as azathiprine and cyclophosphamide; TNF-α inhibitors such as tenidap, anti-TNF antibodies or soluble TNF receptor, and rapamycin (sirolimus or RAPAMUNE®) or derivatives thereof.

The above other therapeutic agents, when employed in combination with the compounds of the present invention, may be used, for example, in those amounts indicated in the *Physicians' Desk Reference* (PDR) or as otherwise determined by one of ordinary skill in the art. In the methods of the present invention, such other therapeutic agent(s) may be administered prior to, simultaneously with, or following the administration of the inventive compounds. The present invention also provides pharmaceutical compositions capable of treating IRAK-4 kinase-associated conditions, including TLR and IL-1 family receptor mediated diseases as described above.

The inventive compositions may contain other therapeutic agents as described above and may be formulated, for example, by employing conventional solid or liquid vehicles or diluents, as well as pharmaceutical additives of a type appropriate to the mode of desired administration (e.g., excipients, binders, preservatives, stabilizers, flavors, etc.) according to techniques such as those well known in the art of pharmaceutical formulation.

Accordingly, the present invention further includes compositions comprising one or more compounds of Formula (I) and a pharmaceutically acceptable carrier.

A "pharmaceutically acceptable carrier" refers to media generally accepted in the art for the delivery of biologically active agents to animals, in particular, mammals. Pharmaceutically acceptable carriers are formulated according to a number of factors well within the purview of those of ordinary skill in the art. These include without limitation the type and nature of the active agent being formulated; the subject to which the agent-containing composition is to be administered; the intended route of administration of the composition; and, the therapeutic indication being targeted. Pharmaceutically acceptable carriers include both aqueous and non-aqueous liquid media, as well as a variety of solid and semi-solid dosage forms. Such carriers can include a number of different ingredients and additives in addition to the active agent, such additional ingredients being included in the formulation for a variety of reasons, e.g., stabilization of the active agent, binders, etc., well known to those of ordinary skill in the art. Descriptions of suitable pharmaceutically acceptable carriers, and factors involved in their selection, are found in a variety of readily available sources such as, for example, *Remington's Pharmaceutical Sciences*, 17th Edition (1985), which is incorporated herein by reference in its entirety.

The compounds of Formula (I) may be administered by any means suitable for the condition to be treated, which may depend on the need for site-specific treatment or quantity of drug to be delivered. Topical administration is generally preferred for skin-related diseases, and systematic treatment preferred for cancerous or pre-cancerous conditions, although other modes of delivery are contemplated. For example, the compounds may be delivered orally, such as in the form of tablets, capsules, granules, powders, or liquid formulations including syrups; topically, such as in the form of solutions, suspensions, gels or ointments; sublingually; bucally; parenterally, such as by subcutaneous, intravenous, intramuscular or intrasternal injection or infusion techniques (e.g., as sterile injectable aq. or non-aq. solutions or suspensions); nasally such as by inhalation spray; topically, such as in the form of a cream or ointment; rectally such as in the form of suppositories; or liposomally. Dosage unit formulations containing non-toxic, pharmaceutically acceptable vehicles or diluents may be administered. The compounds may be administered in a form suitable for immediate release or extended release. Immediate release or extended release may be achieved with suitable pharmaceutical compositions or, particularly in the case of extended release, with devices such as subcutaneous implants or osmotic pumps.

Exemplary compositions for topical administration include a topical carrier such as PLASTIBASE® (mineral oil gelled with polyethylene).

Exemplary compositions for oral administration include suspensions which may contain, for example, microcrystalline cellulose for imparting bulk, alginic acid or sodium alginate as a suspending agent, methylcellulose as a viscosity enhancer, and sweeteners or flavoring agents such as those known in the art; and immediate release tablets which may contain, for example, microcrystalline cellulose, dicalcium phosphate, starch, magnesium stearate and/or lactose and/or other excipients, binders, extenders, disintegrants, diluents and lubricants such as those known in the art. The inventive compounds may also be orally delivered by sublingual and/or buccal administration, e.g., with molded, compressed, or freeze-dried tablets. Exemplary compositions may include fast-dissolving diluents such as mannitol, lactose, sucrose, and/or cyclodextrins. Also included in such formulations may be high molecular weight excipients such as celluloses (AVICEL®) or polyethylene glycols (PEG); an excipient to aid mucosal adhesion such as hydroxypropyl cellulose (HPC), hydroxypropyl methyl cellulose (HPMC), sodium carboxymethyl cellulose (SCMC), and/or maleic anhydride copolymer (e.g., GANTREZ®); and agents to control release such as polyacrylic copolymer (e.g., CARBOPOL 934®). Lubricants, glidants, flavors, coloring agents and stabilizers may also be added for ease of fabrication and use.

Exemplary compositions for nasal aerosol or inhalation administration include solutions which may contain, for example, benzyl alcohol or other suitable preservatives, absorption promoters to enhance absorption and/or bioavailability, and/or other solubilizing or dispersing agents such as those known in the art.

Exemplary compositions for parenteral administration include injectable solutions or suspensions which may contain, for example, suitable non-toxic, parenterally acceptable diluents or solvents, such as mannitol, 1,3-butanediol, water, Ringer's solution, an isotonic sodium chloride solution, or other suitable dispersing or wetting and suspending agents, including synthetic mono- or diglycerides, and fatty acids, including oleic acid.

Exemplary compositions for rectal administration include suppositories which may contain, for example, suitable non-irritating excipients, such as cocoa butter, synthetic glyceride esters or polyethylene glycols, which are solid at ordinary temperatures but liquefy and/or dissolve in the rectal cavity to release the drug.

The therapeutically-effective amount of a compound of the present invention may be determined by one of ordinary skill in the art, and includes exemplary dosage amounts for a mammal of from about 0.05 to 1000 mg/kg; 1-1000 mg/kg; 1-50 mg/kg; 5-250 mg/kg; 250-1000 mg/kg of body weight of active compound per day, which may be administered in a single dose or in the form of individual divided doses, such as from 1 to 4 times per day. It will be understood that the specific dose level and frequency of dosage for any particular subject may be varied and will depend upon a variety of factors, including the activity of the specific compound employed, the metabolic stability and length of action of that compound, the species, age, body weight, general health, sex and diet of the subject, the mode and time of administration, rate of excretion, drug combination, and severity of the particular condition. Preferred subjects for treatment include animals, most preferably mammalian species such as humans, and domestic animals such as dogs, cats, horses, and the like. Thus, when the term "patient" is used herein, this term is intended to include all subjects, most preferably mammalian species that are affected by mediation of IRAK-4 enzyme levels.

Biological Assays

IRAK4 Inhibition Assay

The assays were performed in U-bottom 384-well plates. The final assay volume was 30 μL prepared from 15 μL additions of enzyme and substrates (fluoresceinated peptide and ATP) and test compounds in assay buffer (20 mM HEPES pH 7.2, 10 mM $MgCl_2$. 0.015% Brij 35 and 4 mM DTT). The reaction was initiated by the combination of IRAK4 with substrates and test compounds. The reaction mixture was incubated at room temperature for 60 min. and terminated by adding 45 μL of 35 mM EDTA to each sample. The reaction mixture was analyzed on the Caliper LAB-CHIP® 3000 (Caliper, Hopkinton, Mass.) by electrophoretic separation of the fluorescent substrate and phosphorylated product. Inhibition data were calculated by comparison to no enzyme control reactions for 100% inhibition and vehicle-only reactions for 0% inhibition. The final concentrations of reagents in the assays are ATP, 500 μM; FL-IPTSPITI-TYFFFKKK peptide 1.5 μM; IRAK4, 0.6 nM; and DMSO, 1.6%.

PBMC TLR2 Induced IL-6 Assay

Peripheral blood mononuclear cells (PBMCs) were isolated from human blood containing the anti-coagulant EDTA (2.5 mM) by centrifugation over a FICOLL® gradient. PBMCs (250000 cells/well) were cultured in assay media (RPMI with 10% heat inactivated FCS) with compounds for 30 minutes at 37° C. in a 5% $CO_2$ incubator. Following pretreatment with compounds, cells were stimulated for 5 hours with 10 μg/ml lipoteichoic acid (Invivogen, San Diego, Calif.), a TLR2 agonist. At the end of the culture, plates were centrifuged at 1800 rpm for 10 minutes to pellet the cells. Supernatants were harvested and analyzed for IL-6 levels by ELISA (BD Biosciences, San Jose, Calif.).

The table below lists the IRAK4 $IC_{50}$ values and Cell $IC_{50}$ or $EC_{50}$ values for the following examples of this invention measured in the IRAK4 Inhibition Assay and the PBMC TLR2 Induced IL-6 assay. The compounds of the present invention, as exemplified by the following examples, showed IRAK $IC_{50}$ inhibition values of less than 0.06 μM.

| IRAK4 Inhibition Data | | |
|---|---|---|
| Example No. | IRAK4 $IC_{50}$ (μM) | Cell $IC_{50}$ (or *$EC_{50}$) (μM) |
| 1 | 0.0539 | 0.550 |
| 2 | 0.0020 | 0.453 |
| 3 | 0.0148 | 0.789 |
| 4 | 0.0103 | 0.454 |
| 5 | 0.0056 | 0.588 |
| 6 | 0.0055 | 0.648 |
| 7 | 0.0104 | 0.800 |
| 8 | 0.0307 | 0.433 |
| 9 | 0.0074 | 0.116 |
| 10 | 0.0142 | 0.593 |
| 11 | 0.0111 | 0.320 |
| 12 | 0.0019 | 0.050 |
| 13 | 0.0021 | 0.420 |
| 14 | 0.0018 | 0.043 |
| 15 | 0.0052 | 0.245 |
| 16 | 0.0063 | 0.212 |
| 17 | 0.0096 | 0.382 |
| 18 | 0.0034 | 0.137 |
| 19 | 0.0048 | 0.378 |
| 20 | 0.0117 | 0.647 |
| 21 | 0.0133 | 0.331 |
| 22 | 0.0053 | 0.342 |
| 23 | 0.0233 | 0.032 |
| 24 | 0.0110 | 0.312 |
| 25 | 0.0099 | 0.372 |
| 26 | 0.0048 | 0.139 |
| 27 | 0.0060 | 0.133 |
| 28 | 0.0015 | 0.270 |
| 29 | 0.0012 | 0.111 |
| 30 | 0.0094 | 0.163* |
| 31 | 0.0046 | 0.170* |
| 32 | 0.0125 | 0.199* |
| 33 | 0.0100 | 0.149* |
| 34 | 0.0061 | 0.122* |
| 35 | 0.0126 | 0.350* |
| 36 | 0.0033 | 0.049* |
| 37 | 0.0040 | 0.095* |
| 38 | 0.0045 | 0.453* |
| 39 | 0.0038 | 0.100* |
| 40 | 0.0064 | 0.161* |
| 41 | 0.0199 | 0.160* |
| 42 | 0.0147 | 0.329* |
| 43 | 0.0107 | 0.169* |
| 44 | 0.0078 | 0.393* |
| 45 | 0.0075 | 0.712 |
| 46 | 0.0169 | 0.206* |
| 47 | 0.0019 | 0.069 |
| 48 | 0.0093 | 0.369 |
| 49 | 0.0031 | 0.164 |
| 50 | 0.0094 | 0.085 |
| 51 | 0.0046 | 0.099 |
| 52 | 0.0069 | 0.074 |
| 53 | 0.0081 | 0.517* |
| 54 | 0.0059 | 0.126 |
| 55 | 0.0050 | 0.027 |
| 56 | 0.0050 | 0.041 |
| 57 | 0.0018 | 0.068* |
| 58 | 0.0104 | 0.191 |
| 59 | 0.0074 | 0.060 |
| 60 | 0.0067 | 0.052 |
| 61 | 0.0084 | 0.184 |
| 62 | 0.0017 | 0.052* |
| 63 | 0.0038 | 0.092* |
| 64 | 0.0031 | 0.448 |
| 65 | 0.0029 | 0.156* |
| 66 | 0.0038 | 0.063* |
| 67 | 0.0072 | 0.457* |
| 68 | 0.0027 | 0.165 |
| 69 | 0.0018 | 0.619 |
| 70 | 0.0032 | 0.091* |
| 71 | 0.0028 | 0.394* |
| 72 | 0.0104 | 0.246* |
| 73 | 0.0015 | 0.132* |
| 74 | 0.0027 | 0.084* |
| 75 | 0.0014 | 0.054* |
| 76 | 0.0064 | 0.107* |
| 77 | 0.0078 | 0.216* |
| 78 | 0.0037 | 0.064* |
| 79 | 0.0030 | 0.494* |

IRAK4 Inhibition Data

| Example No. | IRAK4 IC$_{50}$ (µM) | Cell IC$_{50}$ (or *EC$_{50}$) (µM) |
|---|---|---|
| 80 | 0.0070 | 0.335* |
| 81 | 0.0071 | 0.096* |
| 82 | 0.0030 | 0.105* |
| 83 | 0.0073 | 0.771* |
| 84 | 0.0015 | 0.138* |
| 85 | 0.0036 | 0.062* |
| 86 | 0.0048 | 0.349* |
| 87 | 0.0035 | 0.197* |
| 88 | 0.0054 | 0.266* |
| 89 | 0.0145 | 0.491* |
| 90 | 0.0035 | 0.243* |
| 91 | 0.0043 | 0.178* |
| 92 | 0.0127 | 0.269* |
| 93 | 0.0175 | 0.394* |
| 94 | 0.0121 | 0.391* |
| 95 | 0.0071 | 0.501* |
| 96 | 0.0112 | 1.550 |
| 97 | 0.0053 | 0.418 |
| 98 | 0.0075 | 0.690 |
| 99 | 0.0042 | 0.475 |
| 100 | 0.0174 | 0.308* |
| 101 | 0.0056 | 0.380* |
| 102 | 0.0041 | 0.071* |
| 103 | 0.0053 | 0.195* |
| 104 | 0.0086 | 0.199* |
| 105 | 0.0055 | 0.336* |
| 106 | 0.0168 | 0.433* |
| 107 | 0.0091 | 0.757* |
| 108 | 0.0087 | 0.368* |
| 109 | 0.0137 | 0.350* |
| 110 | 0.0157 | 0.705* |
| 111 | 0.0118 | 0.653* |
| 112 | 0.0110 | 0.087* |
| 113 | 0.0170 | 0.558* |
| 114 | 0.0023 | 0.056* |
| 115 | 0.0045 | 0.065* |
| 116 | 0.0028 | 0.130* |
| 117 | 0.0038 | 0.202* |
| 118 | 0.0046 | 0.172* |
| 119 | 0.0105 | 0.736* |
| 120 | 0.0126 | 0.379* |
| 121 | 0.0066 | 0.049* |
| 122 | 0.0033 | 0.056* |
| 123 | 0.0035 | 0.045* |
| 124 | 0.0057 | 0.098* |
| 125 | 0.0036 | 0.085* |
| 126 | 0.0029 | 0.083* |
| 127 | 0.0153 | 0.254* |
| 128 | 0.0046 | 0.224* |
| 129 | 0.0159 | 0.398* |
| 130 | 0.0040 | 0.089* |
| 131 | 0.0106 | 0.137* |
| 132 | 0.0130 | 0.862* |
| 133 | 0.0032 | 0.085* |
| 134 | 0.0052 | 0.203* |
| 135 | 0.0060 | 0.129* |
| 136 | 0.0033 | 0.063* |
| 137 | 0.0041 | 0.072* |
| 138 | 0.0035 | 0.108* |
| 139 | 0.0060 | 0.114* |
| 140 | 0.0073 | 0.241* |
| 141 | 0.0099 | 0.412* |
| 142 | 0.0012 | 0.093* |
| 143 | 0.0029 | 0.126* |
| 144 | 0.0078 | 0.393* |
| 145 | 0.0043 | 0.275* |
| 146 | 0.0085 | 0.509* |
| 147 | 0.0124 | 0.439* |
| 148 | 0.0034 | 0.111* |
| 149 | 0.0030 | 0.193* |
| 150 | 0.0014 | 0.062* |
| 151 | 0.0033 | 0.187* |
| 152 | 0.0053 | 0.260* |
| 153 | 0.0056 | 0.439* |
| 154 | 0.0052 | 0.529* |
| 155 | 0.0043 | 0.309* |
| 156 | 0.0086 | 0.124* |
| 157 | 0.0020 | 0.071* |
| 158 | 0.0023 | 0.102* |
| 159 | 0.0058 | 0.130* |
| 160 | 0.0098 | 0.846* |
| 161 | 0.0155 | 0.303* |
| 162 | 0.0026 | 0.330* |
| 163 | 0.0102 | 0.459* |
| 164 | 0.0080 | 0.174* |
| 165 | 0.0113 | 0.279* |
| 166 | 0.0082 | 0.202* |
| 167 | 0.0130 | 0.638* |
| 168 | 0.0061 | 0.122* |

Methods of Preparation

The compounds of the present invention can be prepared in a number of ways well known to one skilled in the art of organic synthesis. The compounds of the present invention can be synthesized using the methods described below, together with synthetic methods known in the art of synthetic organic chemistry, or variations thereon as appreciated by those skilled in the art. Preferred methods include, but are not limited to, those described below. All references cited herein are hereby incorporated in their entirety herein by reference.

The reactions and techniques described in this section are performed in solvents appropriate to the reagents and materials employed and are suitable for the transformations being effected. Also, in the description of the synthetic methods described below, it is to be understood that all proposed reaction conditions, including choice of solvent, reaction atmosphere, reaction temperature, duration of the experiment and work up procedures, are chosen to be the conditions standard for that reaction, which should be readily recognized by one skilled in the art. It is understood by one skilled in the art of organic synthesis that the functionality present on various portions of the molecule must be compatible with the reagents and reactions proposed. Such restrictions to the substituents that are compatible with the reaction conditions will be readily apparent to one skilled in the art and alternate methods must then be used. This will sometimes require a judgment to modify the order of the synthetic steps or to select one particular process scheme over another in order to obtain a desired compound of the invention. It will also be recognized that another major consideration in the planning of any synthetic route in this field is the judicious choice of the protecting group used for protection of the reactive functional groups present in the compounds described in this invention. An authoritative account describing the many alternatives to the trained practitioner is Greene et al. (*Protective Groups in Organic Synthesis*, Third Edition, Wiley and Sons (1999)).

Compounds of the general Formula (I) can be prepared according to the method outlined in Scheme 1. Hydrolysis of ester (1) to the acid 1.1 followed by reaction with an amine using standard amide bond forming conditions can afford the dichloro amide 1.2. Selective displacement of the C4 chloride by reacting with an amine can afford the mono-chloro product 1.3. Reaction of 1.3 with an appropriate nucleophile, such as an amine, in the presence of a catalyst, such as palladium, can afford compounds of the general formula I.

Scheme 1

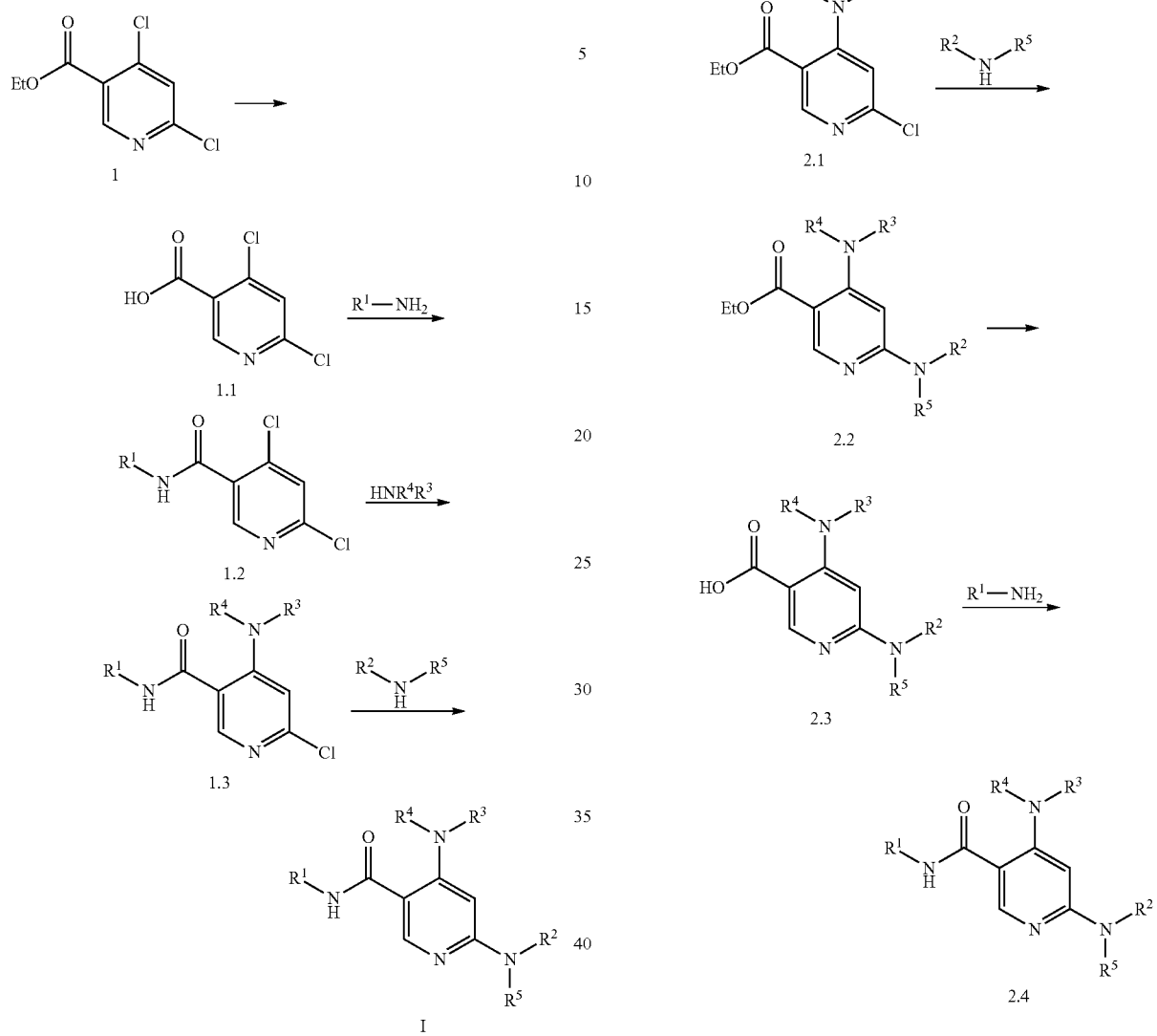

Alternatively, the order of reactions can be modified to change the overall synthesis in order to allow for variations at different positions of the molecule at different stages of the preparation. For example, in Scheme 2, the chloride 1 may be reacted with an amine first to form the monochlorinated ester 2.1. Subsequent reaction with another amine, either in the presence of a metal catalyst or thermally in the presence of acid, may form the disubstituted intermediate 2.2. Hydrolysis of the ester to acid 2.3 followed by amide bond formation can afford the final analog 2.4.

An additional variation on the order of substitution is shown in Scheme 3. First, reacting the dichloride with an amine may afford compound 3.1. Hydrolysis of the ester with a base, such as NaOH or KOH, may afford the acid 3.2. This acid may be reacted with an amine using standard amide bond forming reaction conditions, such as HOBt, EDC and DIPEA, in an appropriate solvent to form the amide 3.3, similar to amide 1.3 in Scheme 1. Subsequent aryl amine or heteroaryl amine coupling in the presence of a metal catalyst such as palladium, may afford the final compound 3.4.

Scheme 2

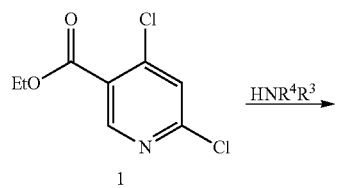

Scheme 3

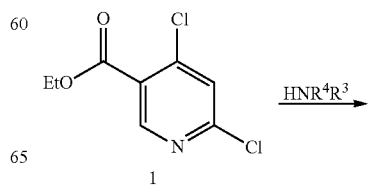

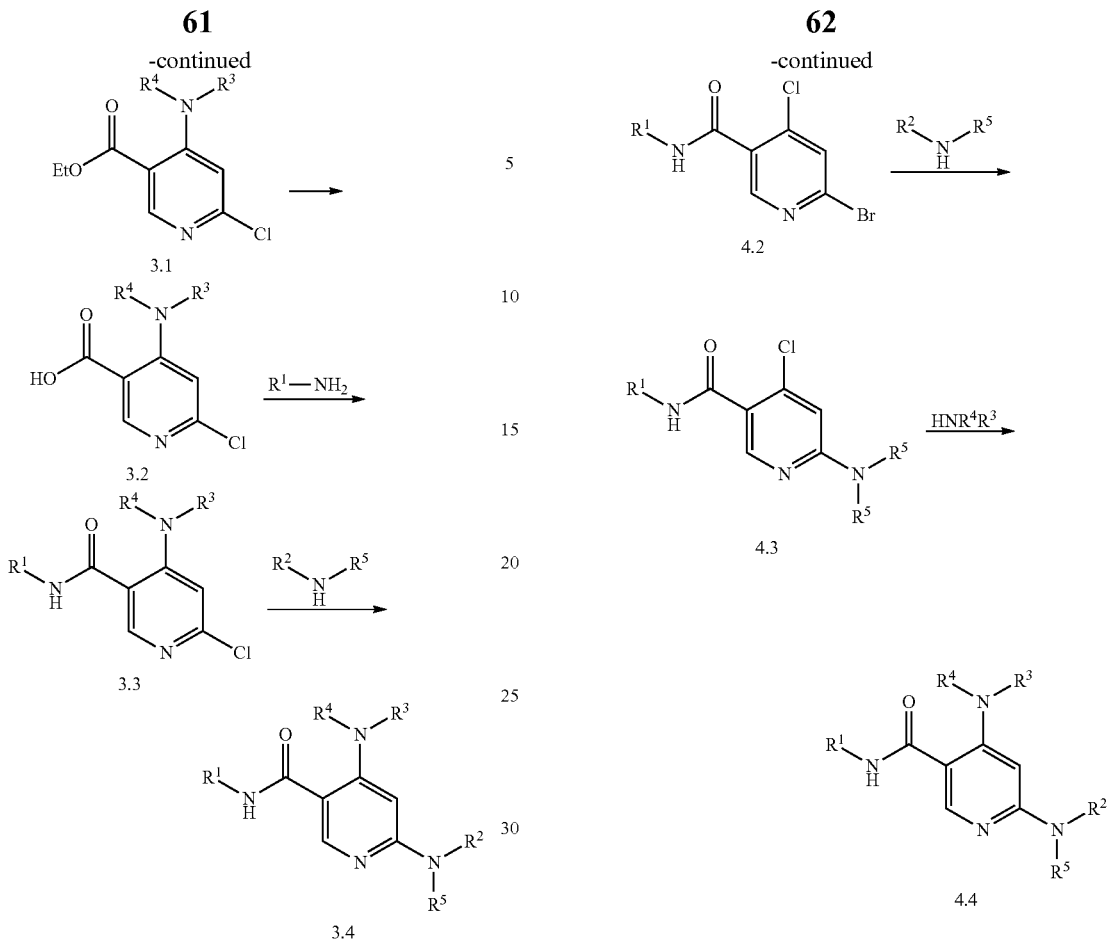

Another variation involves the synthesis of a differentially halogenated pyridine core to allow for variation of the HNR³R⁴ substituent at the last stage of the synthesis. 6-Bromo-4-choronicotinic acid may be reacted with a halogenating reagent, such as oxalyl chloride, to afford the acid chloride 4.1. This may be further reacted with an amine in the presence of a base, such as DIPEA or TEA, in an appropriate solvent, such as DCM, to afford the amide 4.2. Amide 4.2 may be reacted with another amine in the presence of a base, such as Cs₂CO₃ or K₂CO₃ and a metal catalyst, such as Pd, in a solvent to afford compound 4.3. Finally, compound 4.3 may be reacted with an amine in the presence of a base at elevated temperature to afford compound 4.4.

It should be also noted, and obvious to those skilled in the art, that synthetic manipulations of the incorporated $R^1$, $R^2$, $R^3$, $R^4$, and $R^5$ groups is possible. An illustrative example is shown in Scheme 5. The butyl ester incorporated in compound 5.1 may be converted to the acid 5.2 upon treatment with an acid, such as TFA, in an appropriate solvent, such as DCM. Further reaction of 5.2 with an amine in the presence of amide bond forming reagents may afford compounds such as 5.3. It should be obvious to those skilled in the art that other functionalities than a carboxylate may be present for subsequent functionalization. For example, nitro groups can be converted readily to amines and subsequently functionalized, and halogens can be readily converted to aryl amines or nitriles.

Scheme 4

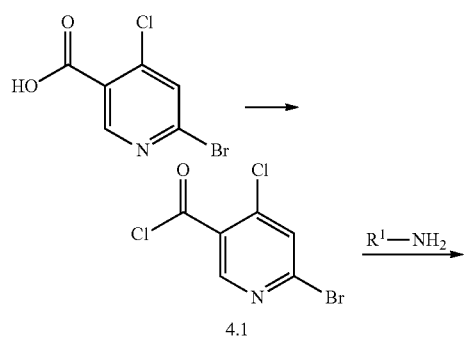

Scheme 5

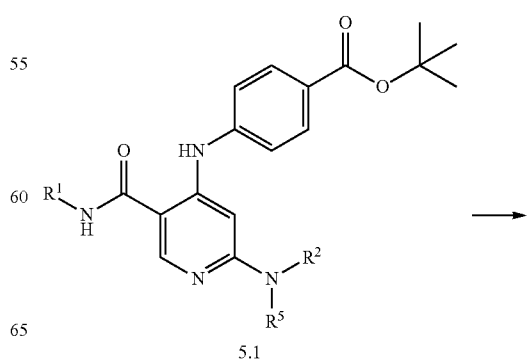

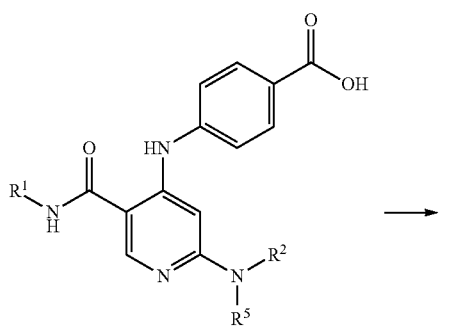

5.2

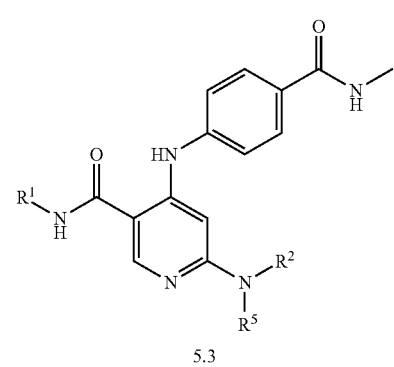

5.3

Another variation on the chemistry in Scheme 5 is outlined in Scheme 6. Alkyl groups may be functionalized, as in the alcohol 6.1, then subsequently transformed via standard chemical manipulations to compounds such as the fluoro analog 6.2. Subsequent conversion of the ester to the acid then amide and amine coupling at the remaining pyridine chloride may afford analogs such as 6.3. It should be obvious to one skilled in the art that these transformations are not limited to the example shown and can be applied to a variety of chemical substrates to afford the desired compounds.

Scheme 6

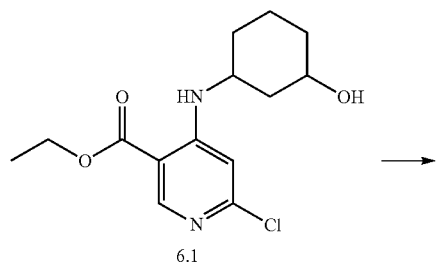

6.1

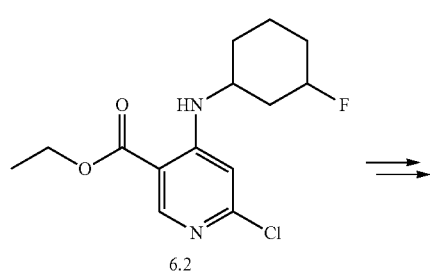

6.2

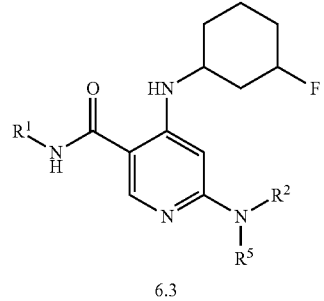

6.3

Additionally, variations to the $R^1$ group can be made via functionalization after incorporating onto the pyridine scaffold. For example, in Scheme 7, an appropriately protected amine is coupled to the pyridine acid via standard amide bond forming conditions to form 7.2. Compound 7.2 may be deprotected to reveal the amine 7.3 which can be reacted with a variety of reagents (acids, acid chlorides, sulfonyl chlorides, isocyanates, aldehydes, etc.) to form compounds of the general formula 7.4.

Scheme 7

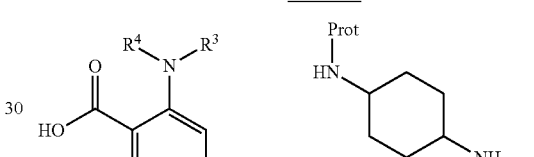

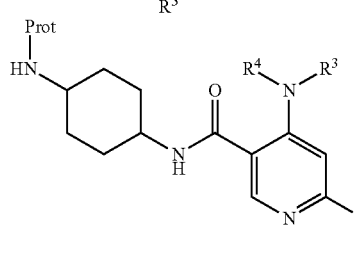

7.2

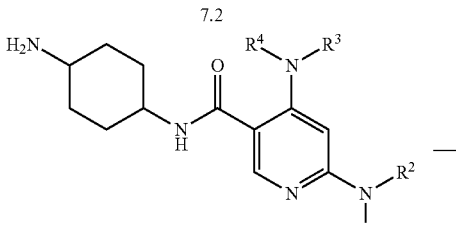

7.3

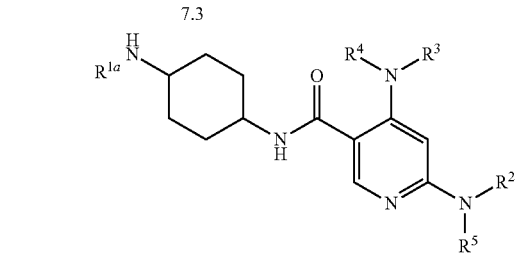

7.4

Similarly, a substituted amino ester may be coupled to the pyridine acid core to furnish the ester 8.1 which may be saponified to the acid 8.2. Subsequent reaction with amines under amide bond forming reaction conditions may form the compounds 8.3.

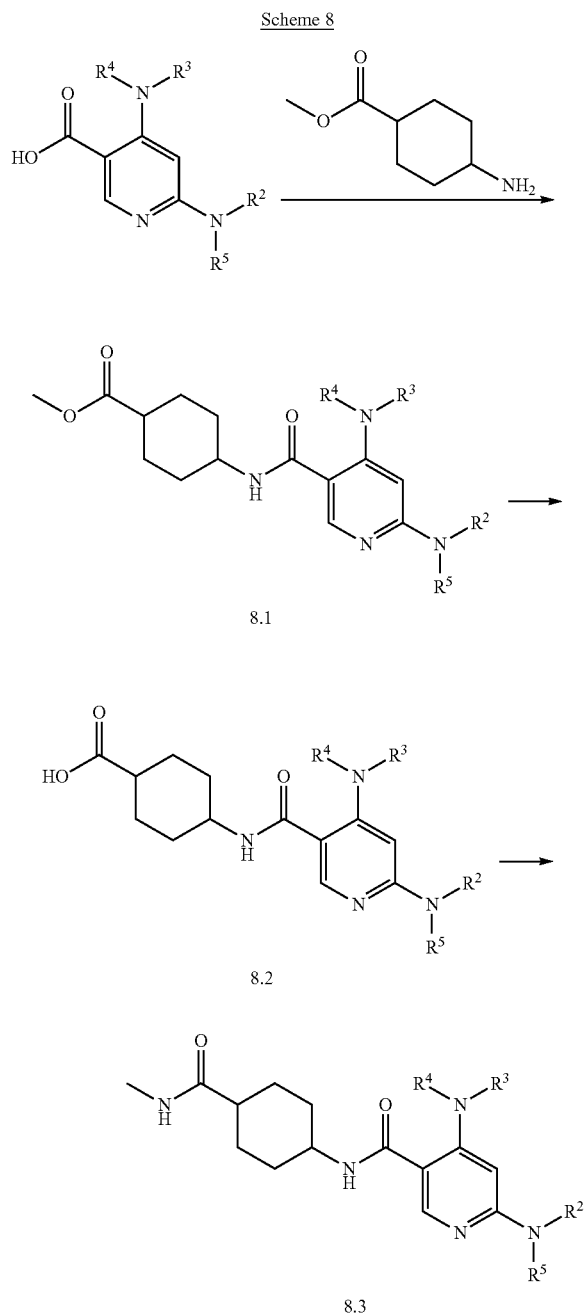

Substitution at either $R^2$ or $R^5$ may be accomplished via the methods outlined in Scheme 9. Preparation of an appropriately functionalized precursor, such as compound 9.1, and reaction with a variety of reagents, such as amines, aryl cross coupling partners, and cyanide may form compounds of the formula 9.2. For example, compound 9.3 may be converted to compound 9.4 via reaction with an amine at elevated temperature.

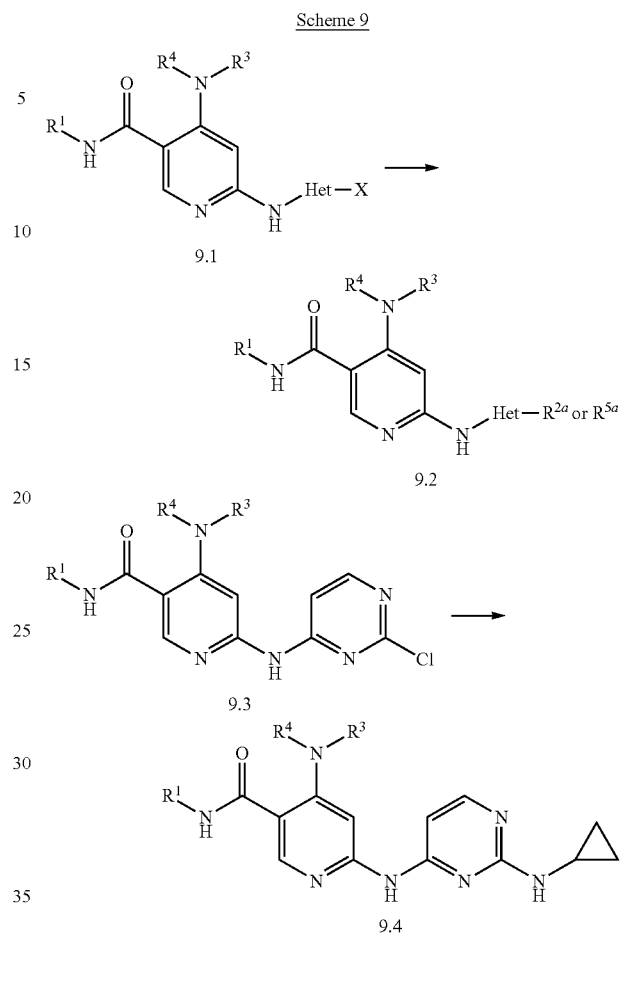

EXAMPLES

Preparation of compounds of Formula (I), and intermediates used in the preparation of compounds of Formula (I), can be prepared using procedures shown in the following Examples and related procedures. The methods and conditions used in these examples, and the actual compounds prepared in these Examples, are not meant to be limiting, but are meant to demonstrate how the compounds of Formula (I) can be prepared. Starting materials and reagents used in these examples, when not prepared by a procedure described herein, are generally either commercially available, or are reported in the chemical literature, or may be prepared by using procedures described in the chemical literature.

In the Examples given, the phrase "dried and concentrated" generally refers to drying of a solution in an organic solvent over either sodium sulfate or magnesium sulfate, followed by filtration and removal of the solvent from the filtrate (generally under reduced pressure and at a temperature suitable to the stability of the material being prepared). Column chromatography was performed with pre-packed silica gel cartridges using an Isco medium pressure chromatography apparatus (Teledyne Corporation), eluting with the solvent or solvent mixture indicated. Preparative high performance liquid chromatography (HPLC) was performed using a reverse phase column (Waters SunFire C18, Waters XBridge C18, PHENOMENEX® Axia $C_{18}$, YMC S5 ODS or the like) of a size appropriate to the quantity of material being separated, generally eluting with a gradient of increasing concentration of methanol or acetonitrile in water, also containing 0.05% or 0.1% trifluoroacetic acid or 10 mM ammonium acetate, at a rate of elution suitable to the column size and separation to be achieved. Chemical names were determined using ChemDraw Ultra, version 9.0.5 (CambridgeSoft). The following abbreviations are used:

ACN=acetonitrile
brine=saturated aqueous sodium chloride
DAST=(diethylamino)sulfur trifluoride
DCM=dichloromethane
DEA=diethylamine
DIPEA=N,N-diisopropylethylamine
DMF=N,N-dimethylformamide
DMSO=dimethyl sulfoxide
EDC=N-(3-dimethylaminopropyl)-N'-ethylcarbodiimide hydrochloride
EtOAc=ethyl acetate
HATU=O-(7-azabenzotriazol-1-yl)-N,N,N',N'-tetramethyluronium hexafluorophosphate
HOBT=1-hydroxybenzotriazole hydrate
LCMS=Liquid Chromatography-Mass Spectroscopy
MeOH=methanol
MTBE=methyl t-butyl ether
$NaHCO_3$ (aq)=saturated aqueous sodium bicarbonate
n-BuLi=n-butyl lithium
$NH_4OAc$=ammonium acetate
$Pd_2(dba)_3$=tris-(dibenzylideneacetone)dipalladium
rt=ambient room temperature (generally about 20-25° C.)
TBAF=tetrabutylammonium fluoride
TEA=triethylamine
TFA=trifluoroacetic acid
THF=tetrahydrofuran HPLC Conditions:

A: XBridge Phenyl (150×4.6 mm), 3.5µ; Solvent A=5% ACN: 95% $H_2O$: 0.05% TFA pH=2.5; Solvent B=95% ACN: 5% $H_2O$: 0.05% TFA pH=2.5; gradient 0-100% B over 15 min; Flow rate: 1.0 µl/min.

B: SunFire C18 (150×4.6 mm), 3.5µ; Solvent A=5% ACN: 95% $H_2O$: 0.05% TFA pH=2.5; Solvent B=95% ACN: 5% $H_2O$: 0.05% TFA pH=2.5; gradient 0-100% B over 30 min.

C: Eclipse XDB C18 (150×4.6 mm) 5µ; Solvent A=20 mM $NH_4OAc$ in water; Solvent B=ACN; gradient 0-100% B over 20 min; Flow rate=1.0 mL/min.

D: ZORBAX® SB C18, 4.6×50 mm, 5 µm; Solvent A=10% MeOH: 90% $H_2O$: 0.1% TFA; Solvent B=90% MeOH: 10% $H_2O$: 0.1% TFA; gradient 0-100% B over 2 min.

E: SunFire C18 (150×4.6 mm), 3.5µ; Solvent A=5% ACN: 95% $H_2O$: 0.05% TFA pH=2.5; Solvent B=95% ACN: 5% $H_2O$: 0.05% TFA pH=2.5; gradient 0-100% B over 15 min.

F: Ascentis Express C18 (4.6×50) mm, 2.7 µm; Solvent A=5% ACN: 95% water: 10 mM $NH_4OAc$; Solvent B=95% ACN: 5% water: 10 mM $NH_4OAc$.gradient 0-100% B over 4 min; Flow rate=4 mL/min. Column temp=45° C.

G: BEH C18 (2.1×50) mm, 1.7 µm; Solvent A=5% ACN: 95% water: 10 mM $NH_4OAc$; Solvent B=95% ACN: 5% water: 10 mM $NH_4OAc$.gradient 0-100% B over 4 min; Flow rate=1.1 mL/min. Column temp=45° C.

H: CHIRALCEL@—OJ-H (250×4.6×5.0p), $CO_2$-3.og (70%), co-solvent-30% (0.5% DEA in methanol).

I: Chiral-OD-H (250×4.6) mm 5µ Mobile Phase A: 0.2 DEA in n-hexane (85); Mobile Phase B: Ethanol(15); Flow: 1.0 ml/min.

J: XBridge Phenyl (4.6×150 mm) 3.5p Mobile Phase A: 10 mM $NH_4HCO_3$ pH 9.5 adjusted using dil. $NH_3$; Mobile Phase B: Methanol; Flow rate: 1 ml/min.

K: SunFire C18 (4.6×150) mm, 3.5 µp Mobile Phase A: 0.05% TFA in water:acetonitrile: 95:05; Mobile Phase B: Acetonitrile: 0.05% TFA in water: 95:05 flow: 1 m\min time B % gradient 0-100% B over 18 min.

L: XBridge (150×4.6 mm) 3.5µ SC/749 Buffer: 0.05% TFA in Water pH 2.5 Mobile Phase A: Buffer: Acetonitrile (95:5) Mobile Phase B: Acetonitrile:Buffer (95:5); Flow: 1.0 ml\min % B 100 time (min) 15.

M: SunFire C18 (150×4.6 mm) 3.5µ, Buffer: 0.05% TFA in water pH adjusted with 2.5 using Dil. Ammonia Solvent A: Buffer:Acetonitrile (95:5), Solvent B: Acetonitrile:Buffer (95:5).

N: CHIRALPAK®-1A (250×4.6 mm) 5 $CO_2$-3.og (70%), co-solvent-30% Mobile Phase A: 0.5% DEA in methanol.

O: Waters Acquity UPLC BEH C18, 2.1×50 mm: Mobile Phase A: 5:95 acetonitrile:water with 0.05% TFA; Mobile Phase B: 95:5 acetonitrile:water with 0.05% TFA; Gradient: 0-100% B over 3 minutes, then a 0.75-minute hold at 100% B; Flow: 1.11 mL/min.

Example 1

6-((5-Cyano-2-pyridinyl)amino)-4-(((1S,2S)-2,3-dihydroxy-1-phenylpropyl)amino)-N-methylnicotinamide

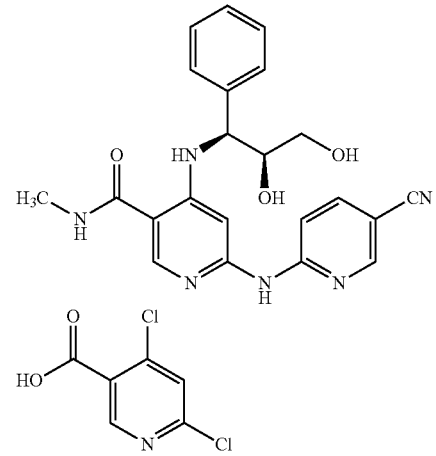

(1)

Step 1: Synthesis of 4,6-dichloronicotinic Acid

Ethyl 4,6-dichloronicotinate in ethanol (20 mL) and water (10 mL) was stirred at ambient temperature. Lithium hydroxide was added to the reaction mixture and stirred at room temperature for 4 h. The solvent was concentrated under reduced pressure, diluted with EtOAc and added water. The aqueous layer was collected and acidified to pH 3-4 using citric acid. The mixture was allowed to stir for 10 min in an ice bath the precipitated product was filtered and dried under vacuum to furnish compound.

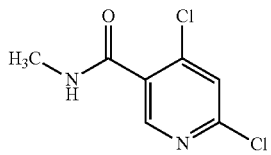

Step 2: Synthesis of 4,6-dichloro-N-methylnicotinamide

To a stirred solution of 4,6-dichloronicotinic acid (2) (10 g, 1 equiv.) in DCM (100 mL), DMF (catalytic amt.) was added at 0° C. Oxalyl chloride (14 mL, 3 equiv.) was added to the reaction mixture. The reaction mixture was allowed to warm to ambient temperature and stirred for 30 min and was then heated at reflux for 2 h. The reaction mixture was concentrated to remove excess of oxalyl chloride and redissolved in DCM (50 mL) and cooled to −20° C. Methyl amine was added in portions to the reaction mixture and stirred at room temperature for 3 h. The reaction was quenched with water followed by NaHCO₃ solution. The layers were separated and the organic layer was dried over anhydrous sodium sulfate, filtered and concentrated to obtain the desired compound, 6-chloro-4-(isopropylamino)nicotinamide. LC/MS: ZORBAX® SB C18, 4.6×50 mm, 5 □μm; Solvent A=10% MeOH: 90% H₂O: 0.1% TFA; Solvent B=90% MeOH: 10% H₂O: 0.1% TFA; gradient 0-100% B over 2 min (3 min run time); retention time: 0.874 min; LCMS (ES-API), m/z 205 (M+H).

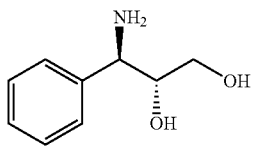 [SMILES: N[C@H](c1ccccc1)[C@@H](O)CO]

Step 3: Synthesis of ((2S,3S)-3-phenyloxiran-2-yl)methanol (−)-DIPT (0.524 g, 0.075 equiv.) was dissolved in DCM (250 mL) and cooled to −30° C. Molecular sieves (1.6 g), titanium (IV) isopropoxide (0.437 mL, 0.05 equiv.) and t-butyl hydroperoxide (TBHP in decane) (5.78 mL, 2 equiv.) were added sequentially. The mixture was allowed to stir for 1 h. (E)-3-phenylprop-2-en-1-ol (4 g, 1 equiv.) in DCM (10 mL) was added to the reaction mixture and stirred for 3 h at −30° C. The reaction was quenched with 8 mL of 10% aqueous NaOH solution followed by brine solution. The reaction mixture was allowed to warm to 10° C. and stirred for 10 min at 10° C. Anhydrous sodium sulfate (2 g) and CELITE® (2 g) were added to the reaction mixture and stirred for another 50 min. The reaction mixture was then filtered through a pad of CELITE®. The residue was washed with ether and the filtrate was concentrated. The crude product was purified by flash column chromatography using ethyl acetate: pet.ether as eluent to afford ((2S,3S)-3-phenyloxiran-2-yl)methanol. ¹H NMR: 400 MHz, CDCl₃: δ 1.19-1.29 (m, 1H), 4.33 (t, J=4.80 Hz, 2H), 6.34-6.41 (m, 1H), 6.61-6.65 (m, 1H), 7.23-7.27 (m, 1H), 7.30-7.38 (m, 4H).

Step 4: Synthesis of (2R,3R)-3-amino-3-phenylpropane-1,2-diol

To a solution of ((2S,3S)-3-phenyloxiran-2-yl)methanol (0.5 g, 1 equiv.) in 2-propanol (5 mL) was added aqueous NH₄OH (10 mL). The reaction mixture was heated at 84° C. for 12 h. The reaction mixture was concentrated and the crude material was azeotroped with toluene (3×30 mL) to afford (2R,3R)-3-amino-3-phenylpropane-1,2-diol. The compound was taken to next step without purification.

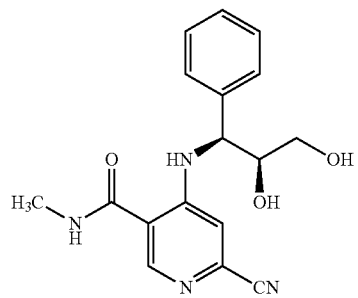 [SMILES: CNC(=O)c1cnc(C#N)cc1N[C@@H](c1ccccc1)[C@H](O)CO]

Step 5

A mixture of 4,6-dichloro-N-methylnicotinamide (410 mg, 2 mmol), (2S,3S)-3-amino-3-phenylpropane-1,2-diol (502 mg, 3 mmol) and DIPEA (419 μL, 2.4 mmol) in DMA (2 mL) was stirred at 110° C. for 6 h. The vessel was allowed to cool to room temperature and the reaction mixture was separated between ethyl acetate and pH 4 solution. The organic portion was washed with pH 4 solution (2×) and the combined aqueous portions were extracted with ethyl acetate (2×). The combined organics were washed with 10% lithium chloride solution and brine, dried over sodium sulfate and concentrated under reduced pressure to afford 6-chloro-4-((1S,2S)-2,3-dihydroxy-1-phenylpropylamino)-N-methylnicotinamide which was used without further purification. ¹H NMR (400 MHz, MeOD) δ ppm 8.23 (1H, s), 7.40-7.47 (2H, m), 7.33-7.40 (2H, m), 7.26-7.33 (1H, m), 6.46 (1H, s), 4.72 (1H, d, J=4.18 Hz), 3.89-4.14 (1H, m), 3.44 (2H, d, J=5.72 Hz), 2.92 (3H, s).

Step 6

A mixture of 6-chloro-4-((1S,2S)-2,3-dihydroxy-1-phenylpropylamino)-N-methylnicotinamide (20 mg, 0.060 mmol), CuI (5.67 mg, 0.030 mmol), Cs₂CO₃ (116 mg, 0.357 mmol) and 6-aminonicotinonitrile (21.3 mg, 0.18 mmol) in a 1 dram vial with NMP (500 μL) was sparged with argon for 5 minutes and Xantphos (6.89 mg, 0.012 mmol) and bis(dibenzylideneactone)palladium (7 mg, 0.012 mmol) were added then argon was filled into the vial. The vessel was heated at 140° C. for 3 hour after which LCMS indicated reaction completion. The contents were diluted in methanol and the desired material was isolated via preparatory HPLC (2.1 mg, 8% yield). LCMS: M+H=419.2; HPLC RT 5.65 min, Condition A; ¹H NMR (500 MHz, MeOD) δ ppm 8.56 (s, 1H), 8.14 (s, 1H), 7.99 (s, 1H), 7.36 (d, J=7.21 Hz, 2H), 7.24-7.32 (m, 2H), 7.11-7.24 (m, 1H), 6.96 (d, J=8.60 Hz, 1H), 6.07 (s, 1H), 4.73-4.85 (m, 1H), 3.81-4.07 (m, 1H), 3.26-3.43 (m, 2H), 2.85 (s, 3H).

Example 2

6-((5-Cyano-2-pyridinyl)amino)-N-((2R)-2-fluoro-3-hydroxy-3-methylbutyl)-4-(isopropylamino)nicotinamide

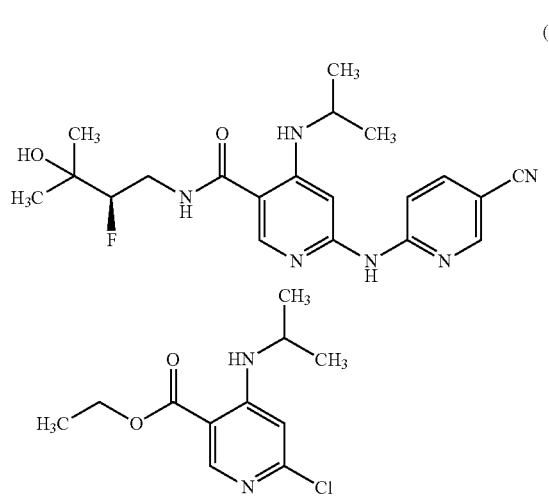

(2)

Step 1: Synthesis of ethyl 6-chloro-4-(isopropylamino)nicotinate

To a solution of ethyl 4,6-dichloronicotinate (1 g, 1 equiv.) in DMA (5 mL) was added DIPEA (3.97 mL, 5 equiv.) and propan-2-amine (0.5 g, 2 equiv.). The mixture was heated at 50° C. for 12 h. The reaction mixture was concentrated under reduced pressure to remove excess solvent. The residue was dissolved in ethyl acetate and washed water followed by brine. The organic layer was collected, dried over $Na_2SO_4$, filtered and concentrated to get the crude product. The product was purified by flash chromatography through silica gel (EtOAC: pet ether as eluent) to afford ethyl 6-chloro-4-(isopropylamino)nicotinate (0.4 g, 36% yield). LC/MS: Acquity BEH C18 2.1×50 mm, 1.8μ; Solvent A=0.1% TFA in water; Solvent B=0.1% TFA in ACN; gradient 0-100% B over 2 min; retention time: 0.90 min; LCMS (ES-API), m/z 243.7 (M+H).

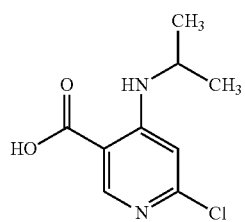

Step 2

To a solution of ethyl 6-chloro-4-(isopropylamino)nicotinate (7 g, 28.8 mmol) in EtOH (70 mL) was added water (30 mL) and LiOH (2.1 g, 87 mmol). The mixture was stirred for 3 h, concentrated and acidified with 1.5 N HCl. The resultant solids were collected and dried to afford 6-chloro-4-)isopropylamino)nicotic acid (5.3 g, 85% yield) as a white solid. LCMS: M+H=215.3; $^1$H NMR (400 MHz, DMSO-$d_6$) δ 13.32 (br s, 1H), 8.51 (s, 1H), 8.19 (d, J=7.6 Hz, 1H), 6.79 (s, 1H), 2.50 (m, 1H), 1.20 (s, 3H), 1.18 (s, 3H).

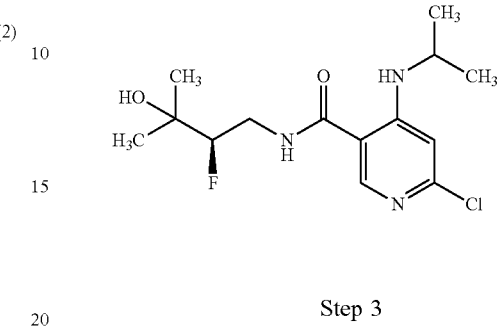

Step 3

To a stirred solution of 6-chloro-4-(isopropylamino)nicotinic acid (2.9 g, 13.51 mmol) in DMF was added (R)-4-amino-3-fluoro-2-methylbutan-2-ol (1.637 g, 13.51 mmol), HATU (6.16 g, 16.21 mmol), DIPEA (9.44 mL, 54.0 mmol) successively and continued stirring for 18 h. The reaction mixture was diluted with ethyl acetate and washed with water (3×). The organic layer was dried over $Na_2SO_4$, concentrated in vacuo to provide the crude compound which was purified via column chromatography (10-40% ethyl acetate/pet ether) to afford (R)-6-chloro-N-(2-fluoro-3-hydroxy-3-methylbutyl)-4-(isopropylamino)nicotinamide (2.8 g, 65% yield) as off-white solid. LCMS: 318.1 (M+H): $^1$H NMR (400 MHz, DMSO-$d_6$) δ 8.75 (t, J=7.6 Hz, 1H), 8.44 (br d, J=10.4 Hz, 1H), 8.38 (s, 1H), 6.71 (s, 1H), 4.24 (m, 1H), 3.64 (m 2H), 3.42 (m, 1H), 1.16 (m, 12H).

Step 4

(R)-6-Chloro-N-(2-fluoro-3-hydroxy-3-methylbutyl)-4-(isopropylamino)nicotinamide (150 mg, 0.472 mmol) was taken in a sealed tube along with Xantphos (137 mg, 0.236 mmol), 6-aminonicotinonitrile (56.2 mg, 0.472 mmol) and $Na_2CO_3$ (150 mg, 1.416 mmol) in dioxin (5 mL) and water (1 mL). The reaction mixture was degassed and $Pd_2(dba)_3$ (216 mg, 0.236 mmol) was added. The reaction mixture was heated to 110° C. for 18 h. The reaction mixture was diluted with ethyl acetate and passed through a small plug of CELITE® with ethyl acetate. The ethyl acetate layer was washed with water, dried and concentrated in vacuum. The crude was purified using 10% methanol in chloroform using combiflash (24 g column) followed by final purification by preparative HPLC to afford (R)-6-((5-cyanopyridin-2-yl)amino)-N-(2-fluoro-3-hydroxy-3-methylbutyl)-4-(isopropylamino)nicotinamide (42 mg, 21% yield). LCMS: 318.1 (M+H): $^1$H NMR (400 MHz, DMSO-$d_6$) 10.24 (s, 1H), 8.66 (s, 1H), 8.54 (t, J=6.0 Hz, 1H), 8.43 (s, 1H), 8.39 (d, J=7.2 Hz, 1H), 8.04 (dd, J=8.8, 2.4 Hz, 1H), 7.84 (d, J=8.8 Hz, 1H), 4.83 (s, 1H), 4.26-4.44 (m, 1H), 3.57-3.75 (m, 2H), 3.40 (M, 1H), 1.23 (s, 3H), 1.22 (s, 3H), 1.17 (s, 3H), 1.16 (s, 3H).

The Examples in the table below were prepared in an analogous fashion to Example 1 and 2, substituting where appropriate, alternate amines in the synthetic sequence.

TABLE 1

| Ex. No. | Structure | HPLC rt (min) | HPLC cond. | LCMS (M + H)+ |
|---|---|---|---|---|
| 3 | 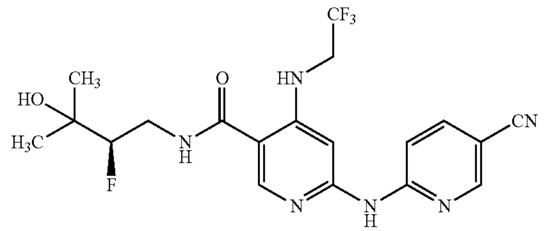 | 6.68 | A | 441.2 |
| 4 | 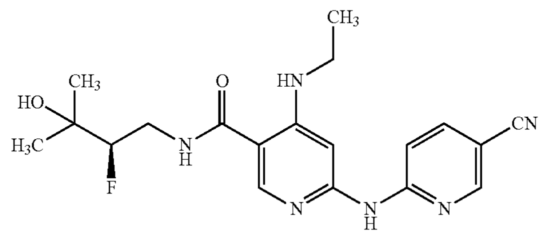 [SMILES: CC(C)(O)[C@H](F)CNC(=O)c1cnc(Nc2ccc(C#N)cn2)cc1NCC(F)(F)F] | 5.08 | M | 387.2 |
| 5 | 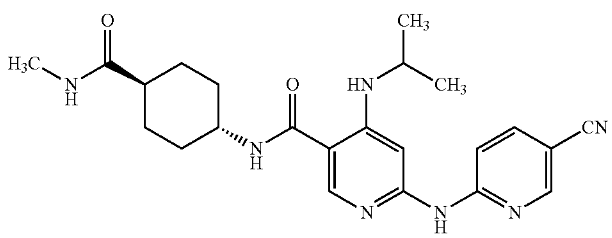 [SMILES: CNC(=O)[C@H]1CC[C@H](NC(=O)c2cnc(Nc3ccc(C#N)cn3)cc2NC(C)C)CC1] | 1.38 | G | 434.1 |
| 6 | 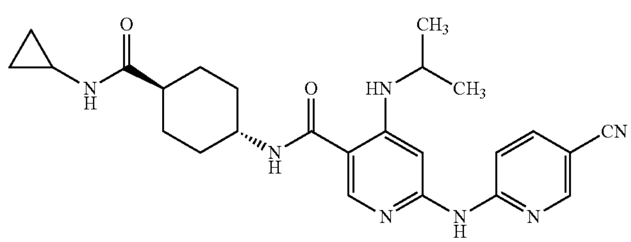 [SMILES: CC(C)Nc1cc(Nc2ccc(C#N)cn2)ncc1C(=O)N[C@H]1CC[C@H](C(=O)NC2CC2)CC1] | 1.48 | B | 462.2 |
| 7 | 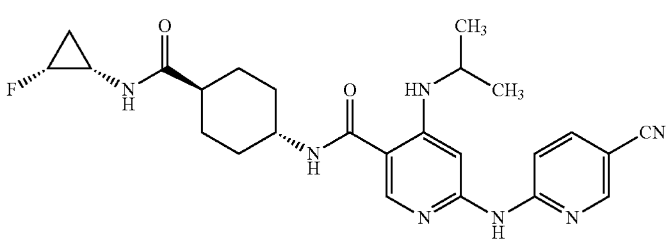 [SMILES: CC(C)Nc1cc(Nc2ccc(C#N)cn2)ncc1C(=O)N[C@H]1CC[C@H](C(=O)N[C@H]2C[C@H]2F)CC1] | 1.49 | B | 480.2 |
| 8 | 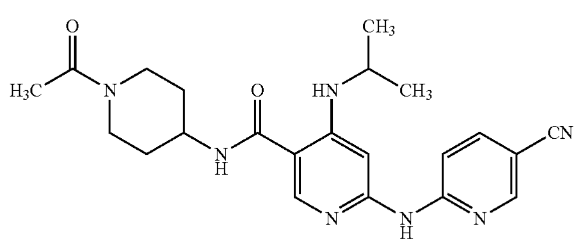 [SMILES: CC(=O)N1CCC(NC(=O)c2cnc(Nc3ccc(C#N)cn3)cc2NC(C)C)CC1] | 1.40 | G | 422.1 |

| Ex. No. | Structure | HPLC rt (min) | HPLC cond. | LCMS (M + H)+ |
|---|---|---|---|---|
| 9 | 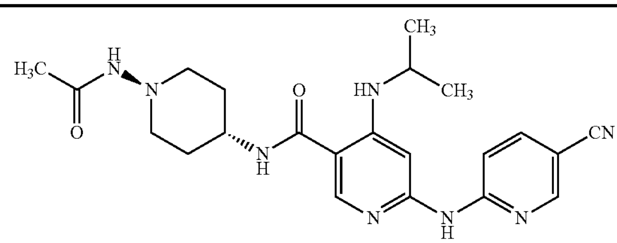 | 1.35 | G | 436.3 |
| 10 | 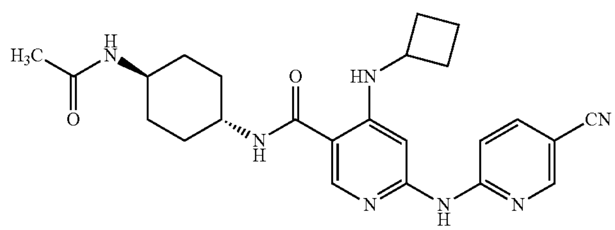 [SMILES: CC(=O)N[C@H]1CC[C@H](NC(=O)c2cnc(Nc3ccc(C#N)cn3)cc2NC2CCC2)CC1] | 1.41 | G | 448.3 |
| 11 | 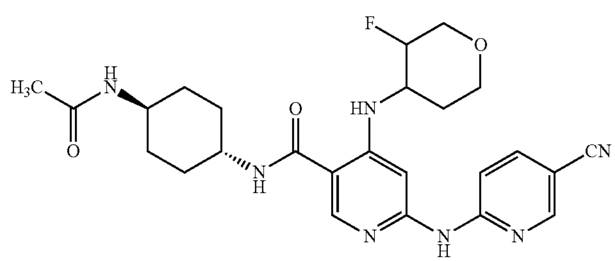 [SMILES: CC(=O)N[C@H]1CC[C@H](NC(=O)c2cnc(Nc3ccc(C#N)cn3)cc2NC2CCOCC2F)CC1] | 1.17 | G | 496.3 |

6-((5-cyano-2-pyridinyl)amino)-N-((2R)-2-fluoro-3-hydroxy-3-methylbutyl)-4-((2,2,2-trifluoroethyl)amino)nicotinamide (3); 6-((5-cyano-2-pyridinyl)amino)-4-(ethylamino)-N-((2R)-2-fluoro-3-hydroxy-3-methylbutyl)nicotinamide (4); 6-((5-cyano-2-pyridinyl)amino)-4-(isopropylamino)-N-(trans-4-(methylcarbamoyl)cyclohexyl)nicotinamide (5); 6-((5-cyanopyridin-2-yl)amino)-N-((1R,4R)-4-(cyclopropylcarbamoyl)cyclohexyl)-4-(isopropylamino) nicotinamide (6); 6-((5-cyano-2-pyridinyl)amino)-N-(trans-4-(((1S,2R)-2-fluorocyclopropyl)carbamoyl)cyclohexyl)-4-(isopropylamino)nicotinamide (7); N-(1-acetyl-4-piperidinyl)-6-((5-cyano-2-pyridinyl)amino)-4-(isopropylamino) nicotinamide (8); N-(trans-4-acetamidocyclohexyl)-6-((5-cyano-2-pyridinyl)amino)-4-(isopropylamino)nicotinamide (9); 6-((5-cyano-2-pyridinyl)amino)-4-(cyclobutylamino)-N-(trans-4-(methylcarbamoyl)cyclohexyl)nicotinamide (10); N-((1R,4R)-4-acetamidocyclohexyl)-6-((5-cyanopyridin-2-yl)amino)-4-(((3S,4R)-3-fluorotetrahydro-2H-pyran-4-yl)amino)nicotinamide (11).

Example 12

6-((3-Chloro-5-cyano-2-pyridinyl)amino)-N-((2R)-2-fluoro-3-hydroxy-3-methylbutyl)-4-(isopropylamino)nicotinamide (12)

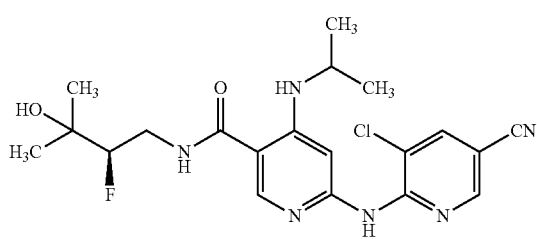

(R)-6-Chloro-N-(2-fluoro-3-hydroxy-3-methylbutyl)-4-(isopropylamino)nicotinamide (25 mg, 0.08 mmol) was taken in dioxane (2.5 mL) and to this 6-amino-5-chloronicotinonitrile (24.16 mg, 0.16 mmol) was added along with Xantphos (23 mg, 0.039 mmol), Na$_2$CO$_3$ (25 mg, 0.24 mmol) and water (0.5 mL). The reaction mixture was degassed for 10 min then added Pd(Ph$_3$P)$_4$ (45.5 mg, 0.039 mmol) was added and further degassed 5 min. The reaction mixture was then heated at 100° C. for 20 minutes then at 140° C. for 20 minutes. Purification via preparative HPLC afforded (R)-6-((3-chloro-5-cyanopyridin-2-yl)amino)-N-(2-fluoro-3-hydroxy-3-methylbutyl)-4-(isopropylamino) nicotinamide (2 mg, 5% yield). LCMS: 435.2 (M+H): $^1$H NMR (500 MHz, 1:1 MeOD:CDCl$_3$) δ 8.76 (s, 1H), 8.55 (s, 1H), 8.28 (s, 1H), 8.02 (s, 1H), 4.45 (ddd, J=10, 50 Hz, 1H), 3.87 (m, 2H), 3.44 (m, 1H), 1.33 (s, 3H), 1.32 (s, 3H), 1.29 (s, 6H).

The Examples in the table below were prepared in an analogous fashion to Example 12, substituting where appropriate, alternate amines in the synthetic sequence.

TABLE 2

| Ex. No. | Structure | HPLC rt (min) | HPLC cond. | LCMS (M + H)+ |
|---|---|---|---|---|
| 13 | 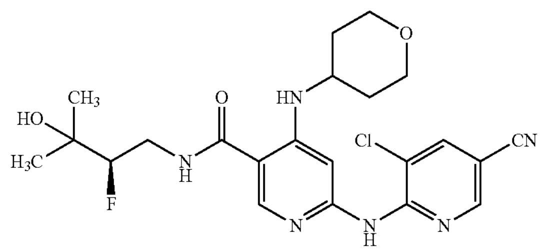 [SMILES: CC(C)(O)[C@H](F)CNC(=O)c1cnc(Nc2ncc(C#N)cc2Cl)cc1NC1CCOCC1] | 9.62 | K | 476.6 (M+) |
| 14 | 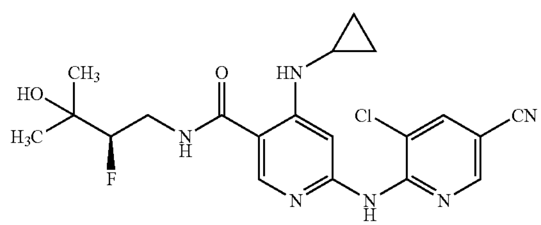 [SMILES: CC(C)(O)[C@H](F)CNC(=O)c1cnc(Nc2ncc(C#N)cc2Cl)cc1NC1CC1] | 1.60 | G | 470.2 |
| 15 | 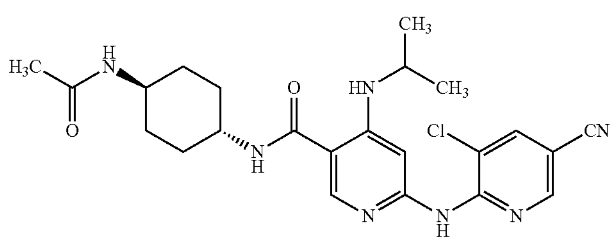 [SMILES: CC(=O)N[C@H]1CC[C@H](NC(=O)c2cnc(Nc3ncc(C#N)cc3Cl)cc2NC(C)C)CC1] | 1.59 | G | 470.2 |
| 16 | 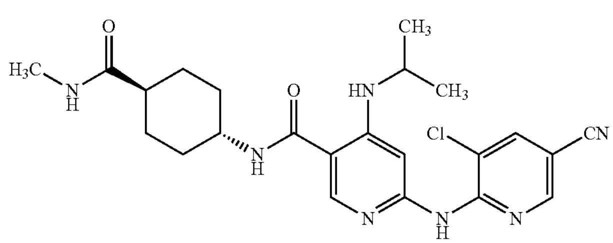 [SMILES: CNC(=O)[C@H]1CC[C@H](NC(=O)c2cnc(Nc3ncc(C#N)cc3Cl)cc2NC(C)C)CC1] | 1.57 | G | 470.2 |
| 17 | 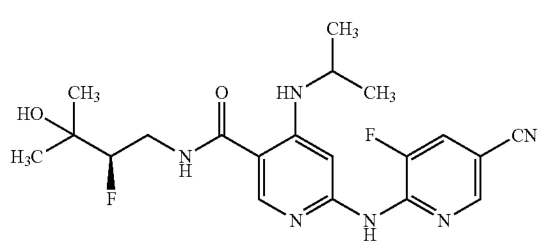 [SMILES: CC(C)Nc1cc(Nc2ncc(C#N)cc2F)ncc1C(=O)NC[C@@H](F)C(C)(C)O] | 1.78 | G | 419.2 |

TABLE 2-continued

| Ex. No. | Structure | HPLC rt (min) | HPLC cond. | LCMS (M + H)+ |
|---|---|---|---|---|
| 18 | 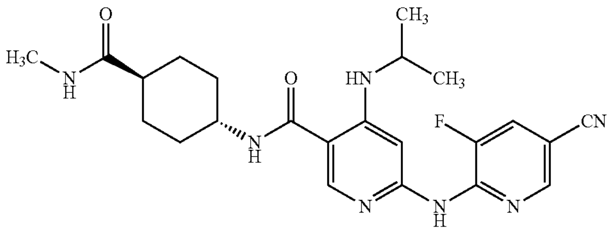 [SMILES: CNC(=O)[C@H]1CC[C@H](NC(=O)c2cnc(Nc3ncc(C#N)cc3F)cc2NC(C)C)CC1] | 1.47 | G | 454.2 |
| 19 | 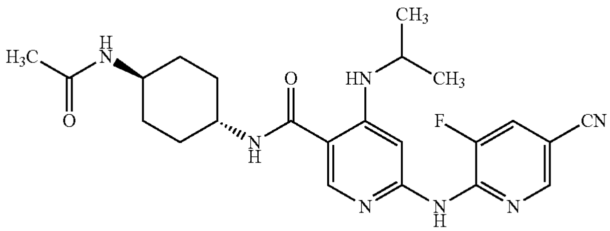 [SMILES: CC(=O)N[C@H]1CC[C@H](NC(=O)c2cnc(Nc3ncc(C#N)cc3F)cc2NC(C)C)CC1] | 1.43 | G | 454.0 |

6-((3-chloro-5-cyano-2-pyridinyl)amino)-N-((2R)-2-fluoro-3-hydroxy-3-methylbutyl)-4-(tetrahydro-2H-pyran-4-ylamino)nicotinamide (13); 6-((3-chloro-5-cyano-2-pyridinyl)amino)-4-(cyclopropylamino)-N-((2R)-2-fluoro-3-hydroxy-3-methylbutyl)nicotinamide (14); N-((1r,4r)-4-acetamidocyclohexyl)-6-((3-chloro-5-cyanopyridin-2-yl)amino)-4-(isopropylamino)nicotinamide (15); 6-((3-chloro-5-cyanopyridin-2-yl)amino)-4-(isopropylamino)-N-((1R,4R)-4-(methylcarbamoyl)cyclohexyl)nicotinamide (16); 6-((5-cyano-3-fluoro-2-pyridinyl)amino)-N-((2R)-2-fluoro-3-hydroxy-3-methylbutyl)-4-(isopropylamino)nicotinamide (17); 6-((5-cyano-3-fluoropyridin-2-yl)amino)-4-(isopropylamino)-N-((1R,4R)-4-(methylcarbamoyl)cyclohexyl)nicotinamide (18); N-(trans-4-acetamidocyclohexyl)-6-((5-cyano-3-fluoro-2-pyridinyl)amino)-4-(isopropylamino)nicotinamide (19).

Example 20

N-((2R)-2-Fluoro-3-hydroxy-3-methylbutyl)-4-(isopropylamino)-6-(4-pyrimidinylamino)nicotinamide (20)

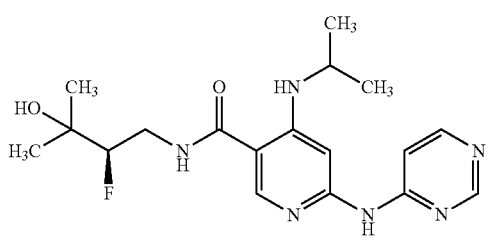

Example 20 was prepared according to the general procedure described for Example 2. HPLC RT 9.54 min, Conditions A. LCMS 377.3 (M+H).

Example 21

4-(Cyclopropylamino)-N-((2R)-2-fluoro-3-hydroxy-3-methylbutyl)-6-(4-pyrimidinylamino)nicotinamide (21)

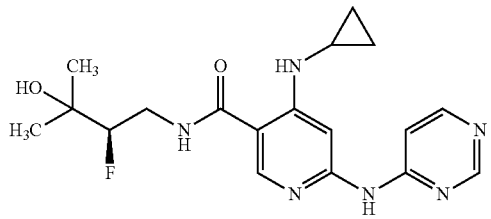

Example 21 was prepared according to the general procedure described for Example 2. HPLC RT 4.32 min, Conditions E. LCMS 375.2 (M+H).

Example 22

6-((5-Cyano-2-pyrimidinyl)amino)-N-((2R)-2-fluoro-3-hydroxy-3-methylbutyl)-4-(isopropylamino)nicotinamide (22)

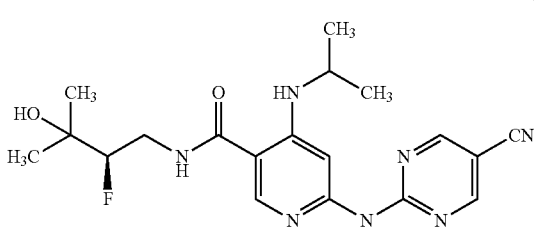

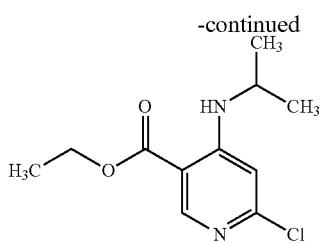

Step 1: Synthesis of ethyl 6-chloro-4-(isopropylamino)nicotinate

To a solution of ethyl 4,6-dichloronicotinate (10 g, 45 mmol) in DMA (40 mL) was added propan-2-amine (5.3 g, 91 mmol) and DIPEA (31.7 mL, 182 mmol). The reaction mixture was stirred at room temperature for 48 h. The reaction mixture was diluted with MTBE and washed water (3×). The organic layer was dried over $Na_2SO_4$, filtered and concentrated to afford the crude product. The product was purified by flash chromatography through silica gel (10% EtOAc:pet ether as eluent) to afford ethyl 6-chloro-4-(isopropylamino)nicotinate (8.3 g, 75% yield) as a crystalline solid. LCMS m/z 243.7 (M+H); $^1$H NMR (400 MHz, DMSO-$d_6$) δ 8.54 (s, 1H), 7.98 (d, J=7.6 Hz, 1H), 6.85 (s, 1H), 4.29 (q, J=7.2 Hz, 2H), 3.86 (m, 1H), 1.32 (d, J=6.8 Hz, 3H), 1.20 (s, 3H), 1.19 (s, 3H).

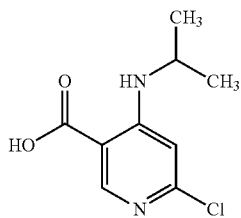

Step 2

Ethyl 6-chloro-4-(isopropylamino)nicotinate (7 g, 28.8 mmol) was synthesized according to the procedure in Example 2, step 2.

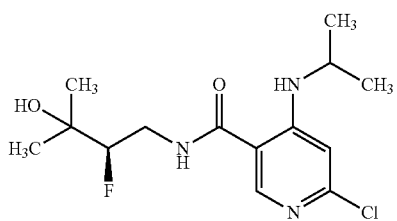 [SMILES: CC(C)Nc1cc(Cl)ncc1C(=O)NC[C@@H](F)C(C)(C)O]

Step 3

6-Chloro-4-(isopropylamino)nicotinic acid (2.9 g, 13.51 mmol) was synthesized according to the procedure in Example 2, step 3.

Step 4

In a 100 mL round bottom flask (R)-6-chloro-N-(2-fluoro-3-hydroxy-3-methylbutyl)-4-(isopropylamino)nicotinamide (10 g, 31.5 mmol) and 2-aminopyrimidine-5-carbonitrile (4.54 g, 37.8 mmol) were taken up in DMA (125 mL) and the suspension purged by bubbling nitrogen through the suspension. $Pd_2(dba)_3$ (0.360 g, 0.393 mmol), Xantphos (0.455 g, 0.787 mmol) and $K_2CO_3$ (8.70 g, 62.9 mmol) were each added sequentially in one portion while the purging process was continued. After the addition, purging was continued for a further 5 min, the needle was then removed from the solution (keeping the reaction under nitrogen atmosphere) and the reaction flask was immersed directly into an oil bath pre-heated to 135° C. for 1 hr. The reaction flask was removed from the heating bath and the reaction mixture was allowed to cool to room temperature. The solvents were removed in vacuo and the resulting solids were purified via column chromatography (100% EtOAc then 10% MeOH/$CH_2Cl_2$). The product containing fractions were then combined with two additional reaction runs (10 g and 5 g scale) and refluxed in acetone for 2 h. The slurry was cooled, filtered and rinsed with acetone to afford the pure product as a white solid after drying (18.5 g, 58% yield). LCMS m/z 402 (M+H)$^+$; $^1$H NMR (400 MHz, DMSO-$d_6$) δ 10.54 (s, 1H), 8.99 (s, 2H), 8.57 (br s, 1H), 8.53-8.40 (m, 2H), 8.46 (s, 1H), 4.81 (s, 1H), 4.36 (m, 1H), 3.84-3.59 (m, 2H), 3.46-3.25 (m, 1H), 1.25 (d, J=6.4 Hz, 6H), 1.21-1.11 (m, 6H).

Preparation of 6-((5-cyano-2-pyrimidinyl)amino)-N-((2R)-2-fluoro-3-hydroxy-3-methylbutyl)-4-(isopropylamino)nicotinamide hydrochloride To a suspension of 6-((5-cyano-2-pyrimidinyl)amino)-N-((2R)-2-fluoro-3-hydroxy-3-methylbutyl)-4-(isopropylamino)nicotinamide (100 mg, 0.249 mmol) in acetone (3 mL) was added HCl (1.2 equivalents, 4N in dioxane). The solids went into solution and the salt began to precipitate after a few minutes of stirring. Stirring was continued for an additional 20 minutes and the solids were filtered, collected and dried under high vacuum to afford 6-((5-cyano-2-pyrimidinyl)amino)-N-((2R)-2-fluoro-3-hydroxy-3-methylbutyl)-4-(isopropylamino)nicotinamide hydrochloride (90 mg, 82% yield) as a white solid. $^1$H NMR (400 MHz, DMSO-$d_6$) δ 11.87 (br s, 1H), 9.22-9.04 (m, 4H), 8.48 (s, 1H), 6.97 (s, 1H), 4.34 (m, 1H), 4.00-3.99 (m, 1H), 3.81-3.61 (m, 3H), 1.28 (d, J=6.4 Hz, 6H), 1.16 (dd, J=−5.9, 1.3 Hz, 6H).

Phosphate Prodrug of 6-((5-cyano-2-pyrimidinyl)amino)-N-((2R)-2-fluoro-3-hydroxy-3-methylbutyl)-4-(isopropylamino)nicotinamide

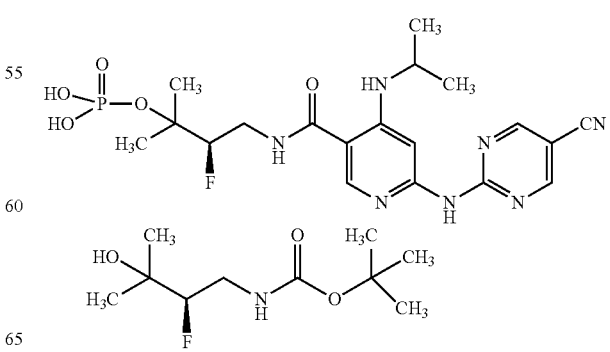

Step 1

To a solution of (R)-4-amino-3-fluoro-2-methylbutan-2-ol (10 g, 83 mmol) in DCM (100 mL) was added TEA (23.01 mL, 165 mmol) and followed by the dropwise addition of BOC$_2$O (21.08 mL, 91 mmol). The reaction was stirred at room temperature for 2 h. The reaction was partitioned between water (100 mL) and DCM (100 mL), and the organic layer was washed with water (2×50 mL), 1.5N HCl solution (2×25 mL) and brine (25 mL). The organic layer was dried over Na$_2$SO$_4$ and concentrated to provide (R)-tert-butyl (2-fluoro-3-hydroxy-3-methylbutyl)carbamate (16.2 g, 89% yield) as a thick colorless oil. $^1$H NMR (400 MHz, DMSO-d$_6$) δ ppm 6.93 (t, J=5.27 Hz, 1H), 4.68-4.73 (m, 1H), 4.06-4.24 (m, 1H), 3.35-3.43 (m, 1H), 2.99-3.12 (m, 1H), 1.37-1.42 (m, 9H), 1.08-1.12 (m, 6H).

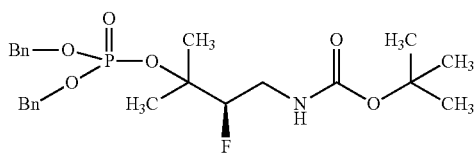 [SMILES: CC(C)(C)OC(=O)NC[C@@H](F)C(C)(C)OP(=O)(OCc1ccccc1)OCc1ccccc1]

Step 2

To a solution of (R)-tert-butyl (2-fluoro-3-hydroxy-3-methylbutyl)carbamate (1.9 g, 8.59 mmol) in DCM (40 mL) was added dibenzyl diisopropylphosphoramidite (4.33 mL, 12.88 mmol) followed by the addition of 1H-tetrazole (1.203 g, 17.17 mmol) at room temperature. The resulting mixture was stirred for 1 h. The reaction was cooled to 0° C. and H$_2$O$_2$ (1.422 mL, 17.17 mmol) was added and the reaction allowed to stir for 1 h at room temperature. The reaction was diluted with DCM (50 mL) and washed with saturated sodium metabisulphate solution (30 mL), brine (20 mL). The organic layer was dried over Na$_2$SO$_4$, concentrated and purified over silica gel eluting 10% EA in DCM to provide (R)-tert-butyl (3-((bis(benzyloxy)phosphoryl)oxy)-2-fluoro-3-methylbutyl)carbamate (2.5 g, 61% yield) as colorless oil. $^1$H NMR (400 MHz, DMSO-d$_6$) δ ppm 7.33-7.42 (m, 9H), 7.08 (t, J=5.52 Hz, 1H), 4.99-5.04 (m, 4H), 4.35-4.52 (m, 1H), 3.35-3.44 (m, 1H), 3.05-3.15 (m, 1H), 1.35-1.51 (m, 15H); LCMS; (M+H) 482.0.

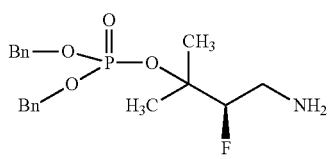 [SMILES: CC(C)(OP(=O)(OCc1ccccc1)OCc1ccccc1)[C@H](F)CN]

Step 3

To a stirred solution of (R)-tert-butyl (3-((bis(benzyloxy)phosphoryl)oxy)-2-fluoro-3-methylbutyl)carbamate (1.6 g, 3.32 mmol) in DCM (3 mL) at 0° C. was added HCl (15 mL, 60.0 mmol, 4M in dioxane) and stirred for 30 min at 0° C. The reaction was concentrated in vacuo and the residue was dissolved in DCM. Aqueous ammonia was added and the layers were separated and the organic layer was dried over Na$_2$SO$_4$ and concentrated to afford (R)-4-amino-3-fluoro-2-methylbutan-2-yl dibenzyl phosphate (1.2 g, 3.15 mmol, 95% yield) as colorless oil. $^1$H NMR (400 MHz, DMSO-d$_6$) δ ppm 7.21-7.43 (m, 11H), 4.94-5.04 (m, 4H), 4.44-4.65 (m, 1H), 3.57-3.74 (m, 2H), 3.44-3.54 (m, 1H), 2.66-3.04 (m, 2H), 1.39-1.52 (m, 6H); LCMS (M+H) 382.2.

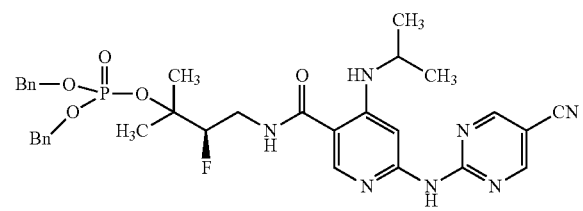 [SMILES: CC(C)Nc1cc(Nc2ncc(C#N)cn2)ncc1C(=O)NC[C@@H](F)C(C)(C)OP(=O)(OCc1ccccc1)OCc1ccccc1]

Step 4

To a solution of 6-((5-cyanopyrimidine-2-yl)amino)-4-(isopropylamino)nicotinic acid (220 mg, 0.738 mmol) and (R)-4-amino-3-fluoro-2-methylbutan-2-yl dibenzyl phosphate (366 mg, 0.959 mmol) in DMF (3 mL) was added DIPEA (0.386 mL, 2.213 mmol) and HATU (561 mg, 1.475 mmol). The reaction was stirred overnight at room temperature. Water (6 mL) was added and the resulting solids were stirred for 5 min then filtered. The solids were washed with hexane (10 mL) and ether (15 mL) and then dried. The material was used directly in the next step without further purification. Crude weight: 190 mg, 30% yield. LCMS (M+H) 661.8.

Step 5

To a solution of (R)-dibenzyl (4-(6-((5-cyanopyrimidine-2-yl)amino)-4-(isopropylamino)nicotinamido)-3-fluoro-2-methylbutan-2-yl)phosphate (120 mg, 0.181 mmol) in 1,2-dichloroethane (4 mL) was added a solution of TFA (2.79 mL, 36.3 mmol) in 10 mL of DCE and the resulting mixture was stirred at 35° C. for 5 hrs. The reaction was concentrated under vacuum at 35° C. then co-distilled with toluene (two times) and CHCl$_3$ (two times) and purified by prep HPLC to get (R)-4-(6-((5-cyanopyrimidine-2-yl)amino)-4-(isopropylamino)nicotinamido)-3-fluoro-2-methylbutan-2-yl dihydrogen phosphate (30 mg, 34% yield) as a white solid. $^1$H NMR (400 MHz, DMSO-d$_6$) δ ppm 8.98 (s, 3H), 8.54-8.58 (m, 2H), 7.56 (s, 1H), 4.50-4.66 (m, 1H), 3.51-3.72 (m, 5H), 1.45 (s, 3H), 1.37 (s, 3H), 1.24 (d, J=6.02 Hz, 6H); LCMS (M+H) 482.2.

Example 23

4-(Cyclopropylamino)-N-((2R)-2-fluoro-3-hydroxy-3-methylbutyl)-6-((4-(3-pyridinyl)-1,3-thiazol-2-yl)amino)nicotinamide (23)

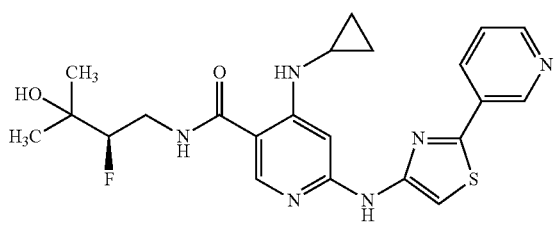

-continued

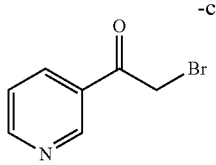

Step 1: Synthesis of 2-bromo-1-(pyridin-3-yl)ethanone

A solution of 1-(pyridin-3-yl)ethanone (4.2 g, 1 equiv.) in 33% HBr in CH$_3$COOH (37 mL) was heated at 70° C. for 5 min. Br$_2$ (1.8 mL, 1.1 equiv.) in 45% HBr (5 mL, 34.7 mmol) was added dropwise to the reaction mixture at 70° C. and stirred for 3 h. The reaction mixture was gradually cooled to room temperature while the product precipitated. The product was filtered and recrystallized using MeOH-hexane (1:1) to obtain 2-bromo-1-(pyridin-3-yl)ethanone (5.6 g, 81% yield). LC/MS: PUROSPHER® Star RP-18, 4×55 mm, 3 µm; Solvent A=10% ACN: 90% H$_2$O: 20 mM NH$_4$OAc; Solvent B=90% ACN: 10% H$_2$O: 20 mM NH$_4$COOAc; gradient 0-100% B over 1.5 min (3.2 min run time); retention time: 1.13 min; LCMS (ES-API), m/z 202 (M+H).

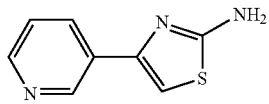 [SMILES: Nc1nc(-c2cccnc2)cs1]

Step 2: Synthesis of 4-(pyridin-3-yl)thiazol-2-amine

To a solution of 2-bromo-1-(pyridin-3-yl)ethanone (2 g, 1 equiv.) in ethanol (18.46 mL), thiourea (0.543 g, 0.7 equiv.) was added. The reaction mixture was heated to reflux for 2 h. After completion of 2 h, the reaction mixture was cooled to 4° C. On cooling the product precipitated out in dihydrobromide salt form. The material obtained was filtered and dried. 4-(pyridin-3-yl)thiazol-2-amine dihydrobromide salt was dissolved in warm water (11 mL) and stirred for 5 min, to this aqueous ammonium hydroxide solution (17 mL) was added and stirred. The desired product slowly precipitated (yellow solid) which was filtered and dried under vacuum to afford 4-(pyridin-3-yl)thiazol-2-amine 2 g, 56% yield). LCMS m/z 178.01 (M+H); $^1$H NMR 400 MHz, CD$_3$OD: δ 8.96 (d, J=0.80 Hz, 1H), 8.44 (dd, J=1.60, 4.80 Hz, 1H), 8.19-8.22 (m, 1H), 7.43-7.47 (m, 1H), 7.05 (s, 1H).

Step 3

Example 23 was prepared according to the general procedure described for Example 2. HPLC RT 8.32 min, Conditions C. LCMS 457.2 (M+H).

Example 24

6-((2-(Cyclopropylamino)-4-pyrimidinyl)amino)-N-((2R)-2-fluoro-3-hydroxy-3-methylbutyl)-4-(isopropylamino)nicotinamide (24)

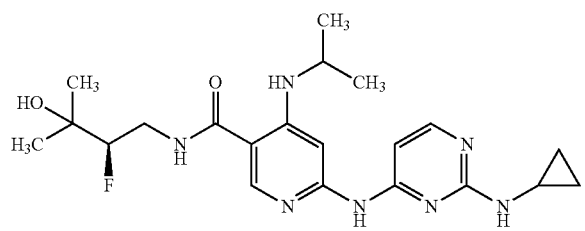

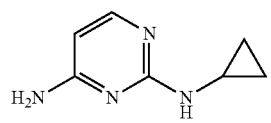

Step 1

To a solution of 2-chloropyrimidin-4-amine (0.5 g, 3.9 mmol) in NMP (5 mL) was added cyclopropyl amine (1.1 g, 19.3 mmol) and the mixture was sealed and heated at 150° C. for 30 min. The mixture was concentrated and partitioned between EA and water. The layers were separated and the organic layer was dried over Na$_2$SO$_4$, filtered and concentrated. The residue was purified via column chromatography (5% MeOH/CHCl$_3$) to afford N2-cyclopropylpyrimidine-2,4-diamine (0.14 g, 23% yield) as a pale yellow oil. LCMS: 151.2 (M+H).

Step 2

Following the procedure outlined for Example 2, N2-cyclopropylpyrimidine-2,4-diamine was reacted with (R)-6-chloro-N-(2-fluoro-3-hydroxy-3-methylbutyl)-4-(isopropylamino)nicotinamide to afford Example 24. LCMS m/z 432.2 (M+H); $^1$H NMR (400 MHz, CD$_3$OD) δ 8.29 (s, 1H), 8.00 (d, J=6.0 Hz, 1H), 7.10 (br s, 1H), 6.54 (d, J=5.6 Hz, 1H), 4.52 (m, 1H), 3.83 (m, 2H), 3.44 (m, 1H), 2.78 (m, 1H), 1.29 (m, 12H), 0.83 (m, 2H), 0.59 (m, 2H).

The Examples in the table below were prepared in an analogous fashion to Example 24, substituting where appropriate, alternate amines in the synthetic sequence.

TABLE 3

| Ex. No. | Structure | HPLC rt (min) | HPLC cond. | LCMS (M + H)+ |
|---|---|---|---|---|
| 25 | 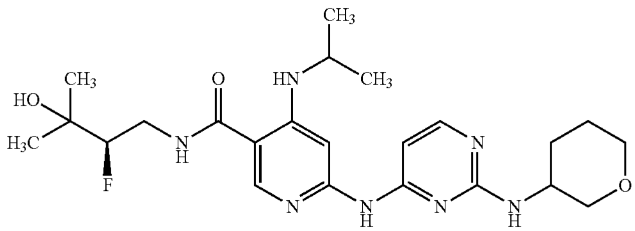 [SMILES: CC(C)Nc1cc(Nc2ccnc(NC3CCCOC3)n2)ncc1C(=O)NC[C@@H](F)C(C)(C)O] | 4.71 | E | 476.8 |
| 26 | 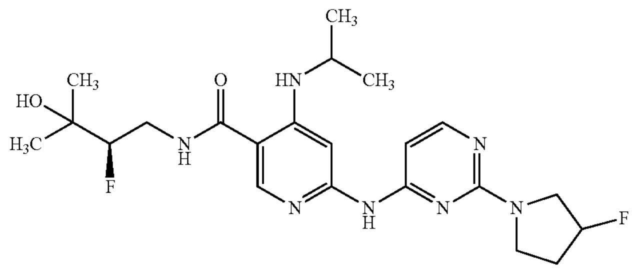 [SMILES: CC(C)Nc1cc(Nc2ccnc(N3CCC(F)C3)n2)ncc1C(=O)NC[C@@H](F)C(C)(C)O] | 9.53 | B | 464.2 |

N-((2R)-2-fluoro-3-hydroxy-3-methylbutyl)-4-(isopropylamino)-6-((2-(tetrahydro-2H-pyran-3-ylamino)-4-pyrimidinyl)amino)nicotinamide (25); N-((2R)-2-fluoro-3-hydroxy-3-methylbutyl)-6-((2-(3-fluoro-1-pyrrolidinyl)-4-pyrimidinyl)amino)-4-(isopropylamino)nicotinamide.

Example 27

6-((5-Cyano-6-((3 S)-3-hydroxy-1-pyrrolidinyl)-2-pyridinyl)amino)-N-((2R)-2-fluoro-3-hydroxy-3-methylbutyl)-4-(isopropylamino)nicotinamide (27)

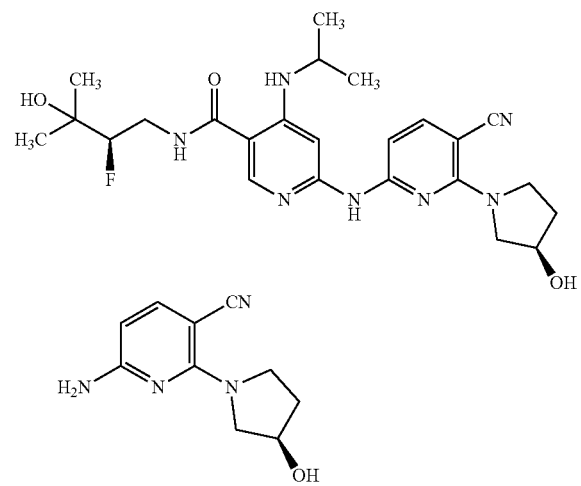

Step 1

6-Amino-2-chloronicotinonitrile (0.100 g, 0.651 mmol) was taken in a sealed tube and dissolved in dioxane (3 mL) and NMP (0.2 mL). To that was added (R)-pyrrolidin-3-ol (0.057 g, 0.651 mmol) and NMP (0.2 mL) and the set up was heated at 150° C. for 18 h. The solvents were evaporated from the reaction mixture and the crude was dissolved in water and made basic by adding NaHCO₃ and was extracted with DCM (3×15 mL). The combined organic layer were dried and evaporated to get the product (80 mg, 42% yield) which was directly in the next reaction. LCMS 205.2 (M+H).

Step 2

Following the procedure outlined for Example 2, (R)-6-amino-2-(3-hydroxypyrrolidin-1-yl)nicotinonitrile was reacted with (R)-6-chloro-N-(2-fluoro-3-hydroxy-3-methylbutyl)-4-(isopropylamino)nicotinamide to afford Example 27. LCMS m/z 486.2 (M+H); HPLC RT 6.80 min, Conditions E.

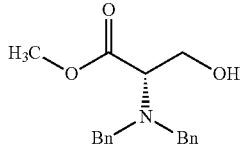 [SMILES: COC(=O)[C@H](CO)N(Cc1ccccc1)Cc1ccccc1]

Synthesis of methyl 2-(dibenzylamino)-3-hydroxypropanoate

To a solution of K₂CO₃ (34.8 g, 2 equiv.) in DMF (280 mL), was added L-serine methyl ester hydrochloride (1 equiv.), potassium iodide (10.8 g, 0.5 equiv.) and benzyl bromide (38 mL, 2.5 equiv.). The mixture was stirred for 16 h at room temperature. The reaction mixture was concentrated under reduced pressure to remove excess of DMF and then diluted with EtOAc. The organic layer was washed with brine and water. The organic layer was separated, dried over anhydrous sodium sulfate, filtered and concentrated. The crude material was purified by column chromatography through silica gel (EtOAC: pet ether as eluent) to afford methyl 2-(dibenzylamino)-3-hydroxypropanoate. $^1$H NMR: 400 MHz, DMSO-d$_6$: δ 2.49 (s, 1H), 3.58-3.59 (m, 1H), 3.67-3.70 (m, 2H), 3.73-3.75 (m, 2H), 3.77-3.80 (m, 3H), 3.90-3.94 (m, 2H), 7.24-7.38 (m, 10H).

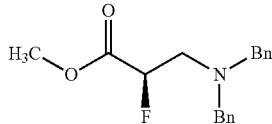 [SMILES: COC(=O)[C@H](F)CN(Cc1ccccc1)Cc1ccccc1]

Synthesis of (R)-methyl 3-(dibenzylamino)-2-fluoropropanoate

To an ice cool solution of methyl 2-(dibenzylamino)-3-hydroxypropanoate (15 g, 1 equiv.) in THF (95 mL), DAST (13.1 mL, 1.23 equiv.) was added dropwise under N$_2$-atmosphere and the reaction mixture was stirred for 14 h at room temperature. The reaction mixture was quenched with aq. 10% NaHCO$_3$ solution at 0° C. and extracted into ethyl acetate (twice). The organic layers were collected, dried over anhydrous sodium sulfate, filtered and concentrated. The crude product was purified by flash column chromatography using silica gel and EtOAc:pet ether to afford (R)-methyl 3-(dibenzylamino)-2-fluoropropanoate. $^1$H NMR: 400 MHz, CDCl$_3$: δ 2.93-3.11 (m, 2H), 3.51-3.55 (m, 2H), 3.70 (s, 3H), 3.82-3.85 (m, 2H), 4.98-5.13 (m, 1H), 7.22-7.34 (m, 10H).

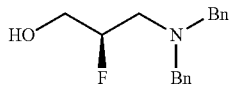 [SMILES: OC[C@H](F)CN(Cc1ccccc1)Cc1ccccc1]

Synthesis of (S)-3-(dibenzylamino)-2-fluoropropan-1-ol

To a stirred solution of LiBH$_4$ (34.5 mL, 1.4 equiv.) in THF (300 mL), (R)-methyl 3-(dibenzylamino)-2-fluoropropanoate (15 g, 1 equiv.), in THF (150 mL), was added dropwise under N$_2$-atm. The reaction mixture was stirred for 16 h at room temperature. The reaction mixture was quenched with saturated solution of ammonium chloride at 0° C. and extracted into ethyl acetate (twice). The organic layers were collected together, dried over anhydrous sodium sulfate, filtered and concentrated. The crude product was purified by flash column chromatography using silica gel and EtOAc:pet ether to afford (R)-3-(dibenzylamino)-2-fluoropropan-1-ol.

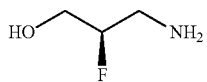

Synthesis of (R)-3-amino-2-fluoropropan-1-ol

To a degassed solution of (R)-3-(dibenzylamino)-2-fluoropropan-1-ol (2 g, 1 equiv.) in ethanol (50 mL), 10% Pd/C (0.2 equiv.) and Pd(OH)$_2$ (0.2 equiv.), were added and the reaction mixture was hydrogenated in an autoclave at 60° C. at 10 Kg (140 psi) pressure for 14 h. The reaction mixture was filtered through CELITE® and the filtrate was concentrated to afford (R)-3-amino-2-fluoropropan-1-ol.

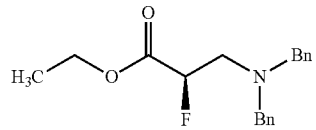 [SMILES: CCOC(=O)[C@H](F)CN(Cc1ccccc1)Cc1ccccc1]

Synthesis of (R)-ethyl 3-(dibenzylamino)-2-fluoropropanoate

Prepared according to the method as described for the synthesis of (R)-methyl 3-(dibenzylamino)-2-fluoropropanoate.

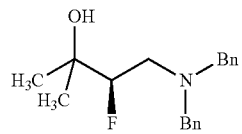

Synthesis of (R)-4-(dibenzylamino)-3-fluoro-2-methylbutan-2-ol

To a solution of (R)-ethyl 3-(dibenzylamino)-2-fluoropropanoate (15 g, 1 equiv.) in THF (150 mL), methyl magnesium bromide (3M in diethyl ether) (15 mL, 2.5 equiv.) was added dropwise at 0° C. under N$_2$ atm. The reaction mixture was slowly allowed to attain room temperature and stirred for 1 h. The reaction mixture was quenched with saturated aqueous ammonium chloride at 0° C. and extracted into ethyl acetate (twice). The organic layers were collected, dried over anhydrous sodium sulfate, filtered and concentrated. The crude product was purified by flash column chromatography using silica gel and EtOAc:pet ether to afford (R)-4-(dibenzylamino)-3-fluoro-2-methylbutan-2-ol. $^1$H NMR: 400 MHz, DMSO-d$_6$: δ 0.92-0.92 (m, 3H), 0.98-0.98 (m, 3H), 2.53-2.94 (m, 2H), 3.51-3.81 (m, 4H), 4.34-4.46 (m, 1H), 4.80 (s, 1H), 7.22-7.40 (m, 10H).

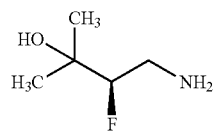

Synthesis of (R)-4-amino-3-fluoro-2-methylbutan-2-ol (R)-4-(dibenzylamino)-3-fluoro-2-methylbutan-2-ol was deprotected using the procedures outlined for the synthesis of (R)-3-amino-2-fluoropropan-1-ol.

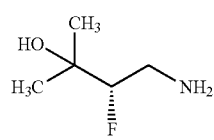

Synthesis of (S)-4-amino-3-fluoro-2-methylbutan-2-ol (S)-4-(Dibenzylamino)-3-fluoro-2-methylbutan-2-ol was prepared in an identical fashion as (R)-4-amino-3-fluoro-2-methylbutan-2-ol starting from D-serine methyl ester.

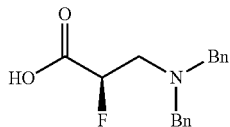

Synthesis of (R)-3-(dibenzylamino)-2-fluoropropanoic Acid

To a solution of (R)-ethyl 3-(dibenzylamino)-2-fluoropropanoate (5.5 g, 1 equiv.) in EtOH (30 mL), LiOH (5 equiv.) dissolved in water (30 mL) was added. The reaction mixture was stirred at room temperature for 12 h. The reaction mixture was concentrated and the residue obtained was dissolved in minimum amount of water and neutralized with 6N HCl resulting in white solid. The precipitate was filtered and dried under vacuum to afford (R)-3-(dibenzylamino)-2-fluoropropanoic acid. LC/MS: Acquity BEH C18 2.1×50 mm, 1.8μ; Solvent A=0.1% TFA in water; Solvent B=0.1% TFA in ACN; gradient 0-100% B over 2 min; retention time: 0.64 min; LCMS (ES-API), m/z 288.8 (M+H).

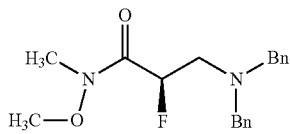

Synthesis of (R)-3-(dibenzylamino)-2-fluoro-N-methoxy-N-methylpropanamide

To a solution of (R)-3-(dibenzylamino)-2-fluoropropanoic acid (1.4 g, 1 equiv.) in DMF (5 mL), N,O-dimethylhydroxylamine.HCl (0.7 g, 1.5 equiv.), EDC.HCl (1.8 g, 2 equiv.) and DIPEA (4.5 mL, 5 equiv.) were added followed by the addition of HOBT (0.65 g, 1 equiv.). The reaction mixture was stirred at room temperature. The reaction mixture was concentrated under reduced pressure to remove excess of DMF and the residue obtained was diluted with ethyl acetate and washed with brine solution followed by water. The organic layer was collected and dried over anhydrous sodium sulfate, filtered and concentrated. The crude material was purified by flash chromatography through silica gel and EtOAC:pet ether as eluent to afford (R)-3-(dibenzylamino)-2-fluoro-N-methoxy-N-methylpropanamide. LC/MS: Acquity BEH C18 2.1×50 mm, 1.8μ; Solvent A=0.1% TFA in water; Solvent B=0.1% TFA in ACN; gradient 0-100% B over 2 min; retention time: 0.71 min; LCMS (ES-API), m/z 331.8 (M+H).

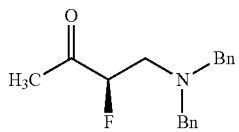

Synthesis of (R)-4-(dibenzylamino)-3-fluorobutan-2-one

A solution of (R)-3-(dibenzylamino)-2-fluoro-N-methoxy-N-methylpropanamide (0.9 g, 1 equiv.) in THF (10 mL) was cooled to 0° C. Methyl magnesium bromide (3 equiv, 3M in diethyl ether) was added to the reaction mixture. After completion of addition the reaction mixture was warmed to room temperature and stirred for 1 h. The reaction was quenched using saturated ammonium chloride solution and extracted with ethyl acetate. The organic layer was collected and dried over anhydrous sodium sulfate, filtered and concentrated to afford the title compound (R)-4-(dibenzylamino)-3-fluorobutan-2-one. LC/MS: Acquity BEH C18 2.1×50 mm, 1.8μ; Solvent A=0.1% TFA in water; Solvent B=0.1% TFA in ACN; gradient 0-100% B over 2 min; retention time: 0.73 min; LCMS (ES-API), m/z 286.8 (M+H).

Synthesis of (R)-1-(dibenzylamino)-2-fluoro-4-methylpentan-3-one and (R)-1-cyclopropyl-3-(dibenzylamino)-2-fluoropropan-1-one These compounds were prepared using the methods described for the synthesis of (R)-4-(dibenzylamino)-3-fluorobutan-2-one using iso-propyl or cyclopropyl Grignard reagents, respectively.

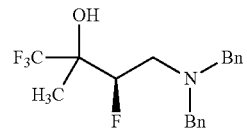 [SMILES: CC(O)([C@H](F)CN(Cc1ccccc1)Cc1ccccc1)C(F)(F)F]

Synthesis of (R)-4-(dibenzylamino)-1,1,1,3-tetrafluoro-2-methylbutan-2-ol

To a solution of (R)-4-(dibenzylamino)-3-fluorobutan-2-one (1.2 g, 1 equiv.) in THF (15 mL), CF$_3$TMS (3 g, 5 equiv.) was added and stirred for 30 min. The reaction mixture was cooled to 0° C. and added TBAF (1M in THF, 21 mL, 5 equiv.) dropwise to the reaction mixture. The reaction mixture was allowed to stir for 16 h at room temperature and quenched with 2 M HCl. The product was extracted into MTBE, and the organic layer was collected and dried over anhydrous sodium sulfate, filtered and concentrated. The crude material was purified by flash chromatography through silica gel and EtOAC:pet ether as eluent to afford the title compound (R)-4-(dibenzylamino)-1,1,1,3-tetrafluoro-2-methylbutan-2-ol as a mixture of diastereomers. LC/MS: Acquity BEH C18 2.1×50 mm, 1.8μ; Solvent A=0.1% TFA in water; Solvent B=0.1% TFA in ACN; gradient 0-100% B over 2 min; retention time: 0.77 min; LCMS (ES-API), m/z 356.8 (M+H).

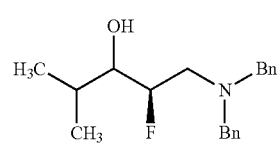 [SMILES: CC(C)C(O)[C@H](F)CN(Cc1ccccc1)Cc1ccccc1]

Synthesis of (2R)-1-(dibenzylamino)-2-fluoro-4-methylpentan-3-ol

To (R)-1-(dibenzylamino)-2-fluoro-4-methylpentan-3-one (0.9 g, 1 equiv.) in THF:MeOH (2:1) (10 mL), NaBH$_4$ (0.2 g, 2 equiv.) was added in portions at 0° C. and allowed to stir for 1 h. The reaction was quenched with saturated NH$_4$Cl solution at ambient temperature and concentrated under reduced pressure to remove excess of solvent. The residue obtained was diluted with ethyl acetate and washed with water. The organic layer was collected and dried over anhydrous sodium sulfate, filtered and concentrated. The material obtained was washed with diethyl ether and dried under vacuum to afford (2R)-1-(dibenzylamino)-2-fluoro-4-methylpentan-3-ol as a mixture of diastereomers. LC/MS: Acquity BEH C18 2.1×50 mm, 1.8μ; Solvent A=0.1% TFA in water; Solvent B=0.1% TFA in ACN; gradient 0-100% B over 2 min; retention time: 0.76 min; LCMS (ES-API), m/z 316.8 (M+H).

Synthesis of (2R)-1-cyclopropyl-3-(dibenzylamino)-2-fluoropropan-1-ol and (3R)-4-(dibenzylamino)-3-fluorobutan-2-ol These compounds were prepared using the methods described for the synthesis of (2R)-1-(dibenzylamino)-2-fluoro-4-methylpentan-3-ol starting from (R)-1-cyclopropyl-3-(dibenzylamino)-2-fluoropropan-1-one and (R)-4-(dibenzylamino)-3-fluorobutan-2-one.

Synthesis of (3R)-2-cyclopropyl-4-(dibenzylamino)-1,1,1,3-tetrafluorobutan-2-ol This compound was prepared using the method described for the synthesis of compound no. (R)-4-(dibenzylamino)-1,1,1,3-tetrafluoro-2-methylbutan-2-ol starting from (R)-1-cyclopropyl-3-(dibenzylamino)-2-fluoropropan-1-one.

Synthesis of (3R)-4-amino-1,1,1,3-tetrafluoro-2-methylbutan-2-ol, (2R)-1-amino-2-fluoro-4-methylpentan-3-ol, (2R)-3-amino-1-cyclopropyl-2-fluoropropan-1-ol, (3R)-4-amino-3-fluorobutan-2-ol, (3R)-4-amino-2-cyclopropyl-1,1,1,3-tetrafluorobutan-2-ol These compounds were prepared using the benzyl deprotection method described for the synthesis of (R)-3-amino-2-fluoropropan-1-ol.

(3R)-4-Amino-1,1,1,3-tetrafluoro-2-methylbutan-2-ol

LC/MS: ELSD method. Retention time: 1.804 min; LCMS (ES-API), m/z 175.6 (M−H).

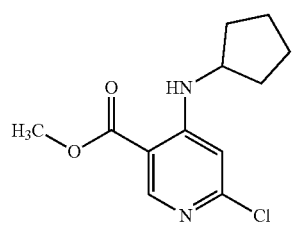 [SMILES: COC(=O)c1cnc(Cl)cc1NC1CCCC1]

Step 1: Methyl 6-chloro-4-(cyclopentylamino)nicotinate

The compound was prepared using the method described for the synthesis of ethyl 6-chloro-4-(isopropylamino)nicotinate starting from methyl 4,6-dichloronicotinate.

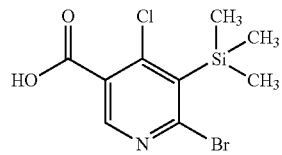

Step 1

A solution of 2,2,6,6-tetramethylpiperidine (23.5 g, 160 mmol) in (THF 250 mL) was cooled to −78° C. under a nitrogen atmosphere. Butyl lithium (9.7 g, 151 mmol) was added dropwise and then allowed to stir at 0° C. for 45 min. The LTMP solution was then cooled to −78° C. and treated dropwise with a solution of 2-bromo-4-fluoro-3-(trimethylsilyl)pyridine (20 g, 76 mmol) in THF (50 mL). The reaction mixture was stirred at −78° C. for 3.5 h and then quenched with dry ice under a nitrogen atmosphere. The reaction mixture was acidified with 5% H$_2$SO$_4$ solution and the aqueous layer was extracted twice with EtOAc. The separated organic layer was dried (Na$_2$SO$_4$) and concentrated to afford the crude product (6-chloro-4-fluoro-5-(trimethylsilyl)nicotinic acid (18.7 g, 80% yield) as a brown oil. This crude product was used directly in the next step. $^1$H NMR (400 MHz, CDCl$_3$) δ 8.66 (s, 1H), 0.59 (s, 9H).

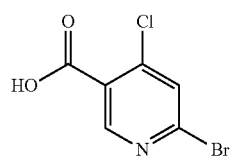 [SMILES: O=C(O)c1cnc(Br)cc1Cl]

Step 2

To solution of 6-chloro-4-bromo-5-(trimethylsilyl)nicotinic acid (4 g, 13 mmol) in MeOH (100 mL) and was added K$_2$CO$_3$ (4 g, 29 mmol). The reaction mixture was stirred at room temperature for 2 h. The reaction mixture was slowly added to ice then acidified with 10% H$_2$SO$_4$. The aqueous layer was extracted twice with EtOAc (50 mL). The separated organic layer was dried (Na$_2$SO$_4$) and concentrated to afford the crude product 6-chloro-4-bromonicotinic acid (2.3 g, 75% yield). LCMS m/z 233.9 (M)+; $^1$H NMR (400 MHz, DMSO-d$_6$) δ 14.05 (br s, 1H), 8.77 (s, 1H), 8.06 (s, 1H).

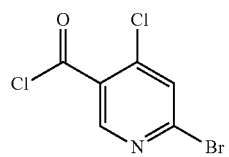 [SMILES: O=C(Cl)c1cnc(Br)cc1Cl]

Step 3

A suspension of 6-bromo-4-chloronicotinic acid (5 g, 21.15 mmol) in DCM (75 mL) was cooled to 0° C. Oxalyl chloride (3.70 ml, 42.3 mmol) was added and the reaction mixture was heated at 50° C. for 1 h. The reaction mixture was cooled to room temperature and the excess oxalyl chloride and DCM was removed by distillation to obtain the acid chloride as a brown oil which was used directly in the next step.

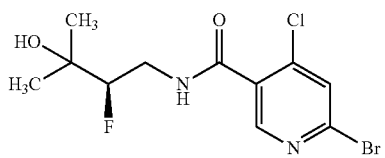 [SMILES: CC(C)(O)[C@H](F)CNC(=O)c1cnc(Br)cc1Cl]

Step 4

(R)-4-Amino-3-fluoro-2-methylbutan-2-ol (2.82 g, 23.26 mmol) in DCM (25 mL) was added TEA (8.84 mL, 63.4 mmol) at 0° C. The acid chloride prepared above was dissolved in DCM (75 mL) and added dropwise at 0° C. to the amine solution. The reaction mixture was stirred for 30 min and allowed to warm to room temperature for 30 min. The reaction mixture was diluted with DCM (150 mL) and washed with water and brine. The organic layer was dried over $Na_2SO_4$, filtered and concentrated to give (R)-6-bromo-4-chloro-N-(2-fluoro-3-hydroxy-3-methylbutyl)nicotinamide (2.7 g, 7.95 mmol, 37.6% yield) as a brown oil. The residue was purified via column chromatography (pet ether: EA, 15-20%). $^1$H NMR (400 MHz, DMSO-$d_6$) δ 8.90 (t, J=5.6 Hz, 1H), 8.47 (s, 1H), 7.91 (s, 1H), 4.84 (s, 1H), 4.31 (ddd, J=49.6, 8.4, 2.0 Hz, 1H), 3.77 (ddd, J=38.4, 14.8, 6.0 Hz, 1H), 3.69 (m, 1H), 1.17 (s, sH), 1.15 (s, 3H).

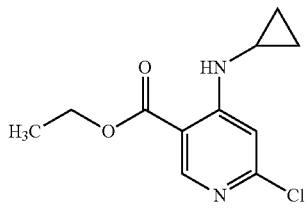 [SMILES: CCOC(=O)c1cnc(Cl)cc1NC1CC1]

To a solution of ethyl 4,6-dichloronicotinate (50 g, 227 mmol) in DMA (500 mL) was added DIPEA (39.7 mL, 227 mmol) and cyclopropyl amine (17.6 mL, 250 mmol). The mixture was then heated at 90° C. for 5 h. The reaction mixture was quenched into crushed ice with stirring. The resulting slurry was stirred and filtered to afford the crude product (42 g, 91% yield) which was used without further purification. LCMS m/z 241.1 (M+H)$^+$. $^1$H NMR (400 MHz, DMSO-$d_6$) δ 8.54 (s, 1H), 8.09 (s, 1H), 7.03 (s, 1H), 4.29 (q, J=7.2 Hz, 2H), 2.61 (m, 1H), 1.31 (t, J=7.2 Hz, 3H), 0.86 (m, 2H), 0.58 (m, 2H).

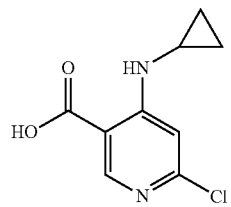 [SMILES: O=C(O)c1cnc(Cl)cc1NC1CC1]

To a solution of ethyl 6-chloro-4-(cyclopropylamino) nicotinate (2 g, 8.31 mmol) in EtOH (14 mL), was added LiOH.H$_2$O (1.02 g, 25 mmol) and water (6 mL, 8.31 mmol). The reaction mixture was stirred at room temperature for 1 h. The solvents were removed in vacuo and the pH adjusted to 3-4 with 1.5 N HCl. The resulting solid was filtered and dried to afford 6-chloro-4-(cyclopropylamino)nicotinic acid (1.5 g, 82% yield) as a white solid. LCMS m/z 213.2 (M+H)$^+$.

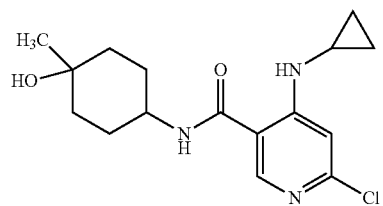 [SMILES: CC1(O)CCC(NC(=O)c2cnc(Cl)cc2NC2CC2)CC1]

To a stirred solution of 6-chloro-4-(cyclopropylamino) nicotinic acid (0.30 g, 1.4 mmol) in DMF (5 mL) was added HATU (0.644 g, 1.7 mmol), DIPEA (0.74 mL, 4.23 mmol) and (1R,4R)-4-amino-1-methylcyclohexanol (0.219 g, 1.693 mmol). The mixture was stirred for 3 hours at room temperature. The DMF was evaporated from the reaction mixture and the residue was partitioned with water and EtOAc. The organic layer was washed with cold water (3 times). The organic layer was dried over Na$_2$SO$_4$ and concentrated under vacuum to get crude compound which was then purified by flash column chromatography (10% MeOH/DCM) to afford 6-chloro-4-(cyclopropylamino)-N-(4-hydroxy-4-methylcyclohexyl)nicotinamide (310 mg, 63% yield). LCMS m/z 324.2 (M+H)$^+$.

Step 4

A solution of 6-chloro-4-(cyclopropylamino)-N-(4-hydroxy-4-methylcyclohexyl)nicotinamide (0.100 g, 0.309 mmol) in dioxane (10 mL) was added benzo[d]thiazol-6-amine (0.056 g, 0.37 mmol), Xantphos (0.071 g, 0.124 mmol) and sodium carbonate (0.131 g, 1.24 mmol). The solution was purged with N$_2$ for 10 mins. Tris(dibenzylideneacetone)dipalladium(0) (0.113 g, 0.124 mmol) was added and the mixture purged with N$_2$ for an additional 10 min. The reaction mixture was heated at 110° C. for 18 h. The mixture was cooled to room temperature and diluted with EtOAc. The mixture was filtered through CELITE® and concentrated to a residue which was purified via preparative HPLC to afford 6-(benzo[d]thiazol-6-ylamino)-4-(cyclopropylamino)-N-(4-hydroxy-4-methylcyclohexyl)nicotinamide (7 mg, 5% yield).

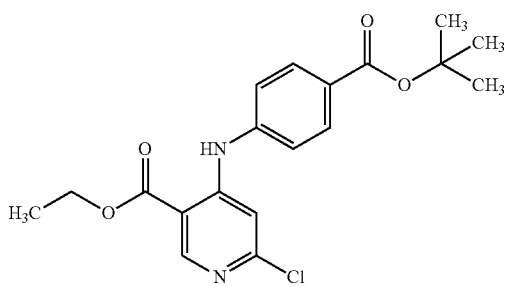 [SMILES: CCOC(=O)c1cnc(Cl)cc1Nc1ccc(C(=O)OC(C)(C)C)cc1]

Step 1: Synthesis of ethyl 4-(4-(tert-butoxycarbonyl)phenylamino)-6-chloronicotinate Followed the same method outlined for the synthesis of Example 5, Step 1 using ethyl 4,6-dichloronicotinate and tert-butyl 4-aminobenzoate. LC/MS: PUROSPHER® Star RP-18, 4×55 mm, 3 μm; Solvent A=10% ACN: 90% $H_2O$: 20 mM $NH_4OAc$; Solvent B=90% ACN: 10% $H_2O$: 20 mM $NH_4COOAc$; gradient 0-100% B over 1.5 min (3.2 min run time); retention time: 2.525 min; LCMS (ES-API), m/z 377.0 (M+H).

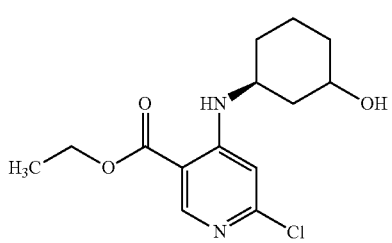 [SMILES: CCOC(=O)c1cnc(Cl)cc1N[C@H]1CCCC(O)C1]

Step 1: Synthesis of ethyl 6-chloro-4-(3-hydroxycyclohexylamino)nicotinate

Followed the same method outlined for the synthesis of Example 5, Step 1 using ethyl 4,6-dichloronicotinate and (3S)-3-aminocyclohexanol. LC/MS: ZORBAX® SB C18, 4.6×50 mm, 5 μm; Solvent A=10% MeOH: 90% $H_2O$: 0.1% TFA; Solvent B=90% MeOH: 10% $H_2O$: 0.1% TFA; gradient 0-100% B over 2 min (3 min run time); retention time: 1.65 min; LCMS (ES-API), m/z 299.0 (M+H).

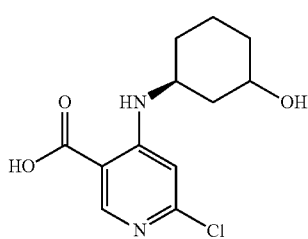 [SMILES: O=C(O)c1cnc(Cl)cc1N[C@H]1CCCC(O)C1]

Step 2: Synthesis of 6-chloro-4-((1S)-3-hydroxycyclohexylamino)nicotinic Acid Followed the same method described for the synthesis of Example 5, Step 3 using 6-chloro-4-(3-hydroxycyclohexylamino)nicotinate. LC/MS: ZORBAX® SB C18, 4.6×50 mm, 5 μm; Solvent A=10% MeOH: 90% $H_2O$: 0.1% TFA; Solvent B=90% MeOH: 10% $H_2O$: 0.1% TFA; gradient 0-100% B over 2 min (3 min run time); retention time: 1.095 min; LCMS (ES-API), m/z 271.0 (M+H).

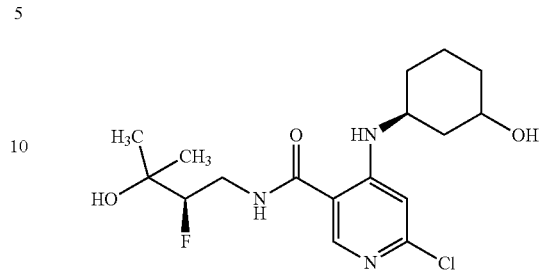

Step 3: Synthesis of 6-chloro-N-(2-fluoro-3-hydroxy-3-methylbutyl)-4-((1S)-3-hydroxycyclohexylamino)nicotinamide Followed the method described for the synthesis of Example 5, Step 4, using (R)-4-amino-3-fluoro-2-methylbutan-2-ol and 6-chloro-4-((1S)-3-hydroxycyclohexylamino) nicotinic acid.

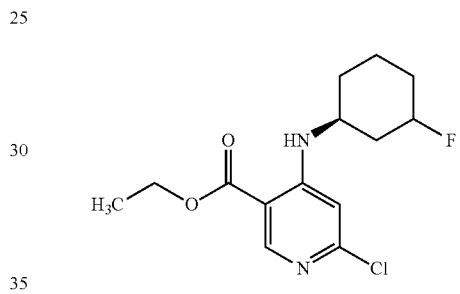

Step 1: Synthesis of ethyl 6-chloro-4-((1S)-3-fluorocyclohexylamino)nicotinate A solution of ethyl 6-chloro-4-((3-hydroxycyclohexyl) amino)nicotinate (0.3 g, 1 equiv.) in DCM (10 mL) was cooled to −78° C. and stirred for 5 min. Xtal-Fluoro-E (1.2 equiv.) was added to the reaction mixture. After completion of addition the reaction mixture was stirred for 5 min. The reaction mixture was quenched with saturated solution of $NH_4Cl$ at −78° C. and extracted with DCM (twice). The organic layers were collected together, dried over anhydrous sodium sulfate and concentrated. The crude material obtained was purified via column chromatography (EtOAc: pet ether) to afford ethyl 6-chloro-4-((1S)-3-fluorocyclohexylamino)nicotinate. LC/MS: ZORBAX® SB C18, 4.6× 50 mm, 5 μm; Solvent A=10% MeOH: 90% $H_2O$: 0.1% TFA; Solvent B=90% MeOH: 10% $H_2O$: 0.1% TFA; gradient 0-100% B over 2 min (3 min run time); retention time: 1.981 min; LCMS (ES-API), m/z 301 (M+H).

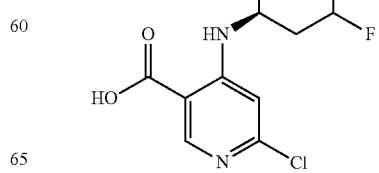

Step 2: Synthesis of 6-chloro-4-((1S)-3-fluorocyclohexylamino)nicotinic Acid

Followed the same method described for the synthesis of Example 5, Step 3 using 6-chloro-4-((1S)-3-fluorocyclohexylamino)nicotinate. LC/MS: ZORBAX® SB C18, 4.6× 50 mm, 5 μm; Solvent A=10% MeOH: 90% H₂O: 0.1% TFA; Solvent B=90% MeOH: 10% H₂O: 0.1% TFA; gradient 0-100% B over 2 min (3 min run time); retention time: 1.393 min; LCMS (ES-API), m/z 273.0 (M+H).

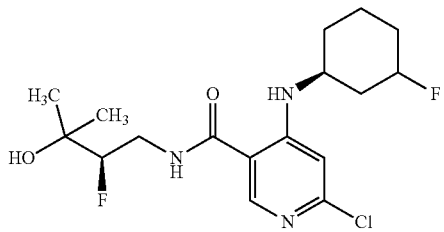 [SMILES: CC(C)(O)[C@H](F)CNC(=O)c1cnc(Cl)cc1N[C@H]1CCCC(F)C1]

Step 3: Synthesis of 6-chloro-N-(2-fluoro-3-hydroxy-3-methylbutyl)-4-((1S)-3-fluorocyclohexylamino)nicotinamide Followed the method described for the synthesis of Example 5, Step 4, using (R)-4-amino-3-fluoro-2-methylbutan-2-ol and 6-chloro-4-((1S)-3-fluorocyclohexylamino)nicotinic acid.

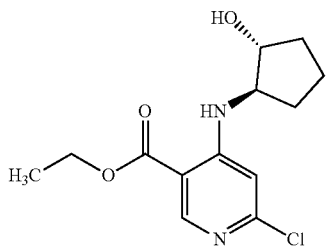 [SMILES: CCOC(=O)c1cnc(Cl)cc1N[C@@H]1CCC[C@H]1O]

Step 1: Synthesis of ethyl 6-chloro-4-((1R,2R)-2-hydroxycyclopentylamino)nicotinate)

Followed the same method outlined for the synthesis of Example 5, Step 1 using ethyl 4,6-dichloronicotinate and (1R,2R)-2-aminocyclopentanol. LC/MS: Ascentis Express C18, 5×2.1 mm, 2.7 μm; Solvent A=2% ACN: 98% H₂O: 10 mM NH₄COOH; Solvent B=98% ACN: 2% H₂O: 10 mM NH₄COOH; gradient 0-100% B over 1.5 min; retention time: 1.786 min; LCMS (ES-API), m/z 285.2 (M+H).

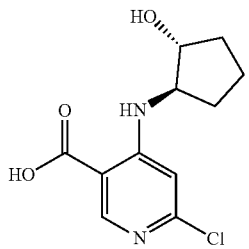 [SMILES: O=C(O)c1cnc(Cl)cc1N[C@@H]1CCC[C@H]1O]

Step 2

Ethyl 6-chloro-4-(((1R,2R)-2-hydroxycyclopentyl)amino)nicotinate (1.3 g, 4.57 mmol) in THF (10 mL), MeOH (4 mL) and water (2 mL) was added LiOH (0.328 g, 13.7 mmol) and stirred at room temperature for 18 h. The organic layer was evaporated and the pH of the crude mixture was adjusted to 6 with 1.5N HCl to precipitate the crude acid. The solids were filtered and dried under vacuum to afford 6-chloro-4-(((1R,2R)-2-hydroxycyclopentyl)amino)nicotinic acid (0.95 mg, 81% yield). LCMS (ES-API), m/z 257.4 (M+H).

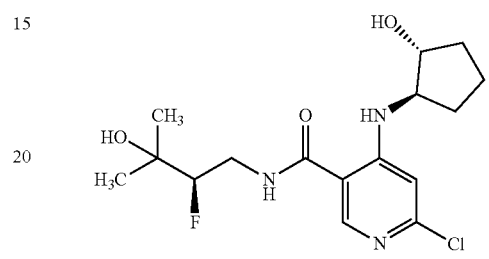

Step 3

A solution of 6-chloro-4-(((1R,2R)-2-hydroxycyclopentyl)amino)nicotinic acid (900 mg, 3.51 mmol) in DMF (10 mL) and (R)-4-amino-3-fluoro-2-methylbutan-2-ol (425 mg, 3.51 mmol) was added HATU (1333 mg, 3.51 mmol) and DIPEA (0.612 mL, 3.51 mmol). The reaction mixture was allowed to stir for 18 h at room temperature. The DMF was removed under vacuum and the crude mass was diluted with water and extracted with ethylacetate. The ethylacetate layer was washed with NaHCO₃, then dried and concentrated to give 1.4 g crude mass which was purified by column chromatography (CHCl₃:MeOH:9.5/0.5) to provide the product. LCMS m/z 360.5 (M+H).

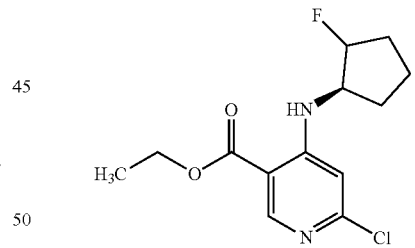

Synthesis of ethyl 6-chloro-4-((1R)-2-fluorocyclopentylamino)nicotinate

A solution of ethyl 6-chloro-4-(((2S)-2-hydroxycyclopentyl)amino)nicotinate (1.0 g, 1 equiv.) in DCM (15 mL) was cooled to ° C. DAST (0.7 mL, 1.5 equiv.) was added dropwise. The reaction mixture was stirred overnight at room temperature. The reaction mixture was again cooled to 0° C. and quenched with 10% NaHCO₃ solution. The product was extracted in DCM. The aqueous layer was washed with DCM (twice). The organic extracts were combined, dried over anhydrous sodium sulfate, filtered and concentrated. The crude product was purified by flash column chromatography using silica gel and EtOAc:pet ether to obtain the desired product. LC/MS: Ascentis Express C18, 5×2.1 mm, 2.7 μm; Solvent A=2% ACN: 98% H₂O: 10 mM NH₄COOH; Solvent B=98% ACN: 2% H₂O: 10 mM NH₄COOH; gradient 0-100% B over 1.5 min; retention time: 2.013 min; LCMS (ES-API), m/z 287.2 (M+H).

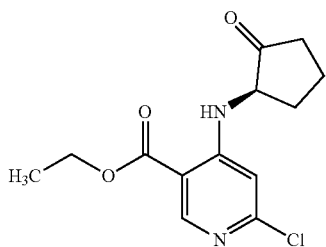 [SMILES: CCOC(=O)c1cnc(Cl)cc1N[C@@H]1CCCC1=O]

Synthesis of (R)-ethyl 6-chloro-4-(2-oxocyclopentylamino)nicotinate

A solution of ethyl 6-chloro-4-(((2S)-2-hydroxycyclopentyl)amino)nicotinate (0.5 g, 1 equiv.) in DCM (20 mL) was added Dess-Martin Periodinane (2.98 g, 4 equiv.) and the reaction mixture was stirred at room temperature for 10 min. The reaction mixture was concentrated and the residue was dissolved in ethyl acetate and filtered through a bed of CELITE®. The filtrate was concentrated. The crude product was purified by flash column chromatography using silica gel and EtOAc:pet ether to obtain the desired product. LC/MS: Ascentis Express C18, 5×2.1 mm, 2.7 m; Solvent A=2% ACN: 98% H₂O: 10 mM NH₄COOH; Solvent B=98% ACN: 2% H₂O: 10 mM NH₄COOH; gradient 0-100% B over 1.5 min; retention time: 1.863 min; LCMS (ES-API), m/z 283.2 (M+H).

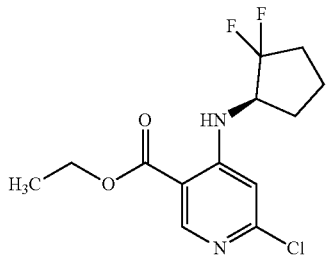 [SMILES: CCOC(=O)c1cnc(Cl)cc1N[C@@H]1CCCC1(F)F]

Synthesis of (R)-ethyl 6-chloro-4-(2,2-difluorocyclopentylamino)nicotinate

Ethyl 6-chloro-4-((2-oxocyclopentyl)amino)nicotinate (0.57 g, 1 equiv.) in DCM (10 mL) was cooled to 0° C. DAST (0.67 mL, 2.5 equiv.) was added dropwise to the reaction mixture and allowed to overnight at room temperature. The reaction mixture was diluted with DCM, quenched with 10% NaHCO₃ at 0° C. The organic layer was collected, dried over anhydrous sodium sulfate, filtered and concentrated. The crude product was purified by flash column chromatography using silica gel and EtOAc:pet ether to obtain the desired product. LC/MS: PUROSPHER® Star RP-18, 4×55 mm, 3 μm; Solvent A=10% ACN: 90% H₂O: 20 mM NH₄OAc; Solvent B=90% ACN: 10% H₂O: 20 mM NH₄COOAc; gradient 0-100% B over 1.5 min (3.2 min run time); retention time: 2.017 min; LCMS (ES-API), m/z 305 (M+H).

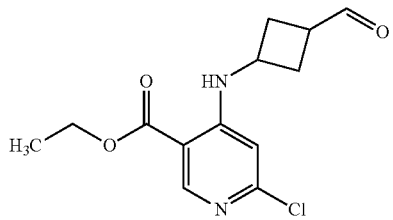 [SMILES: CCOC(=O)c1cnc(Cl)cc1NC1CC(C=O)C1]

Step 1: Synthesis of ethyl 6-chloro-4-(3-formylcyclobutylamino)nicotinate

To a solution of ethyl 6-chloro-4-((3-(hydroxymethyl)cyclobutyl)amino)nicotinate (0.6 g, 1 equiv.) in DCM (35 mL) was added Dess-Martin Periodinane (3.57 g, 4 equiv.) at 0° C. and the reaction mixture was stirred at room temperature for 30 min. The reaction mixture was concentrated. The residue was dissolved in ethyl acetate, filtered through a CELITE® bed, and washed with ethyl acetate. The filtrate was collected and washed with 10% NaHCO₃ solution. The organic layer was collected, dried over anhydrous sodium sulfate, filtered and concentrated. The crude material was purified by flash chromatography using EtOAc: pet ether as eluent to afford ethyl 6-chloro-4-(3-formylcyclobutylamino)nicotinate. LC/MS: PUROSPHER® Star RP-18, 4×55 mm, 3 μm; Solvent A=10% ACN: 90% H₂O: 20 mM NH₄OAc; Solvent B=90% ACN: 10% H₂O: 20 mM NH₄COOAc; gradient 0-100% B over 1.5 min (3.2 min run time); retention time: 1.54 min; LCMS (ES-API), m/z 281.2 (M−H).

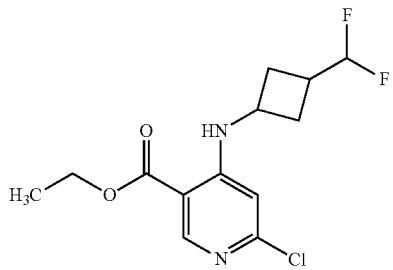 [SMILES: CCOC(=O)c1cnc(Cl)cc1NC1CC(C(F)F)C1]

Step 2: Synthesis of ethyl 6-chloro-4-(3-(difluoromethyl)cyclobutylamino)nicotinate A solution of ethyl 6-chloro-4-((3-formylcyclobutyl)amino)nicotinate (0.11 g, 0.389 mmol) in DCM (5 mL) was cooled to −10° C. DAST (0.103 mL, 0.78 mmol) was added dropwise to the reaction mixture and stirred at room temperature for 5 h. The reaction mixture was quenched with sat NaHCO₃ solution at 0° C. The product was extracted into DCM and the organic extracts collected, dried over anhydrous sodium sulfate, filtered and concentrated. The crude material was purified by flash chromatography using EtOAc: pet ether as eluent to afford ethyl 6-chloro-4-(3-(difluoromethyl)cyclobutylamino)nicotinate. LC/MS: PUROSPHER® Star RP-18, 4×55 mm, 3 μm; Solvent A=10% ACN: 90% H₂O: 20 mM NH₄OAc; Solvent B=90% ACN: 10% H₂O: 20 mM NH₄COOAc; gradient 0-100% B over 1.5 min (3.2 min run time); retention time: 1.975 min; LCMS (ES-API), m/z 305.0 (M+H).

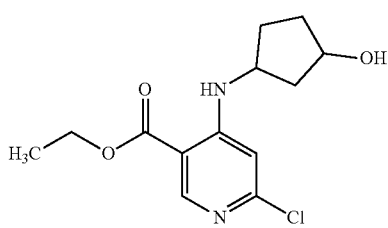 [SMILES: CCOC(=O)c1cnc(Cl)cc1NC1CCC(O)C1]

Step 1: Synthesis of ethyl 6-chloro-4-((1S)-3-hydroxycyclopentylamino)nicotinate This intermediate was prepared from 3-aminocyclopentanol and ethyl 4,6-dichloronicotinate following the standard procedures outlined in Example 5. LC/MS: Acquity BEH C18 2.1×50 mm, 1.8μ; Solvent A=0.1% TFA in water; Solvent B=0.1% TFA in ACN; gradient 0-100% B over 2 min; retention time: 0.70 min; LCMS (ES-API), m/z 285.1 (M+H).

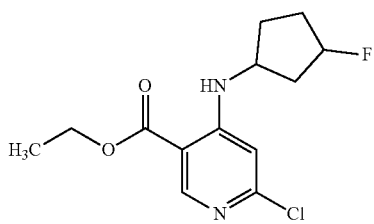 [SMILES: CCOC(=O)c1cnc(Cl)cc1NC1CCC(F)C1]

Step 2: Synthesis of ethyl 6-chloro-4-((1S)-3-fluorocyclopentylamino)nicotinate This intermediate was prepared from the reaction of ethyl 6-chloro-4-(3-hydroxycyclopentylamino)nicotinate and DAST according to the methods outlined for the preparation of ethyl 6-chloro-4-((1R)-2-fluorocyclopentylamino)nicotinate. LC/MS: XBridge Phe 8, ☐4.6×30 mm, 3.5 μm; Solvent A=2% ACN: 98% H₂O: 10 mM NH₄COOH; Solvent B=98% ACN: 2% H₂O: 10 mM NH₄COOH; gradient 0-100% B over 1.5 min (3.2 min run time); retention time: 1.165 min; LCMS (ES-API), m/z 287.0 (M+H).

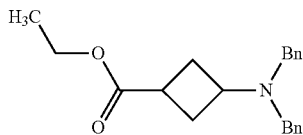 [SMILES: CCOC(=O)C1CC(N(Cc2ccccc2)Cc2ccccc2)C1]

Synthesis of ethyl 3-(dibenzylamino)cyclobutanecarboxylate

Ethyl 3-oxocyclobutanecarboxylate (5.0 g, 1 equiv.) was dissolved in a mixture of 10% aqueous acetic acid (25 mL) and THF (25 mL). Sodium triacetoxyborohydride (14.9 g, 2 equiv.) and dibenzylamine (6.94 g, 1 equiv.) were added sequentially. The reaction mixture was stirred for 14 h at room temperature. The reaction mixture was then concentrated to remove the excess solvent and the residue was dissolved in DCM, washed with water followed by 10% aq NaHCO₃ and brine solution. The organic layer was collected and dried over anhydrous sodium sulfate, filtered and concentrated. The crude product was purified by flash chromatography using silica gel and EtOAc:pet ether as eluent to obtain the required product. ¹H NMR 400 MHz, CD₃OD: δ 1.22-1.26 (m, 3H), 2.03-2.12 (m, 2H), 2.19-2.26 (m, 2H), 2.69-2.71 (m, 1H), 3.11-3.15 (m, 1H), 3.51 (d, J=2.40 Hz, 4H), 4.11 (q, J=7.20 Hz, 2H), 7.22-7.34 (m, 10H).

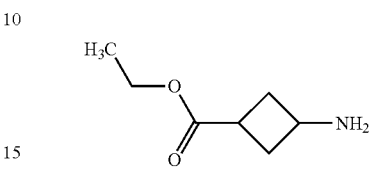

Synthesis of ethyl 3-aminocyclobutanecarboxylate

Ethyl 3-(dibenzylamino)cyclobutane carboxylate (1.0 g, 1 equiv.) dissolved in a mixture of ethanol (48 mL), water (3 mL) and acetic acid (0.2 mL) was degassed with N₂. To the reaction mixture 10% Pd/C (0.5 g, 1.1 equiv.) was added in an inert condition. The reaction mixture was hydrogenated in an autoclave at 42 psi at room temperature for 18 h. The reaction mixture was filtered through CELITE® and concentrated to obtain ethyl 3-aminocyclobutanecarboxylate. ¹H NMR 400 MHz, CD₃OD: δ 1.29-1.30 (m, 3H), 2.23-2.29 (m, 2H), 2.56-2.63 (m, 2H), 2.96-3.01 (m, 1H), 3.63-3.67 (m, 1H), 4.16 (q, J=7.20 Hz, 2H).

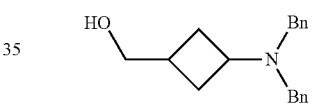

Synthesis of (3-(dibenzylamino)cyclobutyl)methanol

A solution of ethyl 3-(dibenzylamino)cyclobutanecarboxylate (4.0 g, 1 equiv.) in THF (50 mL) was cooled to −10° C. Lithium borohydride (0.404 g, 1.5 equiv.) was added to the reaction mixture in portions. After the addition was complete the reaction mixture was allowed to warm to room temperature and stirred for 18 h. The reaction mixture was diluted with ethyl acetate, cooled to 0° C. and quenched using a saturated solution of NH₄Cl. The organic layer was collected and dried over anhydrous sodium sulfate, filtered and concentrated. The crude product was purified by flash chromatography using silica gel and EtOAc:pet ether as eluent to obtain the required product (3-(dibenzylamino) cyclobutyl)methanol. LC/MS: PUROSPHER® Star RP-18, 4×55 mm, 3 μm; Solvent A=10% ACN: 90% H₂O: 20 mM NH₄OAc; Solvent B=90% ACN: 10% H₂O: 20 mM NH₄COOAc; gradient 0-100% B over 1.5 min (3.2 min run time); retention time: 1.955 min; LCMS (ES-API), m/z 282.2 (M+H).

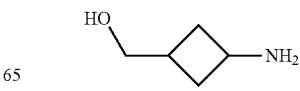

Synthesis of (3-aminocyclobutyl)methanol

Using the reduction procedure described for the preparation of ethyl 3-aminocyclobutanecarboxylate, (3-aminocyclobutyl)methanol was obtained from (3-(dibenzylamino)cyclobutyl)methanol. ¹H NMR 400 MHz, CD₃OD: δ 3.61-3.66 (m, 1H), 3.55 (d, J=5.20 Hz, 2H), 3.33-3.34 (m, 2H), 2.40-2.47 (m, 2H), 2.22-2.38 (m, 2H), 1.92-1.98 (m, 3H).

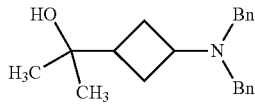 [SMILES: CC(C)(O)C1CC(N(Cc2ccccc2)Cc2ccccc2)C1]

Synthesis of 2-(3-(dibenzylamino)cyclobutyl)propan-2-ol

Ethyl 3-(dibenzylamino)cyclobutanecarboxylate (1.5 g, 4.6 mmol) was dissolved in THF (30 mL) and cooled to −50° C. Methyl magnesium bromide (1.6 mL, 13.9 mmol) was added dropwise and the mixture was stirred at room temperature for 20 h. TLC indicated partial conversion. The reaction mixture was again cooled to −15° C. and an additional 3 eq of methyl magnesium bromide (1.603 mL, 13.91 mmol) was added and the reaction mixture was stirred at room temperature for 3 h. The reaction mixture was cooled to 0° C. and quenched with sat NH₄Cl solution. The aqueous layer was extracted with ethylacetate (3 times) and the combined organic extracts were dried over Na₂SO₄, filtered and concentrated to obtain a liquid as the crude product. The crude product was purified by column chromatography (EA/pet ether 15%) to obtain 2-(3-(dibenzylamino)cyclobutyl)propan-2-ol (1.4 g, 88% yield) as a colorless liquid. LC/MS: PUROSPHER® Star RP-18, 4×55 mm, 3 μm; Solvent A=10% ACN: 90% H₂O: 20 mM NH₄OAc; Solvent B=90% ACN: 10% H₂O: 20 mM NH₄COOAc; gradient 0-100% B over 1.5 min (3.2 min run time); retention time: 2.201 min; LCMS (ES-API), m/z 310.2 (M+H).

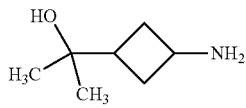

Synthesis of 2-(3-aminocyclobutyl)propan-2-ol 2-(3-(dibenzylamino)cyclobutyl)propan-2-ol (1.6 g, 5.17 mmol) was dissolved in ethanol (45 mL) and added 10% Pd—C (0.8 g, 7.52 mmol), AcOH (4.8 mL) and water (0.32 mL) was added. The reaction mixture was than hydrogenated in an autoclave at 3 kg psi for 18 h. The reaction mixture was filtered through CELITE®, washed with MeOH, and concentrated to obtain a colorless liquid as the product (0.63 g, 94% yield). LCMS m/z 130.1 (M+H); ¹H NMR 400 MHz, CD₃OD: δ 3.53-3.57 (m, 1H), 2.29-2.35 (m, 2H), 2.13-2.20 (m, 1H), 2.02-2.07 (m, 2H), 1.12-1.18 (m, 6H).

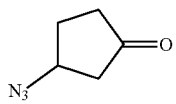

Synthesis of 3-azidocyclopentanone

A solution of cyclopent-2-enone (10 g, 1 equiv.) in DCM (100 mL) and AcOH (35 mL, 5 equiv.) at 0° C. was added trimethyl silyl azide (81 mL, 5 equiv.) followed of TEA (3.4 mL, 0.2 equiv.). The reaction mixture was allowed to stir overnight at room temperature. After complete consumption of the starting material, the reaction was quenched by adding water. The product was extracted into DCM (twice) and the organic layer was collected, dried over anhydrous sodium sulfate, filtered and concentrated to give crude 3-azidocyclopentanone. GCMS: 125 (M): Retention time: 4.445 min.

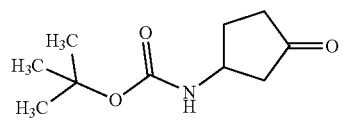

Synthesis of tert-butyl 3-oxocyclopentylcarbamate

A solution of 3-azidocyclopentanone (10 g, 1 equiv.) in EtOAc (80 mL) was added Boc₂O (22.3 mL, 1.2 equiv.). The solution was degassed with N₂ followed by addition of Pd/C (0.850 g, 0.1 equiv.). The reaction mixture was stirred overnight at ambient temperature under H₂ atm (14 psi). The reaction mixture was filtered through CELITE® and the CELITE® bed washed thoroughly with ethyl acetate. The filtrate was concentrated. The residue was triturated with ether:hexane:1:1, filtered and dried to give tert-butyl (3-oxocyclopentyl)carbamate. LC/MS: Ascentis Express C18, 5×2.1 mm, 2.7 μm; Solvent A=2% ACN: 98% H₂O: 10 mM NH₄COOH; Solvent B=98% ACN: 2% H₂O: 10 mM NH₄COOH; gradient 0-100% B over 1.5 min; retention time: 1.6 min; LCMS (ES-API), m/z 200.9 (M+H).

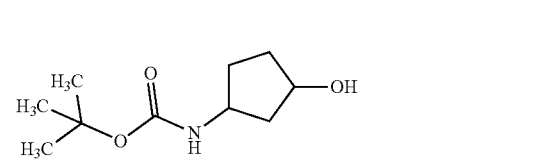

Synthesis of tert-butyl 3-hydroxycyclopentylcarbamate

A solution of tert-butyl (3-oxocyclopentyl)carbamate (2.0 g, 1 equiv.) in MeOH (20 mL) at 0° C. was added NaBH₄ (0.760 g, 2 equiv.). The reaction mixture was stirred for 1 h at room temperature. Methanol was removed under reduced pressure, and the residue was quenched with saturated NH₄Cl and extracted with EtOAc (twice). The organic layer was washed with water and brine, dried over anhydrous sodium sulfate and concentrated. The crude material obtained was purified by column chromatography using silica gel and EtOAc:pet ether as eluent to afford tert-butyl 3-hydroxycyclopentylcarbamate. LC/MS: Ascentis Express C18, 5×2.1 mm, 2.7 μm; Solvent A=2% ACN: 98% H₂O: 10 mM NH₄COOH; Solvent B=98% ACN: 2% H₂O: 10 mM NH₄COOH; gradient 0-100% B over 1.5 min; retention time: 1.6 min; LCMS (ES-API), m/z 201.9 (M+H).

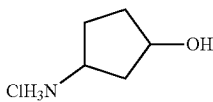

Synthesis of 3-aminocyclopentanol)

A solution of tert-butyl (3-hydroxycyclopentyl)carbamate (1.6 g, 1 equiv.) in DCM (2 mL) was cooled to 0° C. Next, 4 M HCl in dioxane (6 mL) was added to the reaction mixture and stirred for 1 h. Dioxane was removed under vacuum to give 3-aminocyclopentanol hydrochloride. $^1$H NMR 400 MHz, DMSO-d$_6$: δ8.02-8.19 (m, 1H), 4.12-4.23 (m, 2H), 3.43-3.58 (m, 1H), 2.04-2.10 (m, 1H), 1.88-1.94 (m, 2H), 1.66-1.75 (m, 2H), 1.49-1.60 (m, 1H).

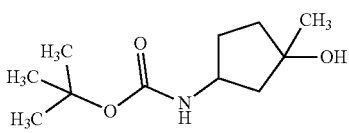

Synthesis of tert-butyl 3-hydroxy-3-methylcyclopentylcarbamate

A solution of tert-butyl (3-oxocyclopentyl)carbamate (0.25 g, 1 equiv.) in THF (10 mL) was cooled 25 to 0° C. Methyl magnesium bromide (3 M in THF) (0.449 g, 3 equiv.) was added and stirred at room temperature for 4 h. After completion of 4 h, the reaction mixture was quenched using sat. NH$_4$Cl solution (20 mL) at 0° C. and stirred at room temperature for 10 min. The product was extracted into ethyl acetate (twice) and the combined organic layers were dried over anhydrous sodium sulfate and concentrated. The crude product was purified by flash column chromatography using silica gel and EtOAc:pet ether to afford tert-butyl (3-hydroxy-3-methylcyclopentyl)carbamate. $^1$H NMR: 400 MHz, DMSO-d$_6$: δ 7.19 (bs, 1H), 4.42 (s, 1H), 3.72-3.85 (m, 1H), 2.08-2.16 (m, 2H), 1.77-1.99 (m, 2H), 1.50-1.66 (m, 2H), 1.33-1.45 (m, 9H), 1.16-1.21 (m, 3H).

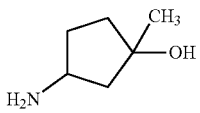

Synthesis of 3-amino-1-methylcyclopentanol

A solution of tert-butyl (3-hydroxy-3-methylcyclopentyl) carbamate (0.12 g) in DCM (10 mL) was treated with methanol hydrochloride (10 mL) at 0° C. The reaction mixture was stirred at room temperature for 4 h. After complete consumption of the starting material the reaction mixture was concentrated. The material obtained was azeotroped with MeOH (twice) and concentrated under reduced pressure to provide 3-amino-1-methylcyclopentanol.

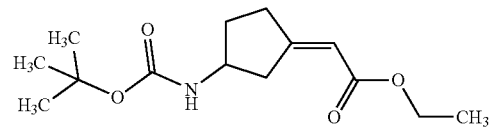 [SMILES: CCOC(=O)/C=C1/CCC(NC(=O)OC(C)(C)C)C1]

Synthesis of ethyl 2-(3-(tert-butoxycarbonylamino)cyclopentylidene)acetate

To a stirred suspension of NaH (72.3 mg, 1.2 equiv.) in THF (10 mL) at 0° C. was added triethyl phosphonoacetate (0.55 mL, 1.1 equiv.) in THF (5 mL) and allowed to stir for 30 min. tert-Butyl (3-oxocyclopentyl)carbamate (500 mg, 1 equiv.) in THF (5 mL) was added to the reaction mixture at 0° C. The reaction mixture was allowed to slowly warm to room temperature and stir for 12 h. The reaction mixture was then concentrated and the residue was diluted with EtOAc and washed with brine solution and water. The organic layer was separated, dried over anhydrous sodium sulfate, filtered and concentrated. The crude material was purified by column chromatography through silica gel and EtOAC:pet ether as eluent to afford ethyl 2-(3-(tert-butoxycarbonylamino)cyclopentylidene)acetate. GCMS: 269 (M); Retention time: 9.051 min.

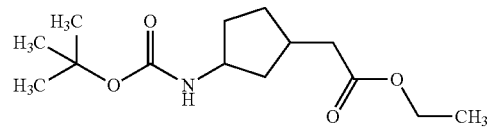 [SMILES: CCOC(=O)CC1CCC(NC(=O)OC(C)(C)C)C1]

Synthesis of ethyl 2-(3-(tert-butoxycarbonylamino)cyclopentyl)acetate

A solution of ethyl 2-(3-(tert-butoxycarbonylamino)cyclopentylidene)acetate (500 mg, 1 equiv.) in MeOH (15 mL) was degassed with N$_2$ followed by addition of PdOH$_2$ (261 mg, 1 equiv.). The reaction mixture was allowed to stir at ambient temperature for 12 h under H$_2$ atm. The reaction mixture was filtered through CELITE®. The filtrate obtained was concentrated to afford ethyl 2-(3-(tert-butoxycarbonylamino)cyclopentyl)acetate. $^1$H NMR: 400 MHz, CDCl$_3$: δ 4.12 (q, J=6.80 Hz, 2H), 3.66 (s, 1H), 2.25-2.41 (m, 4H), 1.85-1.99 (m, 3H), 1.72-1.78 (m, 1H), 1.61-1.65 (m, 1H), 1.44 (s, 9H), 1.22 (t, J=4.40 Hz, 3H).

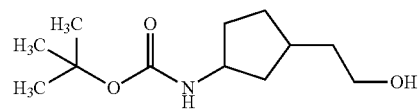 [SMILES: CC(C)(C)OC(=O)NC1CCC(CCO)C1]

Synthesis of tert-butyl 3-(2-hydroxyethyl)cyclopentylcarbamate

To an ice cooled solution of ethyl 2-(3-(tert-butoxycarbonylamino)cyclopentyl)acetate (400 mg, 1 equiv.) in THF was added LAH (112 mg, 2 equiv.) and the reaction mixture was stirred at 0° C. for 1 h. After the completion of 1 h, the reaction was quenched with saturated solution of sodium sulfate and the suspension was filtered. The filtrate was concentrated to provide tert-butyl 3-(2-hydroxyethyl)cyclopentylcarbamate. ¹H NMR: 400 MHz, CDCl₃: δ 3.64-3.61.89-1.99 (m, 2H), 5 (m, 2H), 2.24-2.31 (m, 1H), 2.01-2.10 (m, 1H), 1.60-1.67 (m, 3H), 1.54-1.59 (m, 1H), 1.41 (s, 9H), 1.45-1.32 (m, 3H).

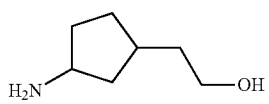

Synthesis of 2-(3-aminocyclopentyl)ethanol tert-Butyl 3-(2-hydroxyethyl)cyclopentylcarbamate was treated with 4 M HCl in dioxane at 0° C. The reaction mixture was stirred for 1 h then concentrated to dryness to furnish 2-(3-aminocyclopentyl)ethanol.

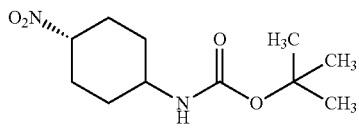

Step 1

To a refluxing solution of mCPBA (0.460 g, 1.867 mmol) in DCE was added tert-butyl ((trans)-4-aminocyclohexyl) carbamate (0.1 g, 0.467 mmol) in DCE. The mixture was refluxed for 3 hours. The reaction was worked up by adding EtOAc, washing with 1N NaOH (3×), and brine (1×). The organic layer was dried (sodium sulfate) and the solvent removed in vacuo to yield 0.0654 g of tert-butyl ((trans)-4-nitrocyclohexyl)carbamate as a yellow viscous oil. ¹H NMR (400 MHz, CDCl₃) δ 3.51 (br. s., 1H), 2.42-2.31 (m, 2H), 2.24-2.15 (m, 2H), 2.04-1.91 (m, 2H), 1.47 (s, 9H), 1.33-1.19 (m, 4H).

tert-Butyl ((trans)-4-nitrocyclohexyl)carbamate (0.0654 g, 0.268 mmol) was dissolved in DCM (1 mL) and to this solution was added HCl (0.669 mL, 2.68 mmol). The contents were stirred overnight at room temperature. TLC in 100% EtOAc shows only baseline product. The solvent was removed in vacuo and the residue re-evaporated from methylene chloride (3×) to remove traces of HCl. There was obtained 0.059 mg of trans-4-nitrocyclohexanamine, HCl as an off-white solid.

Example 28

(28)

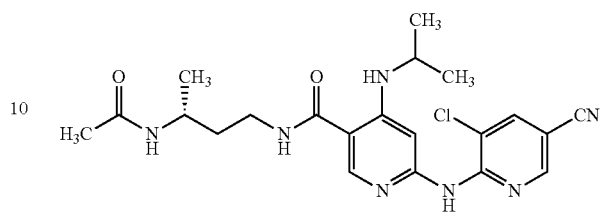

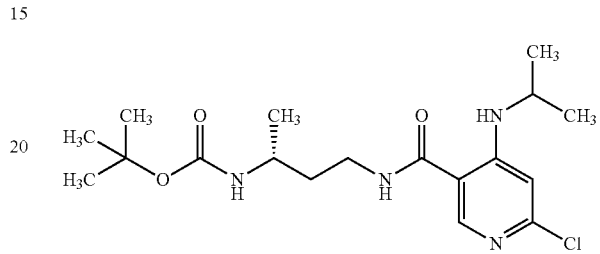

Step 1

6-Chloro-4-(isopropylamino)nicotinic acid (96106-020-01) (150 mg, 0.699 mmol), PyBOP (364 mg, 0.699 mmol) and Hunig's Base (0.366 mL, 2.1 mmol) were mixed in DMF (3 mL) at 25° C. with stirring then (R)-tert-butyl (4-aminobutan-2-yl)carbamate (132 mg, 0.699 mmol) was added. The reaction was stirred for 2 h then added ethyl acetate and rinsed 3 times with 10% LiCl. The organic layer was dried over sodium sulfate and concentrated to give (R)-tert-butyl (4-(6-chloro-4-(isopropylamino)nicotinamido)butan-2-yl)carbamate (250 mg, 84% yield) as a white solid. LCMS 385.20 (M+H)⁺.

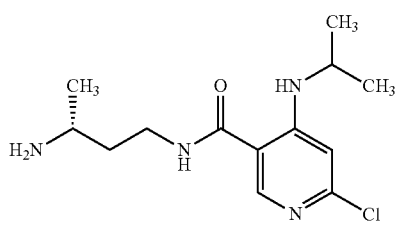 [SMILES: CC(C)Nc1cc(Cl)ncc1C(=O)NCC[C@@H](C)N]

Step 2

(R)-tert-Butyl (4-(6-chloro-4-(isopropylamino)nicotinamido)butan-2-yl)carbamate (250 mg, 0.650 mmol) was dissolved in CH₂Cl₂ (2 mL) at 25° C. with stirring then 4N HCl in dioxane (1.624 mL, 6.50 mmol) was added. After 3 hours the reaction essentially complete by LCMS. Workup entailed concentrating the reaction 5 times from methylene chloride to obtain (R)—N-(3-aminobutyl)-6-chloro-4-(isopropylamino)nicotinamide, 2 HCl (230 mg, 0.611 mmol, 94% yield) as a white glass. LCMS 285.1 (M+H)⁺.

111

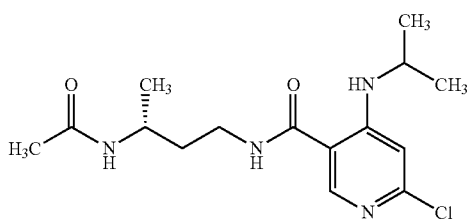 [SMILES: CC(=O)N[C@H](C)CCNC(=O)c1cnc(Cl)cc1NC(C)C]

Step 3

(R)—N-(3-Aminobutyl)-6-chloro-4-(isopropylamino)nicotinamide, 2 HCl (115 mg, 0.321 mmol), PYBOP ((1H-benzo[d][1,2,3]triazol-1-yl)oxy)tri(pyrrolidin-1-yl)phosphonium hexafluorophosphate(V) (167 mg, 0.321 mmol), Hunig's Base (0.168 mL, 0.964 mmol) and acetic acid (19.31 mg, 0.321 mmol) were mixed in DMF (1 mL) at 25° C. with stirring. After 1 hour, LCMS indicates the reaction was nearly complete. Ethyl acetate was added and rinsed 3 times with 10% LiCl to remove the DMF. The organic layer was dried over sodium sulfate and concentrated to give (R)—N-(3-acetamidobutyl)-6-chloro-4-(isopropylamino)nicotinamide (75 mg, 0.207 mmol, 64.2% yield) as an off-white solid. LCMS 327.20 (M+H)+.

Step 4

In a microwave tube, (R)—N-(3-acetamidobutyl)-6-chloro-4-(isopropylamino)nicotinamide (20 mg, 0.061 mmol), 6-amino-5-chloronicotinonitrile (18.80 mg, 0.122 mmol), Pd$_2$dba$_3$ (11.21 mg, 0.012 mmol), Xantphos (14.16 mg, 0.024 mmol) and Cs$_2$CO$_3$ (59.8 mg, 0.184 mmol) were mixed in DMA (1 mL) at room temperature. The reaction vessel was purged with N$_2$ then sealed and heated at 150° C. for a total of 40 minutes. The reaction was filtered, and the filtrate was concentrated under high vacuum and the residue was purified via preparative HPLC to afford (R)—N-(3-acetamidobutyl)-6-((3-chloro-5-cyanopyridin-2-yl)amino)-4-(isopropylamino)nicotinamide, 2 TFA (6 mg, 13% yield). $^1$H NMR (500 MHz, methanol-d$_4$) δ 8.64 (d, J=2.0 Hz, 1H), 8.38 (s, 1H), 8.27 (d, J=2.0 Hz, 1H), 7.65 (s, 1H), 7.14 (s, 1H), 4.05-3.94 (m, 1H), 3.83 (dt, J=12.9, 6.4 Hz, 1H), 3.65-3.55 (m, 1H), 3.18 (ddd, J=14.1, 8.7, 5.9 Hz, 1H), 2.01 (s, 3H), 1.87-1.76 (m, 1H), 1.69-1.59 (m, 1H), 1.42-1.35 (m, 6H), 1.21 (d, J=6.9 Hz, 3H); LCMS 444.2 (M+H)+.

Example 29

(29)

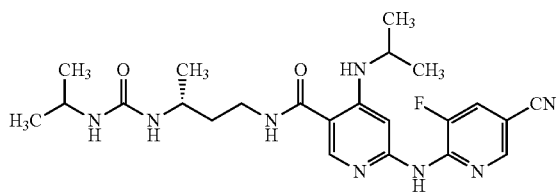

112

-continued

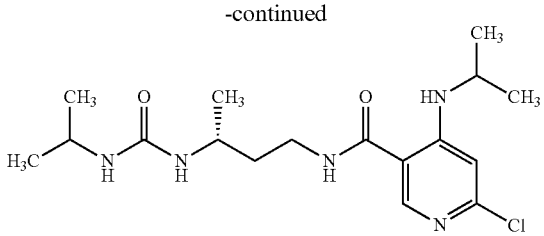

Step 1

(R)—N-(3-Aminobutyl)-6-chloro-4-(isopropylamino)nicotinamide, 2 HCl (115 mg, 0.321 mmol) and Hunig's Base (0.056 mL, 0.321 mmol) were mixed in THF (2 mL) at 25° C. with stirring then 2-isocyanatopropane (27.4 mg, 0.321 mmol) was added. The reaction was stirred for 30 min then concentrated and purified via column chromatography to afford (R)-6-chloro-4-(isopropylamino)-N-(3-(3-isopropylureido)butyl)nicotinamide (75 mg, 0.201 mmol, 62% yield) as a white solid. $^1$H NMR (400 MHz, DMSO-d$_6$) δ 8.55 (t, J=5.4 Hz, 1H), 8.45 (d, J=7.7 Hz, 1H), 8.32 (s, 1H), 6.68 (s, 1H), 5.58 (t, J=8.0 Hz, 2H), 3.81-3.71 (m, 1H), 3.70-3.60 (m, 2H), 3.18 (s, 1H), 3.17-3.05 (m, 1H), 1.55 (dt, J=13.8, 7.1 Hz, 2H), 1.16 (d, J=6.4 Hz, 6H), 1.07-0.98 (m, 9H); LCMS 370.3 (M+H)+.

Step 2

In a microwave tube, (R)-6-chloro-4-(isopropylamino)-N-(3-(3-isopropylureido)butyl)nicotinamide (20 mg, 0.054 mmol), 6-amino-5-fluoronicotinonitrile (14.83 mg, 0.108 mmol), Pd$_2$dba$_3$ (9.90 mg, 10.81 μmol), Xantphos (12.51 mg, 0.022 mmol) and Cs$_2$CO$_3$ (52.9 mg, 0.162 mmol) were mixed in DMA (1 mL) at room temperature. The reaction vessel was purged with N$_2$ then sealed and heated at 150° C. for a total of 40 minutes. The reaction was filtered, and the filtrate was concentrated under high vacuum and the residue was purified via preparative HPLC to afford (R)-6-((5-cyano-3-fluoropyridin-2-yl)amino)-4-(isopropylamino)-N-(3-(3-isopropylureido)butyl)nicotinamide (11.6 mg, 43% yield) $^1$H NMR (500 MHz, methanol-d$_4$) δ 8.44 (d, J=2.0 Hz, 1H), 8.32 (s, 1H), 7.73 (dd, J=10.7, 1.2 Hz, 2H), 7.61 (s, 1H), 3.90-3.74 (m, 3H), 3.66-3.59 (m, 1H), 3.13 (ddd, J=13.9, 8.4, 5.9 Hz, 1H), 1.80-1.70 (m, 1H), 1.61-1.51 (m, 1H), 1.34 (dd, J=6.4, 2.0 Hz, 6H), 1.19-1.10 (m, 9H); LCMS 471.2 (M+H)+.

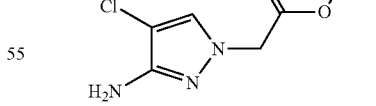

A solution of 2-(3-amino-4-chloro-1H-pyrazol-1-yl)acetic acid (500 mg, 2.85 mmol) was stirred at 25° C. under nitrogen in CH$_2$Cl$_2$ (3 mL) and MeOH (1 mL). The reaction was a partial solution. 2.0M TMS-Diazomethane in hexanes (1.566 mL, 3.13 mmol) was added dropwise. Note: Gas evolution was observed during the addition. Once the addition was complete, the reaction was an amber solution. The reaction was stirred for 1 h then concentrated to afford methyl 2-(3-amino-4-chloro-1H-pyrazol-1-yl)acetate (422 mg, 2.114 mmol, 74.2% yield) of oily tan solids as product which solidified. LCMS 189.90 (M+H)+.

Example 30

(30)

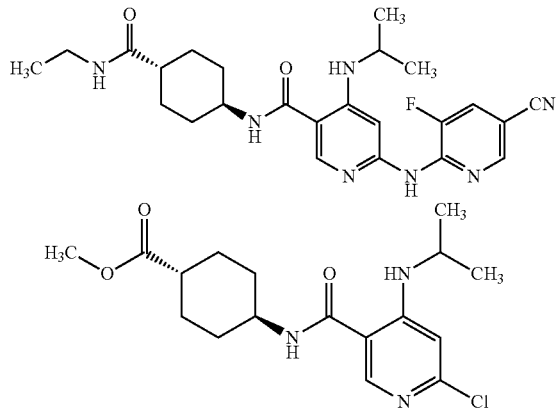

Step 1

A solution of 6-chloro-4-(isopropylamino)nicotinic acid (0.554 g, 2.58 mmol), BOP (1.142 g, 2.58 mmol) and TEA (1.080 mL, 7.75 mmol) in DMF (15 mL) at 25° C. was added (1R,4R)-methyl 4-aminocyclohexanecarboxylate, HCl (0.5 g, 2.58 mmol). The reaction was stirred overnight then added ethyl acetate and rinsed 3 times with 10% LiCl to remove the DMF. The organic layer was dried over sodium sulfate and concentrated to give (1R,4R)-methyl 4-(6-chloro-4-(isopropylamino)nicotinamido)cyclohexane carboxylate (820 mg, 85% yield) as an off-white solid. LCMS 354.10 (M+H)+.

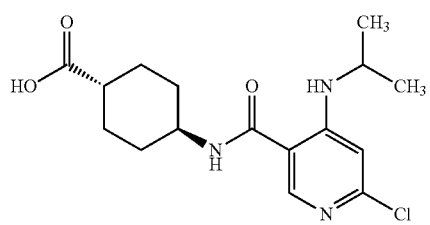 [SMILES: CC(C)Nc1cc(Cl)ncc1C(=O)N[C@H]1CC[C@H](C(=O)O)CC1]

Step 2

(1R,4R)-methyl 4-(6-chloro-4-(isopropylamino)nicotinamido)cyclohexane carboxylate (820 mg, 2.317 mmol) was dissolved in MeOH (10 mL) at 25° C. with stirring then 1.0 N NaOH (4.63 mL, 4.63 mmol) was added. The reaction was stirred for 2 h then concentrated to remove the MeOH. The aqueous pH was adjusted to 4 with 1N HCl with stirring. The resulting solids were filtered, rinsed with water followed by hexanes. The solids were dried under high vacuum to give (1r,4r)-4-(6-chloro-4-(isopropylamino)nicotinamido)cyclohexane carboxylic acid (680 mg, 82% yield). LCMS 340.10 (M+H)+.

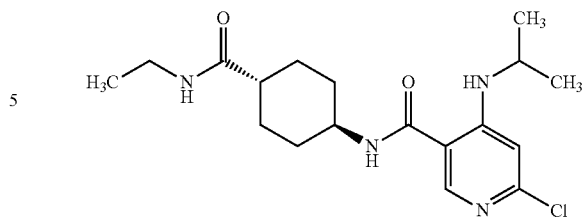

Step 3

(1r,4r)-4-(6-Chloro-4-(isopropylamino)nicotinamido)cyclohexane carboxylic acid (200 mg, 0.589 mmol), BOP (260 mg, 0.589 mmol) and TEA (0.246 mL, 1.766 mmol) were mixed in DMF (5 mL) at 25° C. with stirring then 2.0M ethanamine in THF (0.441 mL, 0.883 mmol) was added. The reaction was stirred overnight, diluted with EA and rinsed 2 times with 10% LiCl to remove the DMF. The organic layer was dried over sodium sulfate and concentrated to give 6-chloro-N-((1R,4R)-4-(ethylcarbamoyl)cyclohexyl)-4-(isopropylamino)nicotinamide (200 mg, 83% yield). LCMS 367.20 (M+H)+.

Step 4

In a microwave vial, 6-chloro-N-((1R,4R)-4-(ethylcarbamoyl)cyclohexyl)-4-(isopropylamino)nicotinamide (25 mg, 0.068 mmol), 6-amino-5-fluoronicotinonitrile (9.34 mg, 0.068 mmol), BrettPhos precatalyst (2.72 mg, 3.41 µmol) and K2CO3 (18.83 mg, 0.136 mmol) were mixed in 6:1 t-BuOH/DMA (2 mL) at room temperature. Nitrogen was bubbled through the mixture for 5 minutes and then the reaction was heated at 145° C. for 15 minutes. The reaction was cooled, filtered, and the filtrate was concentrated. The product was purified via preparative HPLC to afford 6-((5-cyano-3-fluoropyridin-2-yl)amino)-N-((1R,4R)-4-(ethylcarbamoyl)cyclohexyl)-4-(isopropylamino)nicotinamide, 2 TFA (6.6 mg, 13% yield). 1H NMR; LCMS 468.2 (M+H)+.

Example 31

(31)

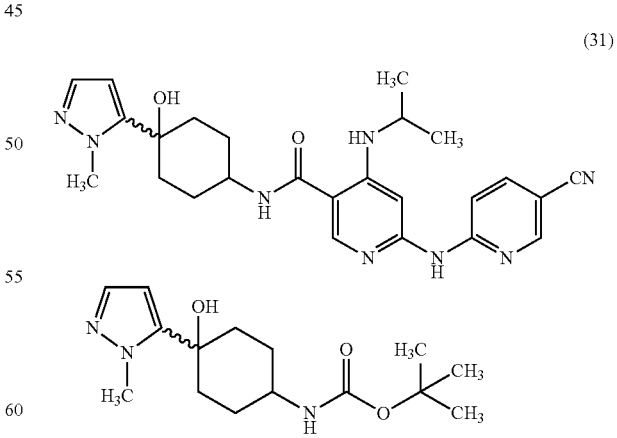

Step 1

A solution of 1-methyl-1H-pyrazole (1.012 mL, 12.18 mmol) in THF (50 mL) was cooled to −78° C. and n-BuLi (4.87 mL, 12.18 mmol) was added. The mixture was allowed to stir at room temperature for 1 hr. Afterwards a solution of tert-butyl (4-oxocyclohexyl)carbamate (1.299 g, 6.09 mmol) in THF (10 mL) was added and the mixture stirred at room temperature overnight. The reaction was worked up by quenching with water, evaporating the THF, adding EtOAc, and washing the product with water (2×). The organic layer was dried (sodium sulfate) and the solvent removed in vacuo to yield 1.061 g of a viscous yellow oil which was purified via column chromatography to afford a mixture of cis and trans isomers (0.85 g, 46% yield). $^1$H NMR (400 MHz, CDCl$_3$-d) δ 7.40-7.33 (m, 1H), 6.24-6.00 (m, 1H), 5.31 (s, 1H), 4.48 (br. s., 1H), 4.12-4.00 (m, 3H), 2.23-1.80 (m, 6H), 1.73-1.59 (m, 2H), 1.50-1.43 (m, 9H). Note that there were two sets of vinyl peaks in a ration of 3:1 designating the ratio of trans/cis products.

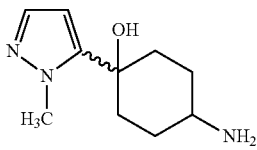

Step 2 tert-Butyl (4-hydroxy-4-(1-methyl-1H-pyrazol-5-yl)cyclohexyl)carbamate (0.85 g, 2.88 mmol) was dissolved in DCM (20 mL) and to this solution was added HCl (4N in dioxane) (7.19 mL, 28.8 mmol). The contents were stirred at room temperature. The reaction appeared to be precipitating and thus a little MeOH was added to help make the product more soluble. The reaction was evaporated and the residue evaporated from methylene chloride 3× to remove traces of HCl. The solid thus obtained was dried under house vacuum to afford 0.75 g of a light yellow solid which was used without further purification: $^1$H NMR (400 MHz, DMSO-d$_6$) δ 8.31-8.14 (m, 3H), 7.39 (d, J=2.0 Hz, 1H), 6.14 (d, J=2.0 Hz, 1H), 3.98 (s, 3H), 3.08-2.95 (m, 1H), 2.08-1.96 (m, 2H), 1.82 (br. s., 5H).

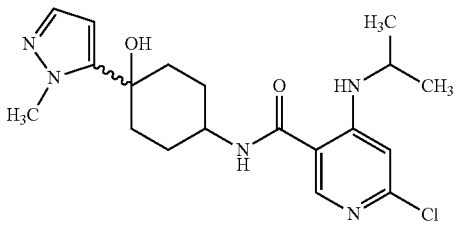 [SMILES: CC(C)Nc1cc(Cl)ncc1C(=O)NC1CCC(O)(c2ccnn2C)CC1]

Step 3

4-Amino-1-(1-methyl-1H-pyrazol-5-yl)cyclohexanol, HCl (200 mg, 0.863 mmol), 6-chloro-4-(isopropylamino)nicotinic acid (185 mg, 0.863 mmol), Hunig's Base (0.754 mL, 4.32 mmol), and PyBOP (898 mg, 1.726 mmol) were mixed and stirred in DMF (3 mL) at room temperature. The reaction was quenched with 1N NaOH, and EtOAc was added. The layers were separated and the organic layer rinsed with 1N NaOH (2×), brine (1×), dried (sodium sulfate) and the solvent removed in vacuo to yield 1.25 g of a brown oily solid. The residue was purified via column chromatography to afford 245 mg (69% yield) of a mixture of 4-5:1 ratio of trans to cis isomers. $^1$H NMR (400 MHz, DMSO-d$_6$) δ 8.46 (d, J=7.7 Hz, 1H), 8.42-8.25 (m, 2H), 7.33-7.19 (m, 1H), 6.74-6.61 (m, 1H), 6.25-6.02 (m, 1H), 5.22-5.08 (m, 1H), 4.01-3.91 (m, 3H), 3.88-3.69 (m, 2H), 2.11-1.60 (m, 7H), 1.20 (d, J=6.6 Hz, 1H), 1.16 (d, J=6.4 Hz, 5H), 1.09-1.09 (m, 1H).

Step 4

A solution of 6-((5-cyanopyridin-2-yl)amino)-4-(isopropylamino)nicotinic acid (50 mg, 0.168 mmol), BOP (82 mg, 0.185 mmol) and TEA (0.047 mL, 0.336 mmol) in DMF (2 mL) at 25° C. was stirred under nitrogen. After a few minutes, 4-amino-1-(1-methyl-1H-pyrazol-5-yl)cyclohexanol. HCl (39.0 mg, 0.168 mmol) was added. The mixture was a light amber solution. The reaction was stirred for 1 h and the crude material was purified directly via preparative HPLC to afford 6-((5-cyanopyridin-2-yl)amino)-N-((1s,4s)-4-hydroxy-4-(1-methyl-1H-pyrazol-5-yl)cyclohexyl)-4-(isopropylamino)nicotinamide (14.4 mg, 17% yield). $^1$H NMR (500 MHz, DMSO-d$_6$) δ 10.18 (s, 1H), 8.64 (d, J=1.8 Hz, 1H), 8.43 (s, 1H), 8.40 (d, J=7.3 Hz, 1H), 8.20 (d, J=7.3 Hz, 1H), 8.03 (dd, J=8.9, 2.1 Hz, 1H), 7.84 (d, J=8.5 Hz, 1H), 7.25 (d, J=1.8 Hz, 1H), 7.08 (s, 1H), 6.09 (d, J=1.8 Hz, 1H), 3.96 (s, 3H), 3.78 (dd, J=7.6, 4.0 Hz, 1H), 3.60 (dq, J=13.0, 6.4 Hz, 1H), 2.03 (d, J=11.6 Hz, 2H), 1.92-1.79 (m, 2H), 1.76-1.61 (m, 4H), 1.21 (d, J=6.1 Hz, 7H).; LCMS 475.2 (M+H)$^+$.

Example 32

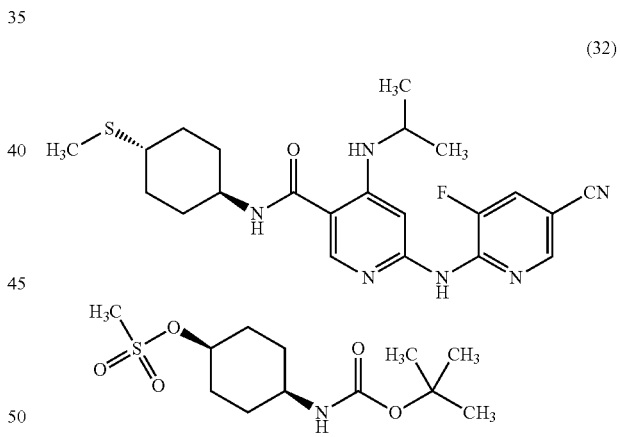

(32)

Step 1

To a stirred solution of tert-butyl ((1s,4s)-4-hydroxycyclohexyl)carbamate (1.00 g, 4.64 mmol) and triethylamine (3.24 mL, 23.22 mmol) in CH$_2$Cl$_2$ (10 mL) at 0° C. were added methanesulfonyl chloride (0.543 ml, 6.97 mmol) dropwise. The mixture was stirred at 0° C. for 15 min then diluted with water. The layers were separated and the organic layer was rinsed with saturated sodium bicarbonate (1×) followed by brine (1×). The organic layer was dried over Na$_2$SO$_4$ and concentrated to provide (1S,4S)-4-((tert-butoxycarbonyl)amino)cyclohexyl methanesulfonate (3.20 g, 89% yield) as a light amber solid. LCMS (TFA) 238.0 (M+H-t-butyl)$^+$.

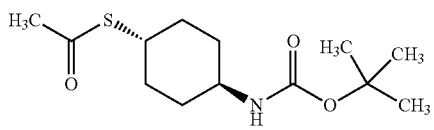 [SMILES: CC(=O)S[C@H]1CC[C@H](NC(=O)OC(C)(C)C)CC1]

Step 2

To a stirred solution of (1S,4S)-4-((tert-butoxycarbonyl)amino)cyclohexyl methanesulfonate (3.20 g, 10.91 mmol) in DMF (40 mL) at room temperature was added potassium thioacetate (1.869 g, 16.36 mmol). The reaction was heated at 80° C. behind a safety shield for 7 hours, then at room temperature for 48 hours. The reaction mixture was diluted with ethyl acetate and rinsed with 10% LiCl (2×), saturated ammonium chloride (1×), saturated sodium bicarbonate (1×), and brine (2×). The organic layer was dried over $Na_2SO_4$ and concentrated to provide a dark oil as crude product. Purification via column chromatography provided S-((1R,4R)-4-((tert-butoxycarbonyl)amino)cyclohexyl)ethanethioate (820 mg, 27.5% yield). LCMS (TFA) 218.0 (M+H-t-butyl)⁺.

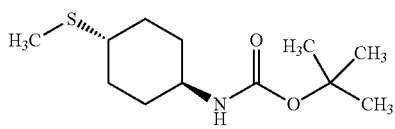 [SMILES: CS[C@H]1CC[C@H](NC(=O)OC(C)(C)C)CC1]

Step 3

To a stirred solution of S-((1R,4R)-4-((tert-butoxycarbonyl)amino)cyclohexyl)ethanethioate (820 mg, 3.00 mmol) in MeOH (5 mL) at room temperature was added sodium methoxide (648 mg, 12.00 mmol) followed by iodomethane (0.281 mL, 4.50 mmol). The flask was then capped with a stopper and stirred for 16 hours. The reaction mixture was diluted with water then extracted with ethyl acetate (3×). The combined organic layer was rinsed with saturated ammonium chloride (1×), saturated sodium bicarbonate (1×), and brine (1×). The organic layer was dried over $Na_2SO_4$ and concentrated to provide tert-butyl ((1R,4R)-4-(methylthio)cyclohexyl)carbamate (650 mg, 79% yield) of amber solids. LCMS (TFA) 190.0 (M+H)⁺.

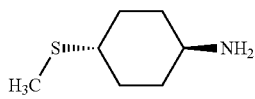

Step 4

To a stirred solution of tert-butyl ((1R,4R)-4-(methylthio)cyclohexyl)carbamate (650 mg, 2.65 mmol) in dioxane (5 mL) and methanol (1 mL) at room temperature was added 4N HCl in dioxane (3.31 mL, 13.24 mmol). After 20 hours, the reaction was concentrated from methylene chloride (5×) to provide (1R,4R)-4-(methylthio)cyclohexanamine, HCl (490 mg, 92% yield) of tan solids as product

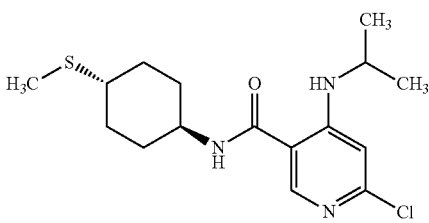 [SMILES: CS[C@H]1CC[C@H](NC(=O)c2cnc(Cl)cc2NC(C)C)CC1]

Step 5

To a stirred solution of 6-chloro-4-(isopropylamino)nicotinic acid (236 mg, 1.101 mmol), BOP (487 mg, 1.101 mmol) and TEA (0.307 mL, 2.201 mmol) in DMF (0.5 mL) at 25° C. was added (1r,4r)-4-(methylthio)cyclohexanamine, HCl (200 mg, 1.101 mmol). After 2 hours, the reaction mixture was diluted with ethyl acetate and rinsed with 10% LiCl (2×), saturated sodium bicarbonate (1×) and finally 10% LiCl (1×). The organic layer was dried over $Na_2SO_4$ and concentrated to provide tert-butyl ((1R,4R)-4-(methylcarbamoyl)cyclohexyl)carbamate (320 mg, 77% yield) of an amber oil as product. LCMS 342.2 (M+H)⁺.

Step 6

A mixture of 6-chloro-4-(isopropylamino)-N-((1R,4R)-4-(methylthio)cyclohexyl)nicotinamide (100 mg, 0.292 mmol), 6-amino-5-fluoronicotinonitrile (48.1 mg, 0.351 mmol), $K_2CO_3$ (29.4 mg, 0.213 mmol), and 6:1 t-BuOH/DMA (2 mL) were mixed in a 5 mL microwave vial containing a magnetic stir bar and degassed with bubbling nitrogen for 5 minutes. The mixture was treated with BrettPhos precatalyst (23.36 mg, 0.029 mmol) and degassed for another 5 minutes. The vial was sealed and the reaction heated in the microwave with stirring at 145° C. for 40 minutes. The reaction was filtered, purified via preparative HPLC to afford the product (16.8 mg, 12% yield). $^1H$ NMR (500 MHz, DMSO-$d_6$) δ 9.04 (d, J=7.3 Hz, 1H), 8.69 (d, J=7.3 Hz, 1H), 8.61 (d, J=1.8 Hz, 1H), 8.45-8.37 (m, 2H), 7.95 (s, 1H), 7.04 (s, 1H), 3.71 (dd, J=12.8, 6.7 Hz, 2H), 2.57-2.52 (m, 1H), 2.09-1.98 (m, 5H), 1.90 (d, J=12.2 Hz, 2H), 1.44-1.20 (n, 11H). LCMS 443.2 (M+H)⁺.

Example 33

(33)

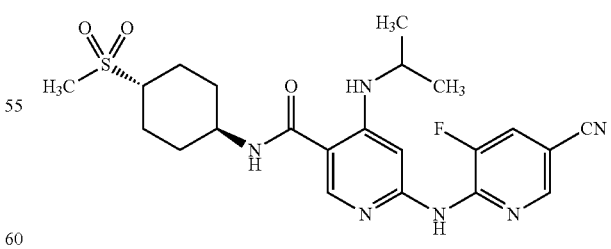

A solution of 6-((5-cyano-3-fluoropyridin-2-yl)amino)-4-(isopropylamino)-N-((1R,4R)-4-(methylthio)cyclohexyl) nicotinamide (50 mg, 0.113 mmol) in MeOH (3.5 mL) at 0° C. was added OXONE® (139 mg, 0.226 mmol) in water (1.5 mL). Stirring was continued at room temperature for 1 h then another aliquot of OXONE® (0.3 equiv) was added.

The reaction was stirred for an additional 48 hour. The solids were filtered and rinsed with MeOH. The filtrate was concentrated and extracted with CH₂Cl₂. The organic extract was dried (Na₂SO₄), filtered and concentrated. The product was purified via preparative HPLC to afford 6-((5-cyano-3-fluoropyridin-2-yl)amino)-4-(isopropylamino)-N-((1R,4R)-4-(methylsulfonyl)cyclohexyl)nicotinamide (11.3 mg, 19% yield). $^1$H NMR (500 MHz, DMSO-$d_6$) δ 8.53 (d, J=1.2 Hz, 1H), 8.44 (d, J=6.7 Hz, 1H), 8.39 (s, 1H), 8.23 (d, J=7.9 Hz, 1H), 8.15 (d, J=11.0 Hz, 1H), 7.42 (s, 1H), 3.78-3.68 (m, 1H), 3.63 (dq, J=12.8, 6.3 Hz, 1H), 3.16 (d, J=3.7 Hz, 1H), 3.04 (t, J=11.9 Hz, 1H), 2.93 (s, 3H), 2.13 (d, J=11.6 Hz, 2H), 1.98 (d, J=10.4 Hz, 2H), 1.56-1.44 (m, 2H), 1.44-1.35 (m, 2H), 1.22 (d, J=6.1 Hz, 6H); LCMS 475.1 (M+H)⁺.

Example 34

(34)

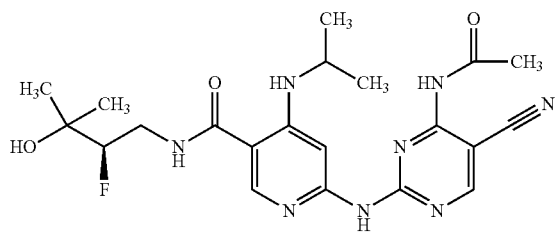

(R)-6-((4-Amino-5-cyanopyrimidine-2-yl)amino)-N-(2-fluoro-3-hydroxy-3-methylbutyl)-4-(isopropylamino)nicotinamide (60 mg, 0.144 mmol) and Hunig's Base (0.025 mL, 0.144 mmol) was dissolved in DMF (2 mL) at room temperature with stirring then added acetyl chloride (10.24 μl, 0.144 mmol). The reaction was stirred for 1 hour. The reaction was then filtered, and the filtrate was purified via preparative HPLC to afford the product (2.9 mg, 4% yield). $^1$H NMR (500 MHz, DMSO-$d_6$) δ 8.68 (s, 1H), 8.53 (d, J=7.3 Hz, 1H), 8.43 (s, 2H), 8.37 (s, 1H), 8.29 (d, J=7.3 Hz, 1H), 7.94 (s, 1H), 7.59 (br. s., 2H), 4.84 (s, 1H), 4.37 (d, J=9.2 Hz, 0.5H), 4.27 (d, J=9.2 Hz, 0.5H), 3.91-3.81 (m, 1H), 3.74-3.58 (m, 1H), 3.34-3.26 (m, 1H), 2.36 (s, 1H), 1.19 (d, J=6.1 Hz, 5H), 1.15 (d, J=6.1 Hz, 7H); LCMS 459.2 (M+H)⁺.

Example 35

(35)

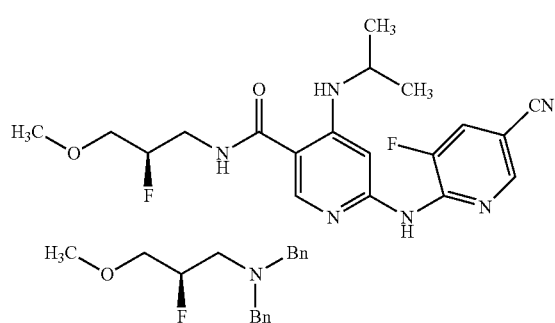

Step 1

To a solution of (R)-3-(dibenzylamino)-2-fluoropropan-1-ol (400 mg, 1.463 mmol) in THF (10 mL) at 0° C. under nitrogen was added NaH (70.2 mg, 1.756 mmol). The mixture was stirred for 10 min then added MeI (0.092 mL, 1.463 mmol). After 1 hour additional DMF (1 mL) was added. Over the course of the next 2 hours, 1 additional NaH and MeI (1 equiv) was added in two portions. The reaction was then quenched with water, diluted with EtOAc and washed with 10% LiCl to remove the DMF. The organic layer was dried over sodium sulfate and concentrated to give (R)—N,N-dibenzyl-2-fluoro-3-methoxypropan-1-amine (400 mg, 86% yield). LCMS 287.70 (M+H)⁺.

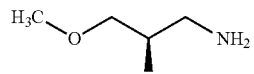

Step 2

Under a nitrogen atmosphere, a Parr bottle was carefully charged with 10% Pd—C (74.1 mg, 0.070 mmol), and the catalyst was carefully wetted with methanol (10 mL). The vessel was charged with a solution of (R)—N,N-dibenzyl-2-fluoro-3-methoxypropan-1-amine (400 mg, 1.392 mmol) in methanol (10 mL) and the mixture was degassed and backfilled with H₂ and pressurized to 50 psi for 4 h. The mixture was degassed with nitrogen, and the reaction mixture was filtered under nitrogen through fiberglass filter paper, being sure not to let the cake dry out. The filter cake was thoroughly rinsed with methanol (25 mL total rinse volume), and the combined filtrate and rinsing were concentrated in vacuo to obtain (R)-2-fluoro-3-methoxypropan-1-amine (125 mg, 75% yield) as a colorless oil.

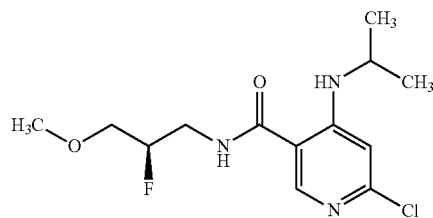 [SMILES: COC[C@H](F)CNC(=O)c1cnc(Cl)cc1NC(C)C]

Step 3

A solution of 6-chloro-4-(isopropylamino)nicotinic acid (250 mg, 1.167 mmol), BOP (516 mg, 1.167 mmol) and TEA (0.325 mL, 2.334 mmol) in DMF (5 mL) was added (R)-2-fluoro-3-methoxypropan-1-amine (125 mg, 1.167 mmol). The reaction was stirred for 18 h. The mixture was diluted with EtOAc and washed 2 times with 10% LiCl to remove the DMF, followed by 1 time with saturated sodium carbonate, and finally 1 time with 10% LiCl. The organic layer was dried over sodium sulfate and concentrated to afford (R)-6-chloro-N-(2-fluoro-3-methoxypropyl)-4-(isopropylamino)nicotinamide (300 mg, 72% yield).

Step 4

In a 5 mL microwave vial, a mixture of (R)-6-chloro-N-(2-fluoro-3-methoxypropyl)-4-(isopropylamino)nicotinamide (35 mg, 0.115 mmol), 6-amino-5-fluoronicotinonitrile (15.80 mg, 0.115 mmol) and $K_2CO_3$ (31.8 mg, 0.230 mmol) were mixed at room temperature in 6:1 tert-butanol/DMA (2 mL) and was degassed with bubbling nitrogen for 5 minutes. The mixture was treated with BrettPhos precatalyst (4.60 mg, 5.76 µmol), degassed for another 5 minutes, and the vial was sealed. The reaction was heated via microwave with stirring at 145° C. for 15 minutes. The reaction was cooled, filtered, and the filtrate was concentrated under high vacuum then the residue was dissolved in DMF for purification. The product was isolated via preparative HPLC to afford (R)-6-((5-cyano-3-fluoropyridin-2-yl)amino)-N-(2-fluoro-3-methoxypropyl)-4-(isopropylamino)nicotinamide (11.8 mg, 25% yield).

Example 36

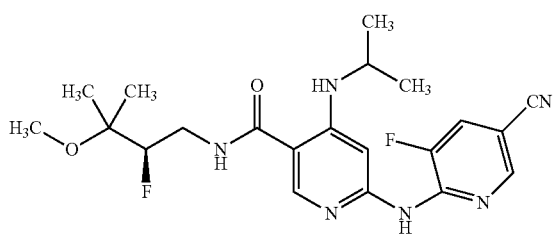

(36)

Example 36 was prepared in an analogous fashion as Example 35 starting from (R)-4-(dibenzylamino)-3-fluoro-2-methylbutan-2-ol. LCMS 433.3 (M+H)+; HPLC RT 1.73 min, conditions G.

Example 37

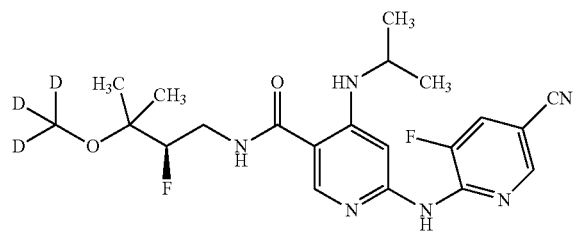

(37)

Example 37 was prepared in an analogous fashion as Example 36 starting from (R)-4-(dibenzylamino)-3-fluoro-2-methylbutan-2-ol and $CD_3I$. LCMS 436.4 (M+H)+; HPLC RT 1.85 min, conditions G.

Example 38

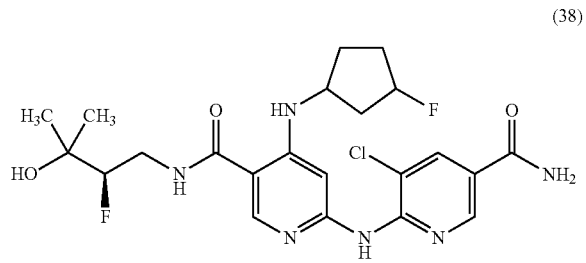 [SMILES: CC(C)(O)[C@H](F)CNC(=O)c1cnc(Nc2ncc(C(N)=O)cc2Cl)cc1NC1CCC(F)C1]

(38)

To a solution of 6-chloro-N—((R)-2-fluoro-3-hydroxy-3-methylbutyl)-4-((3-fluorocyclopentyl)amino)nicotinamide (200 mg, 0.553 mmol) and 6-amino-5-chloronicotinonitrile (85 mg, 0.553 mmol) in 1,4-dioxane (4 mL) was added $Cs_2CO_3$ (540 mg, 1.658 mmol) and Xantphos (128 mg, 0.221 mmol) and 0.5 mL of water. The reaction was then purged with nitrogen for 20 mins, then $Pd_2(dba)_3$ (202 mg, 0.221 mmol) was added and again purged for 15 mins. The reaction mixture was heated at 110° C. overnight. The reaction mixture was cooled, filtered through CELITE® and diluted with EtOAc (50 mL). The organic layer was washed with water (10 mL) and brine solutions (10 mL). The organic layer was dried over $Na_2SO_4$, filtered and concentrated to give the crude compound which was purified over silica gel eluting 10% methanol in DCM to get mixture of nitrile containing diastereomers and 2 nitrile hydrolysis diastereomers which were purified via preparative SFC chromatography. The desired diastereomer was isolated as a white solid (4 mg, 1.5% yield). LCMS 497.2 (M+H)+; HPLC RT 6.15 min, conditions A, 12 min gradient.

Example 39

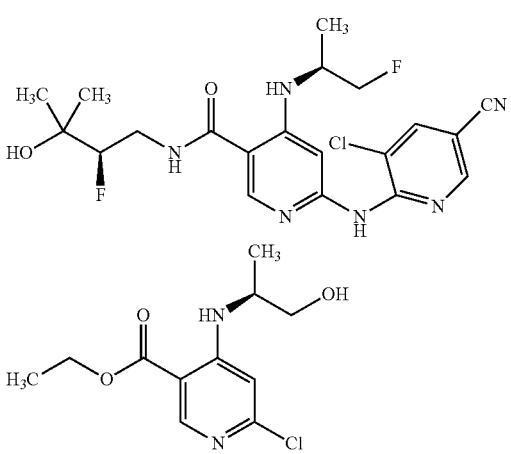

(39)

Step 1

To a stirred solution of ethyl 4,6-dichloronicotinate (1.0 g, 4.54 mmol) in DMA (5 mL) was added DIPEA (2.381 mL, 13.63 mmol) and (S)-2-aminopropan-1-ol (0.424 mL, 5.45 mmol). The reaction mixture was stirred for 3 h at 100° C., cooled to room temperature and the solvents removed in vacuo. The residue was added water and extracted with ethyl acetate. The organic solution was dried over anhydrous Na₂SO₄, filtered, and concentrated. The product was purified via column chromatography to afford (S)-ethyl 6-chloro-4-((1-hydroxypropan-2-yl)amino)nicotinate (1.1 g, 93% yield). ¹H NMR (400 MHz, DMSO-d₆) δ ppm 8.53 (s, 1H) 8.22 (d, J=8.03 Hz, 1H) 8.20-8.24 (m, 1H) 6.87 (s, 1H) 6.85-6.88 (m, 1H) 4.97-4.97 (m, 1H) 4.99 (t, J=5.27 Hz, 1H) 4.30 (q, J=−7.03 Hz, 1H) 4.26-4.33 (m, 2H) 3.73-3.82 (m, 1H) 3.39-3.52 (m, 2H) 1.29-1.34 (m, 3H) 1.16 (m, 3H); LCMS 259.3 (M+H)⁺.

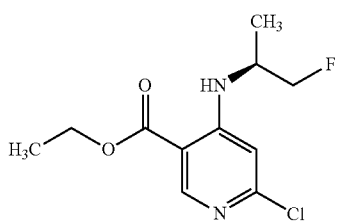 [SMILES: CCOC(=O)c1cnc(Cl)cc1N[C@@H](C)CF]

Step 2

To a stirred solution of (S)-ethyl-6-chloro-4-((1-hydroxypropan-2-yl)amino)nicotinate (2 g, 7.73 mmol) in THF (15 mL) at −78° C. was added DAST (2.55 mL, 19.33 mmol). The reaction mixture was then allowed to warm to room temperature and stir overnight. The reaction was quenched with 10% aq NaHCO₃ and extracted with EtOAc. The organic layer was dried over anhydrous Na₂SO₄, filtered, and concentrated to afford the crude material which was purified via column chromatography to afford the product (1.2 g, 60% yield). LCMS 261.0 (M+H)⁺.

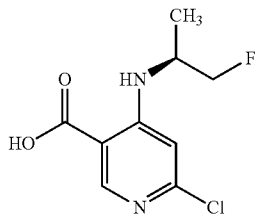

Step 3

To a solution of (S)-ethyl 6-chloro-4-((1-fluoropropan-2-yl)amino)nicotinate (1.3 g, 4.99 mmol) in ethanol (10 mL), was added LiOH (0.615 g, 14.96 mmol) and water (3 mL, 4.99 mmol) and the reaction was stirred at room temperature for 1 h. TLC showed absence of SM. The mixture was concentrated and acidified to a pH of 3-4 using 1.5N HCl. The resulting solid was filtered to afford (S)-6-chloro-4-((1-fluoropropan-2-yl)amino)nicotinic acid (1.0 g, 41% yield) as an off-white solid. LCMS 233.2 (M+H)⁺.

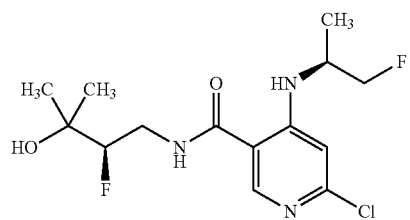 [SMILES: C[C@@H](CF)Nc1cc(Cl)ncc1C(=O)NC[C@@H](F)C(C)(C)O]

Step 4

To as solution of(S)-6-chloro-4-((1-fluoropropan-2-yl) amino)nicotinic acid (0.650 g, 2.79 mmol) in DMF (6 mL) was added DIPEA (1.952 mL, 11.18 mmol), (R)-4-amino-3-fluoro-2-methylbutan-2-ol (0.406 g, 3.35 mmol) and HATU (1.062 g, 2.79 mmol) and the reaction mass was stirred at room temperature for 1 h. The reaction was diluted with water (50 mL) and extracted with ethyl acetate. The combined organic extracts was washed with 10% sodium bicarbonate, dried over sodium sulphate and concentrated. The crude material was purified via column chromatography to afford 6-chloro-N—((R)-2-fluoro-3-hydroxy-3-methylbutyl)-4-(((S)-1-fluoropropan-2-yl)amino)nicotinamide (0.4 g, 42% yield) as a pale yellow oil. LCMS 336.2 (M+H)⁺.

Step 5

To a solution of 6-chloro-N—((R)-2-fluoro-3-hydroxy-3-methylbutyl)-4-(((S)-1-fluoropropan-2-yl)amino)nicotinamide (0.1 g, 0.298 mmol) in dioxane (1 mL) was added 6-amino-5-chloronicotinonitrile (0.055 g, 0.357 mmol), cesium carbonate (0.291 g, 0.893 mmol), water (0.5 mL, 0.298 mmol) and Xantphos (0.017 g, 0.030 mmol). The mixture was degassed then added Pd₂(dba)₃ (0.014 g, 0.015 mmol) after which the reaction was degassed further and heated to 110° C. for 18 h. The reaction was cooled and filtered through CELITE®. The CELITE® bed was washed with ethyl acetate and the combined filtrate was concentrated. Minimum DCM was then added to the reaction mass to dissolve it followed by the addition of Pet ether. The resulting solid was allowed to settle down and the Pet ether layer was decanted. This process was repeated 2-3 times to afford the crude solids which was further purified by prep HPLC to provide a pale brown oil which was further purified by Prep HPLC to get afford 6-((3-chloro-5-cyanopyridin-2-yl)amino)-N—((R)-2-fluoro-3-hydroxy-3-methylbutyl)-4-(((S)-1-fluoropropan-2-yl)amino)nicotinamide (4 mg, 3% yield) as an off-white solid. ¹H NMR (400 MHz, methanol-d₄) δ 8.61 (s, 1H), 8.36 (s, 1H), 8.21 (s, 1H), 7.76-7.98 (m, 1H), 4.96-5.08 (m, 1H), 4.56-4.66 (m, 1H), 4.41-4.56 (m, 1H), 4.29-4.41 (m, 1H), 3.79-3.99 (m, 1H), 3.40-3.62 (m, 3H), 3.37 (s, 3H), 1.35-1.57 (m, 3H), 1.30 (d, J=1.51 Hz, 6H); LCMS 453.2 (M+H)⁺.

Example 40

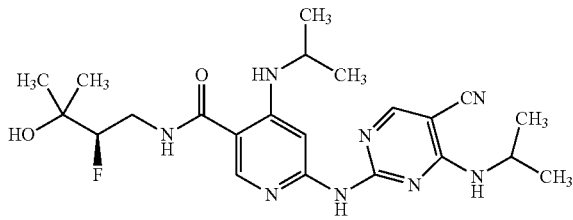
(40)

Example 40 was prepared according to the method described for Example 27. LCMS 459.3 (M+H)⁺; HPLC RT 7.18 min, conditions A.

Example 41

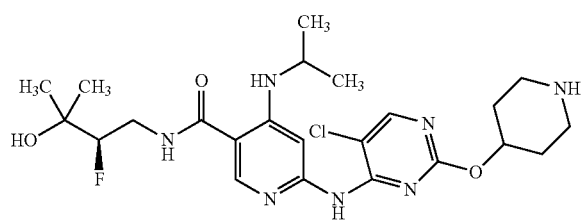
(41)

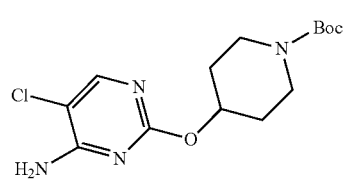

Step 1

A solution of tert-butyl 4-hydroxypiperidine-1-carboxylate (0.614 g, 3.05 mmol) in THF (50 mL) was added KOtBu (0.342 g, 3.05 mmol) and stirred for 30 mins then 2,5-dichloropyrimidin-4-amine (0.5 g, 3.05 mmol) was added. The reaction mixture was heated at reflux overnight. The reaction was cooled, diluted with ethylacetate and washed with water. The organic layer was dried over anhydrous Na₂SO₄, filtered, and concentrated to obtain an orange solid. The crude product was purified by column chromatography to obtain tert-butyl 4-((4-amino-5-chloropyrimidin-2-yl)oxy)piperidine-1-carboxylate (0.72 g, 72% yield) as a white solid. ¹H NMR (400 MHz, CDCl₃) δ 5.24 (br. s., 1H), 5.04-5.11 (m, 1H), 3.84 (m, 3H), 3.24-3.34 (m, 1H), 3.04 (ddd, J=3.50, 9.82, 13.45 Hz, 1H), 1.70-2.01 (m, 4H), 1.50 (s, 9H); LCMS 329.2 (M+H)⁺.

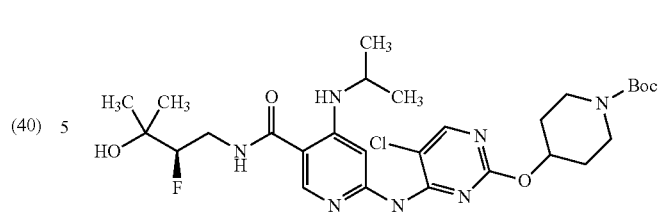

Step 2

A solution of (R)-6-chloro-N-(2-fluoro-3-hydroxy-3-methylbutyl)-4-(isopropylamino)nicotinamide (0.110 g, 0.346 mmol) and tert-butyl 4-((4-amino-5-chloropyrimidin-2-yl)oxy)piperidine-1-carboxylate (0.114 g, 0.346 mmol) in 1,4-dioxane (10 mL) was added Na₂CO₃ (0.110 g, 1.038 mmol) and water (1 mL). The reaction was purged with N₂ then added Xantphos (0.050 g, 0.087 mmol) followed by Pd₂(dba)₃ (0.079 g, 0.087 mmol) and again purged with N₂ for 5 mins. The reaction mixture was heated at 110° C. overnight. The reaction mixture was cooled, diluted with DCM, filtered through CELITE®, and concentrated to obtain a brown liquid as the crude product which was purified by column chromatography to obtain a yellow solid (28 mg, 13% yield). ¹H NMR (400 MHz, methanol-d₄) δ 8.34 (s, 1H), 8.29 (s, 1H), 7.71 (s, 1H), 5.26 (br. s., 1H), 4.33-4.51 (m, 1H), 3.76-3.95 (m, 2H), 3.62 (d, J=9.54 Hz, 2H), 3.40-3.56 (m, 4H), 1.92-2.02 (m, 2H), 1.77-1.88 (m, 2H), 1.50 (s, 9H), 1.34 (d, J=6.02 Hz, 6H), 1.30 (d, J=2.01 Hz, 6H); LCMS 611.2 (M+2H)⁺.

Step 3

(R)-tert-Butyl 4-((5-chloro-4-((5-((2-fluoro-3-hydroxy-3-methylbutyl)carbamoyl)-4-(isopropylamino)pyridin-2-yl)amino)pyrimidin-2-yl)oxy)piperidine-1-carboxylate (0.02 g, 0.033 mmol) in DCM (5 mL) was cooled to 0° C. and added TFA (0.5 µl, 6.49 µmol). The reaction mixture was stirred at room temperature overnight. The solvent was evaporated and the crude product was purified by Prep TLC plate (MeOH/CHCl₃ 9%) to afford the product. ¹H NMR (400 MHz, methanol-d₄) δ 8.34 (s, 1H), 8.30 (s, 1H), 7.64 (s, 1H), 5.27-5.34 (m, 1H), 4.33-4.50 (m, 1H), 3.74-3.94 (m, 2H), 3.47 (ddd, J=9.04, 14.56, 16.56 Hz, 1H), 3.35-3.39 (m, 1H), 3.20 (td, J=4.89, 13.30 Hz, 2H), 2.06-2.22 (m, 4H), 1.35 (d, J=6.53 Hz, 6H), 1.30 (d, J=1.51 Hz, 6H); LCMS 510.0 (M+H)⁺.

Example 42

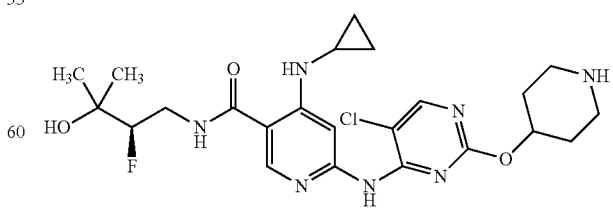
(42)

Example 42 was prepared according to the method described for Example 41. LCMS 508.2 (M+H)⁺; HPLC RT 8.11 min, conditions K.

Example 43

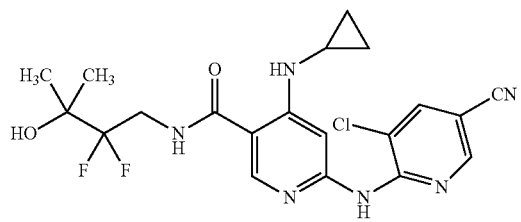

(43)

Step 1

To a stirred suspension of Zn dust (4.98 g, 76 mmol) in THF (100 mL) was added TMS-Cl (9.73 mL, 76 mmol) followed by the addition of ethyl 2-bromo-2,2-difluoroacetate (3.40 g, 16.75 mmol). The mixture was stirred for 15 minutes, then a solution of N-((1H-benzo[d][1,2,3]triazol-1-yl)methyl)-N-benzyl-1-phenylmethanamine (5 g, 15.22 mmol) in THF (50 mL) was added slowly. The reaction mixture was stirred for 2 hours. The reaction was quenched slowly by the addition of 10% sodium-bi-carbonate solution and extracted with ethyl acetate (3×200 mL). The combined organic layers were washed with water, dried over sodium sulphate and concentrated. The crude material was purified via column chromatography to afford ethyl 3-(dibenzylamino)-2,2-difluoropropanoate (5 g, 95% yield) as a pale yellow oil. LCMS 334.2 (M+H).

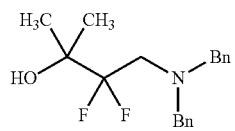

Step 2

To a solution of ethyl 3-(dibenzylamino)-2,2-difluoropropanoate (8 g, 24.00 mmol) in THF (80 mL) at 0° C. was added methyl MgBr (24 mL, 72.0 mmol) dropwise. After completion of addition the reaction was stirred at room temperature for 1 h. The reaction was cooled to 0° C. and quenched with the addition of ammonium chloride solution. The aqueous layer was extracted with ethyl acetate (3×200 mL). The combined organic layers were washed with water, dried over sodium sulphate and concentrated. The crude material was purified via column chromatography to afford 4-(dibenzylamino)-3,3-difluoro-2-methylbutan-2-ol (5 g, 64% yield) as a pale yellow oil. LCMS 320.2 (M+H)$^+$.

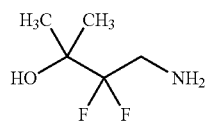

Step 3

To a solution of 4-(dibenzylamino)-3,3-difluoro-2-methylbutan-2-ol (5 g, 15.65 mmol) in MeOH was added Pd/C (2.5 g, 23.49 mmol) and palladium hydroxide (2.5 g, 15.65 mmol) and the reaction mass was hydrogenated at room temperature for 4 h. The reaction was filtered through CELITE® and the filtrate was concentrated to get 4-amino-3,3-difluoro-2-methylbutan-2-ol as a pale yellow oil (2 g, 91% yield). $^1$H NMR (MeOD$_4$, 400 MHz) δ 3.14 (t, J=16.4 Hz, 2H), 1.30 (s, 6H).

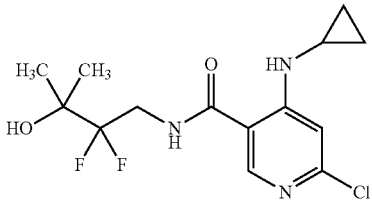 [SMILES: CC(C)(O)C(F)(F)CNC(=O)c1cnc(Cl)cc1NC1CC1]

Step 4

To a solution of 6-chloro-4-(cyclopropylamino)nicotinic acid (1 g, 4.70 mmol) in DMF (10 mL) was added DIPEA (2.46 mL, 14.11 mmol), 4-amino-3,3-difluoro-2-methylbutan-2-ol (0.79 g, 5.64 mmol) and HATU (1.79 g, 4.70 mmol) and the reaction was stirred at room temperature for 2 h. The reaction mass was diluted with water and extracted with ethyl acetate (3×75 ml). The combined organics were washed with 10% sodium-bi-carbonate and water then dried over sodium sulphate and concentrated to afford 6-chloro-N-(2,2-difluoro-3-hydroxy-3-methylbutyl)-4 (isopropylamino)nicotinamide (1.30 g, 60% yield).

Step 5

To a solution of 6-chloro-4-(cyclopropylamino)-N-(2,2-difluoro-3-hydroxy-3-methylbutyl)nicotinamide (0.2 g, 0.599 mmol) in dioxane (5 mL) was added 6-amino-5-chloronicotinonitrile (0.110 g, 0.719 mmol), Cs$_2$CO$_3$ (0.586 g, 1.798 mmol) and Xantphos (0.277 g, 0.479 mmol) and the reaction was degassed. Pd$_2$dba$_3$ (0.219 g, 0.240 mmol) was added and the mixture degassed again then heated at 110° C. in a sealed tube overnight. The reaction was cooled and filtered through CELITE® and purified via preparative HPLC to afford 6-((3-chloro-5-cyanopyridin-2-yl)amino)-4-(cyclopropylamino)-N-(2,2-difluoro-3-hydroxy-3-methylbutyl)nicotinamide (61 mg, 18% yield). $^1$H NMR (400 MHz, methanol-d$_4$) δ 8.68 (s, 1H), 8.42 (s, 1H), 8.24 (s, 1H), 7.47 (s, 1H), 4.01 (t, J=16 Hz, 1H), 2.67-2.73 (s, 1H), 1.35 (m, 6H), 1.01-1.06 (m, 2H), 0.75-0.77 (n, 2H); LCMS 451.1 (M+H)$^+$.

Example 44

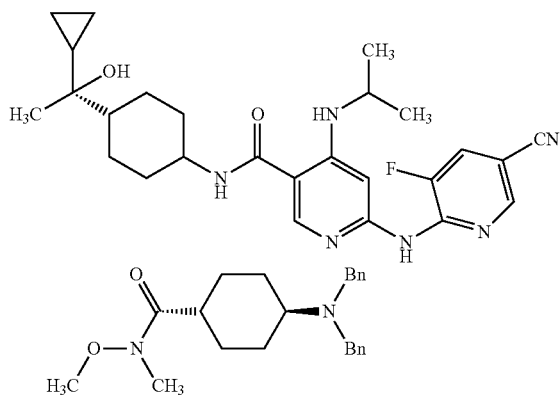

(44)

Step 1

To a stirred suspension of 4-(dibenzylamino)cyclohexanecarboxylic acid (1.5 g, 4.64 mmol) in DMF (15 mL) was added HATU (3.53 g, 9.28 mmol) and DIPEA (4.05 mL, 23.19 mmol). The reaction was stirred for 5 min then added N,O-dimethylhydroxylamine hydrochloride (2.26 g, 23.2 mmol). The reaction was stirred for 3 h, added water and extracted into EtOAc. The combined organic layers were dried ($Na_2SO_4$), filtered and concentrated. The product was purified via column chromatography to afford 4-(dibenzylamino)-N-methoxy-N-methylcyclohexanecarboxamide (0.9 g, 54% yield). $^1$H NMR (400 MHz, DMSO-$d_6$) δ 7.27-7.40 (m, 8H), 7.18-7.24 (m, 2H), 3.66 (s, 3H), 3.60 (s, 4H), 3.06 (s, 3H), 2.62 (br. s., 1H), 2.41 (t, J=11.80 Hz, 1H), 1.87 (d, J=10.04 Hz, 2H), 1.76 (d, J=11.04 Hz, 2H), 1.40-1.54 (m, 2H), 1.14-1.27 (m, 2H); LCMS 367.0 (M+H)+.

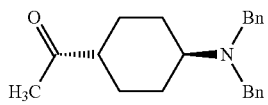

Step 2

To a stirred solution of 4-(dibenzylamino)-N-methoxy-N-methylcyclohexanecarboxamide (800 mg, 2.183 mmol) in dry THF (16 mL) at 0° C. was added methyl MgBr (1.091 mL, 3.27 mmol). The reaction was then allowed to warm to room temperature and stirred for 2 h. The reaction was cooled in an ice bath and quenched with saturated $NH_4Cl$. The combined organic layers were dried ($Na_2SO_4$), filtered and concentrated. The product was purified via column chromatography to afford 1-(4-(dibenzylamino)cyclohexyl)ethanone. LCMS 322.4 (M+H)$^+$.

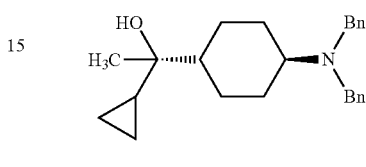

Step 3

To a stirred solution of 1-(4-(dibenzylamino)cyclohexyl)ethanone (1.2 g, 3.73 mmol) in dry THF (24 mL) was added cyclopropyl magnesium bromide (14.93 mL, 7.47 mmol) dropwise at 0° C. The reaction was then allowed to warm to room temperature and stirred for 3 h. The reaction was cooled in an ice bath and quenched with saturated $NH_4Cl$. The combined organic layers were dried ($Na_2SO_4$), filtered and concentrated. The product was purified via column chromatography to afford 1-cyclopropyl-1-(4-(dibenzylamino)cyclohexyl)ethanol as a mixture of diastereomers. LCMS 364.3 (M+H)$^+$.

Step 4

A solution of 1-cyclopropyl-1-((1s,4s)-4-(dibenzylamino)cyclohexyl)ethanol (1.2 g, 3.30 mmol) in MeOH (24 mL) was added Pd/C (0.527 g, 0.495 mmol) and stirred for 16 h under hydrogen atmosphere at RT. The reaction mixture was filtered through CELITE® and the filtrate concentrated to afford 1-((1s,4s)-4-aminocyclohexyl)-1-cyclopropylethanol as a mixture of diastereomers (95% yield). $^1$H NMR (300 MHz, DMSO-$d_6$) δ 3.57 (s, 1H), 1.80 (m, 4H), 1.00-1.22 (m, 4H), 0.91-0.99 (m, 6H), 0.71-0.83 (m, 1H), 0.33 (t, J=6.04 Hz, 1H), 0.13-0.26 (m, 3H).

The Examples in the table below were prepared in an analogous fashion to the previously described Examples, substituting where appropriate, alternate amines in the synthetic sequence.

TABLE 4

| Ex. No. | Structure | HPLC rt (min) | HPLC cond. | LCMS (M + H)$^+$ |
|---|---|---|---|---|
| 45 | (Abs) | 8.13 | K | 393.2 |

TABLE 4-continued
| Ex. No. | Structure | | HPLC rt (min) | HPLC cond. | LCMS (M + H)+ |
|---|---|---|---|---|---|
| 46 | 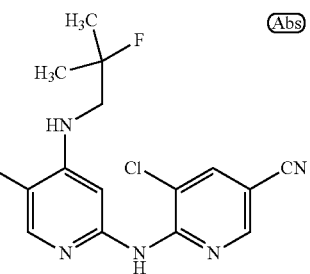 | (Abs) | 6.369 | E | 467.2 |
| 47 | 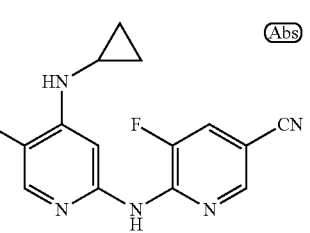 | (Abs) | 5.47 | E | 417.2 |
| 48 | 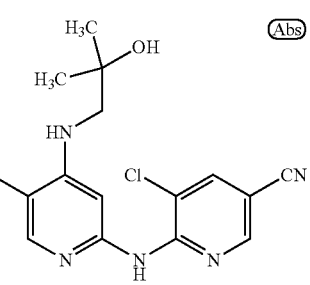 | (Abs) | 6.56 | A | 464.4 |
| 49 | 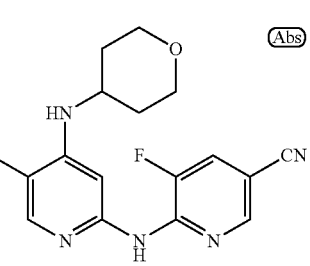 | (Abs) | 9.67 | K | 461.2 |
| 50 | 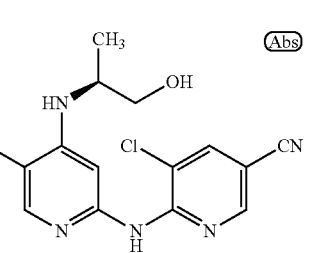 | (Abs) | 9.23 | K | 451.2 |
| 51 | 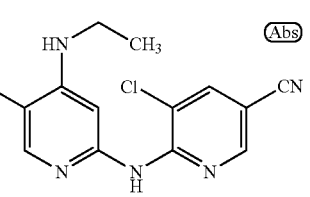 | (Abs) | 6.57 | A | 421.2 |

TABLE 4-continued

| Ex. No. | Structure | HPLC rt (min) | HPLC cond. | LCMS (M + H)+ |
|---|---|---|---|---|
| 52 | 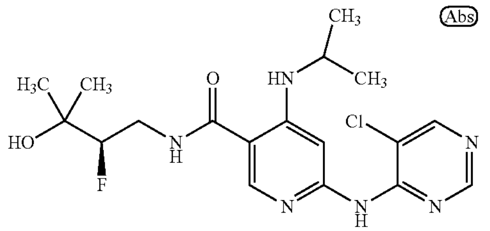 [SMILES: CC(C)Nc1cc(Nc2ncncc2Cl)ncc1C(=O)NC[C@@H](F)C(C)(C)O] | 11.09 | A | 411.2 |
| 53 | 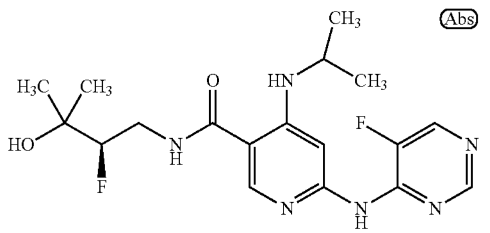 [SMILES: CC(C)Nc1cc(Nc2ncncc2F)ncc1C(=O)NC[C@@H](F)C(C)(C)O] | 8.59 | K | 395.5 |
| 54 | 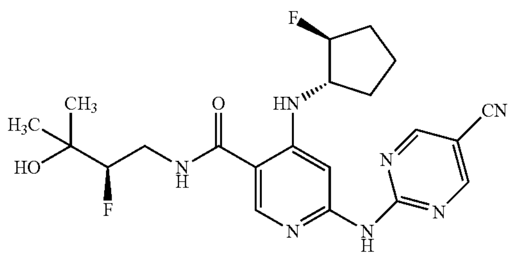 [SMILES: CC(C)(O)[C@H](F)CNC(=O)c1cnc(Nc2ncc(C#N)cn2)cc1N[C@H]1CCC[C@@H]1F] | 1.42 | L | 446.2 |
| 55 | 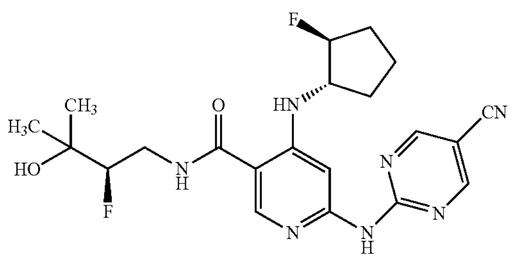 [SMILES: CC(C)(O)[C@H](F)CNC(=O)c1cnc(Nc2ncc(C#N)cn2)cc1N[C@H]1CCC[C@@H]1F] | 1.47 | L | 446.2 |
| 56 | 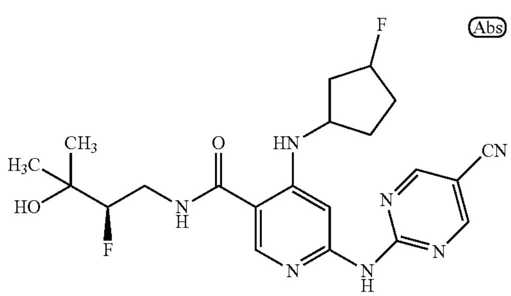 [SMILES: CC(C)(O)[C@H](F)CNC(=O)c1cnc(Nc2ncc(C#N)cn2)cc1NC1CCC(F)C1] | 1.34 | L | 446.2 |
| 57 | 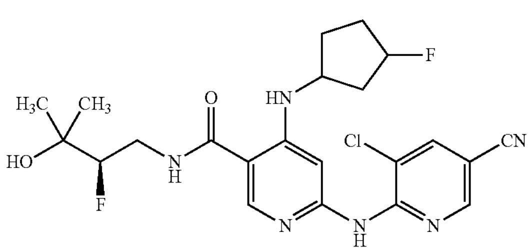 [SMILES: CC(C)(O)[C@H](F)CNC(=O)c1cnc(Nc2ncc(C#N)cc2Cl)cc1NC1CCC(F)C1] | 7.33 | A | 479.2 |

TABLE 4-continued
| Ex. No. | Structure | HPLC rt (min) | HPLC cond. | LCMS (M + H)+ |
|---|---|---|---|---|
| 58 | 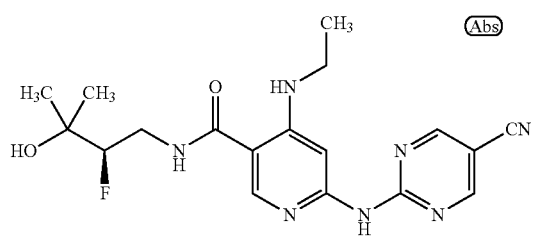 [SMILES: CCNc1cc(Nc2ncc(C#N)cn2)ncc1C(=O)NC[C@@H](F)C(C)(C)O] (Abs) | 1.25 | G | 388.1 |
| 59 | 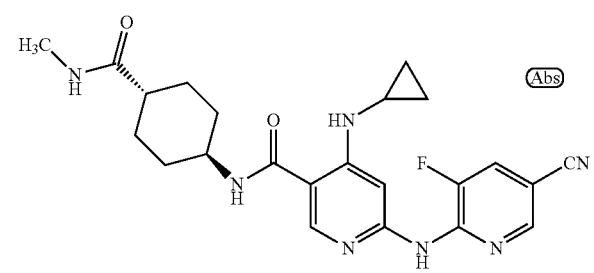 [SMILES: CNC(=O)[C@H]1CC[C@H](NC(=O)c2cnc(Nc3ncc(C#N)cc3F)cc2NC2CC2)CC1] (Abs) | 1.34 | G | 452.1 |
| 60 | 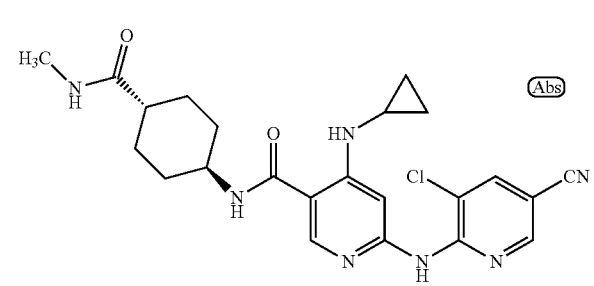 [SMILES: CNC(=O)[C@H]1CC[C@H](NC(=O)c2cnc(Nc3ncc(C#N)cc3Cl)cc2NC2CC2)CC1] (Abs) | 1.47 | G | 468.1 |
| 61 | 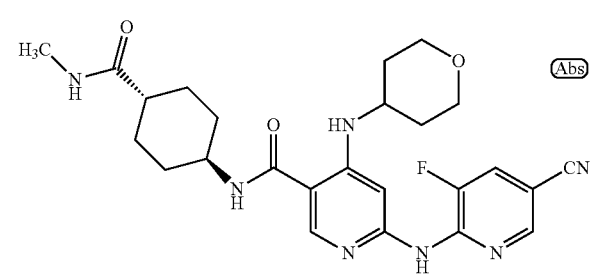 [SMILES: CNC(=O)[C@H]1CC[C@H](NC(=O)c2cnc(Nc3ncc(C#N)cc3F)cc2NC2CCOCC2)CC1] (Abs) | 1.23 | G | 496.2 |
| 62 | 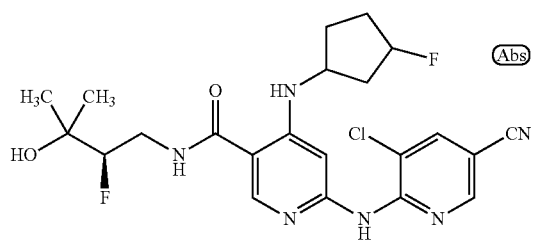 [SMILES: CC(C)(O)[C@H](F)CNC(=O)c1cnc(Nc2ncc(C#N)cc2Cl)cc1NC1CCC(F)C1] (Abs) | 7.28 | A | 479.2 |
| 63 | 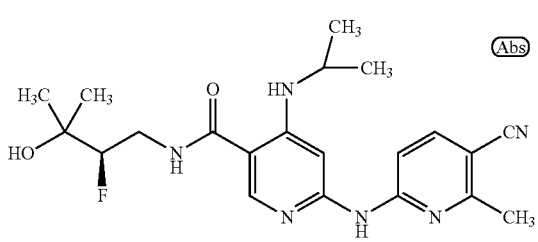 [SMILES: Cc1nc(Nc2cc(NC(C)C)c(C(=O)NC[C@@H](F)C(C)(C)O)cn2)ccc1C#N] (Abs) | 6.98 | A | 415.3 |

TABLE 4-continued

| Ex. No. | Structure | HPLC rt (min) | HPLC cond. | LCMS (M + H)+ |
|---|---|---|---|---|
| 64 | 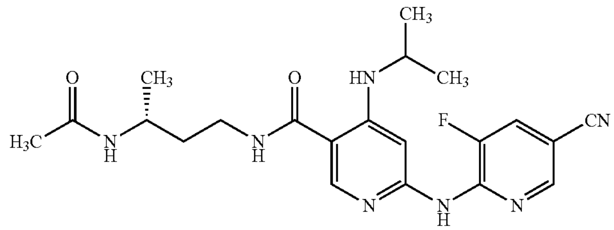 [SMILES: CC(=O)N[C@H](C)CCNC(=O)c1cnc(Nc2ncc(C#N)cc2F)cc1NC(C)C] | 1.38 | G | 428.1 |
| 65 | 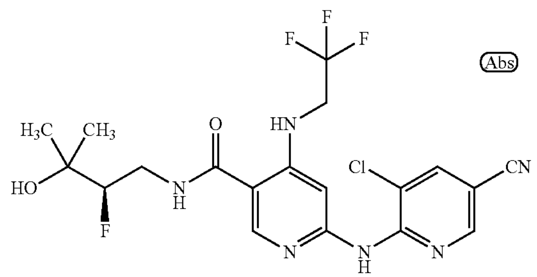 [SMILES: CC(C)(O)[C@H](F)CNC(=O)c1cnc(Nc2ncc(C#N)cc2Cl)cc1NCC(F)(F)F] | 7.23 | A | 475.1 |
| 66 | 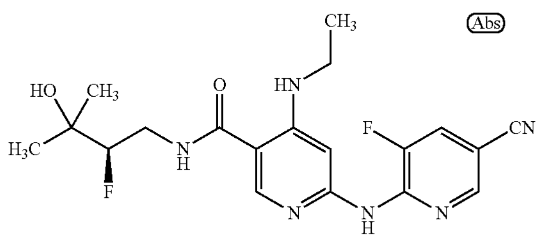 [SMILES: CCNc1cc(Nc2ncc(C#N)cc2F)ncc1C(=O)NC[C@@H](F)C(C)(C)O] | 9.79 | K | 405.2 |
| 67 | 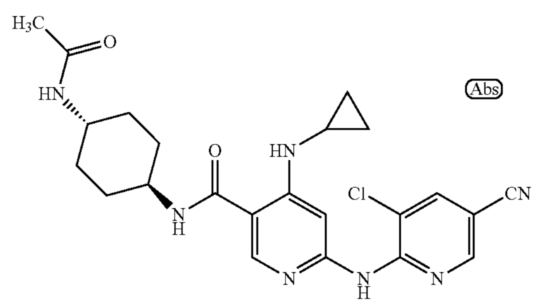 [SMILES: CC(=O)N[C@H]1CC[C@H](NC(=O)c2cnc(Nc3ncc(C#N)cc3Cl)cc2NC2CC2)CC1] | 1.46 | G | 468.2 |
| 68 | 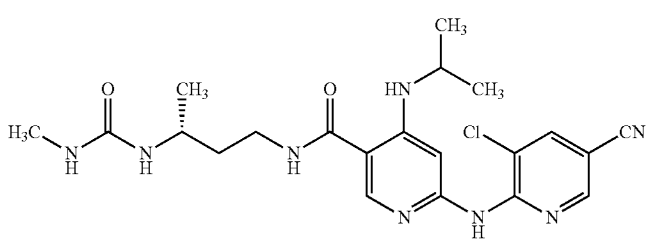 [SMILES: CNC(=O)N[C@H](C)CCNC(=O)c1cnc(Nc2ncc(C#N)cc2Cl)cc1NC(C)C] | 1.65 | G | 488.2 |
| 69 | 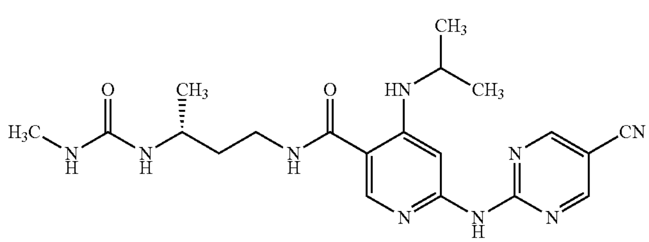 [SMILES: CNC(=O)N[C@H](C)CCNC(=O)c1cnc(Nc2ncc(C#N)cn2)cc1NC(C)C] | 1.43 | G | 453.4 |

TABLE 4-continued

| Ex. No. | Structure | HPLC rt (min) | HPLC cond. | LCMS (M + H)+ |
|---|---|---|---|---|
| 70 | 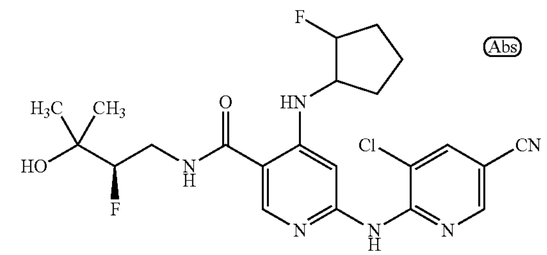 [SMILES: CC(C)(O)[C@H](F)CNC(=O)c1cnc(Nc2ncc(C#N)cc2Cl)cc1NC1CCCC1F] | 7.81 | A | 479.2 |
| 71 | 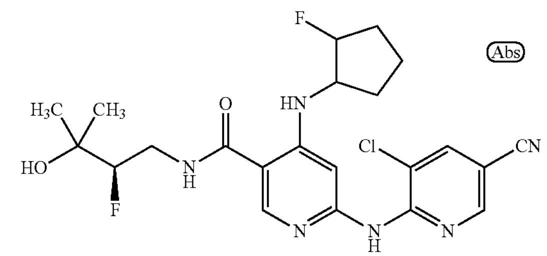 [SMILES: CC(C)(O)[C@H](F)CNC(=O)c1cnc(Nc2ncc(C#N)cc2Cl)cc1NC1CCCC1F] | 7.79 | A | 479.2 |
| 72 | 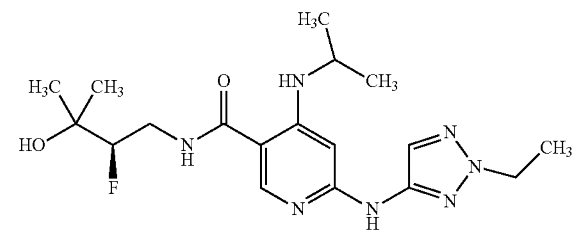 [SMILES: CCn1ncc(Nc2cc(NC(C)C)c(C(=O)NC[C@@H](F)C(C)(C)O)cn2)n1] | 1.33 | G | 394.1 |
| 73 | 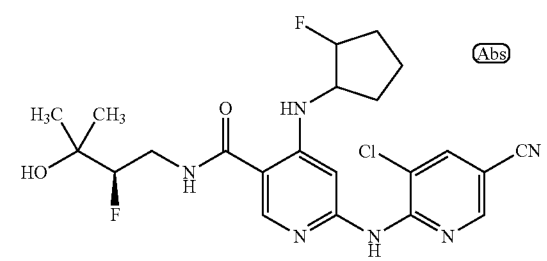 [SMILES: CC(C)(O)[C@H](F)CNC(=O)c1cnc(Nc2ncc(C#N)cc2Cl)cc1NC1CCCC1F] | 6.65 | E | 479.7 |
| 74 | 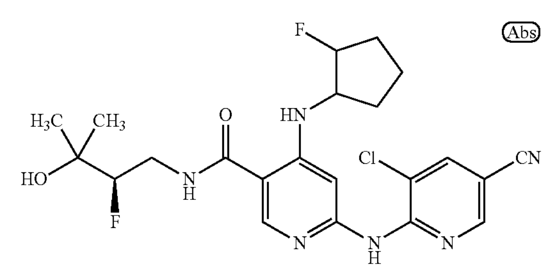 [SMILES: CC(C)(O)[C@H](F)CNC(=O)c1cnc(Nc2ncc(C#N)cc2Cl)cc1NC1CCCC1F] | 7.63 | A | 479.7 |
| 75 | 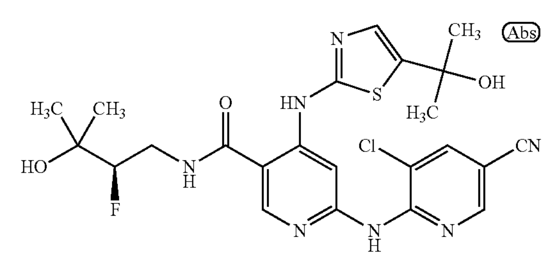 [SMILES: CC(C)(O)c1cnc(Nc2cc(Nc3ncc(C#N)cc3Cl)ncc2C(=O)NC[C@@H](F)C(C)(C)O)s1] | 6.42 | E | 534.2 |

TABLE 4-continued
| Ex. No. | Structure | HPLC rt (min) | HPLC cond. | LCMS (M + H)+ |
|---|---|---|---|---|
| 76 | 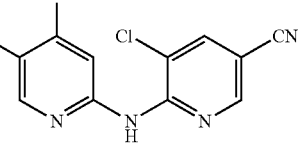 | 5.42 | B | 477.2 |
| 77 | 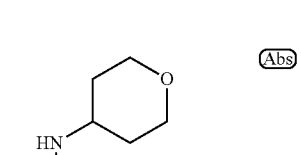 | 1.4 | G | 512.3 |
| 78 | 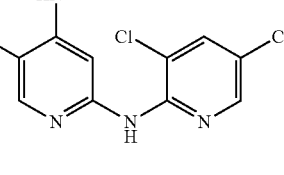 | 5.41 | B | 477.2 |
| 79 | 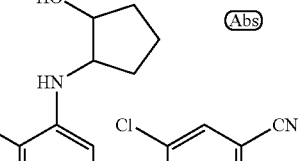 | 6.48 | A | 495.2 |
| 80 | 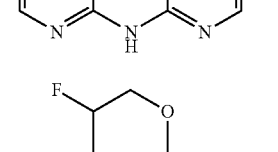 | 5.95 | E | 410.2 (M − H)+ |
| 81 | 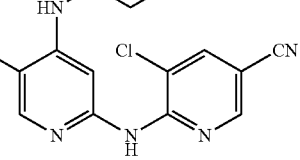 | 11.96 | K | 408.5 |

TABLE 4-continued
| Ex. No. | Structure | HPLC rt (min) | HPLC cond. | LCMS (M + H)+ |
|---|---|---|---|---|
| 82 | 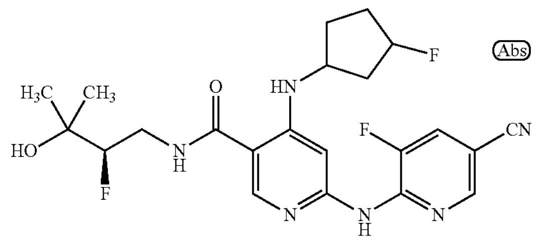 [SMILES: CC(C)(O)[C@H](F)CNC(=O)c1cnc(Nc2ncc(C#N)cc2F)cc1NC1CCC(F)C1] | 7.10 | A | 463.7 |
| 83 | 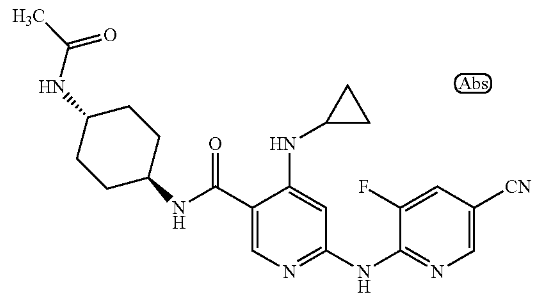 [SMILES: CC(=O)N[C@H]1CC[C@H](NC(=O)c2cnc(Nc3ncc(C#N)cc3F)cc2NC2CC2)CC1] | 1.33 | G | 452.3 |
| 84 | 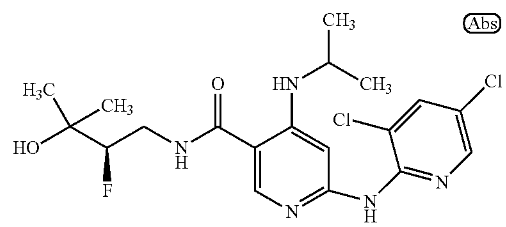 [SMILES: CC(C)Nc1cc(Nc2ncc(Cl)cc2Cl)ncc1C(=O)NC[C@@H](F)C(C)(C)O] | 2.01 | G | 444.2 |
| 85 | 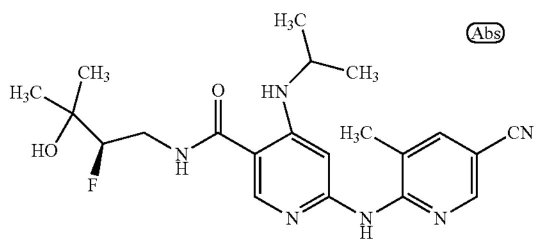 [SMILES: Cc1cc(C#N)cnc1Nc1cc(NC(C)C)c(C(=O)NC[C@@H](F)C(C)(C)O)cn1] | 7.13 | A | 413.6 (M − H)+ |
| 86 | 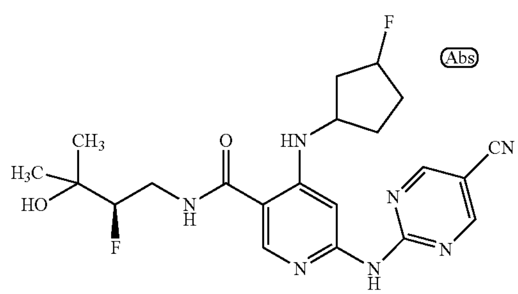 [SMILES: CC(C)(O)[C@H](F)CNC(=O)c1cnc(Nc2ncc(C#N)cn2)cc1NC1CCC(F)C1] | 7.4 | H | 446.2 |
| 87 | 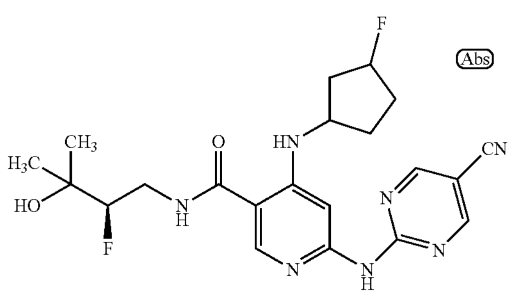 [SMILES: CC(C)(O)[C@H](F)CNC(=O)c1cnc(Nc2ncc(C#N)cn2)cc1NC1CCC(F)C1] | 8.6 | H | 446.2 |

TABLE 4-continued
| Ex. No. | Structure | HPLC rt (min) | HPLC cond. | LCMS (M + H)+ |
|---|---|---|---|---|
| 88 | 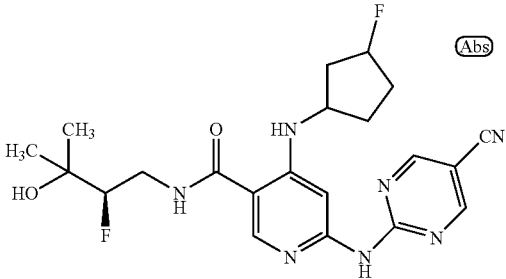 [SMILES: CC(C)(O)[C@H](F)CNC(=O)c1cnc(Nc2ncc(C#N)cn2)cc1NC1CCC(F)C1] | 9.2 | H | 446.2 |
| 89 | 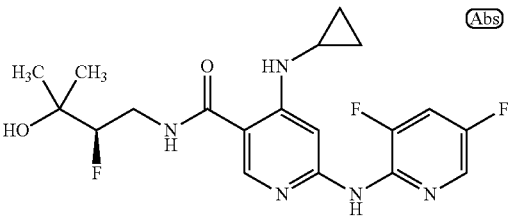 [SMILES: CC(C)(O)[C@H](F)CNC(=O)c1cnc(Nc2ncc(F)cc2F)cc1NC1CC1] | 6.44 | A | 410.2 |
| 90 | 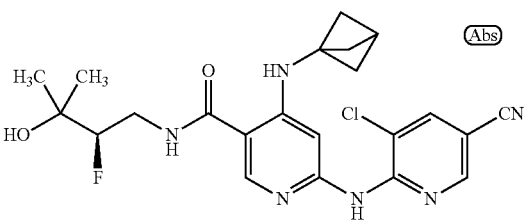 [SMILES: CC(C)(O)[C@H](F)CNC(=O)c1cnc(Nc2ncc(C#N)cc2Cl)cc1NC12CC(C1)C2] | 1.86 | G | 459.1 |
| 91 | 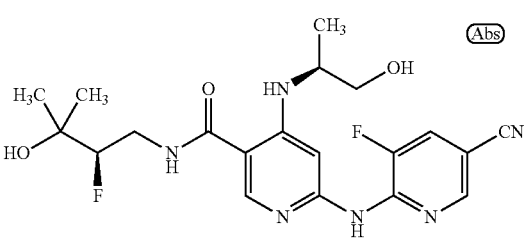 [SMILES: C[C@@H](CO)Nc1cc(Nc2ncc(C#N)cc2F)ncc1C(=O)NC[C@@H](F)C(C)(C)O] | 5.39 | A | 435.6 |
| 92 | 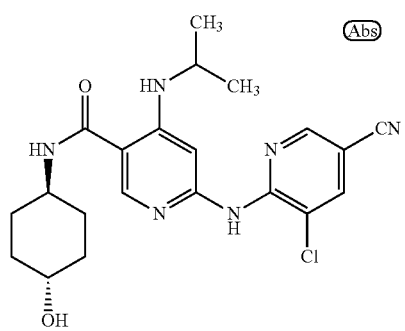 [SMILES: CC(C)Nc1cc(Nc2ncc(C#N)cc2Cl)ncc1C(=O)N[C@H]1CC[C@H](O)CC1] | 11.55 | K | 429.2 |
| 93 | 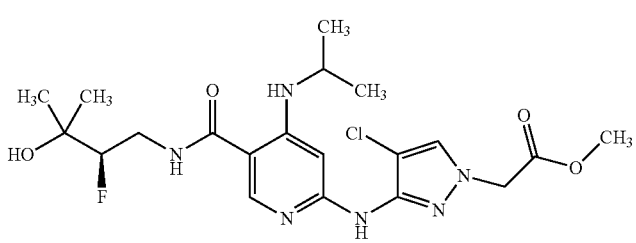 [SMILES: COC(=O)Cn1cc(Cl)c(Nc2cc(NC(C)C)c(C(=O)NC[C@@H](F)C(C)(C)O)cn2)n1] | 0.71 | O, 2 min grad | 471.2 |

TABLE 4-continued

| Ex. No. | Structure | HPLC rt (min) | HPLC cond. | LCMS (M + H)+ |
|---|---|---|---|---|
| 94 | 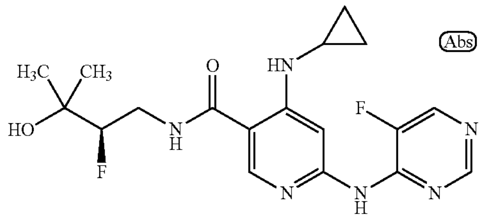 [SMILES: CC(C)(O)[C@H](F)CNC(=O)c1cnc(Nc2ncncc2F)cc1NC1CC1] | 9.37 | A | 393.1 |
| 95 | 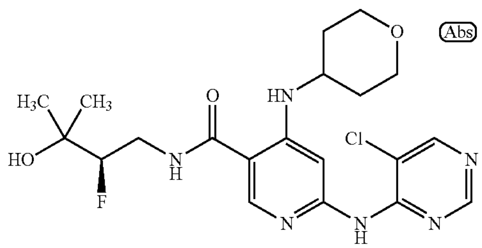 [SMILES: CC(C)(O)[C@H](F)CNC(=O)c1cnc(Nc2ncncc2Cl)cc1NC1CCOCC1] | 9.51 | K | 451.2 (M − H)+ |
| 96 | 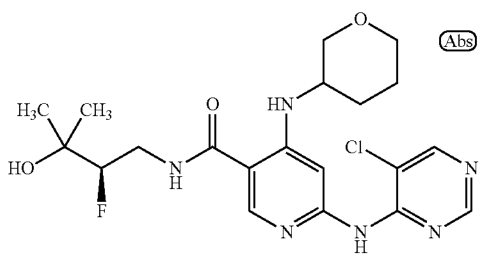 [SMILES: CC(C)(O)[C@H](F)CNC(=O)c1cnc(Nc2ncncc2Cl)cc1NC1CCCOC1] | 9.98 | K | 453.4 |
| 97 | 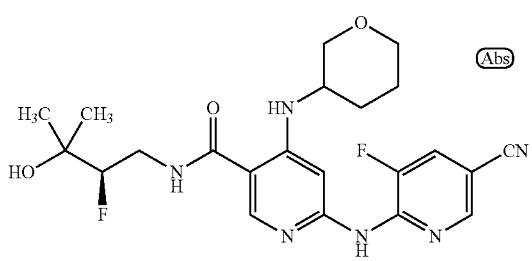 [SMILES: CC(C)(O)[C@H](F)CNC(=O)c1cnc(Nc2ncc(C#N)cc2F)cc1NC1CCCOC1] | 10.87 | K | 461.5 |
| 98 | 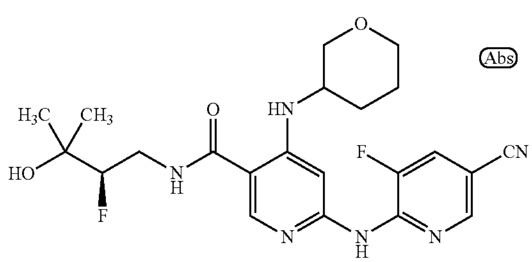 [SMILES: CC(C)(O)[C@H](F)CNC(=O)c1cnc(Nc2ncc(C#N)cc2F)cc1NC1CCCOC1] | 10.83 | K | 461.5 |
| 99 | 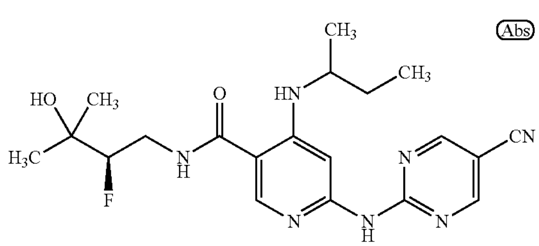 [SMILES: CCC(C)Nc1cc(Nc2ncc(C#N)cn2)ncc1C(=O)NC[C@@H](F)C(C)(C)O] | 6.57 | A | 414.2 (M − H)+ |

TABLE 4-continued
| Ex. No. | Structure | HPLC rt (min) | HPLC cond. | LCMS (M + H)+ |
|---|---|---|---|---|
| 100 |  (Abs) | 10.17 | A, 18 min grad | 428.6 |
| 101 |  (Abs) | 9.76 | A, 18 min grad | 418.6 |
| 102 | 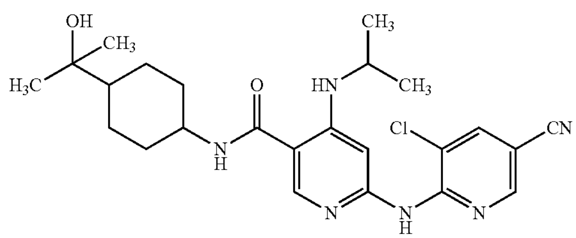 [SMILES: CC(C)Nc1cc(Nc2ncc(C#N)cc2Cl)ncc1C(=O)NC1CCC(C(C)(C)O)CC1] | 7.83 | A | 472 (M − H) |
| 103 | 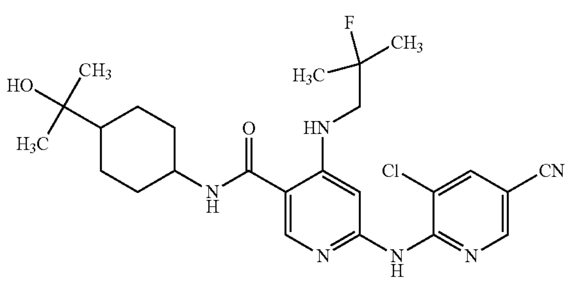 [SMILES: CC(C)(F)CNc1cc(Nc2ncc(C#N)cc2Cl)ncc1C(=O)NC1CCC(C(C)(C)O)CC1] | 7.92 | A | 501.2 (M − H) |
| 104 | 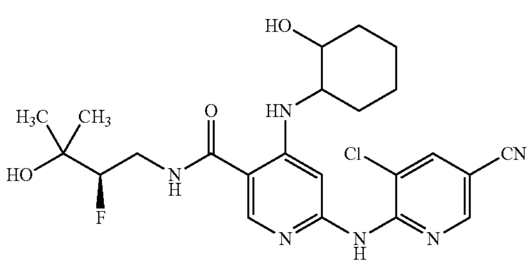 [SMILES: CC(C)(O)[C@H](F)CNC(=O)c1cnc(Nc2ncc(C#N)cc2Cl)cc1NC1CCCCC1O] | 6.95 | A | 491.2 |
| 105 |  (Abs) | 10.13 | K | 409.8 |

TABLE 4-continued

| Ex. No. | Structure | HPLC rt (min) | HPLC cond. | LCMS (M + H)+ |
|---|---|---|---|---|
| 106 | 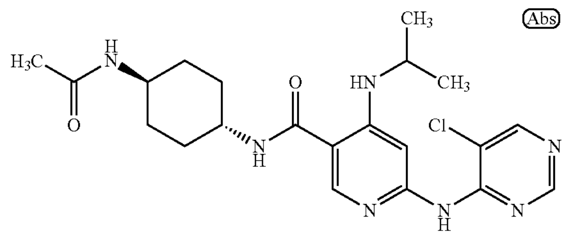 [SMILES: CC(=O)N[C@H]1CC[C@H](NC(=O)c2cnc(Nc3ncncc3Cl)cc2NC(C)C)CC1] | 5.36 | E | 446.9 |
| 107 | 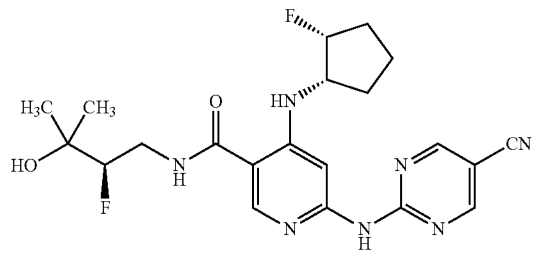 [SMILES: CC(C)(O)[C@H](F)CNC(=O)c1cnc(Nc2ncc(C#N)cn2)cc1N[C@H]1CCC[C@H]1F] | 6.69 | A | 446.5 |
| 108 | 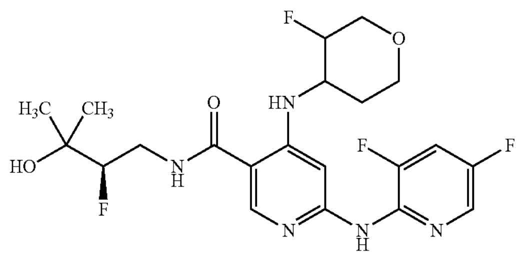 [SMILES: CC(C)(O)[C@H](F)CNC(=O)c1cnc(Nc2ncc(F)cc2F)cc1NC1CCOCC1F] | 5.88 | A | 472.4 |
| 109 | 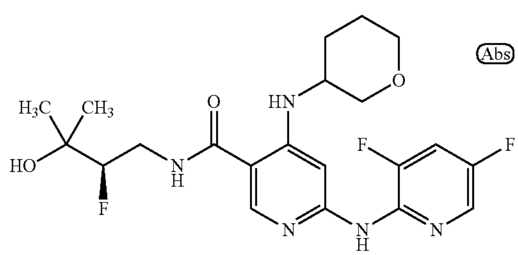 [SMILES: CC(C)(O)[C@H](F)CNC(=O)c1cnc(Nc2ncc(F)cc2F)cc1NC1CCCOC1] | 6.20 | A | 454.4 |
| 110 | 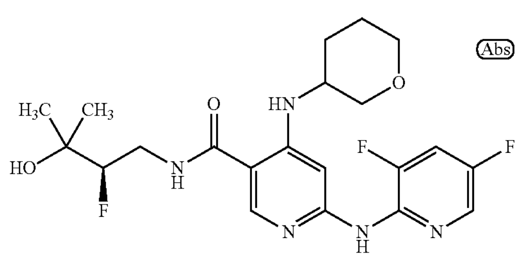 [SMILES: CC(C)(O)[C@H](F)CNC(=O)c1cnc(Nc2ncc(F)cc2F)cc1NC1CCCOC1] | 6.20 | A | 454.4 |
| 111 | 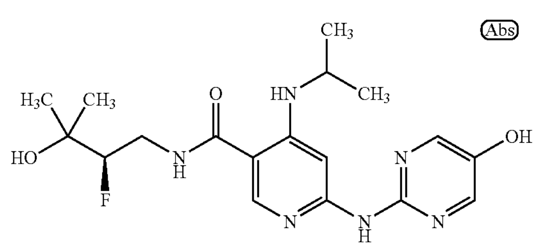 [SMILES: CC(C)Nc1cc(Nc2ncc(O)cn2)ncc1C(=O)NC[C@@H](F)C(C)(C)O] | 0.46 | O, 2 min grad | 393.2 |

TABLE 4-continued

| Ex. No. | Structure | HPLC rt (min) | HPLC cond. | LCMS (M + H)+ |
|---|---|---|---|---|
| 112 | 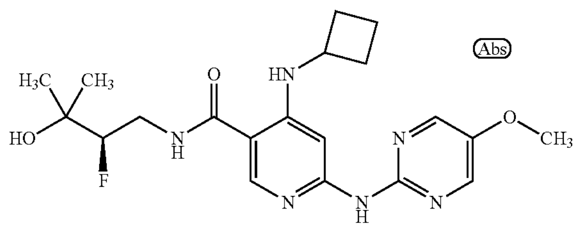 [SMILES: COc1cnc(Nc2cc(NC3CCC3)c(C(=O)NC[C@@H](F)C(C)(C)O)cn2)nc1] | 1.41 | G | 418.9 |
| 113 | 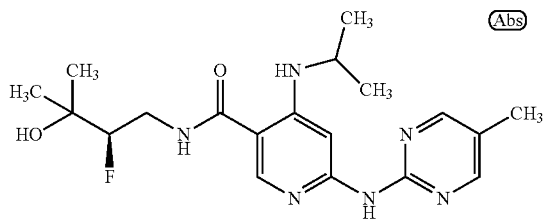 [SMILES: Cc1cnc(Nc2cc(NC(C)C)c(C(=O)NC[C@@H](F)C(C)(C)O)cn2)nc1] | 1.50 | G | 391.2 |
| 114 | 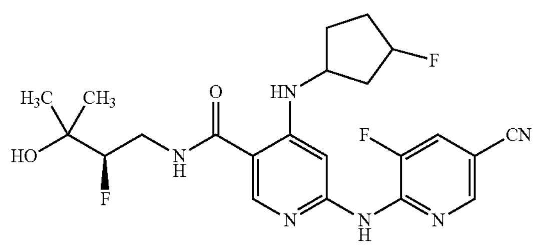 [SMILES: CC(C)(O)[C@H](F)CNC(=O)c1cnc(Nc2ncc(C#N)cc2F)cc1NC1CCC(F)C1] | 6.84 | A | 463.5 |
| 115 | 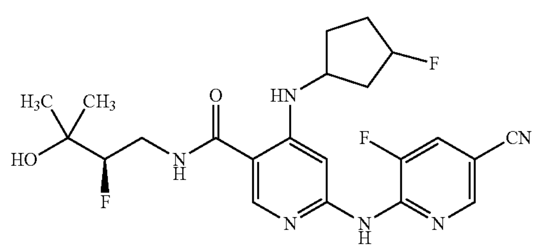 [SMILES: CC(C)(O)[C@H](F)CNC(=O)c1cnc(Nc2ncc(C#N)cc2F)cc1NC1CCC(F)C1] | 6.86 | A | 461.4 (M − H)+ |
| 116 | 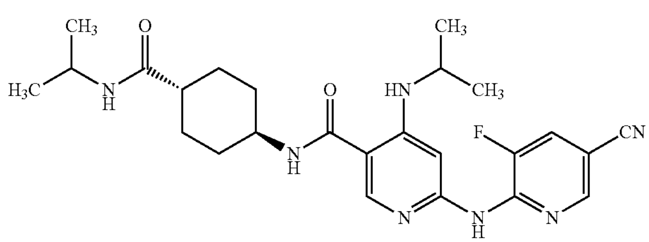 [SMILES: CC(C)Nc1cc(Nc2ncc(C#N)cc2F)ncc1C(=O)N[C@H]1CC[C@H](C(=O)NC(C)C)CC1] | 1.77 | G | 482.2 |
| 117 | 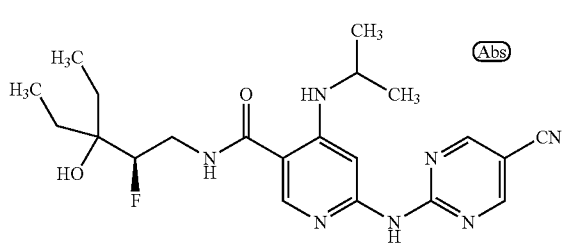 [SMILES: CCC(O)(CC)[C@H](F)CNC(=O)c1cnc(Nc2ncc(C#N)cn2)cc1NC(C)C] | 6.54 | E | 430 |

TABLE 4-continued

| Ex. No. | Structure | HPLC rt (min) | HPLC cond. | LCMS (M + H)+ |
|---|---|---|---|---|
| 118 | 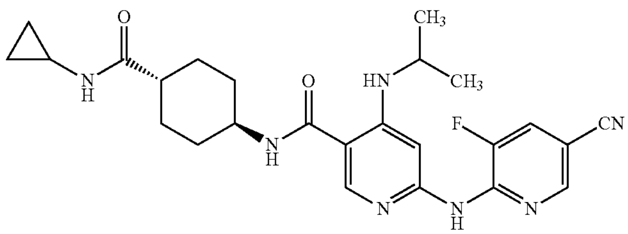 [SMILES: CC(C)Nc1cc(Nc2ncc(C#N)cc2F)ncc1C(=O)N[C@H]1CC[C@H](C(=O)NC2CC2)CC1] | 1.49 | G | 480.3 |
| 119 | 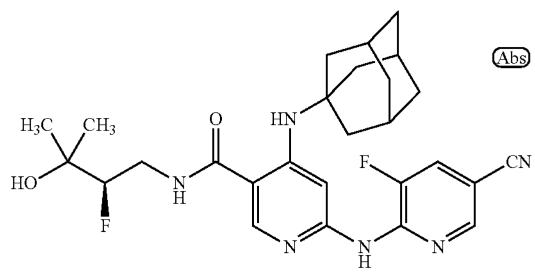 [SMILES: CC(C)(O)[C@H](F)CNC(=O)c1cnc(Nc2ncc(C#N)cc2F)cc1NC12CC3CC(CC(C3)C1)C2] | 2.05 | G | 511.3 |
| 120 | 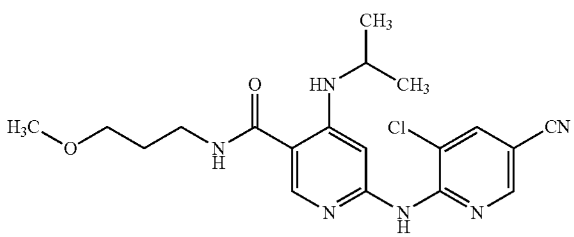 [SMILES: COCCCNC(=O)c1cnc(Nc2ncc(C#N)cc2Cl)cc1NC(C)C] | 1.36 | G | 423.2 |
| 121 | 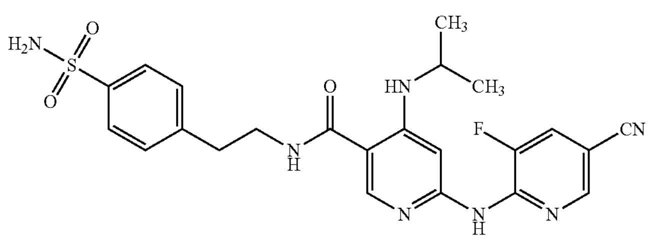 [SMILES: CC(C)Nc1cc(Nc2ncc(C#N)cc2F)ncc1C(=O)NCCc1ccc(S(N)(=O)=O)cc1] | 8.68 | A | 498.2 |
| 122 | 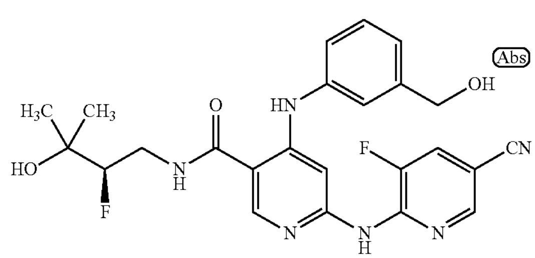 [SMILES: CC(C)(O)[C@H](F)CNC(=O)c1cnc(Nc2ncc(C#N)cc2F)cc1Nc1cccc(CO)c1] | 1.36 | G | 483.1 |
| 123 | 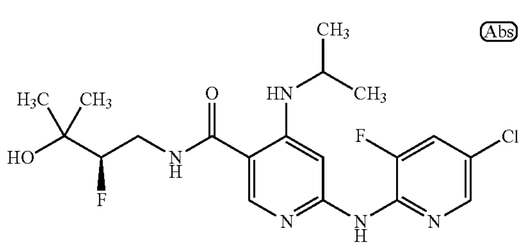 [SMILES: CC(C)Nc1cc(Nc2ncc(Cl)cc2F)ncc1C(=O)NC[C@@H](F)C(C)(C)O] | 7.32 | A | 428 |

TABLE 4-continued
| Ex. No. | Structure | HPLC rt (min) | HPLC cond. | LCMS (M + H)+ |
|---|---|---|---|---|
| 124 | 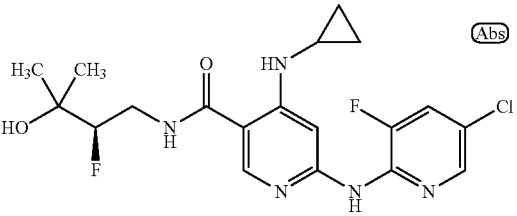 [SMILES: CC(C)(O)[C@H](F)CNC(=O)c1cnc(Nc2ncc(Cl)cc2F)cc1NC1CC1] | 7.04 | A | 426 |
| 125 | 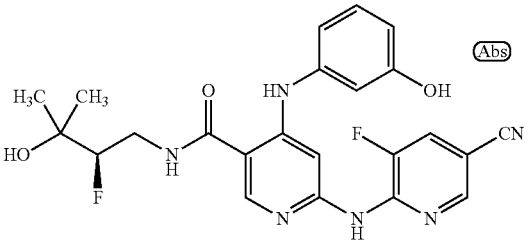 [SMILES: CC(C)(O)[C@H](F)CNC(=O)c1cnc(Nc2ncc(C#N)cc2F)cc1Nc1cccc(O)c1] | 1.32 | G | 469.2 |
| 126 | 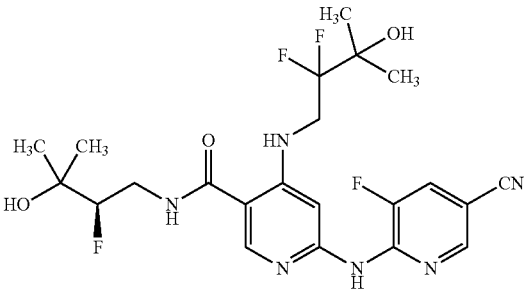 [SMILES: CC(C)(O)[C@H](F)CNC(=O)c1cnc(Nc2ncc(C#N)cc2F)cc1NCC(F)(F)C(C)(C)O] | 5.79 | E | 498.9 |
| 127 | 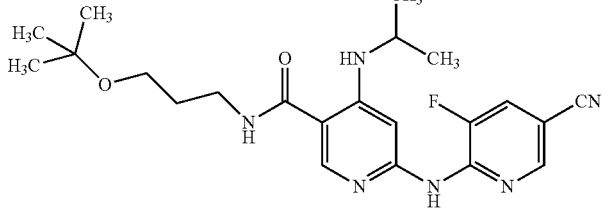 | 2.00 | G | 429.2 |
| 128 | 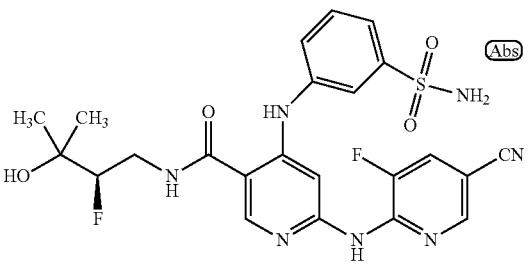 [SMILES: CC(C)(O)[C@H](F)CNC(=O)c1cnc(Nc2ncc(C#N)cc2F)cc1Nc1cccc(S(N)(=O)=O)c1] | 1.28 | G | 532.1 |
| 129 | 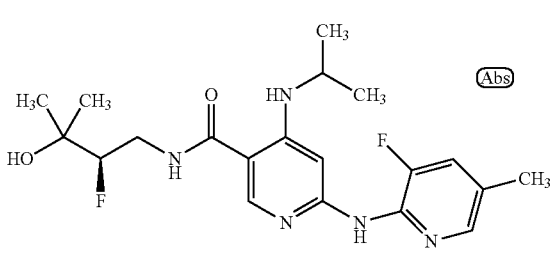 [SMILES: Cc1cnc(Nc2cc(NC(C)C)c(C(=O)NC[C@@H](F)C(C)(C)O)cn2)c(F)c1] | 1.51 | G | 408.3 |

TABLE 4-continued
| Ex. No. | Structure | HPLC rt (min) | HPLC cond. | LCMS (M + H)+ |
|---|---|---|---|---|
| 130 | 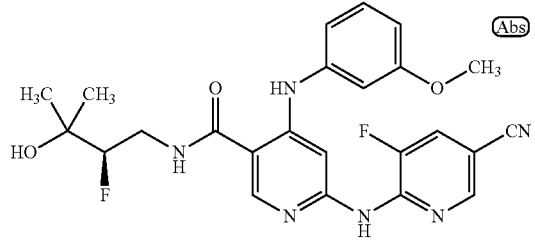 [SMILES: COc1cccc(Nc2cc(Nc3ncc(C#N)cc3F)ncc2C(=O)NC[C@@H](F)C(C)(C)O)c1] | 1.64 | G | 483.2 |
| 131 | 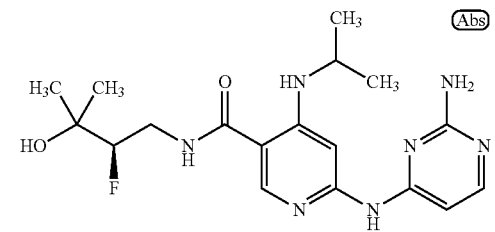 [SMILES: CC(C)Nc1cc(Nc2ccnc(N)n2)ncc1C(=O)NC[C@@H](F)C(C)(C)O] | 0.99 | G | 392.3 |
| 132 | 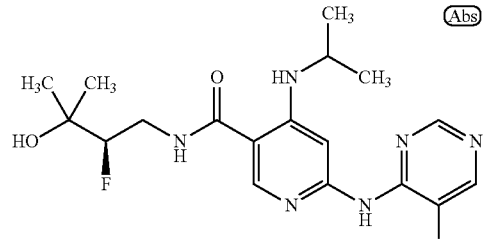 | 1.04 | G | 392.3 |
| 133 | 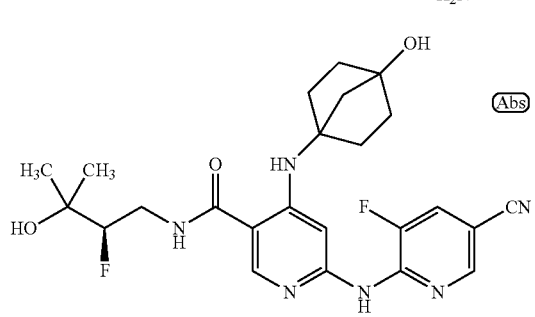 | 1.26 | G | 487.2 |
| 134 | 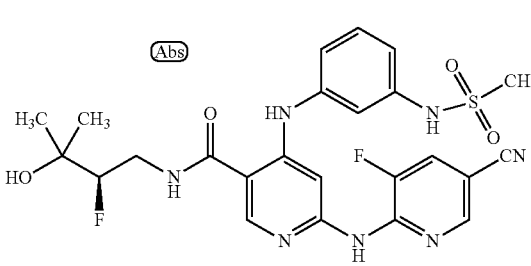 | 1.34 | G | 546.2 |
| 135 | 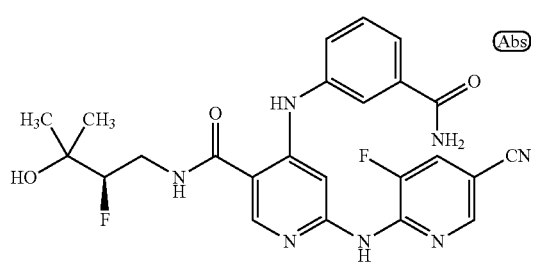 [SMILES: CC(C)(O)[C@H](F)CNC(=O)c1cnc(Nc2ncc(C#N)cc2F)cc1Nc1cccc(C(N)=O)c1] | 1.21 | G | 496.1 |

TABLE 4-continued
| Ex. No. | Structure | HPLC rt (min) | HPLC cond. | LCMS (M + H)+ |
|---|---|---|---|---|
| 136 | 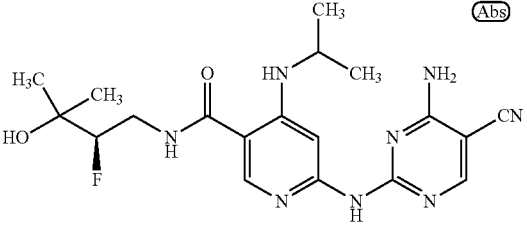 [SMILES: CC(C)Nc1cc(Nc2ncc(C#N)c(N)n2)ncc1C(=O)NC[C@@H](F)C(C)(C)O] | 1.24 | G | 417.2 |
| 137 | 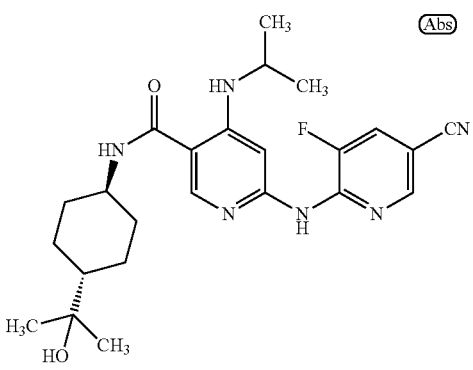 [SMILES: CC(C)Nc1cc(Nc2ncc(C#N)cc2F)ncc1C(=O)N[C@H]1CC[C@H](C(C)(C)O)CC1] | 1.76 | F | 455.2 |
| 138 | 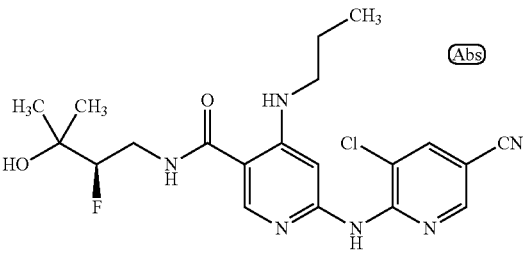 [SMILES: CCCNc1cc(Nc2ncc(C#N)cc2Cl)ncc1C(=O)NC[C@@H](F)C(C)(C)O] | 1.71 | G | 435.2 |
| 139 | 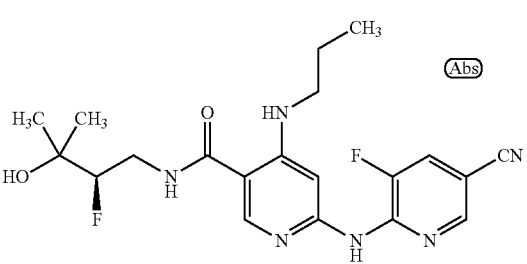 [SMILES: CCCNc1cc(Nc2ncc(C#N)cc2F)ncc1C(=O)NC[C@@H](F)C(C)(C)O] | 1.56 | G | 419.3 |
| 140 | 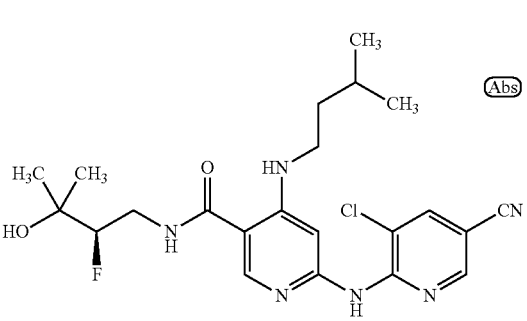 [SMILES: CC(C)CCNc1cc(Nc2ncc(C#N)cc2Cl)ncc1C(=O)NC[C@@H](F)C(C)(C)O] | 1.48 | G | 463.2 |

TABLE 4-continued
| Ex. No. | Structure | HPLC rt (min) | HPLC cond. | LCMS (M + H)+ |
|---|---|---|---|---|
| 141 | 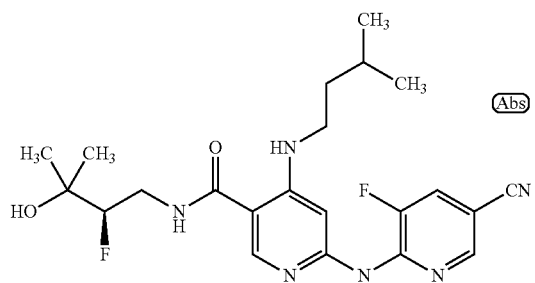 | 1.84 | G | 447.3 |
| 142 | 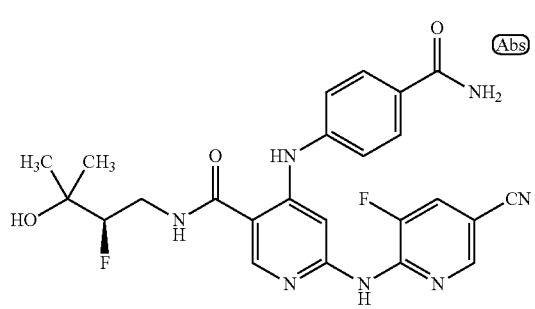 [SMILES: CC(C)(O)[C@H](F)CNC(=O)c1cnc(Nc2ncc(C#N)cc2F)cc1Nc1ccc(C(N)=O)cc1] | 1.15 | G | 496.2 |
| 143 | 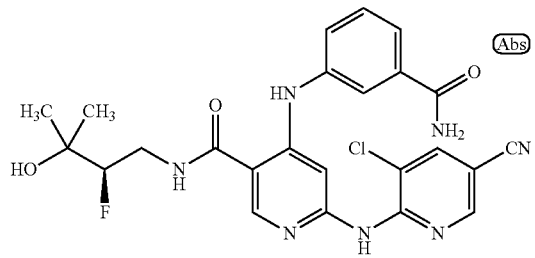 [SMILES: CC(C)(O)[C@H](F)CNC(=O)c1cnc(Nc2ncc(C#N)cc2Cl)cc1Nc1cccc(C(N)=O)c1] | 1.3 | G | 512.3 |
| 144 | 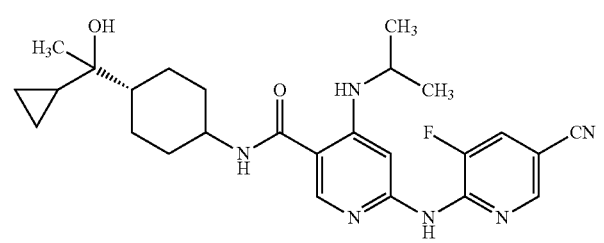 | 7.66 | E | 481 |
| 145 | 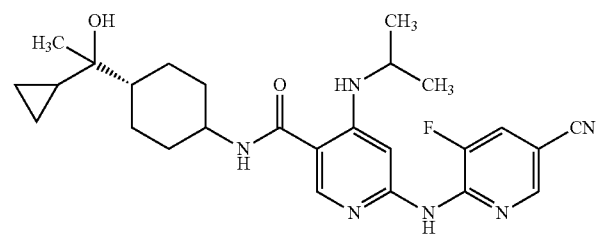 | 7.64 | E | 481 |

TABLE 4-continued
| Ex. No. | Structure | HPLC rt (min) | HPLC cond. | LCMS (M + H)+ |
|---|---|---|---|---|
| 146 | 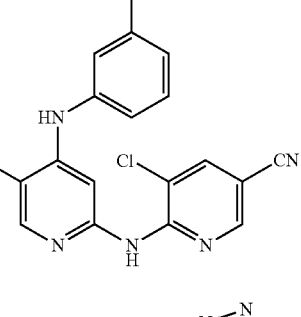 | 1.55 | G | 551.2 |
| 147 | 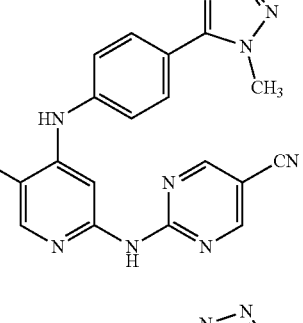 | 1.29 | G | 518.2 |
| 148 | 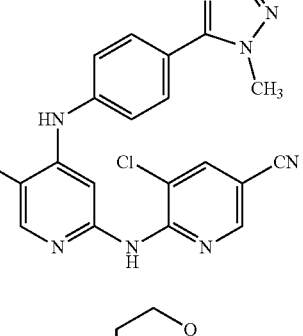 | 1.53 | G | 551.3 |
| 149 | 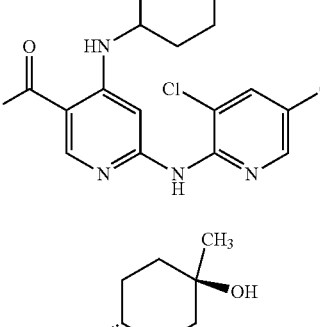 | 1.49 | G | 533.2 |
| 150 | 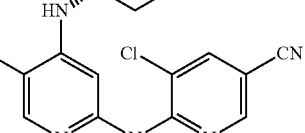 | 1.56 | G | 505.1 |

TABLE 4-continued

| Ex. No. | Structure | HPLC rt (min) | HPLC cond. | LCMS (M + H)+ |
|---|---|---|---|---|
| 151 | 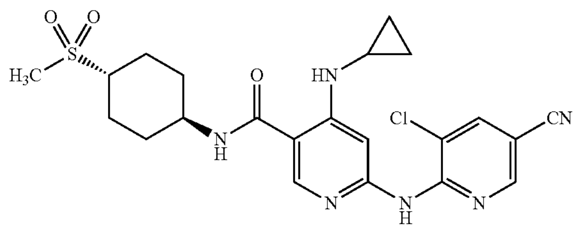 [SMILES: CS(=O)(=O)[C@H]1CC[C@H](NC(=O)c2cnc(Nc3ncc(C#N)cc3Cl)cc2NC2CC2)CC1] | 1.54 | G | 489.3 |
| 152 | 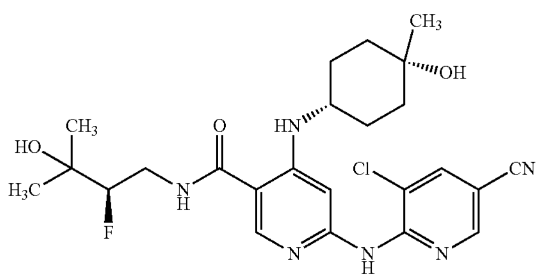 [SMILES: CC(C)(O)[C@H](F)CNC(=O)c1cnc(Nc2ncc(C#N)cc2Cl)cc1N[C@H]1CC[C@@](C)(O)CC1] | 1.34 | G | 505.2 |
| 153 | 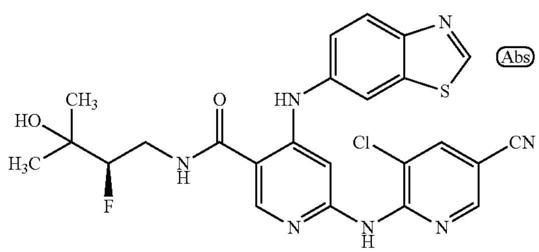 [SMILES: CC(C)(O)[C@H](F)CNC(=O)c1cnc(Nc2ncc(C#N)cc2Cl)cc1Nc1ccc2ncsc2c1] | 1.66 | G, 3 min grad | 526.1 |
| 154 | 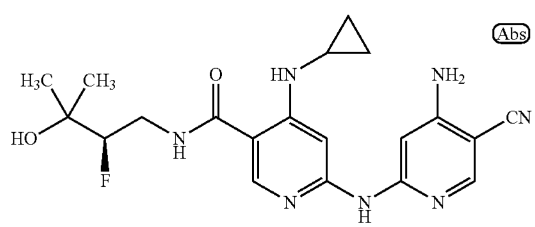 [SMILES: CC(C)(O)[C@H](F)CNC(=O)c1cnc(Nc2cc(N)c(C#N)cn2)cc1NC1CC1] | 1.24 | G | 415.2 |
| 155 | 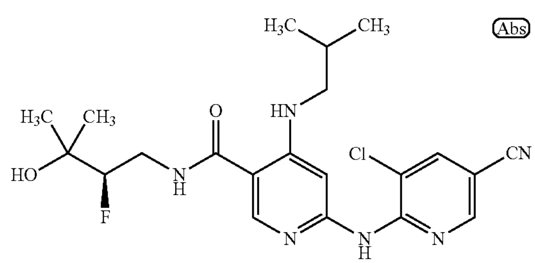 [SMILES: CC(C)CNc1cc(Nc2ncc(C#N)cc2Cl)ncc1C(=O)NC[C@@H](F)C(C)(C)O] | 1.85 | G | 449.1 |
| 156 | 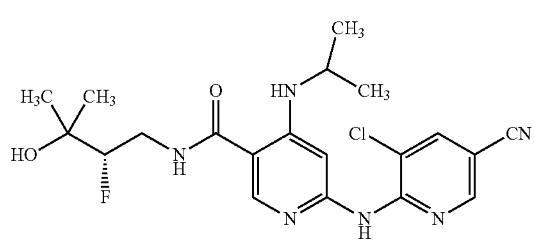 [SMILES: CC(C)Nc1cc(Nc2ncc(C#N)cc2Cl)ncc1C(=O)NC[C@H](F)C(C)(C)O] | 7.41 | A | 435 |

TABLE 4-continued

| Ex. No. | Structure | HPLC rt (min) | HPLC cond. | LCMS (M + H)+ |
|---|---|---|---|---|
| 157 | 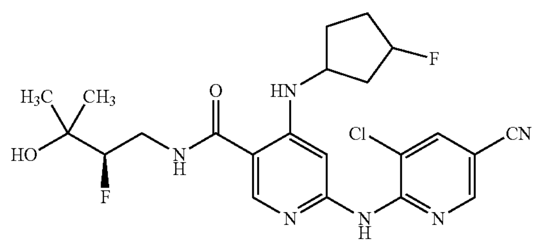 [SMILES: CC(C)(O)[C@H](F)CNC(=O)c1cnc(Nc2ncc(C#N)cc2Cl)cc1NC1CCC(F)C1] | 8.90 | A | 479.2 |
| 158 | 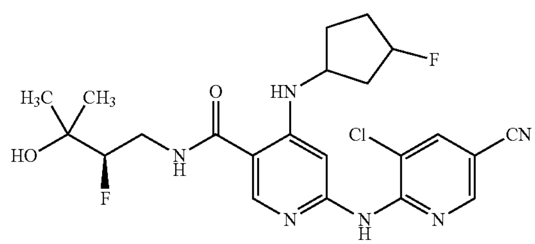 [SMILES: CC(C)(O)[C@H](F)CNC(=O)c1cnc(Nc2ncc(C#N)cc2Cl)cc1NC1CCC(F)C1] | 7.70 | A | 479 |
| 159 | 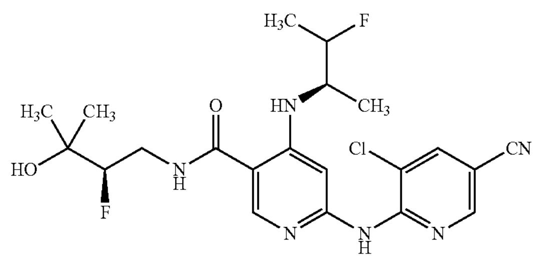 [SMILES: CC(F)[C@@H](C)Nc1cc(Nc2ncc(C#N)cc2Cl)ncc1C(=O)NC[C@@H](F)C(C)(C)O] | 6.54 | E | 467.2 |
| 160 | 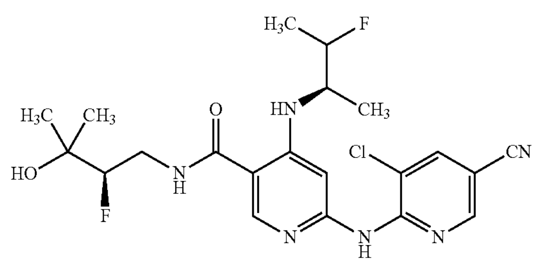 [SMILES: CC(F)[C@@H](C)Nc1cc(Nc2ncc(C#N)cc2Cl)ncc1C(=O)NC[C@@H](F)C(C)(C)O] | 6.50 | E | 467.2 |
| 161 | 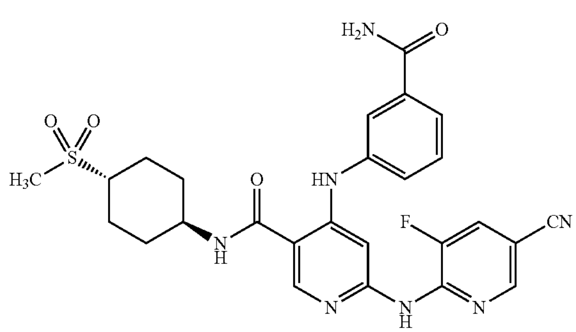 [SMILES: CS(=O)(=O)[C@H]1CC[C@H](NC(=O)c2cnc(Nc3ncc(C#N)cc3F)cc2Nc2cccc(C(N)=O)c2)CC1] | 1.17 | G | 552.2 |

TABLE 4-continued

| Ex. No. | Structure | HPLC rt (min) | HPLC cond. | LCMS (M + H)+ |
|---|---|---|---|---|
| 162 | 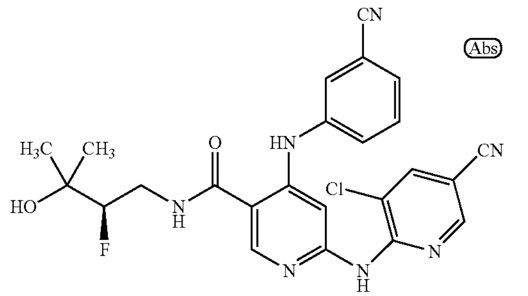 [SMILES: CC(C)(O)[C@H](F)CNC(=O)c1cnc(Nc2ncc(C#N)cc2Cl)cc1Nc1cccc(C#N)c1] | 1.66 | G | 494.2 |
| 163 | 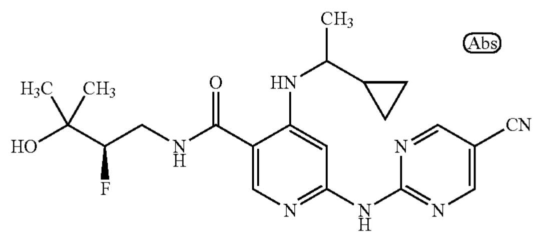 [SMILES: CC(Nc1cc(Nc2ncc(C#N)cn2)ncc1C(=O)NC[C@@H](F)C(C)(C)O)C1CC1] | 6.99 | A | 428.2 |
| 164 | 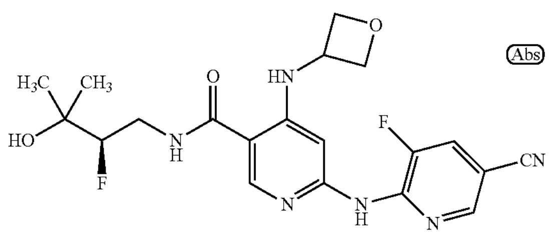 [SMILES: CC(C)(O)[C@H](F)CNC(=O)c1cnc(Nc2ncc(C#N)cc2F)cc1NC1COC1] | 1.1 | G | 433.2 |
| 165 | 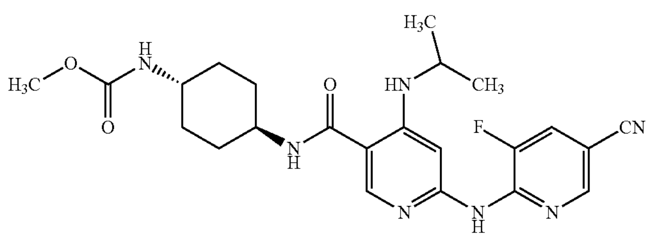 [SMILES: COC(=O)N[C@H]1CC[C@H](NC(=O)c2cnc(Nc3ncc(C#N)cc3F)cc2NC(C)C)CC1] | 1.66 | G | 470.2 |
| 166 | 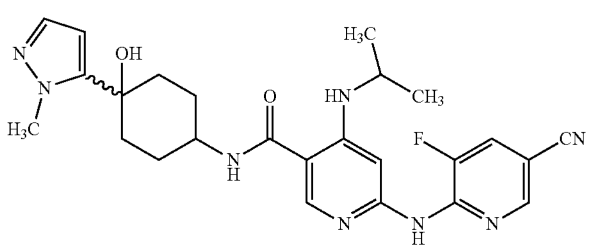 [SMILES: CC(C)Nc1cc(Nc2ncc(C#N)cc2F)ncc1C(=O)NC1CCC(O)(c2ccnn2C)CC1] | 1.63 | G | 493.2 |
| 167 | 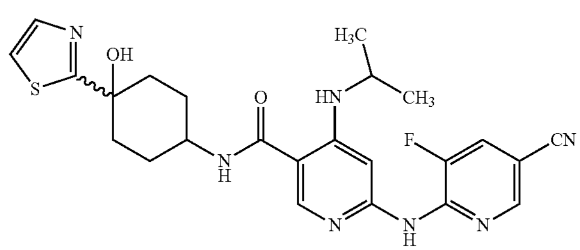 [SMILES: CC(C)Nc1cc(Nc2ncc(C#N)cc2F)ncc1C(=O)NC1CCC(O)(c2nccs2)CC1] | 1.66 | G | 496.1 |

TABLE 4-continued

| Ex. No. | Structure | HPLC rt (min) | HPLC cond. | LCMS (M + H)+ |
|---|---|---|---|---|
| 168 | 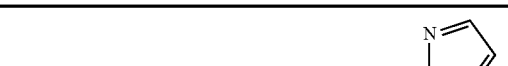 | 1.77 | G | 535.4 |

What is claimed is:
1. A compound of Formula (II)

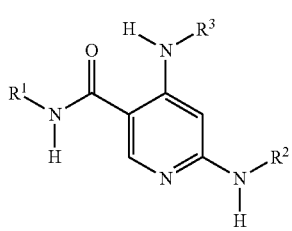

or a stereoisomer or pharmaceutically-acceptable salt thereof, wherein:
$R^1$ is:
(a) $C_{2-3}$ hydroxyalkyl substituted with zero to 4 $R^{1a}$ wherein $R^{1a}$ is independently selected from F, Cl, —OH, —CHF$_2$, —CN, —CF$_3$, —OCH$_3$, and cyclopropyl;
(b) $C_{1-3}$ alkyl substituted with —O($C_{1-3}$ alkyl) and zero to 4 $R^{1a}$ wherein $R^{1a}$ is independently selected from F, Cl, —OH, —CHF$_2$, —CN, —CF$_3$, and cyclopropyl;
(c) $C_{4-8}$ alkyl substituted with zero to 7 $R^{1a}$ wherein $R^{1a}$ is independently selected from F, Cl, —OH, —CHF$_2$, —CF$_3$, —CN, —OCH$_3$, cyclopropyl, and —OP(O)(OH)$_2$;
(d) —(CH$_2$)$_{2-4}$NHC(O)(C$_{1-6}$ alkyl), —(CH$_2$)$_2$CH(CH$_3$)NHC(O)(C$_{1-6}$ alkyl), —(CH$_2$)$_2$CH(CH$_3$)NHC(O)(CH$_2$)$_{0-1}$NH(C$_{1-6}$ alkyl), or —(CH$_2$)$_2$CH(CH$_3$)NHC(O)(CH$_2$)$_{0-1}$N(C$_{1-4}$ alkyl)$_2$;
(e) cyclohexyl substituted with zero to 2 substituents independently selected from —OH, —OCH$_3$, $C_{1-6}$ alkyl, $C_{1-6}$ hydroxyalkyl, —C(O)NH$_2$, —C(O)NH(C$_{1-3}$ alkyl), —C(O)NH(C$_{1-6}$ hydroxyalkyl), —C(O)NH(C$_{3-6}$ cycloalkyl), —C(O)NH(C$_{3-6}$ fluoro cycloalkyl), —NHC(O)(C$_{1-3}$ alkyl), —NHC(O)O(C$_{1-3}$ alkyl), —NHS(O)$_2$CH$_3$, —S(O)$_2$NH$_2$, —S(O)$_2$(C$_{1-3}$ alkyl), —S(C$_{1-3}$ alkyl), and $C_{1-3}$ alkyl substituted with —OH and cyclopropyl; or
(f) —(CH$_2$)$_2$(phenyl) wherein said phenyl is substituted with —C(O)NH$_2$, —C(O)NH(C$_{1-3}$ alkyl), or —S(O)$_2$NH$_2$;
$R^2$ is pyridinyl substituted with zero to 2 substituents independently selected from F, Cl, —OH, —CN, $C_{1-3}$ alkyl, —CH$_2$C(O)OCH$_3$, —O(C$_{1-3}$ alkyl), —NH$_2$, —NH(C$_{1-3}$ alkyl), —NH(cyclopropyl), —C(O)NH$_2$, and —NHC(O)(C$_{1-3}$ alkyl); and
$R^3$ is oxetanyl, tetrahydropyranyl, or fluoro tetrahydropyranyl.

2. The compound according to claim 1 or a stereoisomer or pharmaceutically-acceptable salt thereof, wherein:
$R^1$ is:
(a) $C_{1-3}$ alkyl substituted with —O($C_{1-3}$ alkyl) and zero to 4 $R^{1a}$ wherein $R^{1a}$ is independently selected from F, —OH, and —CF$_3$;
(b) $C_{4-8}$ alkyl substituted with zero to 5 $R^{1a}$ wherein $R^{1a}$ is independently selected from F, Cl, —OH, —CHF$_2$, —CF$_3$, —CN, —OCH$_3$, cyclopropyl, and —OP(O)(OH)$_2$;

(c) —(CH$_2$)$_{2-4}$NHC(O)(C$_{1-3}$ alkyl), —(CH$_2$)$_2$CH(CH$_3$)NHC(O)(C$_{1-3}$ alkyl), —(CH$_2$)$_2$CH(CH$_3$)NHC(O)NH(C$_{1-3}$ alkyl), or —(CH$_2$)$_2$CH(CH$_3$)NHC(O)N(C$_{1-3}$ alkyl)$_2$;

(d) cyclohexyl substituted with zero to 2 substituents independently selected from —OH, —OCH$_3$, C$_{1-3}$ alkyl, —OCH$_3$, C$_{1-3}$ hydroxyalkyl, —C(O)NH$_2$, —C(O)NH(C$_{1-3}$ alkyl), —C(O)NH(C$_{3-5}$ cycloalkyl), —C(O)NH(fluoro cyclopropyl), —NHC(O)(C$_{1-3}$ alkyl), —NHC(O)O(C$_{1-3}$ alkyl), —S(O)$_2$NH$_2$, —S(O)$_2$(C$_{1-2}$ alkyl), —S(C$_{1-2}$ alkyl), and C$_{1-3}$ alkyl substituted with —OH and cyclopropyl; or (e) —(CH$_2$)$_2$(phenyl) wherein said phenyl is substituted with —C(O)NH$_2$, —C(O)NH(CH$_3$), or —S(O)$_2$NH$_2$; and R$^2$ is pyridinyl substituted with zero to 2 substituents independently selected from F, Cl, —OH, —CN, C$_{1-3}$ alkyl, —CH$_2$C(O)OCH$_3$, —O(C$_{1-3}$ alkyl), or —C(O)NH$_2$.

3. The compound according to claim 1 or a stereoisomer or pharmaceutically-acceptable salt thereof, wherein:
R$^1$ is: —CH$_2$CHFC(CH$_3$)$_2$OH, —CH$_2$CHFC(CH$_3$)$_2$OCH$_3$, —CH$_2$CHFC(CH$_2$CH$_3$)$_2$OH, —CH$_2$CHFCH$_2$OCH$_3$, —(CH$_2$)$_3$OCH$_3$, —(CH$_2$)$_3$OC(CH$_3$)$_3$, —CH$_2$CF$_2$C(CH$_3$)$_2$OH, —(CH$_2$)$_2$CH(CH$_3$)NHC(O)CH$_3$, —(CH$_2$)$_2$CH(CH$_3$)NHC(O)NHCH(CH$_3$)$_2$, —CH$_2$CHFC(CH$_3$)$_2$OP(O)(OH)$_2$,

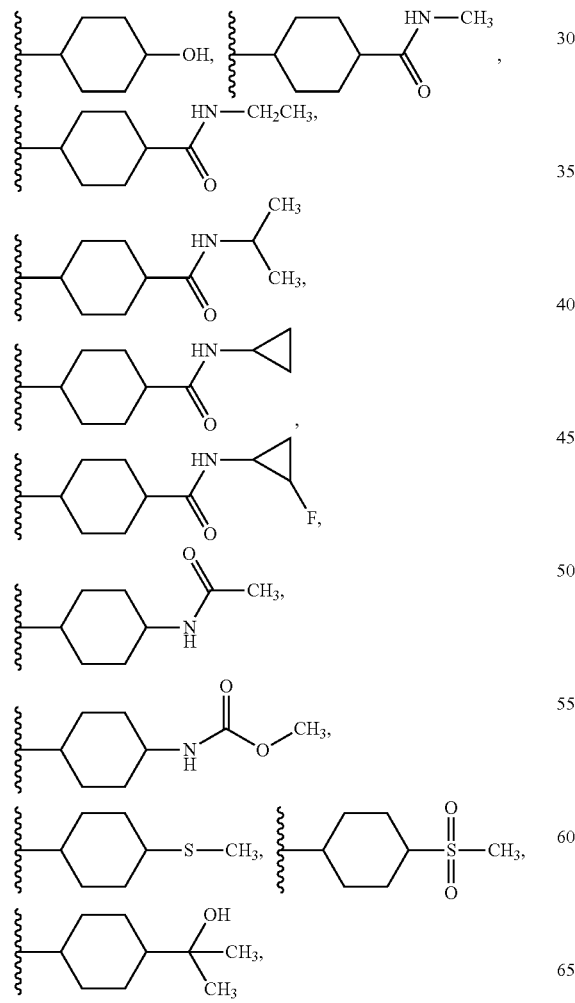

and R$^2$ is

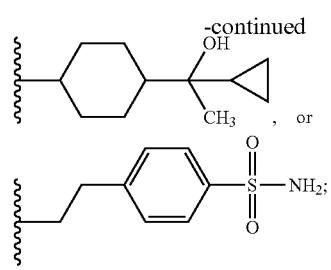

4. The compound according to claim 1 or a stereoisomer or pharmaceutically-acceptable salt thereof, wherein R$^1$ is:
(a) C$_{1-3}$ alkyl substituted with —O(C$_{1-3}$ alkyl) and zero to 4 R$^{1a}$ wherein R$^{1a}$ is independently selected from F, —OH, and —CF$_3$;

(b) C$_{4-8}$ alkyl substituted with zero to 5 R$^{1a}$ wherein R$^{1a}$ is independently selected from F, Cl, —OH, —CHF$_2$, —CF$_3$, —CN, —OCH$_3$, cyclopropyl, and —OP(O)(OH)$_2$; or (c) —(CH$_2$)$_{2-4}$NHC(O)(C$_{1-3}$ alkyl), —(CH$_2$)$_2$CH(CH$_3$)NHC(O)(C$_{1-3}$ alkyl), —(CH$_2$)$_2$CH(CH$_3$)NHC(O)NH(C$_{1-3}$ alkyl), or —(CH$_2$)$_2$CH(CH$_3$)NHC(O)N(C$_{1-3}$ alkyl)$_2$.

5. The compound according to claim 1 for a stereoisomer or pharmaceutically-acceptable salt thereof, wherein R$^1$ is cyclohexyl substituted with zero to 2 substituents independently selected from —OH, —OCH$_3$, C$_{1-3}$ alkyl, —OCH$_3$, C$_{1-3}$ hydroxyalkyl, —C(O)NH$_2$, —C(O)NH(C$_{1-3}$ alkyl), —C(O)NH(C$_{3-5}$ cycloalkyl), —C(O)NH(fluoro cyclopropyl), —NHC(O)(C$_{1-3}$ alkyl), —NHC(O)O(C$_{1-3}$ alkyl), —S(O)$_2$NH$_2$, —S(O)$_2$(C$_{1-2}$ alkyl), —S(C$_{1-2}$ alkyl), and C$_{1-3}$ alkyl substituted with —OH and cyclopropyl.

6. The compound according to claim 1 or a stereoisomer or pharmaceutically-acceptable salt thereof, wherein $R^3$ is

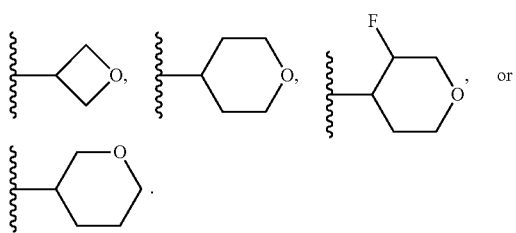

7. The compound according to claim 1 or a stereoisomer or pharmaceutically-acceptable salt thereof, wherein $R^2$ is

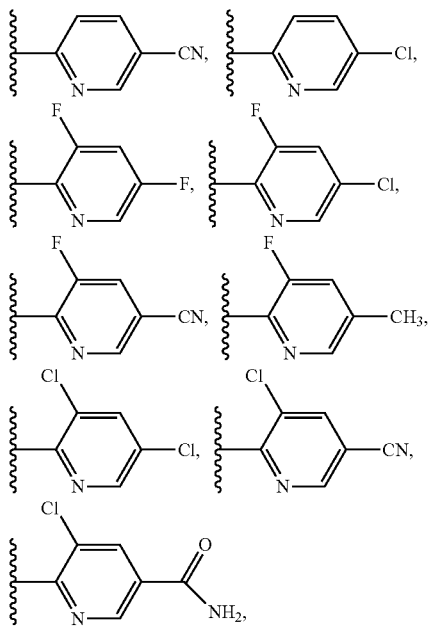

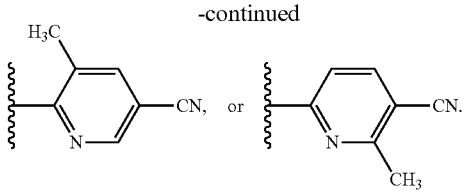

8. A compound according to claim 1 or a pharmaceutically-acceptable salt thereof, selected from:
- (R)-6-((5-cyano-3-fluoropyridin-2-yl)amino)-N-(2-fluoro-3-hydroxy-3-methylbutyl)-4-((tetrahydro-2H-pyran-4-yl)amino)nicotinamide (49);
- 6-((5-cyano-3-fluoropyridin-2-yl)amino)-N-((1r,4r)-4-(methylcarbamoyl) cyclohexyl)-4-((tetrahydro-2H-pyran-4-yl)amino)nicotinamide (61);
- N-((1r,4r)-4-acetamidocyclohexyl)-6-((3-chloro-5-cyanopyridin-2-yl)amino)-4-((tetrahydro-2H-pyran-4-yl)amino)nicotinamide (77);
- 6-((3-chloro-5-cyanopyridin-2-yl)amino)-N—((R)-2-fluoro-3-hydroxy-3-methylbutyl)-4-((3-fluorotetrahydro-2H-pyran-4-yl)amino)nicotinamide (79);
- 6-((5-cyano-3-fluoropyridin-2-yl)amino)-N—((R)-2-fluoro-3-hydroxy-3-methylbutyl)-4-((tetrahydro-2H-pyran-3-yl)amino)nicotinamide (97-98);
- 6-((3,5-difluoropyridin-2-yl)amino)-N—((R)-2-fluoro-3-hydroxy-3-methylbutyl)-4-((3-fluorotetrahydro-2H-pyran-4-yl)amino)nicotinamide (108);
- 6-((3,5-difluoropyridin-2-yl)amino)-N—((R)-2-fluoro-3-hydroxy-3-methylbutyl)-4-((tetrahydro-2H-pyran-3-yl)amino)nicotinamide (109-110);
- 6-((3-chloro-5-cyanopyridin-2-yl)amino)-N-((1 r,4r)-4-(methylsulfonyl)cyclohexyl)-4-((tetrahydro-2H-pyran-4-yl)amino)nicotinamide (149); and
- (R)-6-((5-cyano-3-fluoropyridin-2-yl)amino)-N-(2-fluoro-3-hydroxy-3-methylbutyl)-4-(oxetan-3-ylamino)nicotinamide (164).

9. A pharmaceutical composition comprising one or more compounds according to claim 1 or a pharmaceutically-acceptable salt thereof; and a pharmaceutically acceptable carrier or diluent.

* * * * *

UNITED STATES PATENT AND TRADEMARK OFFICE
CERTIFICATE OF CORRECTION

PATENT NO. : 10,544,133 B2
APPLICATION NO. : 16/009389
DATED : January 28, 2020
INVENTOR(S) : Bhide et al.

Page 1 of 1

It is certified that error appears in the above-identified patent and that said Letters Patent is hereby corrected as shown below:

In the Claims

In Claim 5, Column 176, Line 59, delete "for" and insert -- or --.

In Claim 8, Column 178, Line 32, delete "-((1 r,4r)-" and insert -- -((1r,4r)- --, therefor.

Signed and Sealed this
Eighth Day of December, 2020

Andrei Iancu
*Director of the United States Patent and Trademark Office*

SEQUENCE LISTING

<160> NUMBER OF SEQ ID NOS: 1

<210> SEQ ID NO 1
<211> LENGTH: 18
<212> TYPE: PRT
<213> ORGANISM: Homo sapiens

<400> SEQUENCE: 1

Phe Leu Ile Pro Thr Ser Pro Ile Thr Thr Thr Tyr Phe Phe Phe Lys
1               5                   10                  15

Lys Lys